United States Patent
Crawford et al.

(10) Patent No.: US 8,888,713 B2
(45) Date of Patent: Nov. 18, 2014

(54) SAFETY BLOOD COLLECTION ASSEMBLY WITH INDICATOR

(75) Inventors: Jamieson Crawford, Demarest, NJ (US); Robert Ellis, Wayne, NJ (US); Bradley M. Wilkinson, North Haledon, NJ (US); Benjamin Bartfeld, Pompton Lakes, NJ (US); C. Mark Newby, Tuxedo, NY (US); Chee Leong Alvin Tan, Singapore (SG); Jon Moh, Singapore (SG); Stanley Sim, Singapore (SG); Neville Yu Leng Chia, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 493 days.

(21) Appl. No.: 12/206,299

(22) Filed: Sep. 8, 2008

(65) Prior Publication Data

US 2009/0204026 A1      Aug. 13, 2009

Related U.S. Application Data

(63) Continuation-in-part of application No. 12/044,469, filed on Mar. 7, 2008.

(60) Provisional application No. 60/893,519, filed on Mar. 7, 2007, provisional application No. 60/941,870, filed on Jun. 4, 2007.

(51) Int. Cl.
| | |
|---|---|
| *A61B 5/00* | (2006.01) |
| *B65D 81/00* | (2006.01) |
| *A61B 5/15* | (2006.01) |
| *A61M 5/32* | (2006.01) |
| *A61M 5/50* | (2006.01) |

(52) U.S. Cl.
CPC ............ *A61M 5/3216* (2013.01); *A61B 5/1422* (2013.01); *A61M 5/3202* (2013.01); *A61B 5/1444* (2013.01); *A61M 5/5086* (2013.01); *A61M 2005/3217* (2013.01)
USPC .......................................................... 600/576

(58) Field of Classification Search
USPC .................................................. 600/576–579
See application file for complete search history.

(56) References Cited

U.S. PATENT DOCUMENTS

| | | | |
|---|---|---|---|
| 4,106,497 A | 8/1978 | Percarpio | |
| 4,207,870 A | 6/1980 | Eldridge | |

(Continued)

FOREIGN PATENT DOCUMENTS

| | | | |
|---|---|---|---|
| EP | 0060385 A1 | 9/1982 | |
| EP | 1579805 A1 | 9/2005 | |

(Continued)

OTHER PUBLICATIONS

U.S. Appl. No. 11/572,220, filed Aug. 26, 2008; Swenson.

(Continued)

*Primary Examiner* — Jeffrey G Hoekstra
*Assistant Examiner* — Michael C Stout
(74) *Attorney, Agent, or Firm* — The Webb Law Firm

(57) ABSTRACT

A blood collection assembly includes a housing and a cannula extending distally from the housing including a patient end, and a cannula shield removably engaged with a portion of the housing. The cannula shield is capable of shielding at least the patient end of the cannula, and includes a safety shield engagement. The assembly includes a pivoting safety shield engaged with a portion of the housing, which is transitionable from a retracted position in which the patient end of the cannula is exposed, to an extended position in which the patient end of the cannula is shielded by at least a portion of the safety shield. The safety shield includes at least one locking tab releasably engageable with the safety shield engagement, wherein the locking tab is fixedly engageable with a portion of the housing in the extended position.

29 Claims, 118 Drawing Sheets

(56) References Cited

U.S. PATENT DOCUMENTS

| | | |
|---|---|---|
| 4,305,406 A | 12/1981 | Megahed |
| 4,572,210 A | 2/1986 | McKinnon |
| 4,573,976 A | 3/1986 | Sampson et al. |
| 4,641,663 A | 2/1987 | Juhn |
| 4,795,443 A | 1/1989 | Permenter et al. |
| 4,813,426 A | 3/1989 | Haber et al. |
| 4,840,619 A | 6/1989 | Hughes |
| 4,887,998 A | 12/1989 | Martin et al. |
| 4,894,055 A | 1/1990 | Sudnak |
| 4,900,307 A | 2/1990 | Kulli |
| 4,923,477 A | 5/1990 | Horvath |
| 4,994,046 A | 2/1991 | Wesson et al. |
| 5,015,241 A | 5/1991 | Feimer |
| 5,195,985 A | 3/1993 | Hall |
| 5,215,534 A | 6/1993 | De Harde et al. |
| 5,219,333 A | 6/1993 | Sagstetter et al. |
| 5,222,502 A | 6/1993 | Kurose |
| 5,242,417 A | 9/1993 | Paudler |
| 5,246,428 A * | 9/1993 | Falknor ............... 604/198 |
| 5,256,153 A | 10/1993 | Hake |
| 5,295,970 A | 3/1994 | Clinton et al. |
| 5,295,975 A | 3/1994 | Lockwood, Jr. |
| 5,303,713 A | 4/1994 | Kurose |
| 5,312,372 A | 5/1994 | DeHarde et al. |
| 5,318,547 A | 6/1994 | Altschuler |
| 5,336,199 A | 8/1994 | Castillo et al. |
| 5,348,544 A | 9/1994 | Sweeney et al. |
| 5,356,392 A | 10/1994 | Firth et al. |
| 5,389,085 A | 2/1995 | D'Alessio et al. |
| 5,403,286 A | 4/1995 | Lockwood, Jr. |
| 5,411,492 A | 5/1995 | Sturman et al. |
| 5,439,449 A | 8/1995 | Mapes et al. |
| 5,466,223 A | 11/1995 | Bressler et al. |
| 5,501,675 A | 3/1996 | Erskine |
| 5,542,932 A | 8/1996 | Daugherty |
| 5,549,558 A | 8/1996 | Martin |
| 5,595,566 A | 1/1997 | Vallelunga et al. |
| 5,599,313 A * | 2/1997 | Gyure et al. ............ 604/192 |
| 5,607,402 A | 3/1997 | Dufresne et al. |
| RE35,539 E | 6/1997 | Bonaldo |
| 5,662,617 A | 9/1997 | Odell et al. |
| 5,665,075 A * | 9/1997 | Gyure et al. ............ 604/263 |
| 5,669,889 A * | 9/1997 | Gyure et al. ............ 604/263 |
| 5,672,161 A | 9/1997 | Allen et al. |
| 5,676,658 A | 10/1997 | Erskine |
| 5,681,295 A * | 10/1997 | Gyure et al. ............ 604/263 |
| 5,687,740 A | 11/1997 | Sheridan |
| 5,688,241 A | 11/1997 | Asbaghi |
| 5,695,474 A | 12/1997 | Daugherty |
| 5,702,369 A | 12/1997 | Mercereau |
| 5,704,920 A | 1/1998 | Gyure |
| 5,718,239 A | 2/1998 | Newby et al. |
| 5,733,265 A * | 3/1998 | Bachman et al. ............ 604/263 |
| 5,755,522 A | 5/1998 | Ito |
| 5,795,336 A | 8/1998 | Romano et al. |
| 5,879,337 A | 3/1999 | Kuracina et al. |
| 5,893,845 A | 4/1999 | Newby et al. |
| 5,910,130 A | 6/1999 | Caizza et al. |
| 5,921,964 A | 7/1999 | Martin |
| 5,957,892 A | 9/1999 | Thorne |
| 5,984,899 A | 11/1999 | D'Alessio et al. |
| D422,700 S | 4/2000 | Crawford et al. |
| 6,149,629 A | 11/2000 | Wilson et al. |
| 6,171,284 B1 | 1/2001 | Kao et al. |
| 6,183,445 B1 | 2/2001 | Lund et al. |
| D442,280 S | 5/2001 | Crawford et al. |
| 6,224,576 B1 * | 5/2001 | Thorne et al. ............ 604/198 |
| 6,254,575 B1 * | 7/2001 | Thorne et al. ............ 604/198 |
| 6,261,263 B1 | 7/2001 | Huet et al. |
| 6,261,265 B1 | 7/2001 | Mosseri |
| 6,298,541 B1 | 10/2001 | Newby et al. |
| 6,344,032 B1 * | 2/2002 | Perez et al. ............ 604/198 |
| 6,419,658 B1 | 7/2002 | Restelli et al. |
| 6,436,086 B1 | 8/2002 | Newby et al. |
| 6,440,104 B1 | 8/2002 | Newby et al. |
| 6,471,677 B2 | 10/2002 | Domici, Jr. |
| 6,475,191 B2 | 11/2002 | Tamura et al. |
| 6,485,469 B1 | 11/2002 | Stewart et al. |
| 6,524,277 B1 | 2/2003 | Chang |
| 6,533,760 B2 | 3/2003 | Leong |
| 6,554,807 B2 | 4/2003 | Gollobin |
| 6,575,939 B1 | 6/2003 | Brunel |
| 6,592,556 B1 * | 7/2003 | Thorne ............... 604/192 |
| 6,623,456 B1 | 9/2003 | Holdaway et al. |
| 6,623,461 B1 | 9/2003 | Wilkinson et al. |
| 6,635,032 B2 | 10/2003 | Ward, Jr. |
| 6,641,555 B1 | 11/2003 | Botich et al. |
| 6,648,855 B2 | 11/2003 | Crawford et al. |
| 6,648,856 B1 | 11/2003 | Argento |
| 6,659,983 B2 | 12/2003 | Crawford et al. |
| 6,695,819 B2 * | 2/2004 | Kobayashi ............... 604/192 |
| 6,699,217 B2 | 3/2004 | Bennett et al. |
| 6,712,792 B2 | 3/2004 | Leong |
| 6,716,199 B2 | 4/2004 | DeHarde et al. |
| 6,761,704 B2 | 7/2004 | Crawford |
| 6,773,419 B2 | 8/2004 | Crawford et al. |
| 6,780,169 B2 | 8/2004 | Crawford |
| 6,805,689 B2 | 10/2004 | Chen |
| 6,811,545 B2 | 11/2004 | Vaillancourt |
| 6,835,190 B2 | 12/2004 | Nguyen |
| 6,837,877 B2 | 1/2005 | Zurcher |
| 6,846,302 B2 | 1/2005 | Shemesh et al. |
| 6,860,872 B2 | 3/2005 | Teichert |
| 6,869,415 B2 | 3/2005 | Asbaghi |
| 6,905,483 B2 | 6/2005 | Newby et al. |
| 6,918,891 B2 * | 7/2005 | Bressler et al. ............ 604/198 |
| 6,958,054 B2 | 10/2005 | Fitzgerald |
| 6,974,423 B2 | 12/2005 | Zurcher |
| 6,984,223 B2 | 1/2006 | Newby et al. |
| 6,997,913 B2 | 2/2006 | Wilkinson |
| 7,001,363 B2 | 2/2006 | Ferguson et al. |
| 7,083,600 B2 | 8/2006 | Meloul |
| 7,101,355 B2 * | 9/2006 | Doyle ............... 604/192 |
| 7,128,726 B2 | 10/2006 | Crawford et al. |
| 7,147,624 B2 | 12/2006 | Hirsiger et al. |
| 7,160,267 B2 | 1/2007 | Brown |
| 7,163,526 B2 | 1/2007 | Leong et al. |
| 7,201,740 B2 | 4/2007 | Crawford |
| 7,211,065 B2 | 5/2007 | Miller |
| 7,223,258 B2 | 5/2007 | Crawford |
| 7,226,432 B2 | 6/2007 | Brown |
| 7,361,159 B2 | 4/2008 | Fiser et al. |
| 7,396,343 B2 | 7/2008 | Brown |
| 7,428,773 B2 | 9/2008 | Newby et al. |
| 7,524,308 B2 | 4/2009 | Conway |
| 7,537,581 B2 * | 5/2009 | Hwang ............... 604/110 |
| D604,836 S | 11/2009 | Crawford et al. |
| D604,837 S | 11/2009 | Crawford et al. |
| D604,838 S | 11/2009 | Crawford et al. |
| D604,839 S | 11/2009 | Crawford et al. |
| D605,287 S | 12/2009 | Crawford et al. |
| 7,670,320 B2 | 3/2010 | Iwase et al. |
| 7,727,190 B2 | 6/2010 | Miller |
| 7,766,879 B2 * | 8/2010 | Tan et al. ............ 604/168.01 |
| 7,938,808 B2 | 5/2011 | Pessin |
| 8,066,679 B2 * | 11/2011 | Hwang ............... 604/198 |
| RE43,473 E | 6/2012 | Newby et al. |
| 8,282,605 B2 | 10/2012 | Tan et al. |
| 2001/0021827 A1 * | 9/2001 | Ferguson et al. ............ 604/198 |
| 2002/0004650 A1 | 1/2002 | Kuracina et al. |
| 2002/0055716 A1 | 5/2002 | Nakagami |
| 2002/0103464 A1 | 8/2002 | Crawford et al. |
| 2002/0103465 A1 | 8/2002 | Crowford et al. |
| 2002/0107488 A1 | 8/2002 | Ranford |
| 2002/0151856 A1 | 10/2002 | Gollobin |
| 2002/0193748 A1 | 12/2002 | Cocker et al. |
| 2003/0028171 A1 | 2/2003 | DeHarde et al. |
| 2003/0036730 A1 | 2/2003 | Teichert |
| 2003/0050608 A1 | 3/2003 | Brown |
| 2003/0055385 A1 | 3/2003 | Schooler et al. |
| 2003/0078544 A1 | 4/2003 | Chen |
| 2003/0093009 A1 * | 5/2003 | Newby et al. ............ 600/576 |
| 2003/0105414 A1 * | 6/2003 | Leong ............... 600/576 |
| 2003/0114797 A1 | 6/2003 | Vaillancourt et al. |

(56) References Cited

U.S. PATENT DOCUMENTS

| | | |
|---|---|---|
| 2003/0120222 A1 | 6/2003 | Vaillancourt |
| 2003/0176842 A1 | 9/2003 | Wilkinson et al. |
| 2003/0191438 A1* | 10/2003 | Ferguson et al. ............ 604/198 |
| 2003/0199827 A1 | 10/2003 | Thorne |
| 2003/0216687 A1 | 11/2003 | Hwang |
| 2003/0220614 A1* | 11/2003 | Crawford ...................... 604/192 |
| 2003/0229315 A1* | 12/2003 | Leong et al. .................. 604/263 |
| 2003/0229316 A1 | 12/2003 | Hwang et al. |
| 2004/0024370 A1 | 2/2004 | Wilkinson et al. |
| 2004/0059302 A1 | 3/2004 | Crawford et al. |
| 2004/0092872 A1 | 5/2004 | Botich et al. |
| 2004/0102740 A1 | 5/2004 | Meloul |
| 2004/0111068 A1* | 6/2004 | Swenson ....................... 604/263 |
| 2004/0193120 A1 | 9/2004 | Ferguson et al. |
| 2004/0204681 A1 | 10/2004 | Thoresen et al. |
| 2004/0210197 A1 | 10/2004 | Conway |
| 2005/0004524 A1 | 1/2005 | Newby et al. |
| 2005/0059936 A1 | 3/2005 | Fiser et al. |
| 2005/0065482 A1* | 3/2005 | Hauri et al. ................... 604/263 |
| 2005/0124944 A1* | 6/2005 | Hwang .......................... 604/263 |
| 2005/0165353 A1 | 7/2005 | Pessin |
| 2005/0187493 A1* | 8/2005 | Swenson et al. ............. 600/576 |
| 2005/0228345 A1 | 10/2005 | Yang et al. |
| 2005/0245868 A1 | 11/2005 | Brown |
| 2005/0245869 A1 | 11/2005 | Brown |
| 2005/0245870 A1 | 11/2005 | Brown |
| 2005/0245879 A9 | 11/2005 | Crawford |
| 2005/0245885 A1 | 11/2005 | Brown |
| 2005/0283093 A1* | 12/2005 | Conway et al. .............. 600/576 |
| 2006/0015073 A9* | 1/2006 | Ferguson et al. ............ 604/198 |
| 2006/0036217 A1 | 2/2006 | Doyle |
| 2006/0036219 A1* | 2/2006 | Alvin ............................ 604/272 |
| 2006/0079847 A1 | 4/2006 | Crawford |
| 2006/0129064 A1 | 6/2006 | Conway et al. |
| 2006/0189934 A1 | 8/2006 | Kuracina et al. |
| 2006/0189936 A1 | 8/2006 | Carlyon et al. |
| 2006/0224122 A1* | 10/2006 | Bosel et al. .................. 604/192 |
| 2006/0270947 A1* | 11/2006 | Crawford et al. ............ 600/576 |
| 2006/0276756 A1 | 12/2006 | Francavilla |
| 2007/0021724 A1* | 1/2007 | Bressler et al. .............. 604/263 |
| 2007/0027430 A1 | 2/2007 | Hommann |
| 2007/0106220 A1 | 5/2007 | Brown |
| 2007/0106224 A1* | 5/2007 | Hwang .......................... 604/192 |
| 2007/0167914 A1 | 7/2007 | Leong et al. |
| 2007/0282275 A1* | 12/2007 | Ferguson et al. ............. 604/198 |
| 2008/0015513 A1 | 1/2008 | Westbye et al. |
| 2008/0086085 A1 | 4/2008 | Brown |
| 2008/0177202 A1 | 7/2008 | Brown |
| 2008/0221528 A1 | 9/2008 | Lanz |
| 2008/0269691 A1 | 10/2008 | Cowe |
| 2008/0306452 A1 | 12/2008 | Crawford |
| 2008/0319345 A1 | 12/2008 | Swenson |
| 2008/0319346 A1 | 12/2008 | Crawford et al. |
| 2009/0204026 A1 | 8/2009 | Crawford et al. |
| 2009/0227896 A1 | 9/2009 | Tan et al. |
| 2010/0063455 A1 | 3/2010 | Moyer et al. |
| 2010/0191189 A1 | 7/2010 | Harding et al. |
| 2010/0262038 A1 | 10/2010 | Tan et al. |
| 2011/0118674 A1 | 5/2011 | Doyle |

FOREIGN PATENT DOCUMENTS

| | | |
|---|---|---|
| EP | 1665986 B1 | 6/2009 |
| JP | 5711660 A | 1/1982 |
| JP | 5711661 A | 1/1982 |
| JP | 5789869 A | 6/1982 |
| JP | 6285172 A | 10/1994 |
| JP | 2005176928 A | 7/2005 |
| JP | 2005-270671 A | 10/2005 |
| JP | 2005349196 A | 12/2005 |
| JP | 2006-150083 A | 6/2006 |
| WO | 9629107 A1 | 9/1996 |
| WO | 2006007556 A2 | 1/2006 |
| WO | 2006022716 A1 | 3/2006 |
| WO | 2009110922 A1 | 9/2009 |

OTHER PUBLICATIONS

U.S. Appl. No. 12/044,354, filed Mar. 7, 2008; Tan.
U.S. Appl. No. 12/044,469, filed Mar. 7, 2008; Crawford.
U.S. Appl. No. 12/206,273, filed Sep. 8, 2008; Tan.
U.S. Appl. No. 29/304,786, filed Mar. 7, 2008; Crawford.
U.S. Appl. No. 29/304,794, filed Mar. 7, 2008; Crawford.
U.S. Appl. No. 29/304,796, filed Mar. 7, 2008; Crawford.
U.S. Appl. No. 29/304,801, filed Mar. 7, 2008; Crawford.
U.S. Appl. No. 29/304,807, filed Mar. 7, 2008; Crawford.

* cited by examiner

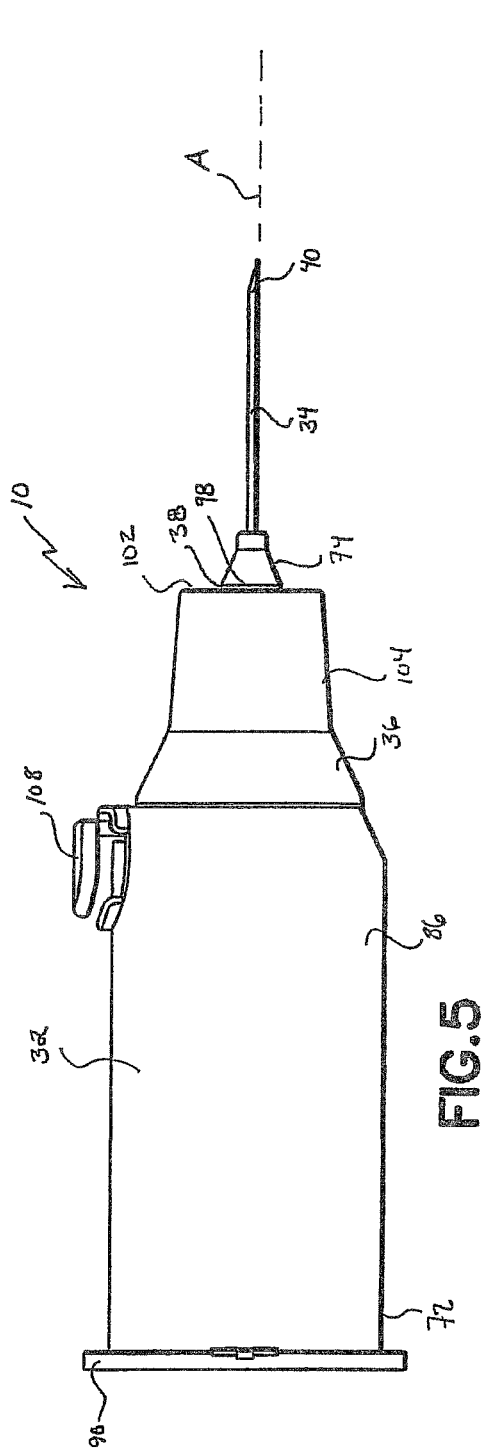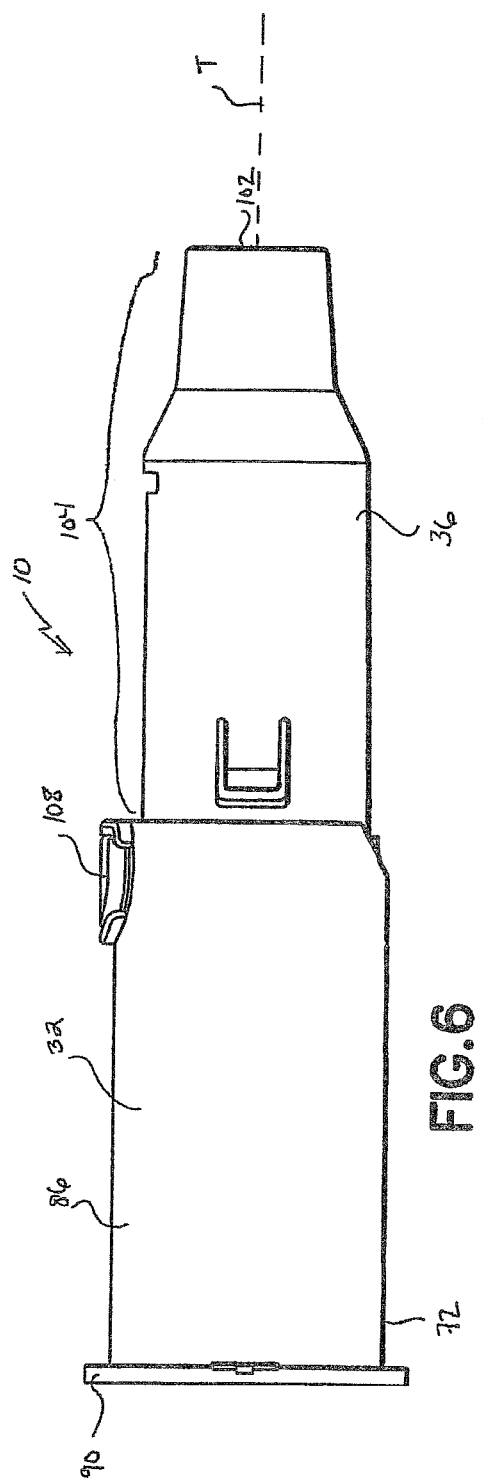

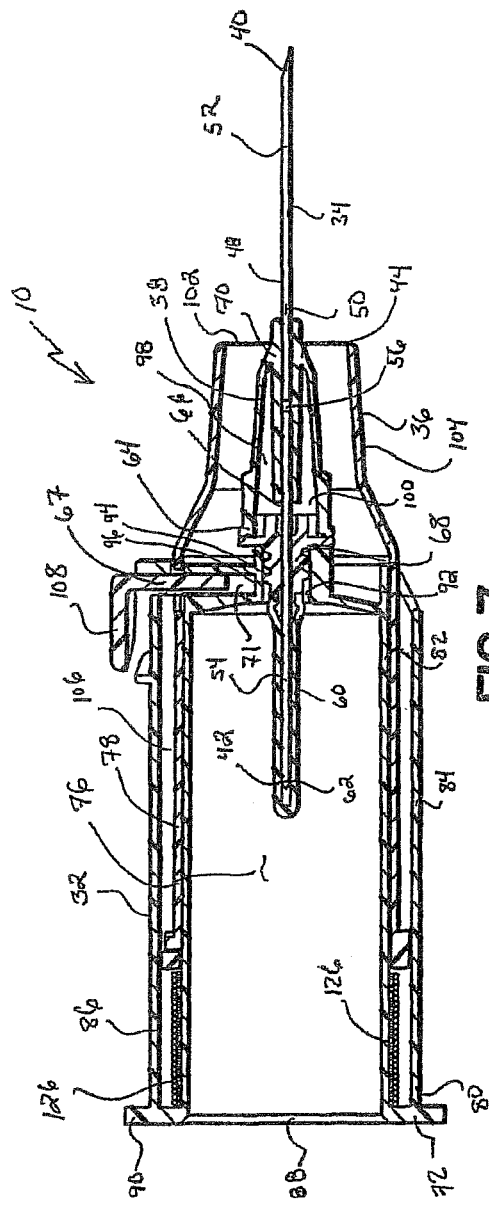
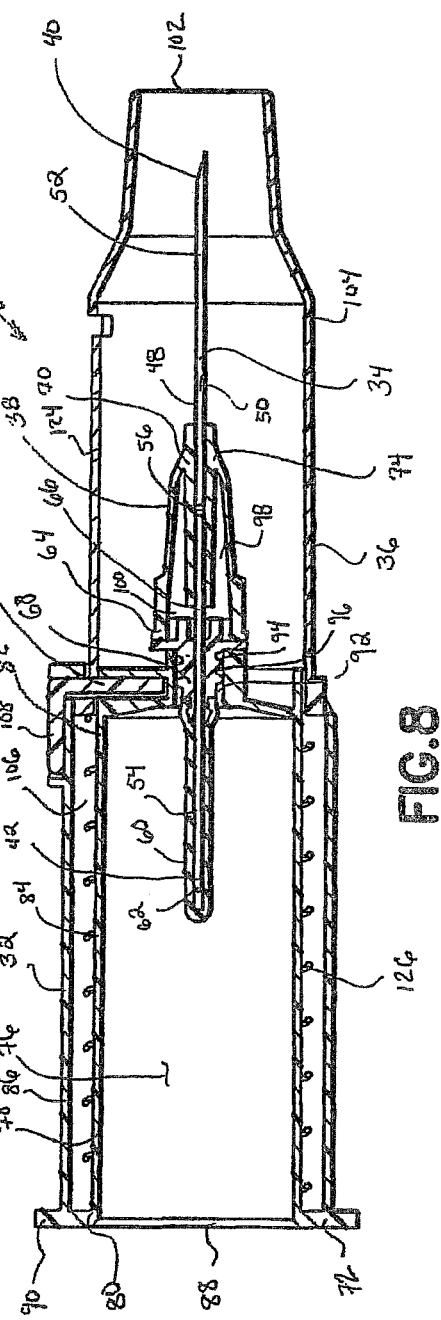
FIG. 7
FIG. 8

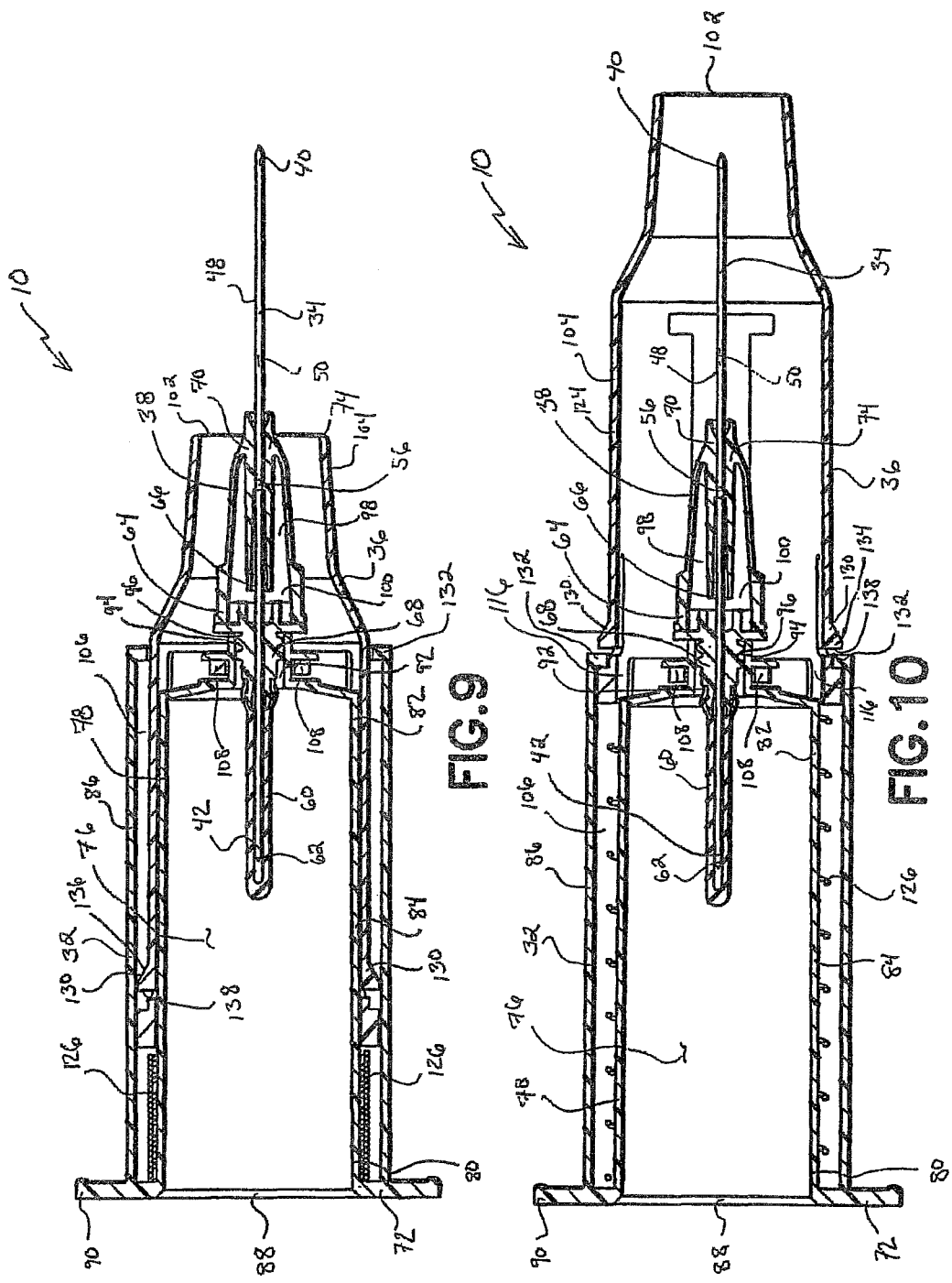

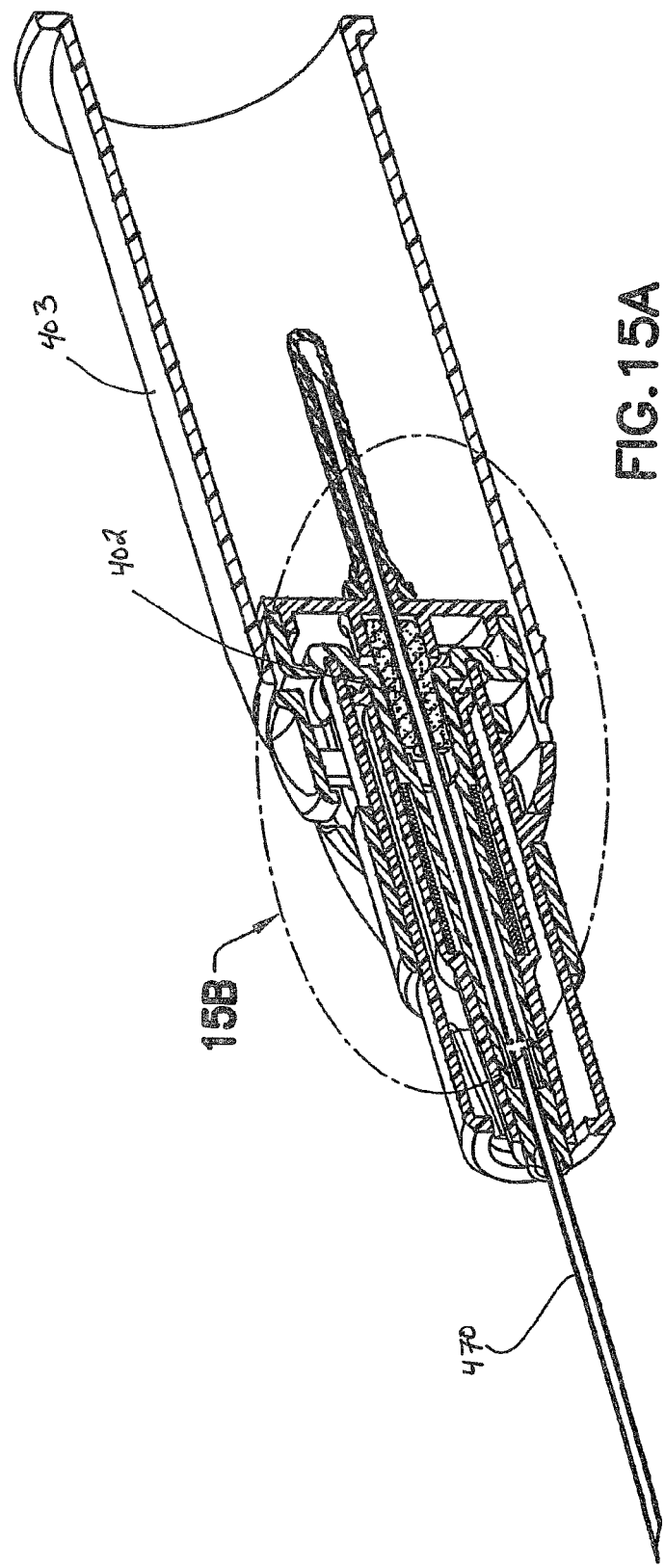

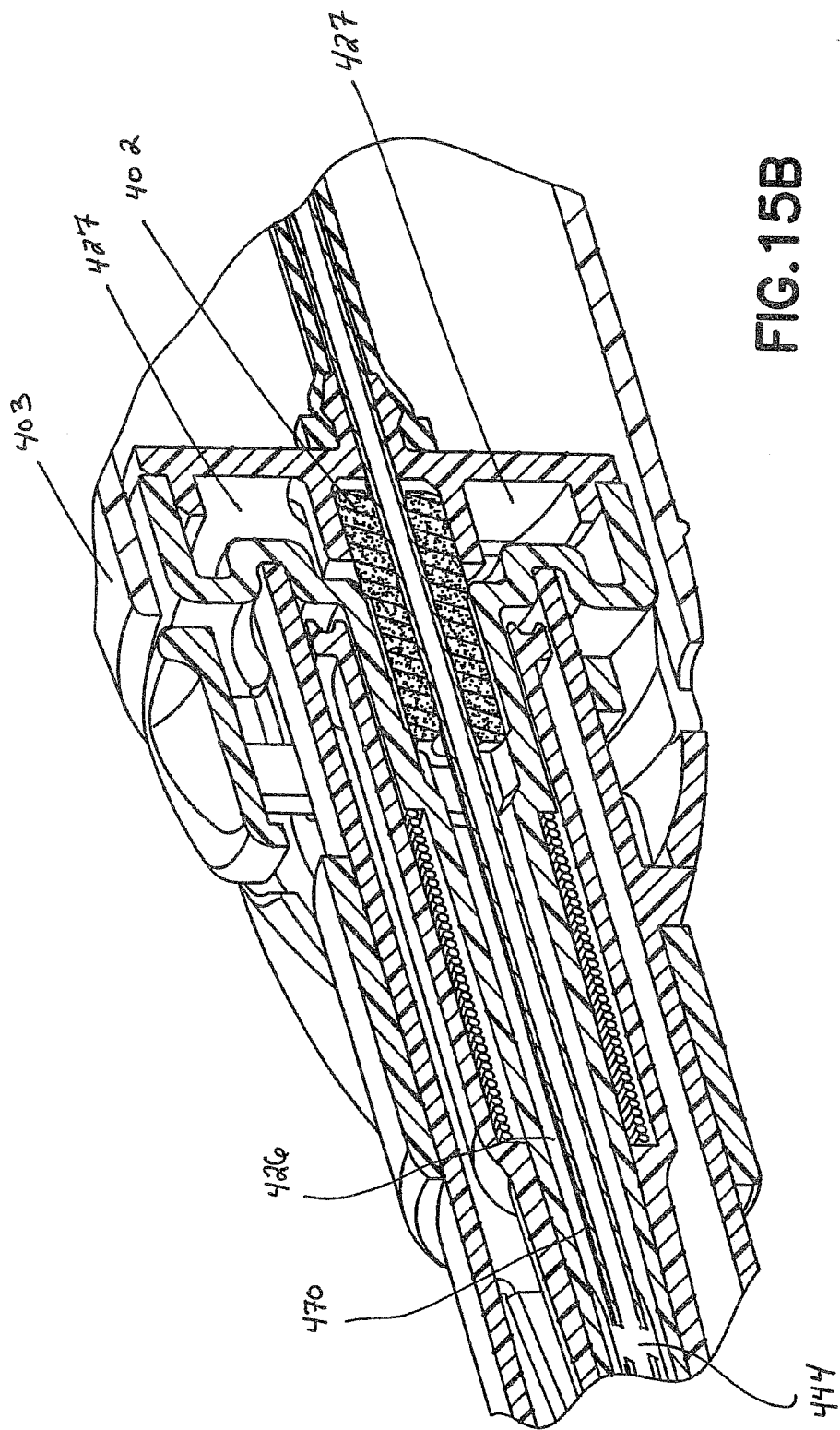

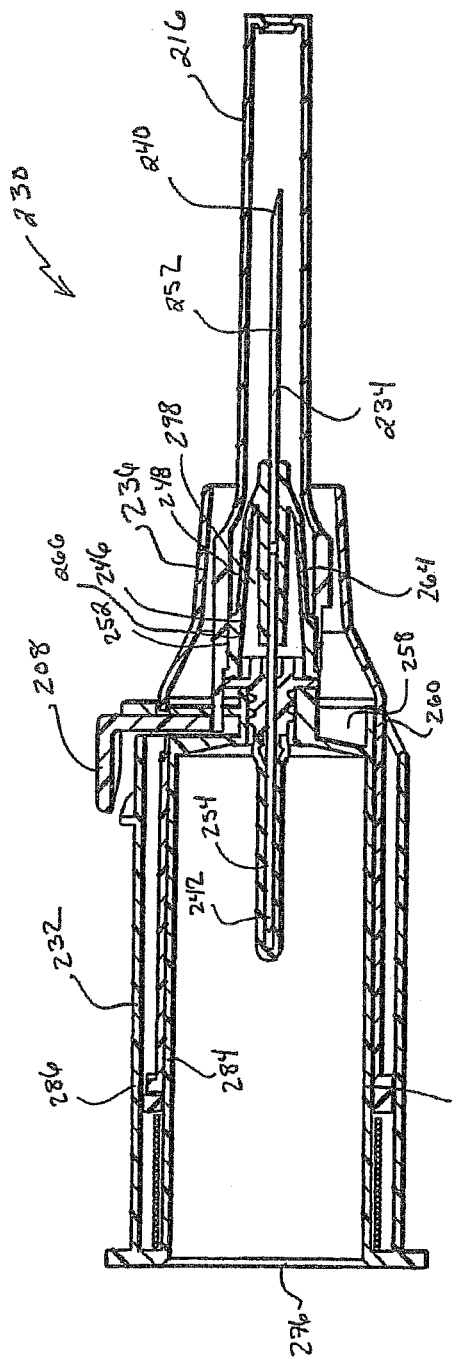

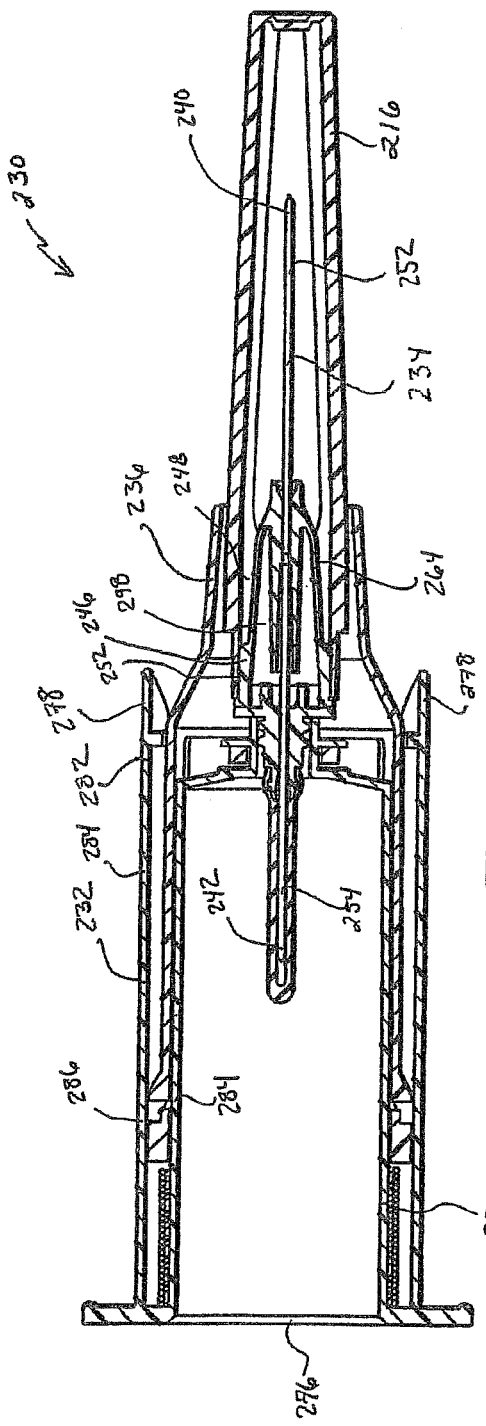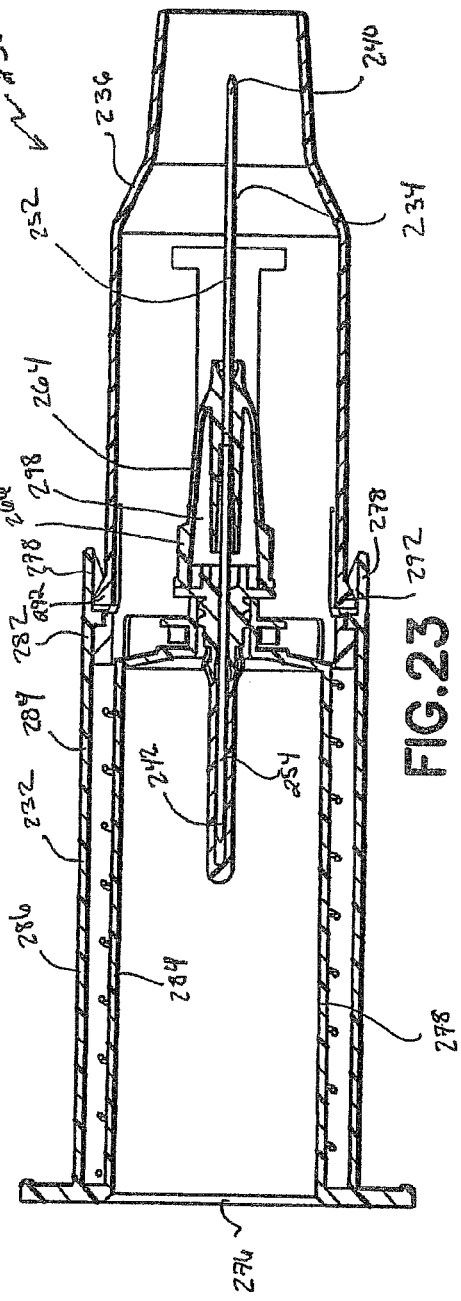

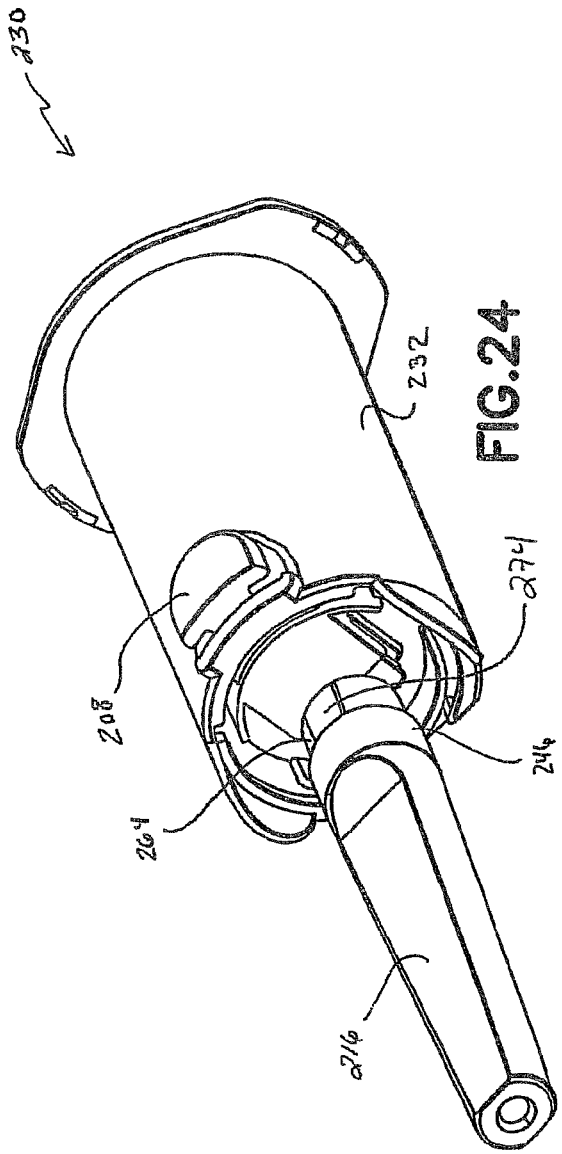
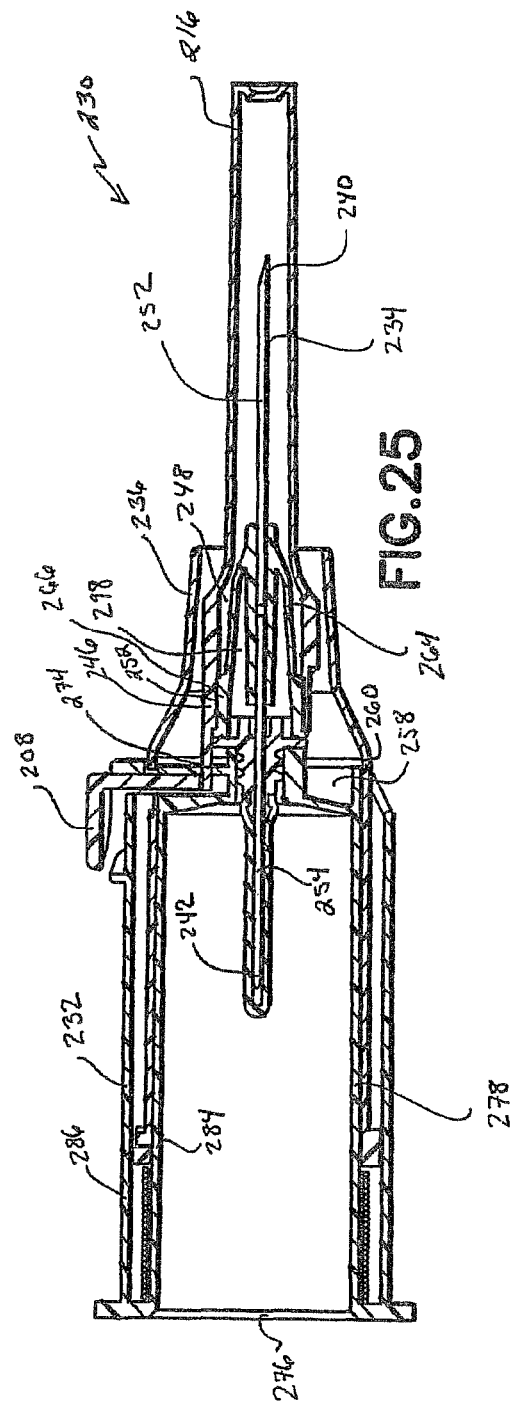

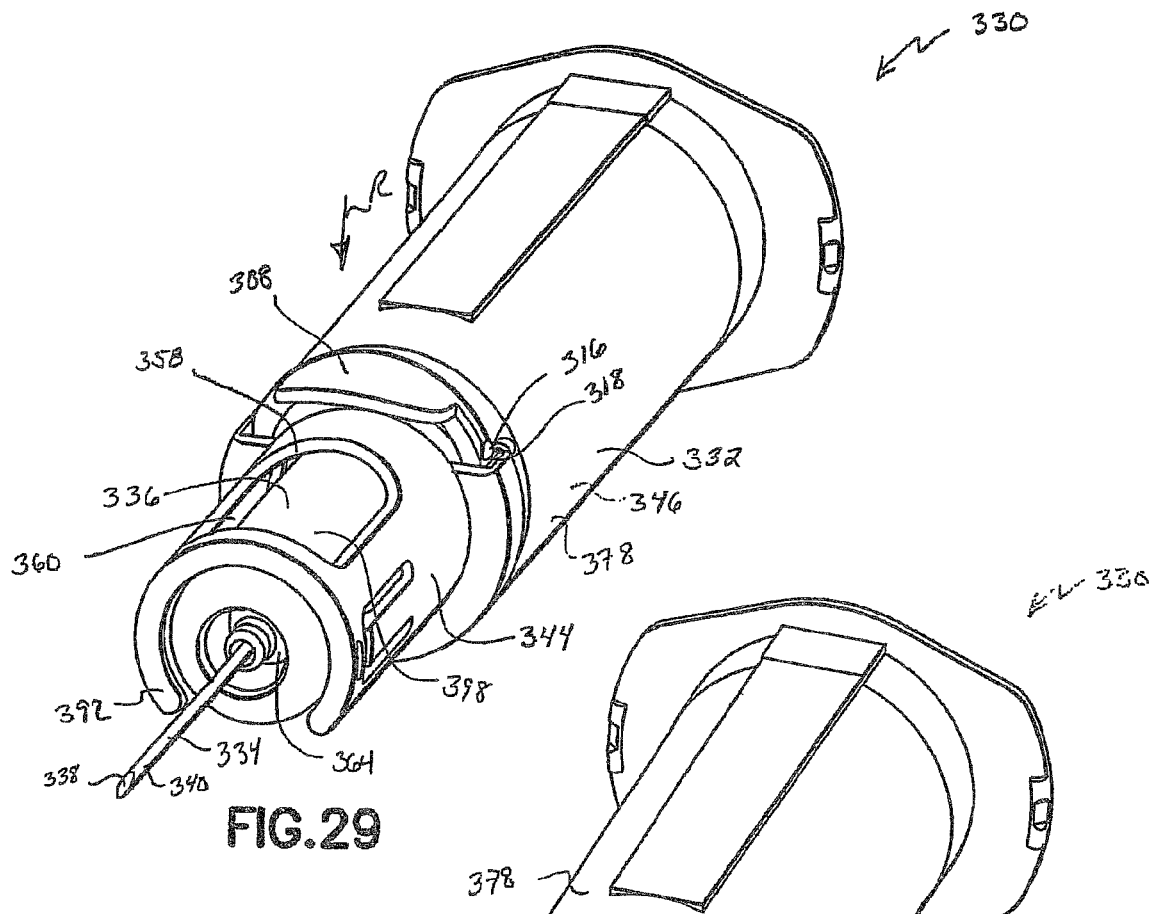
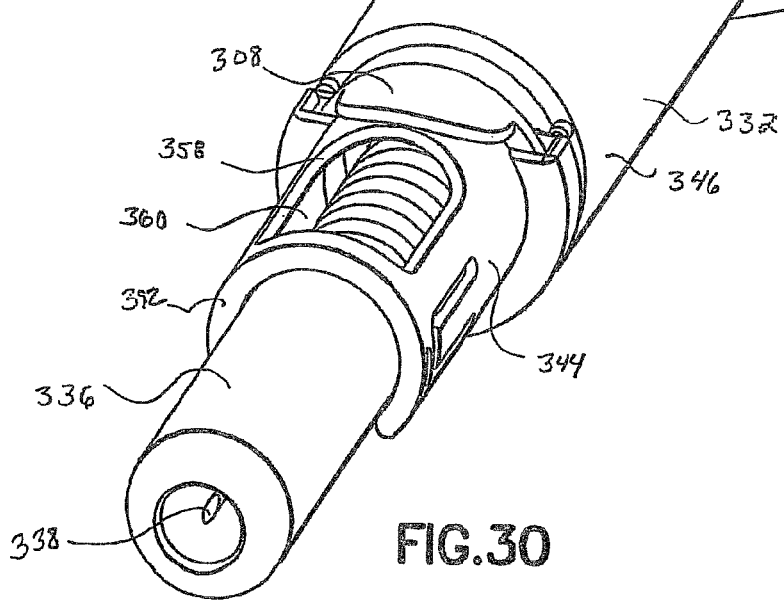

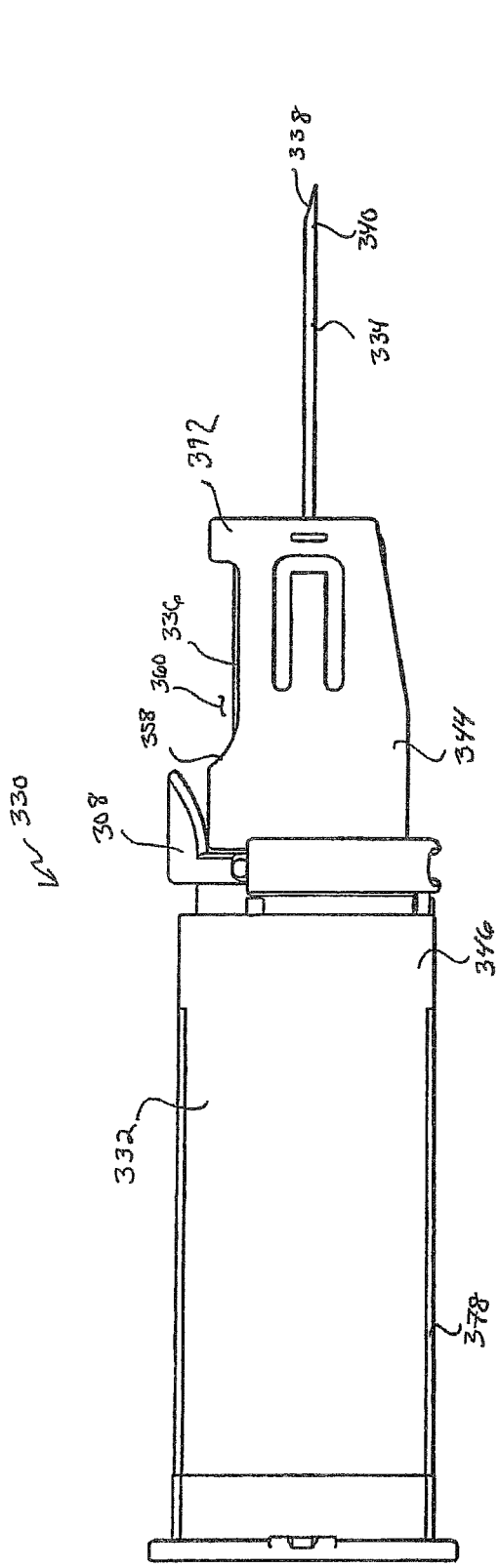
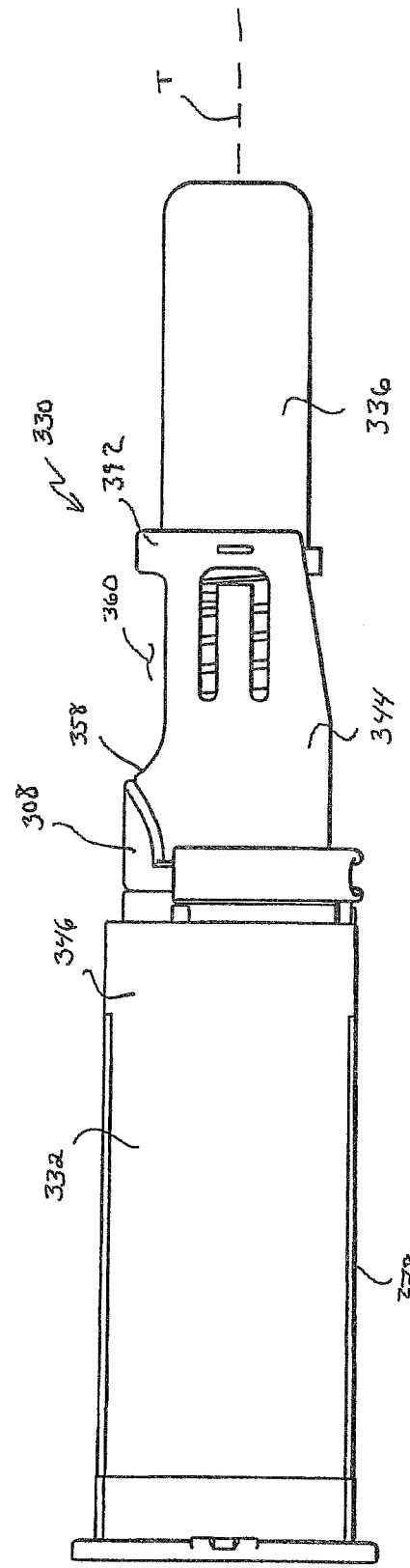
FIG.31
FIG.32

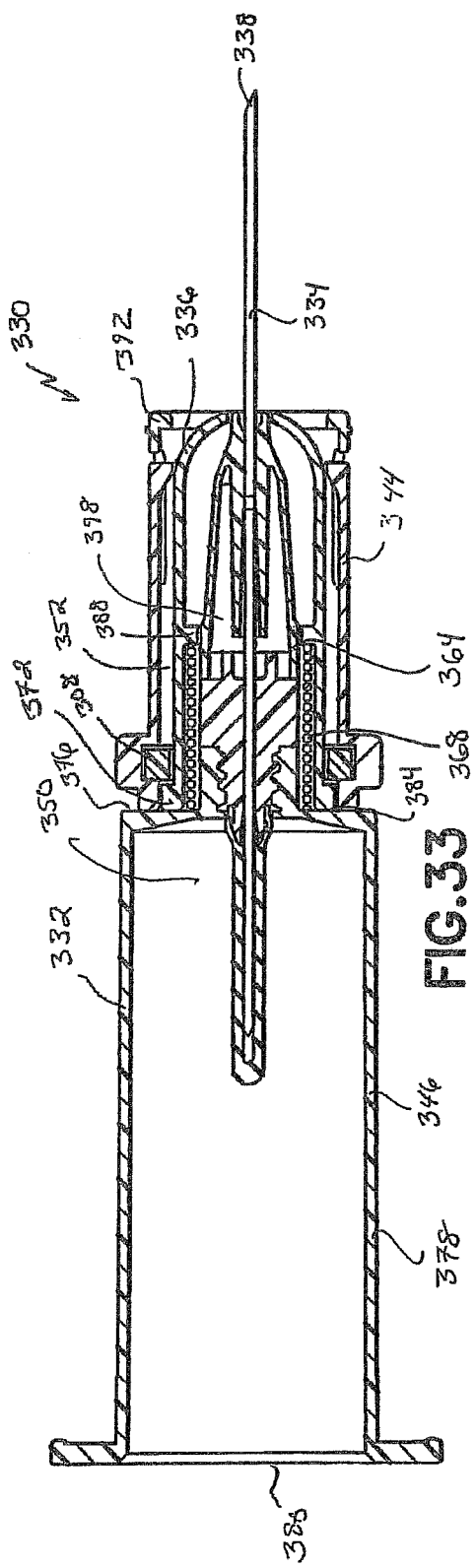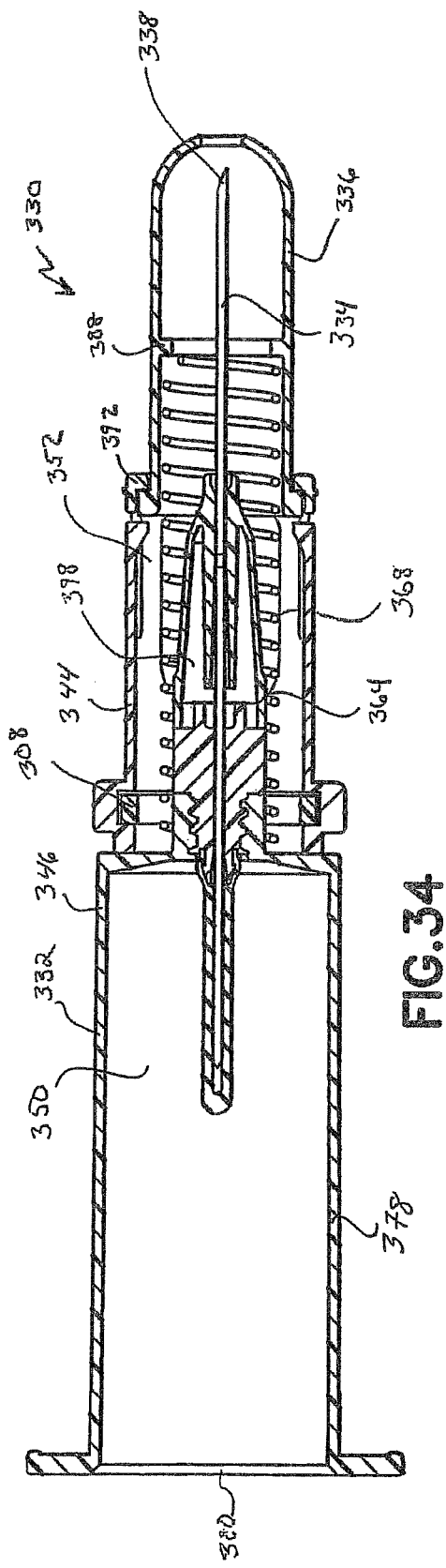

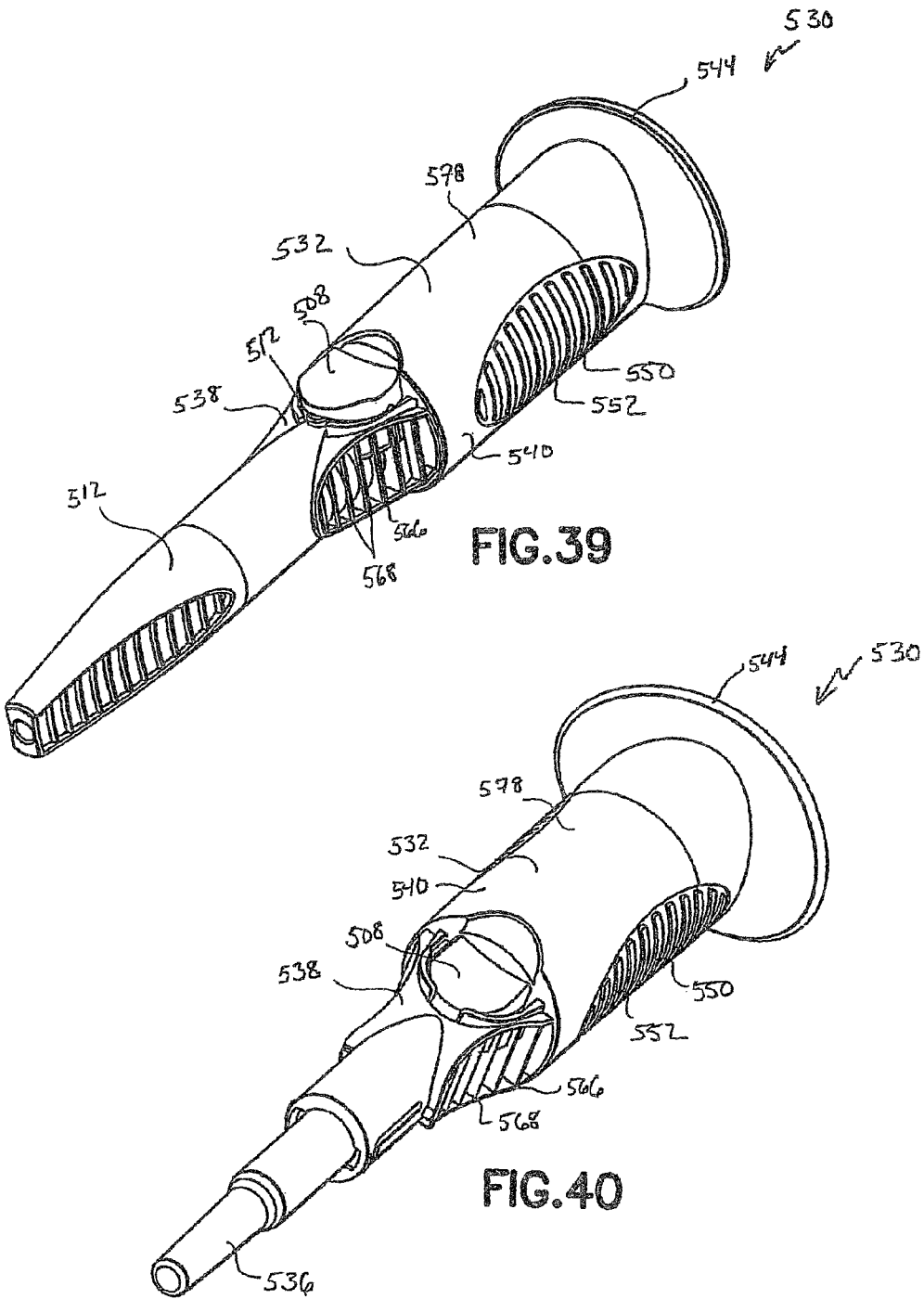

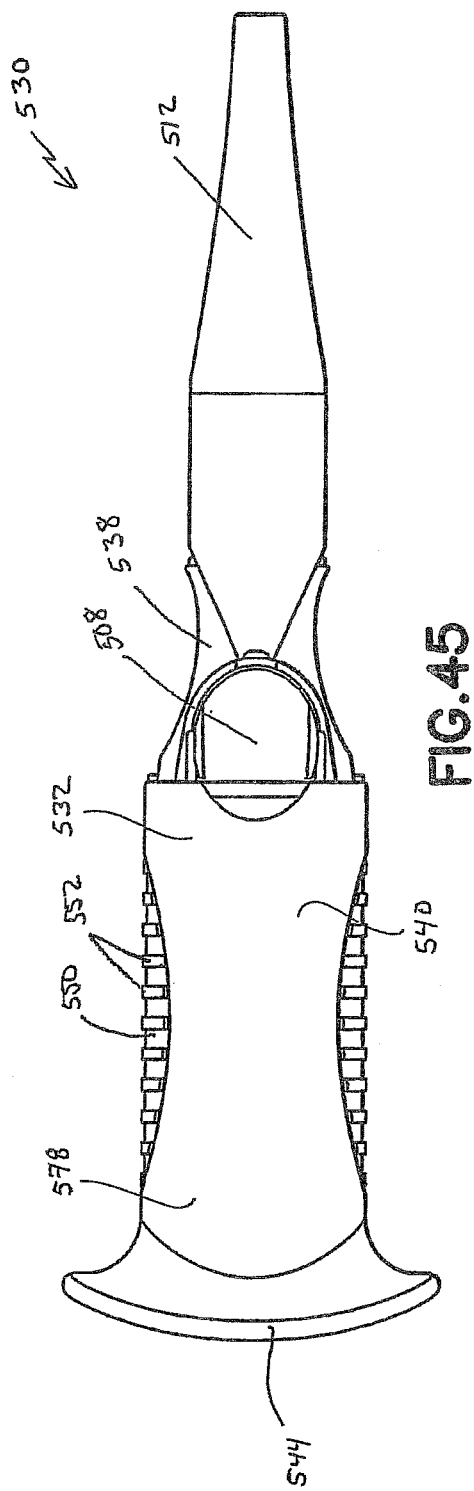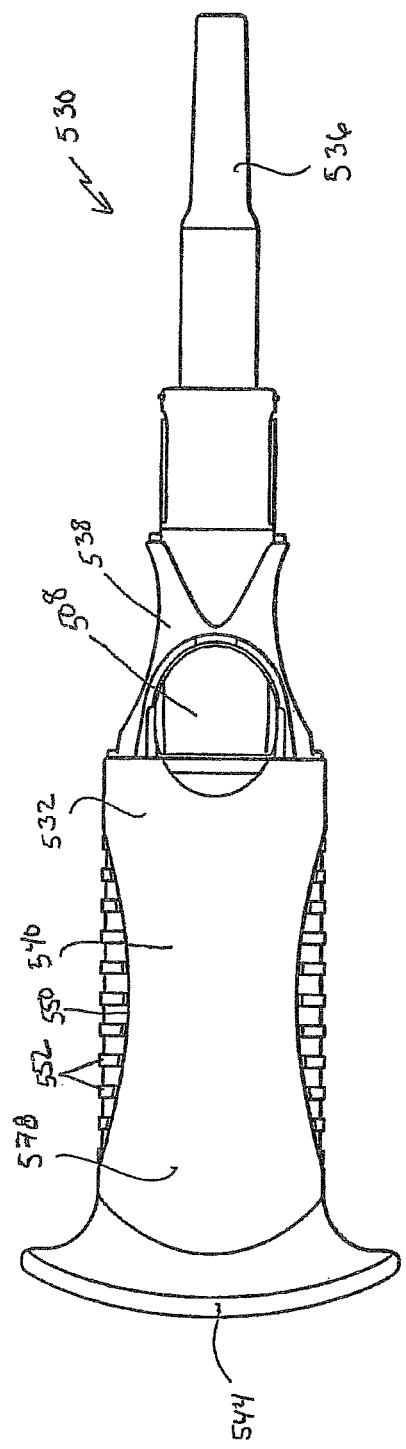

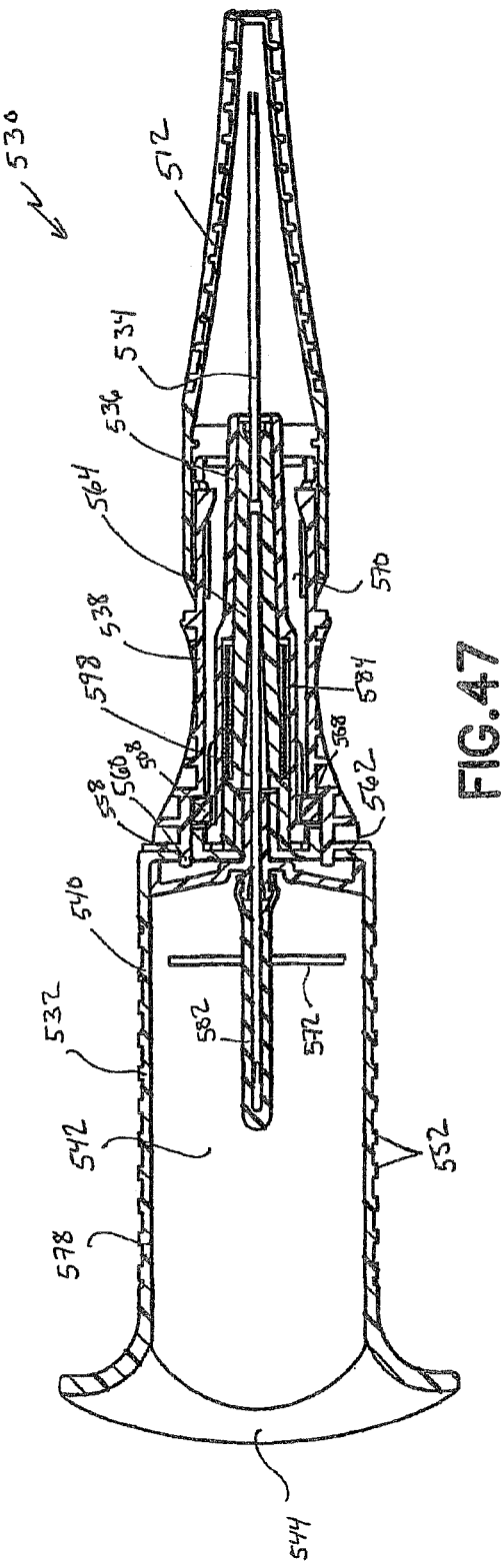
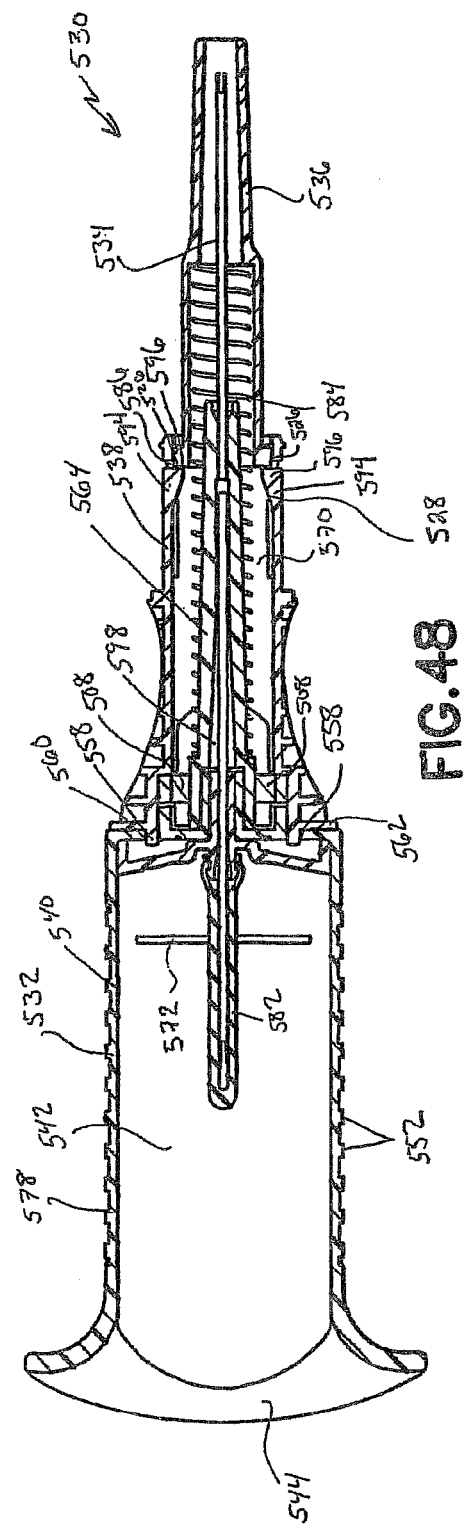
FIG. 47
FIG. 48

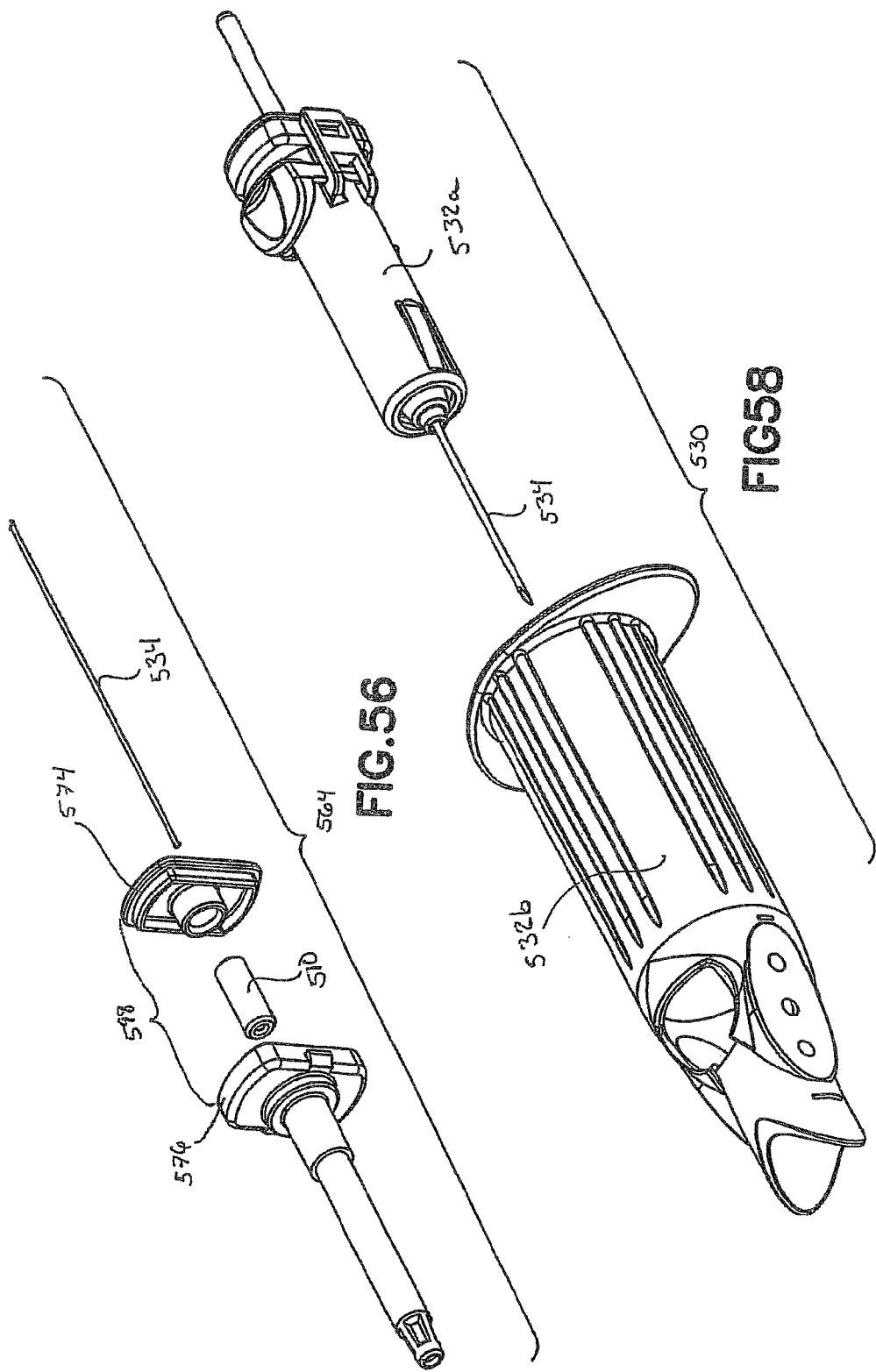

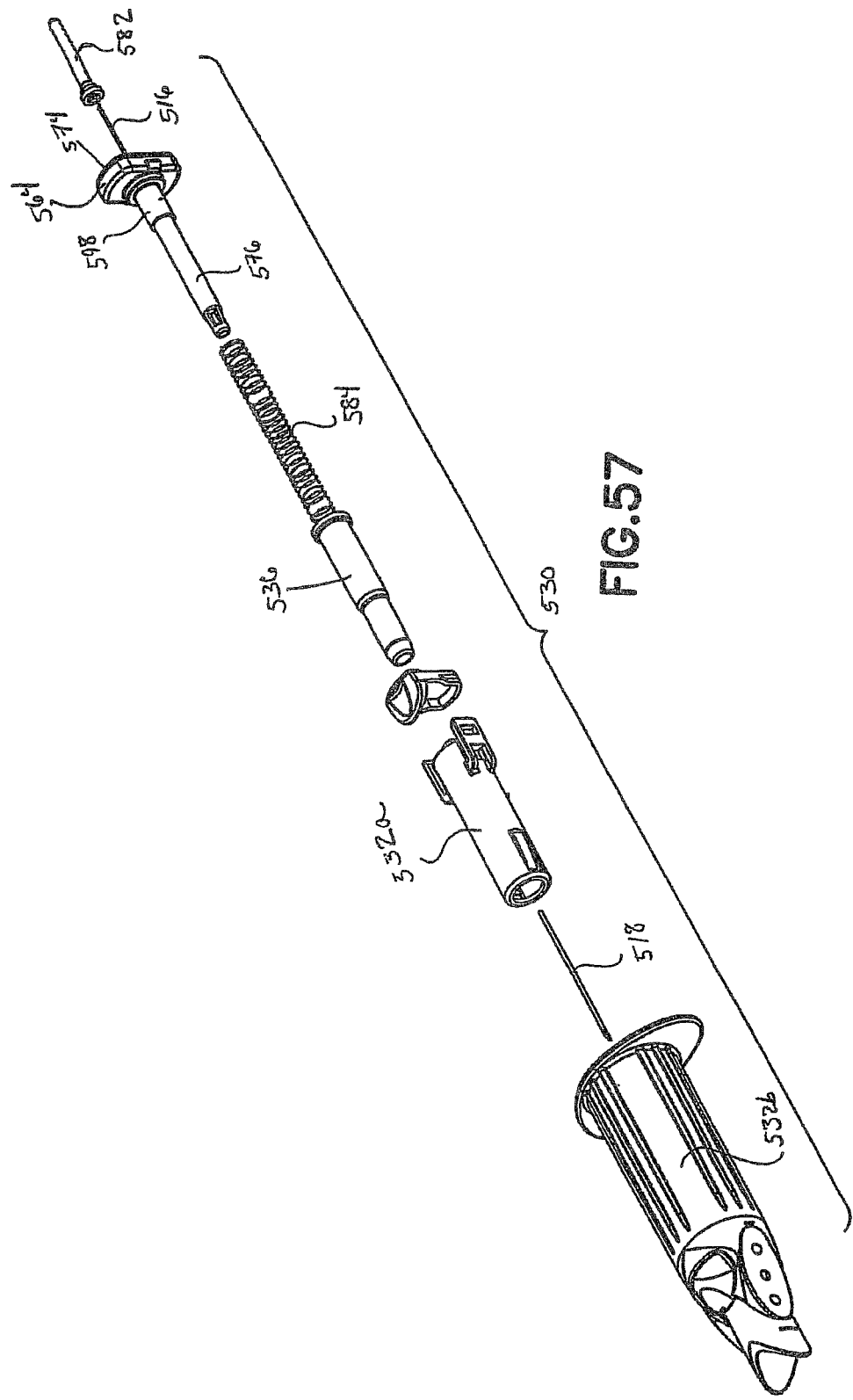

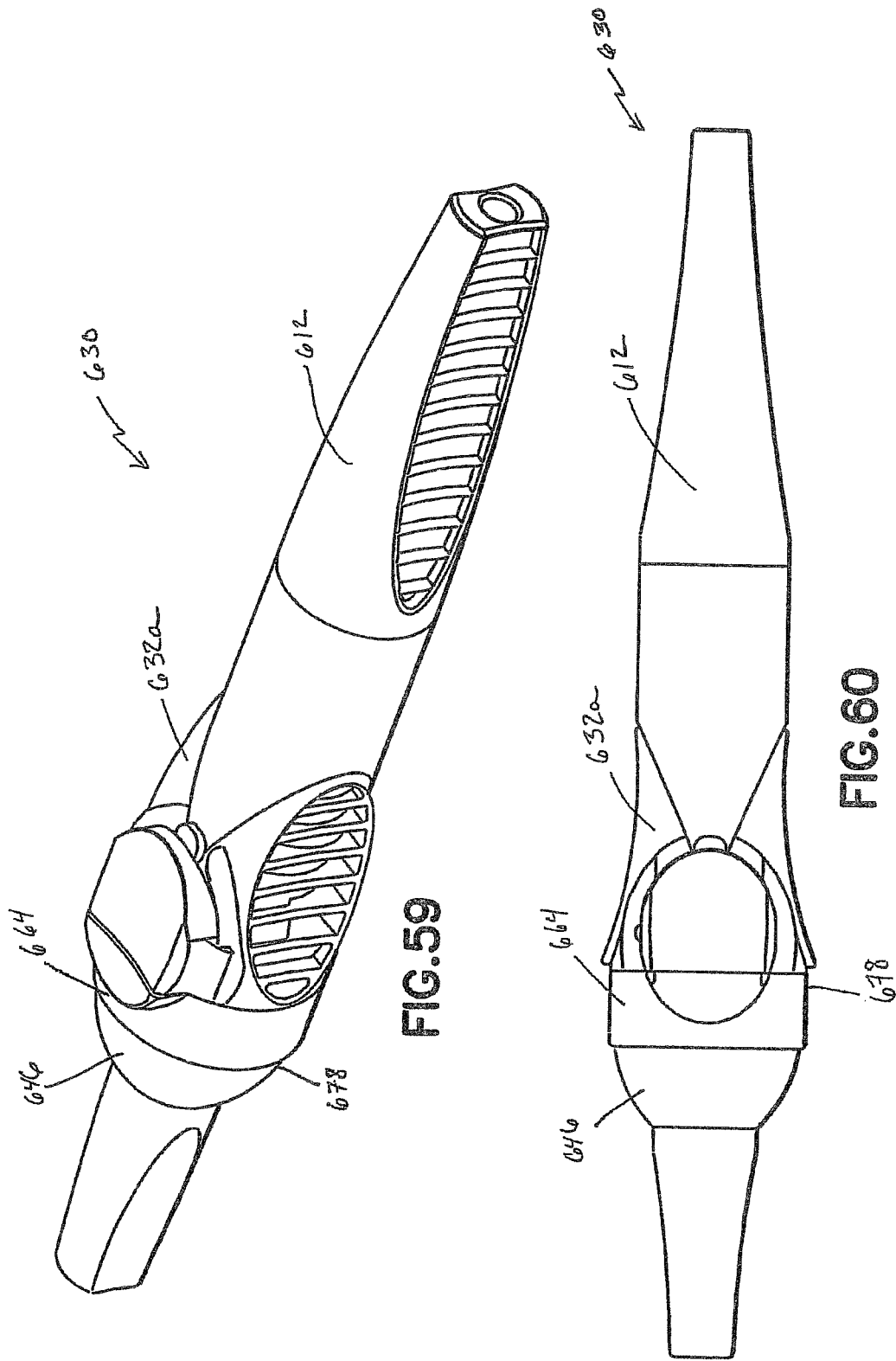

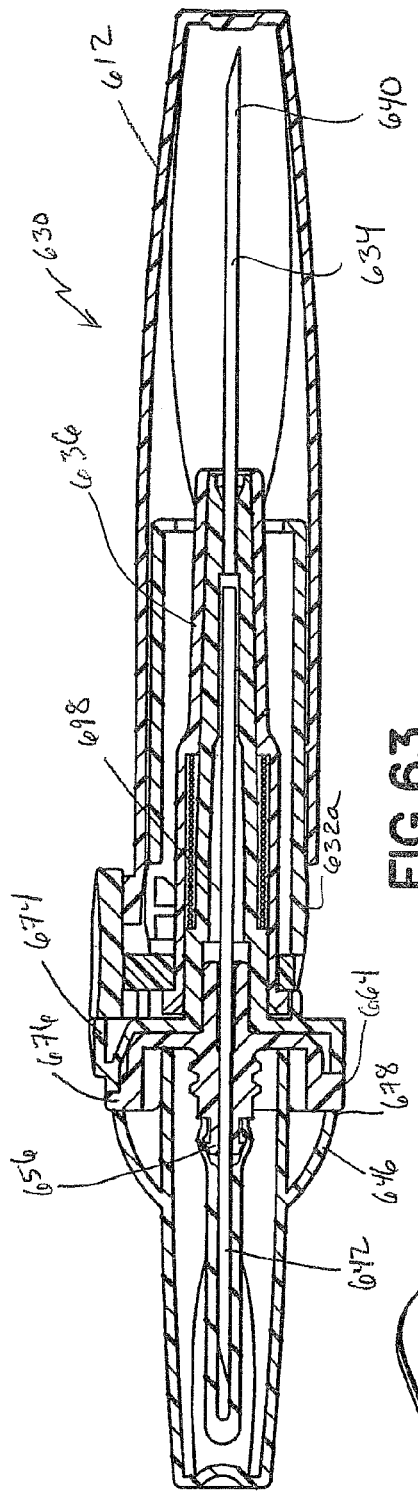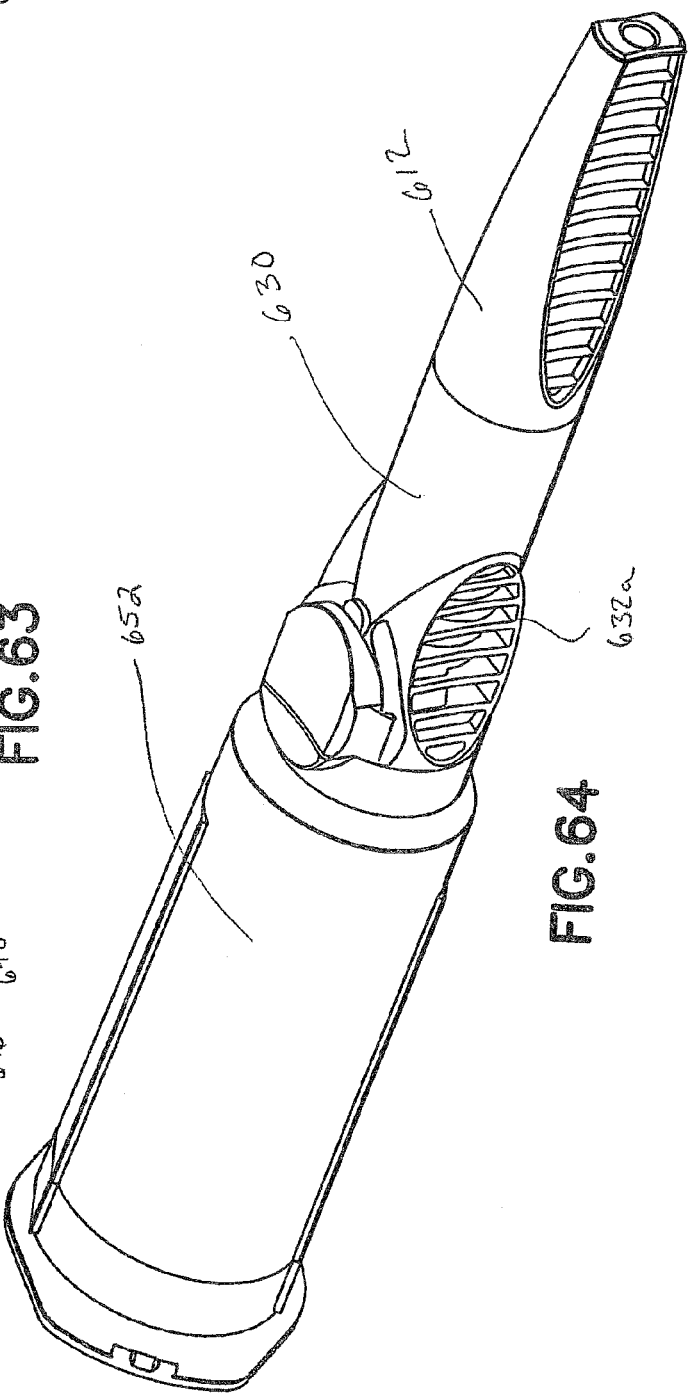

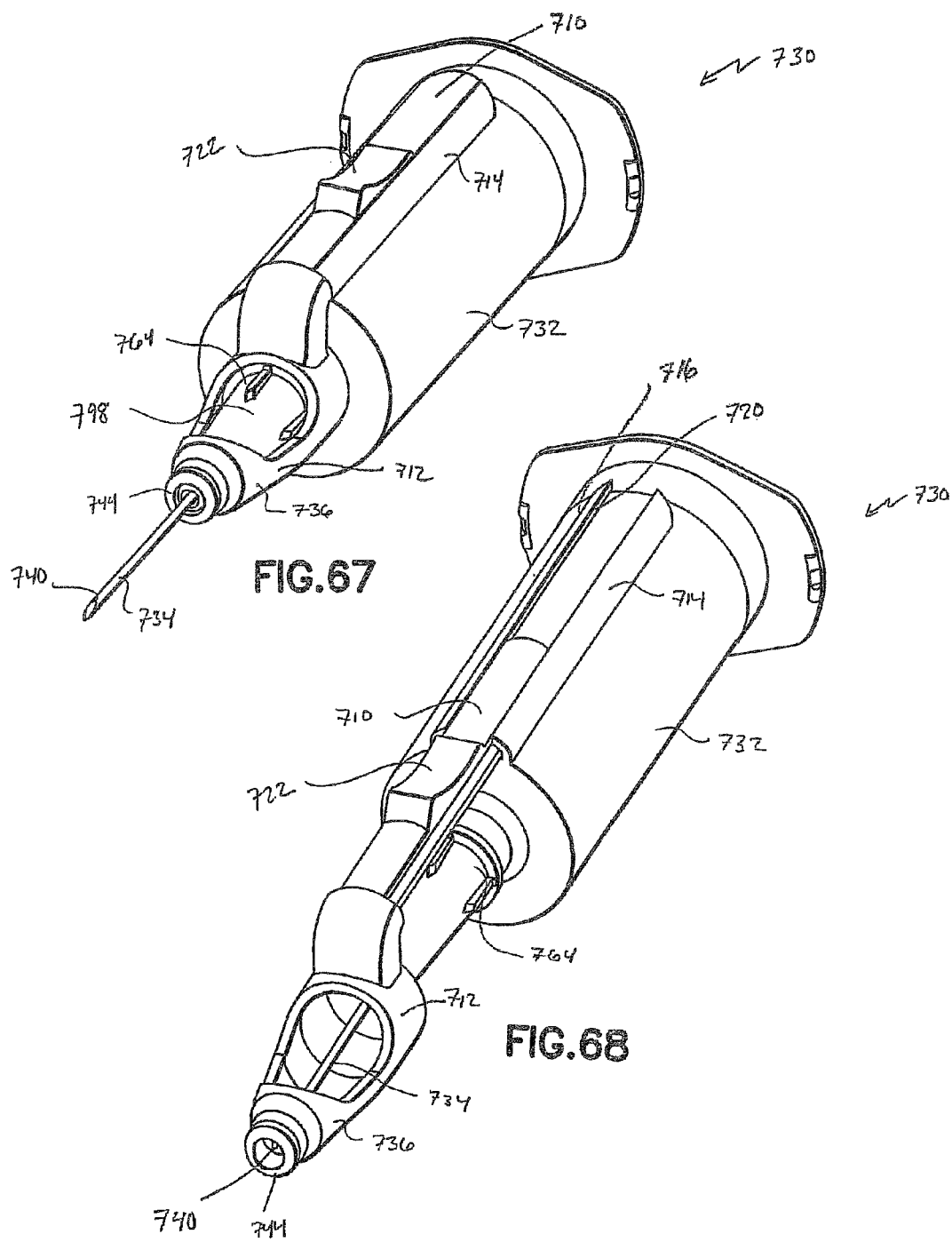

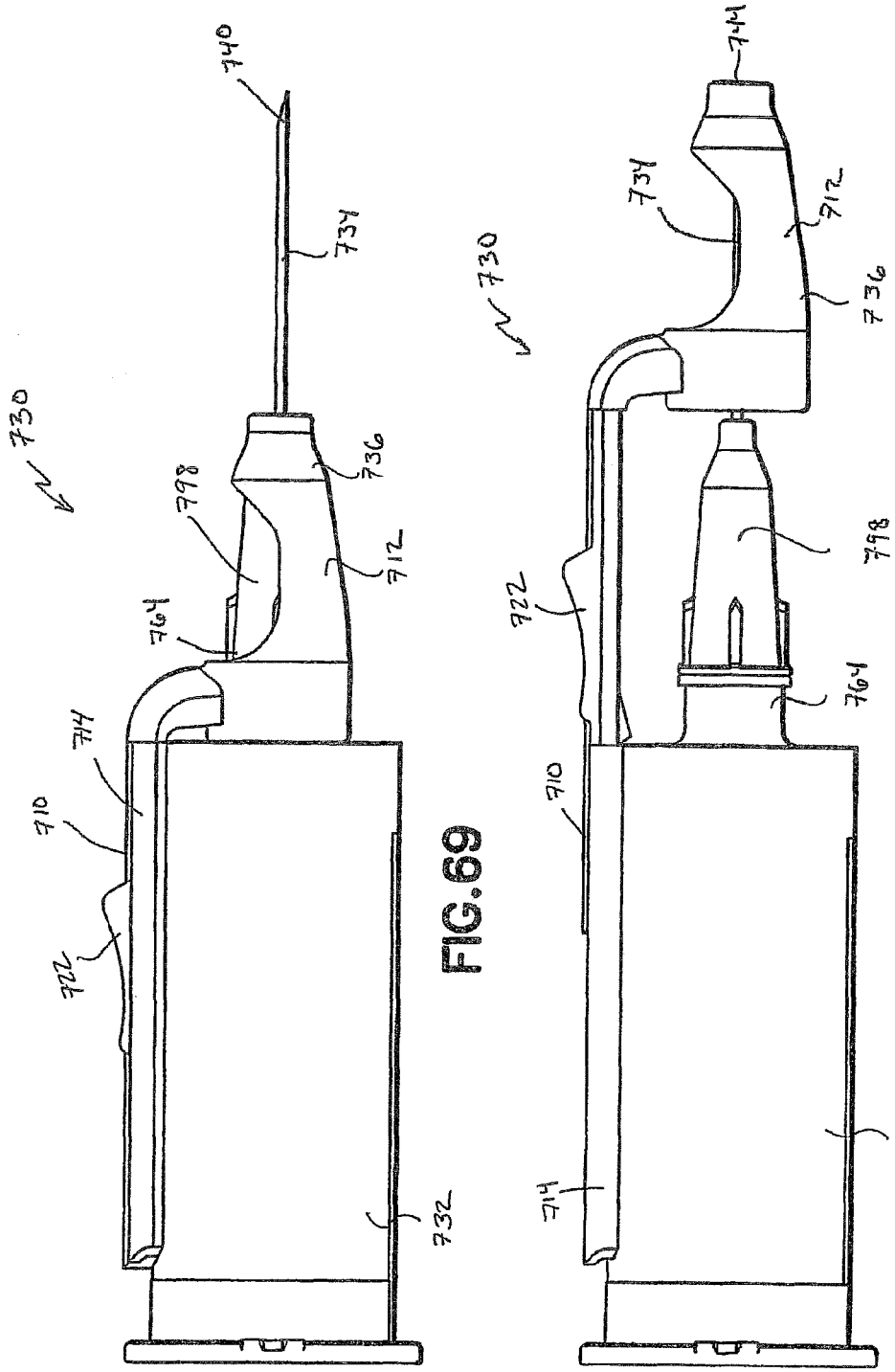

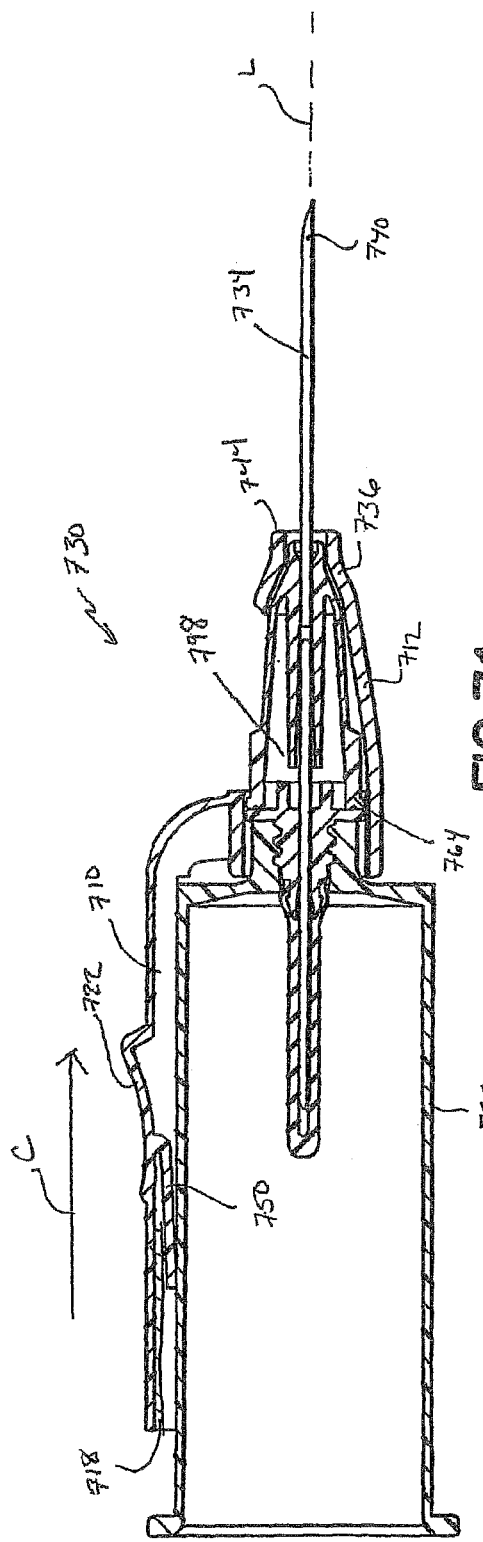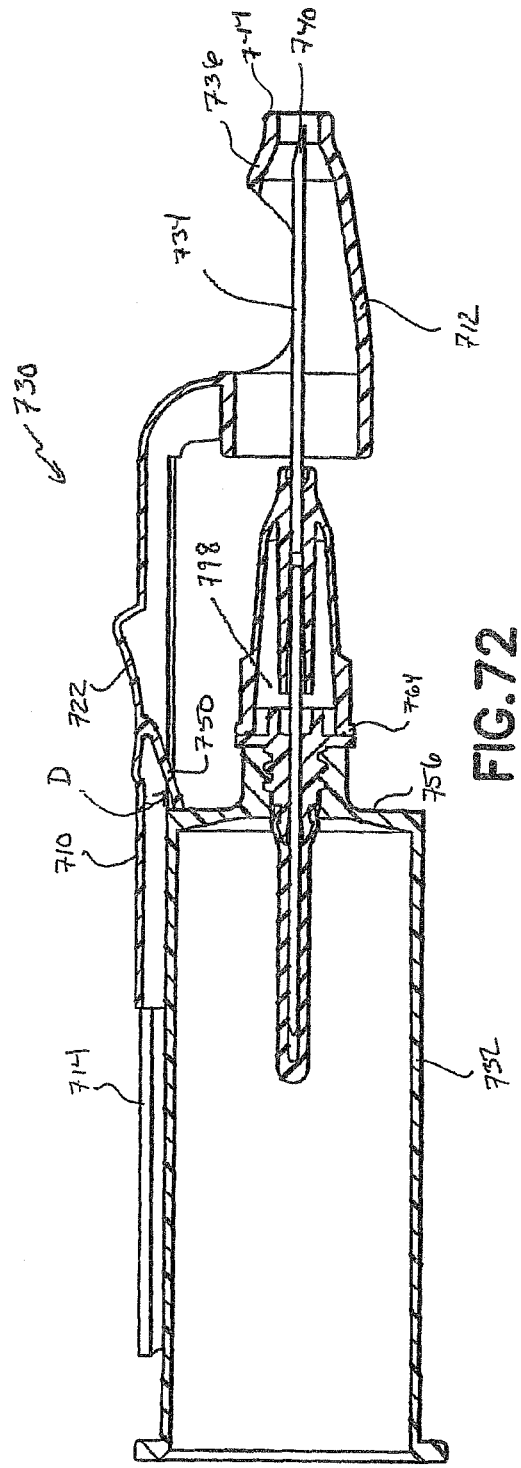

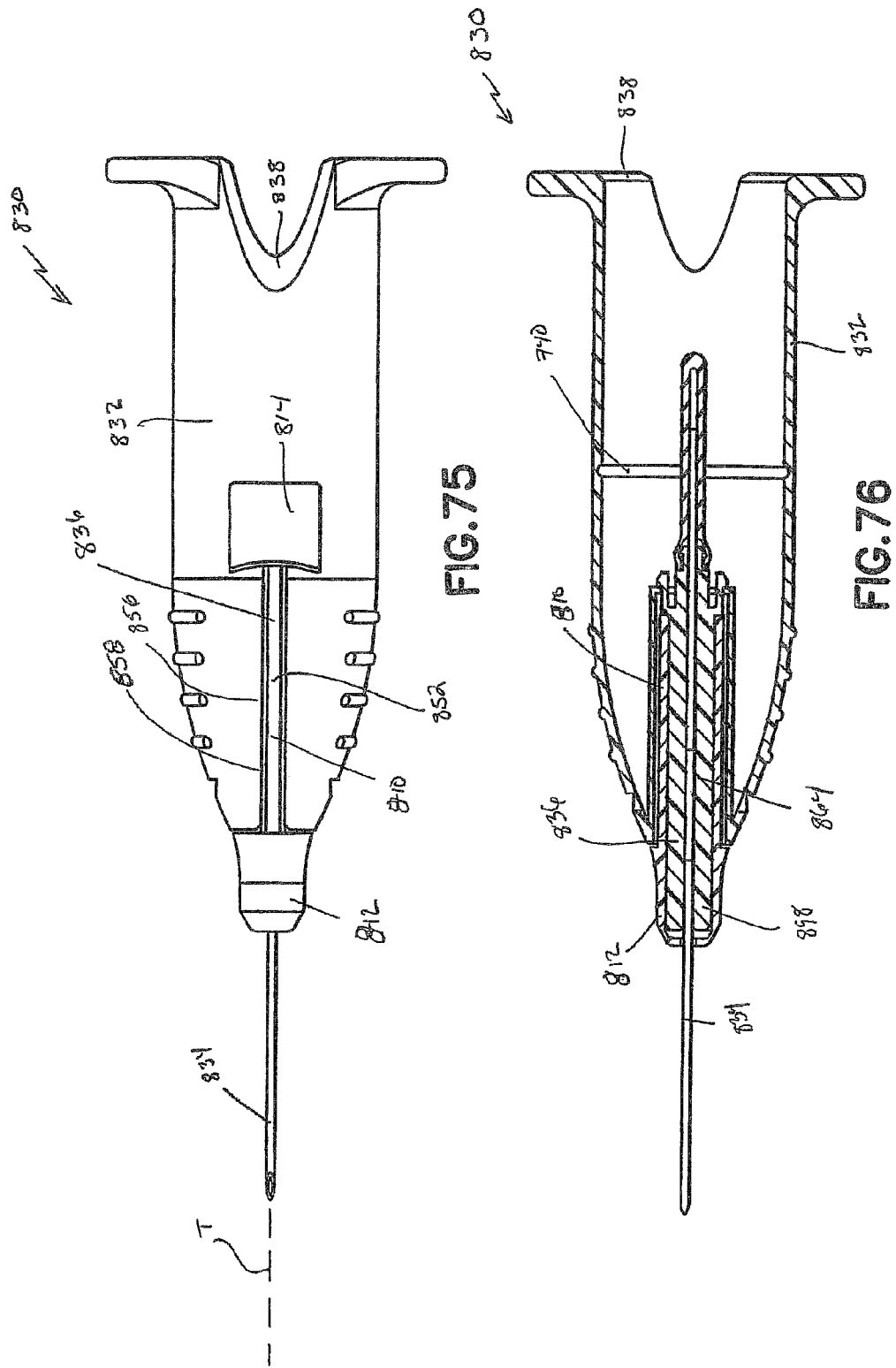

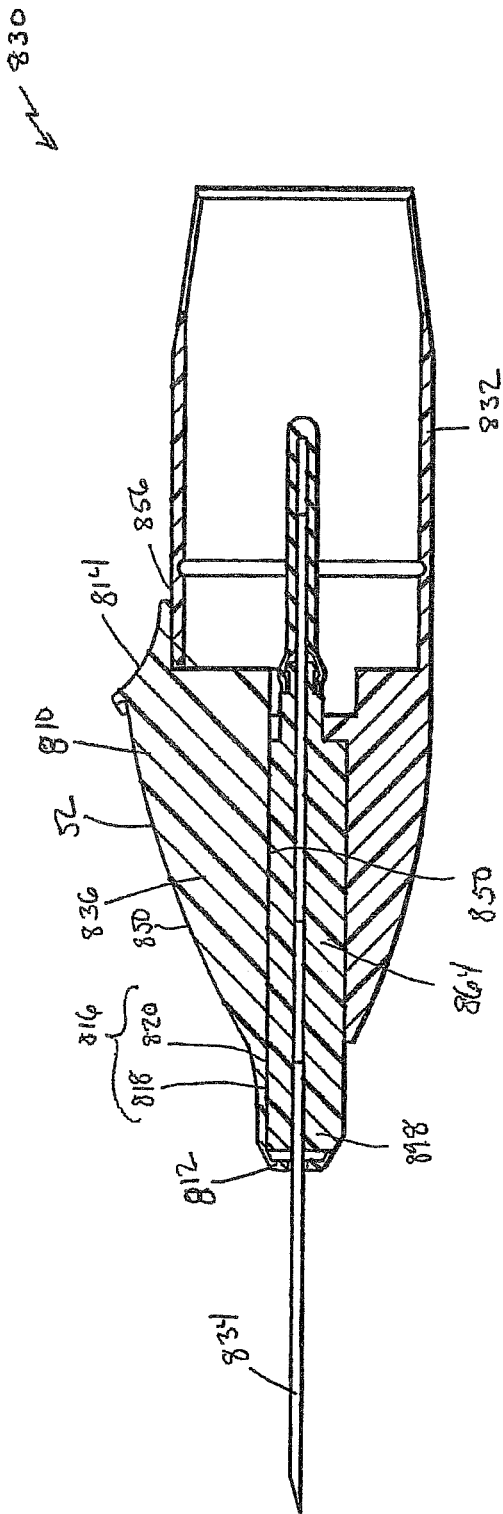
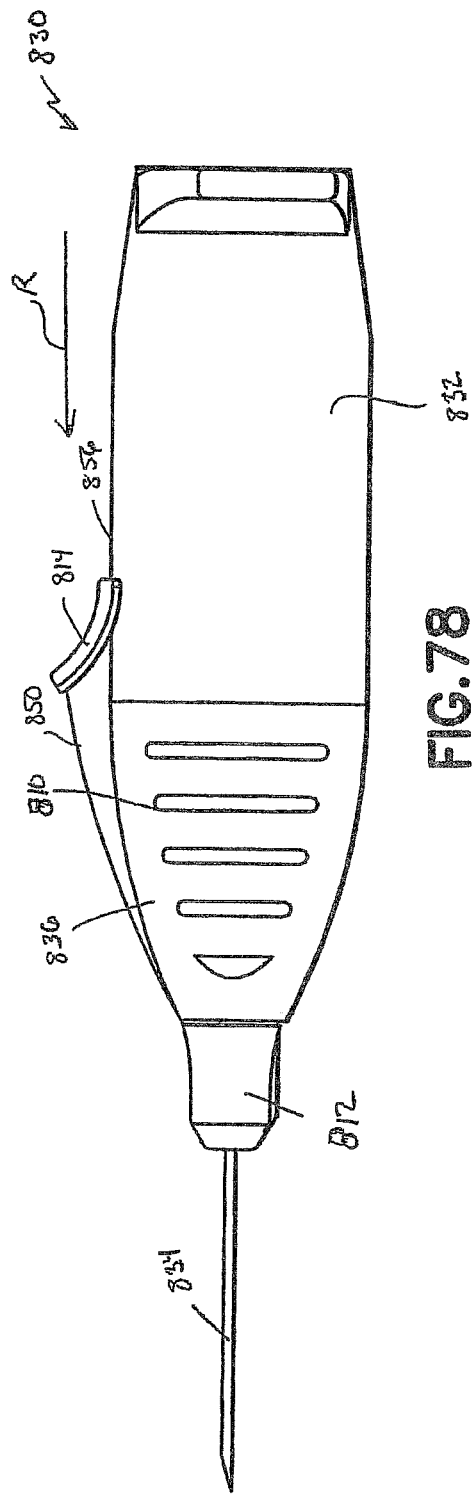

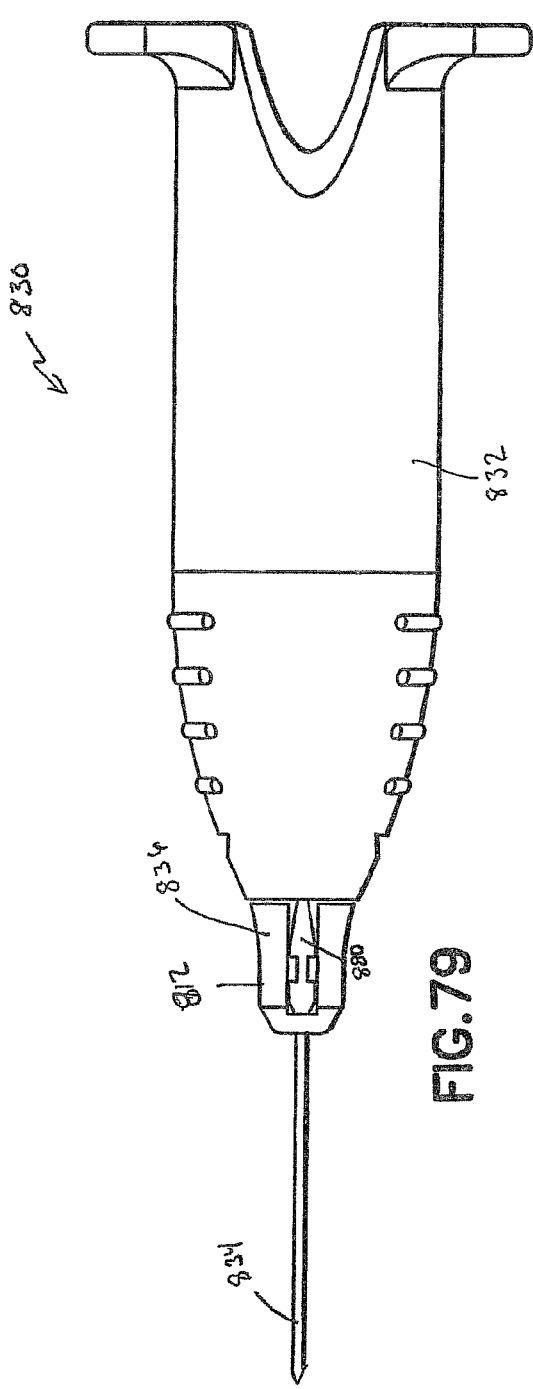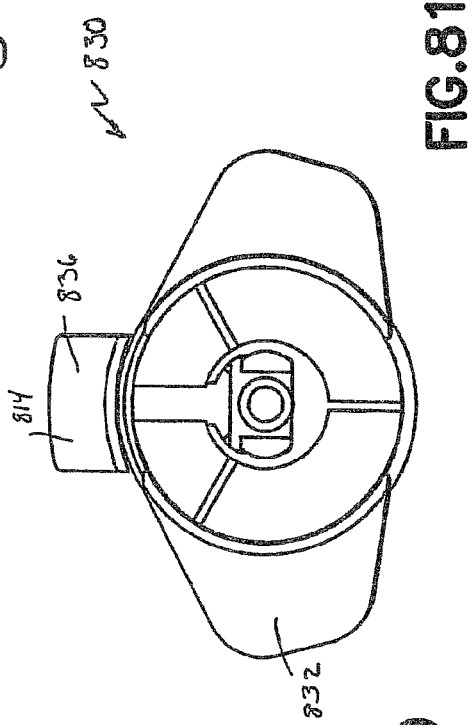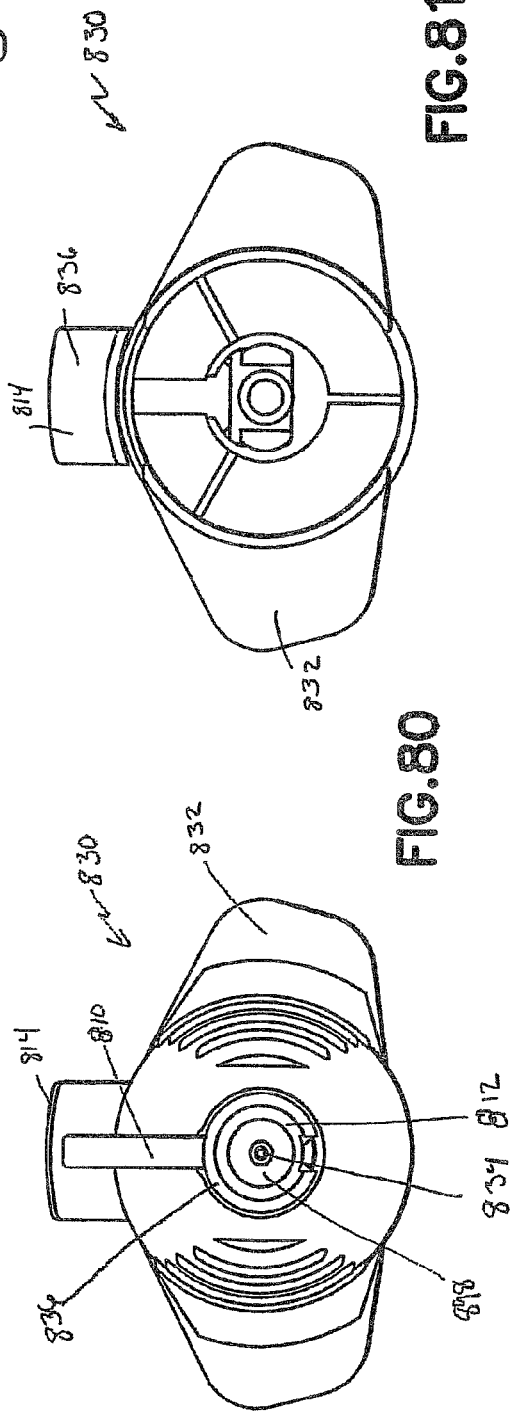

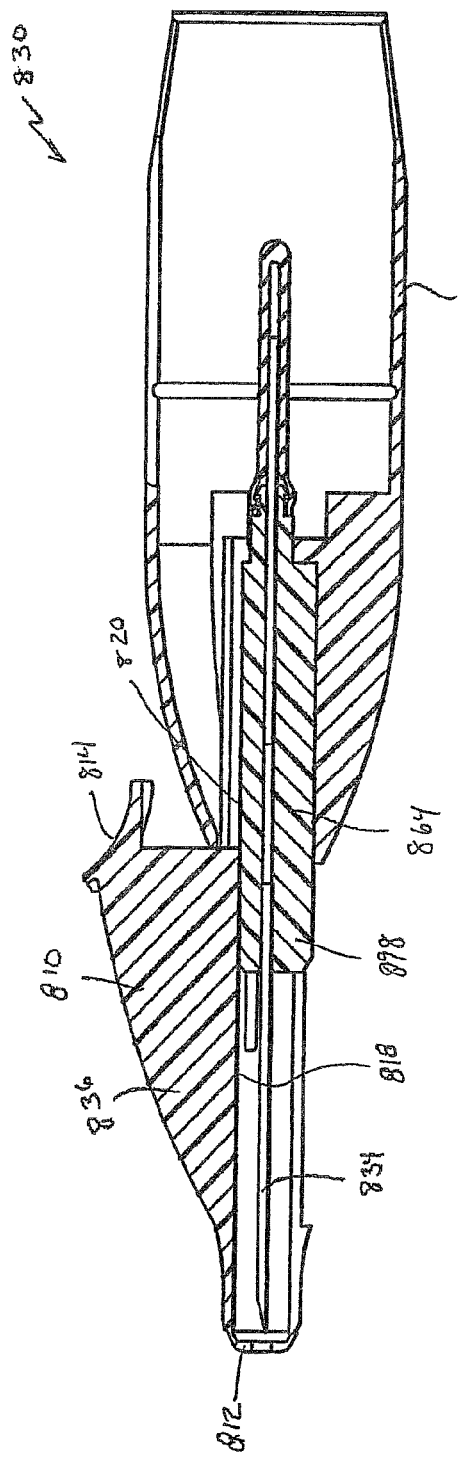
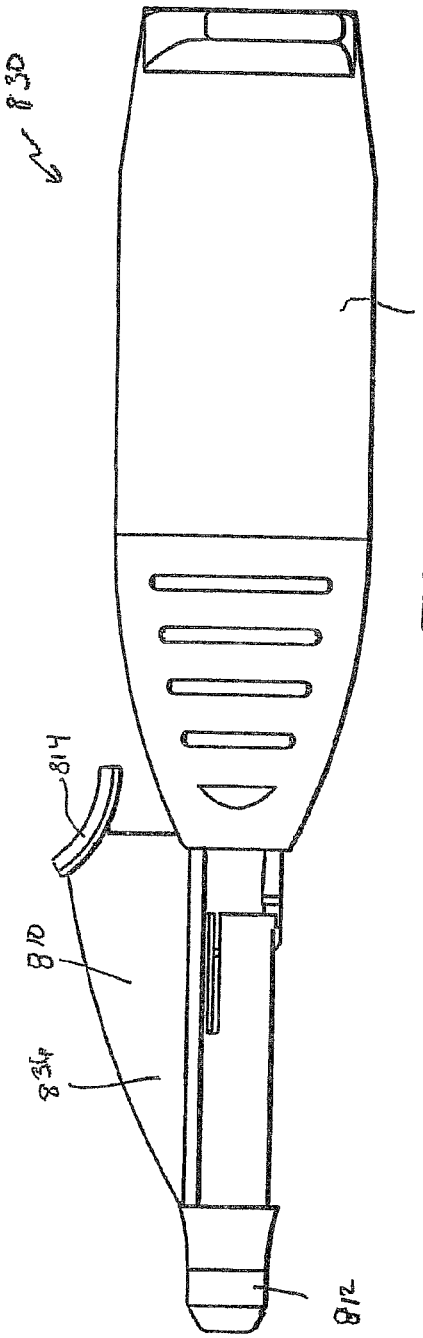
FIG.84
FIG.85

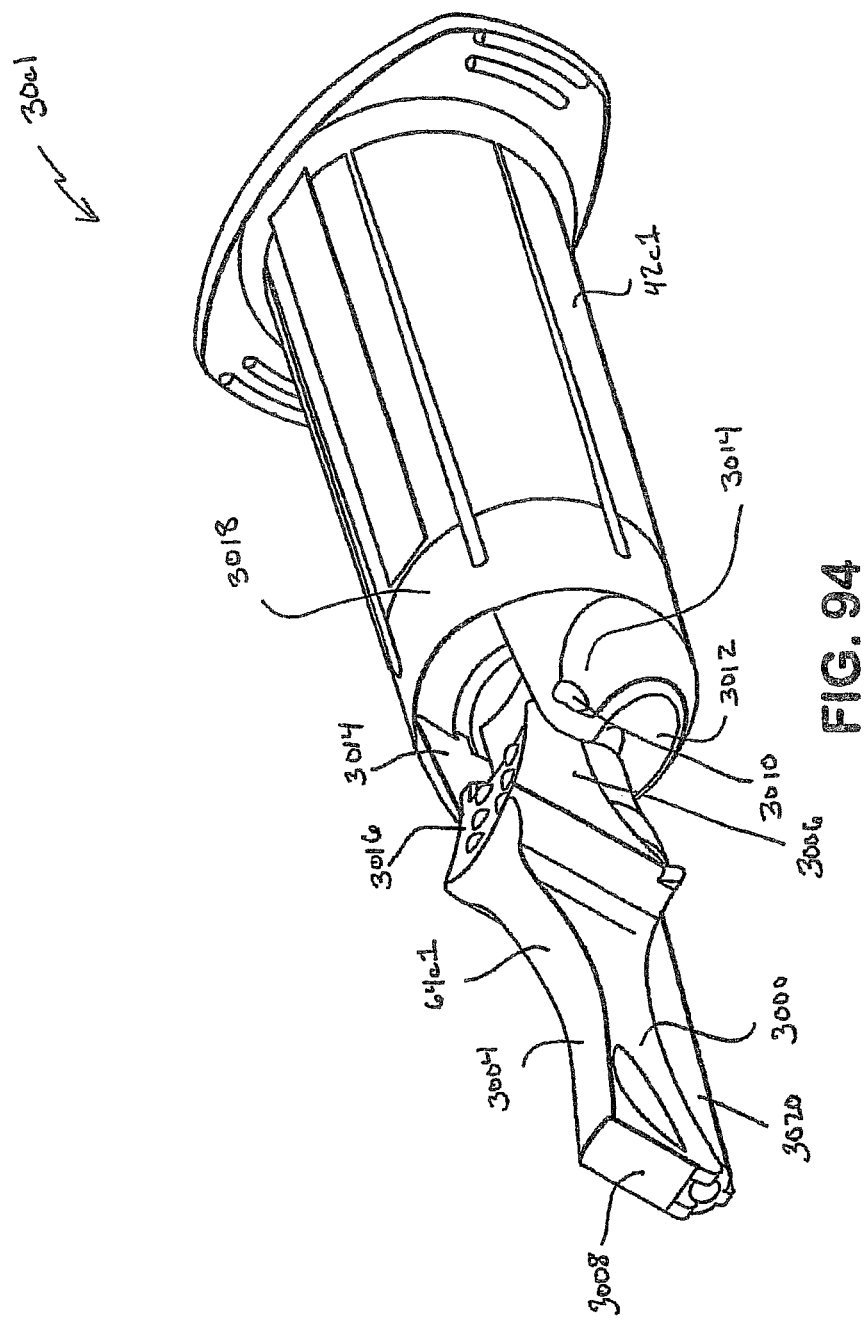

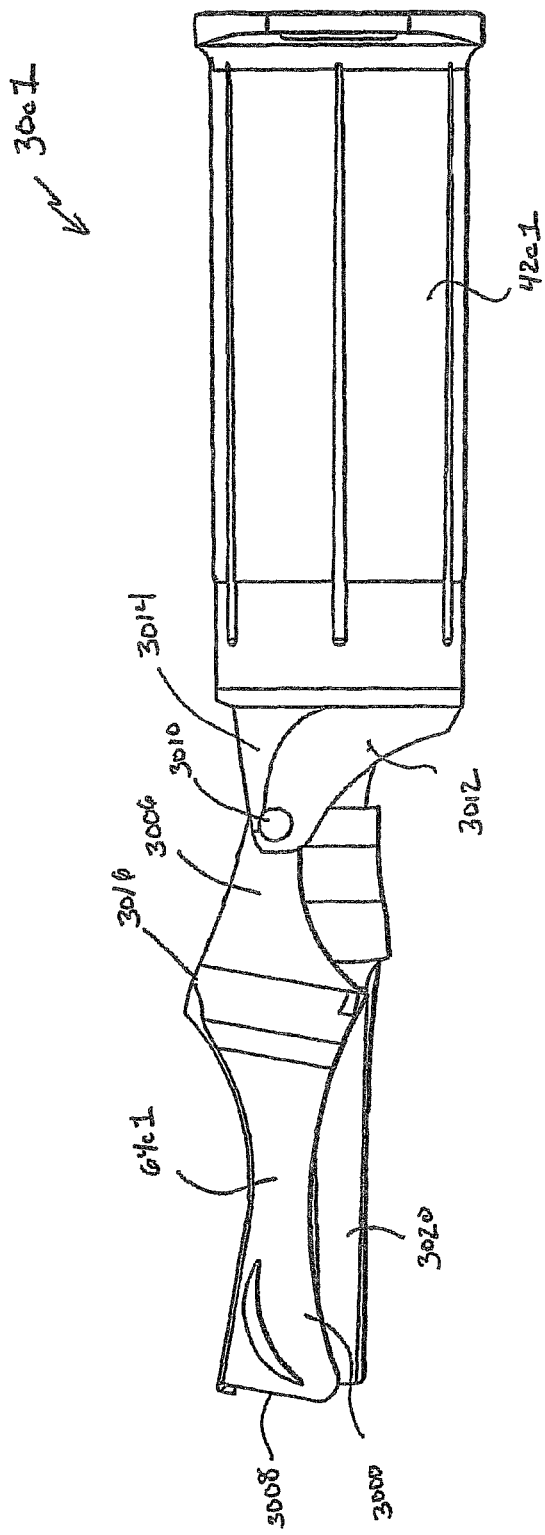

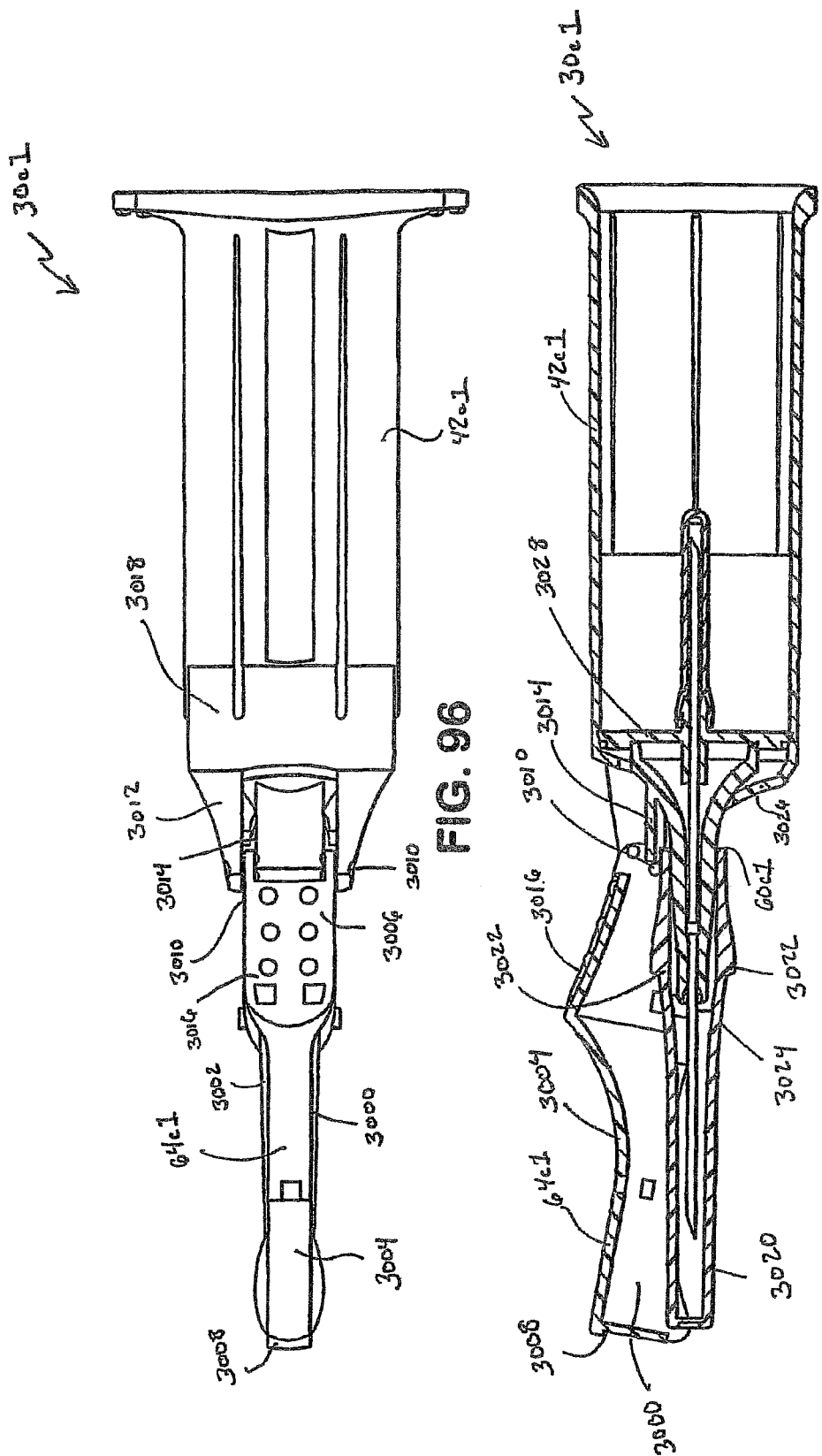

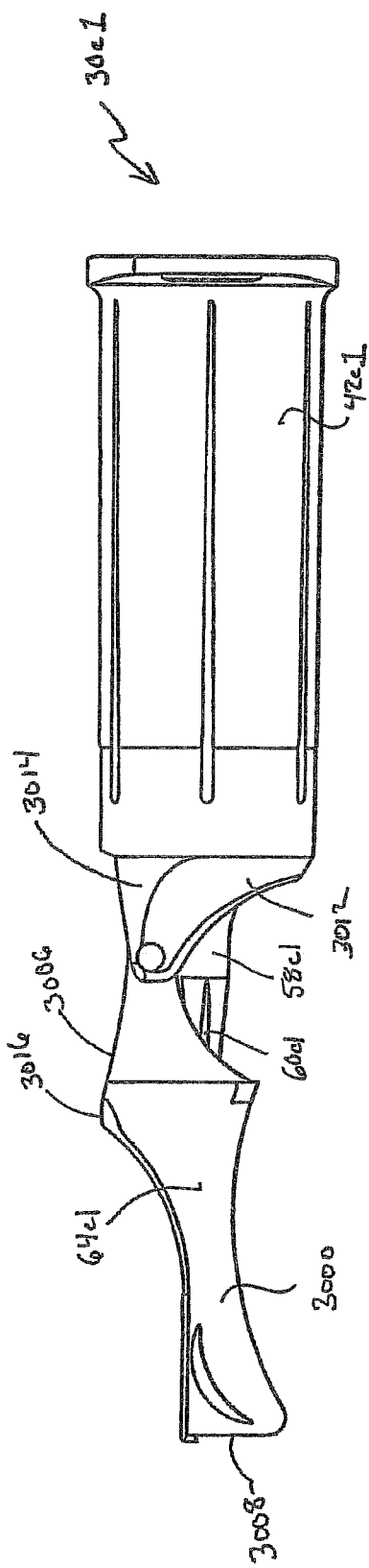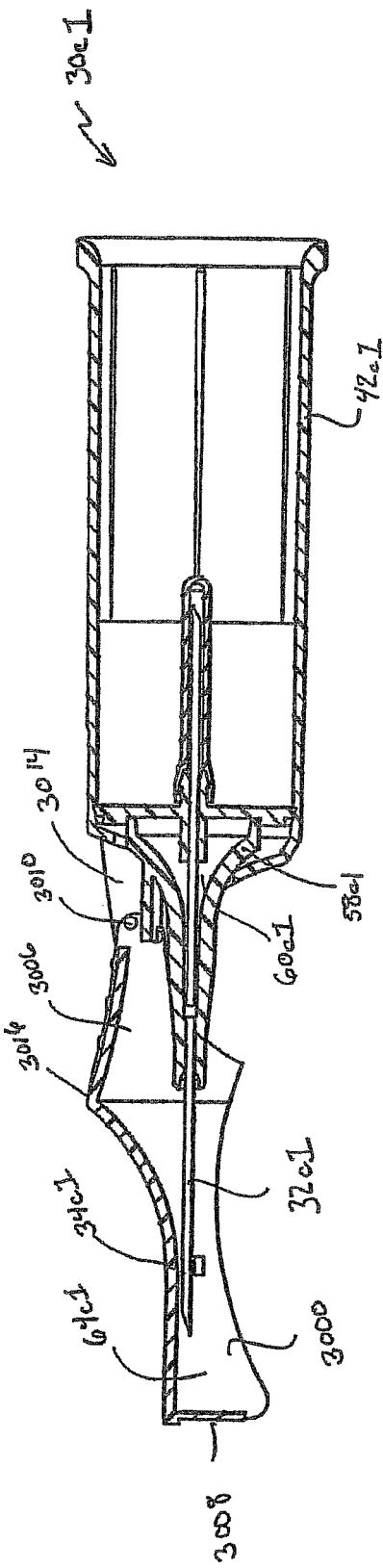
FIG. 103
FIG. 104

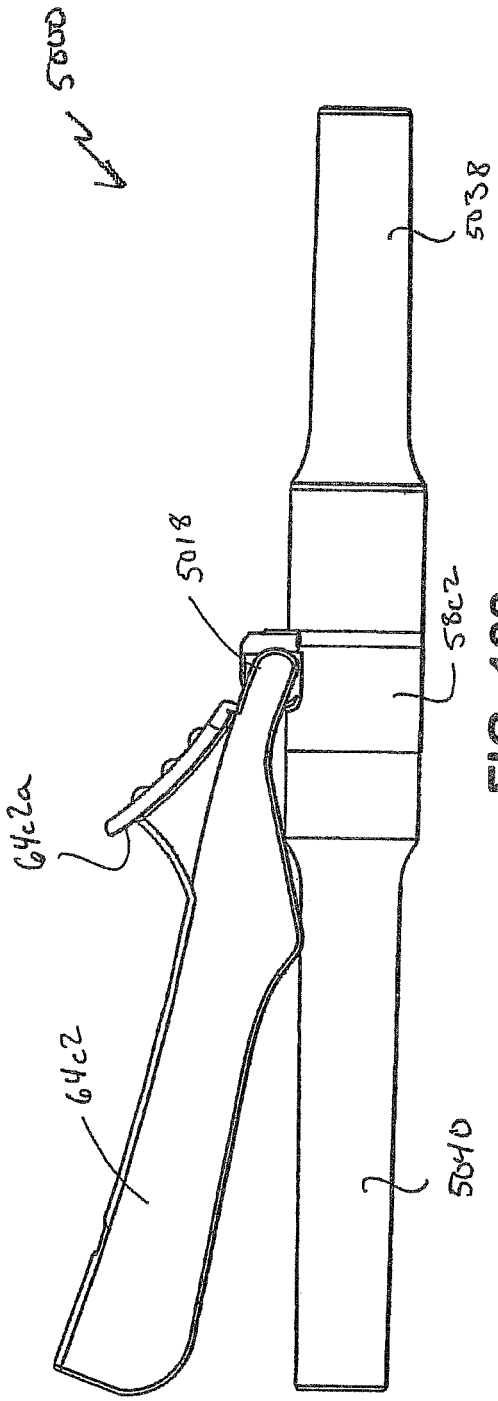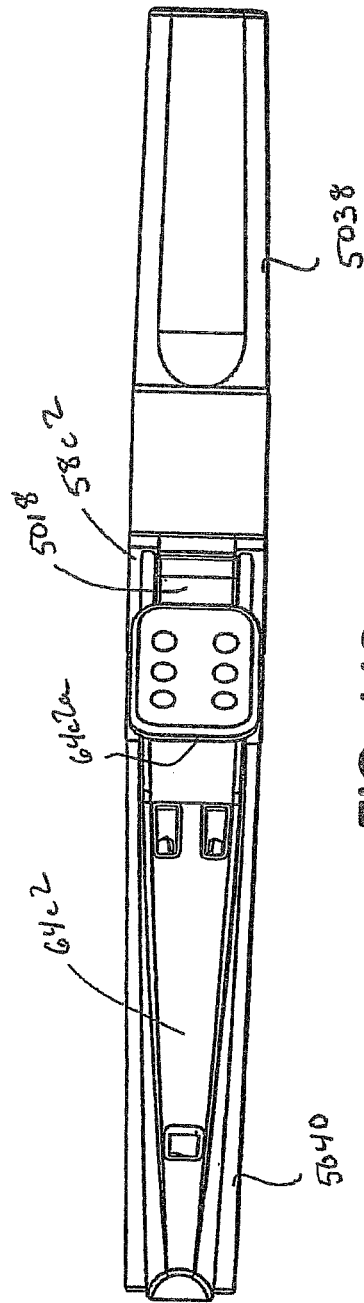

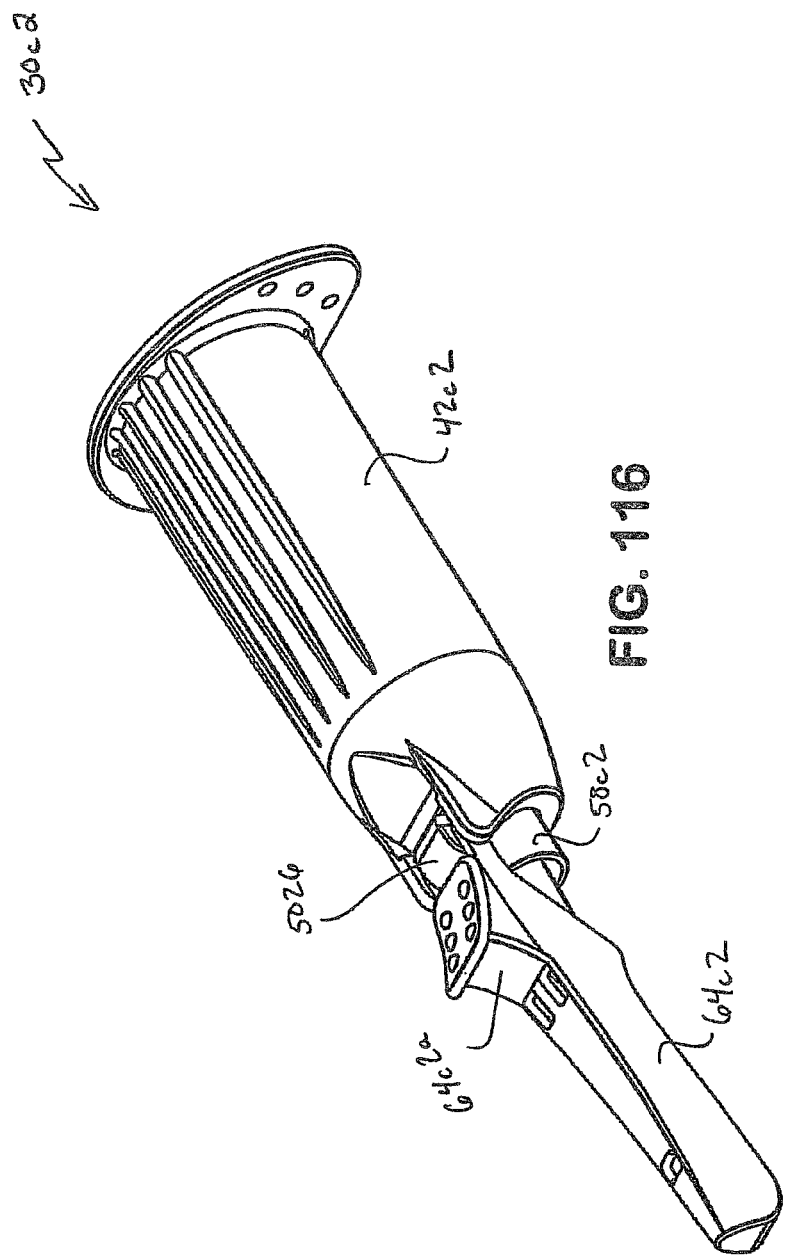

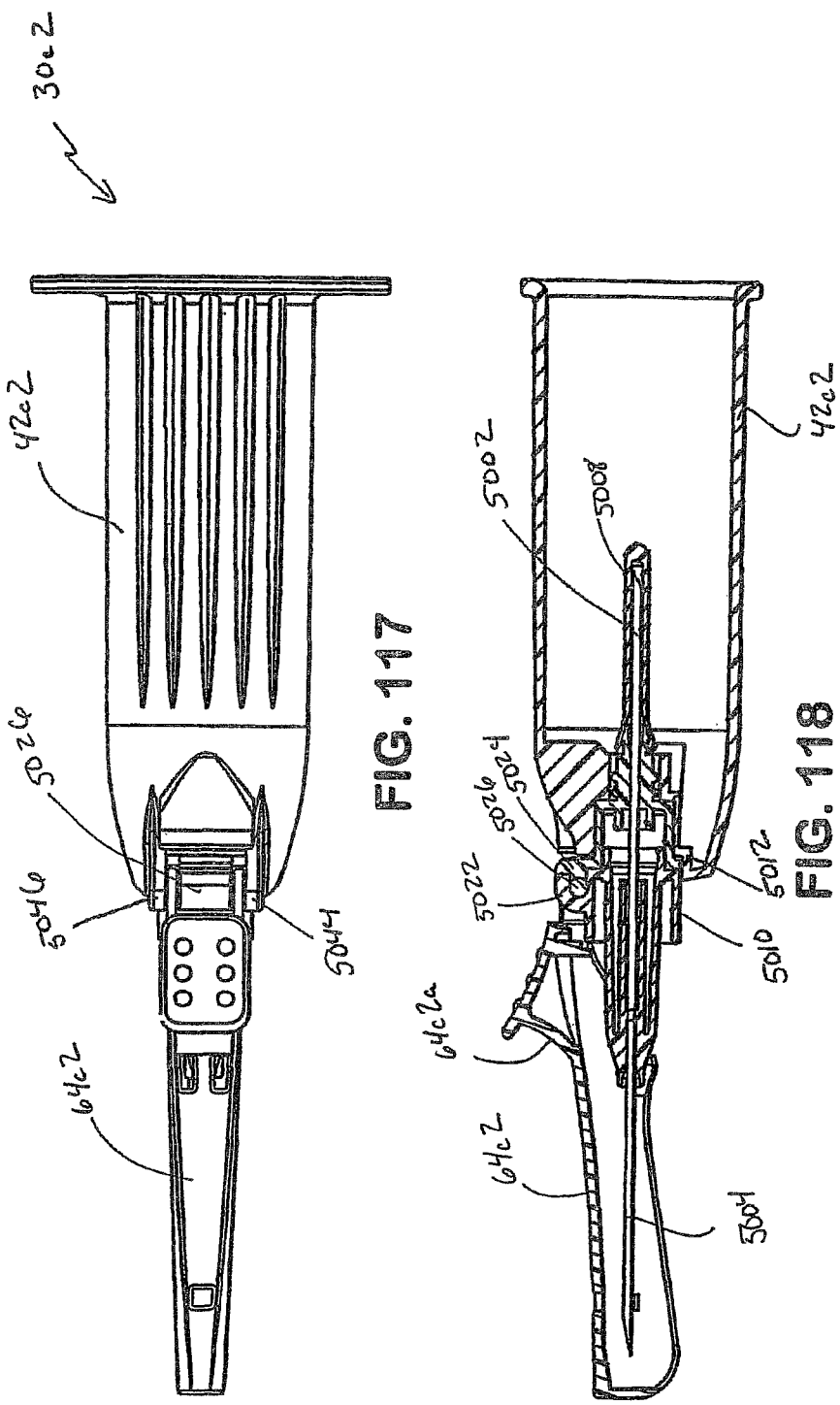

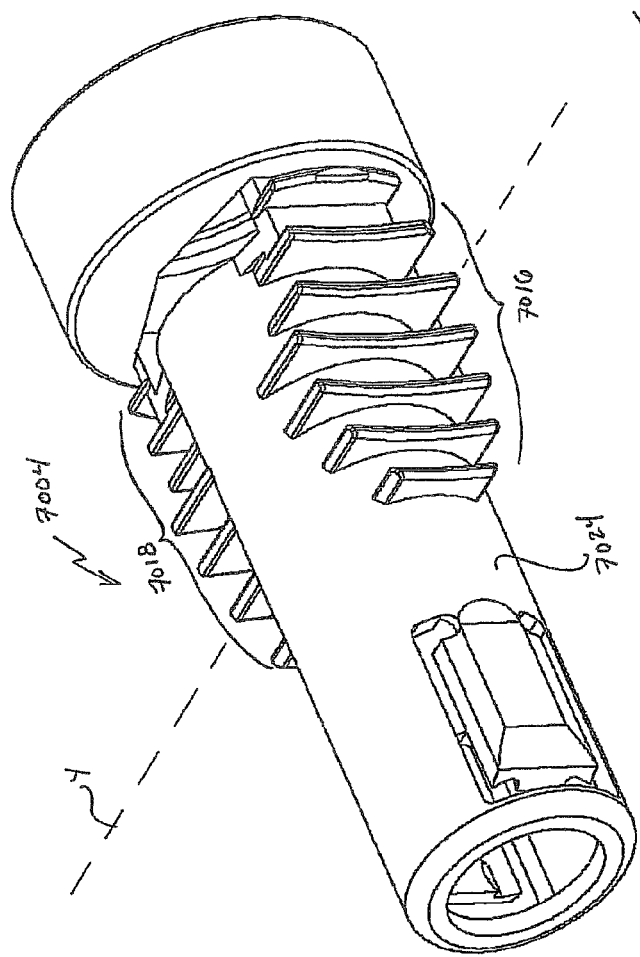
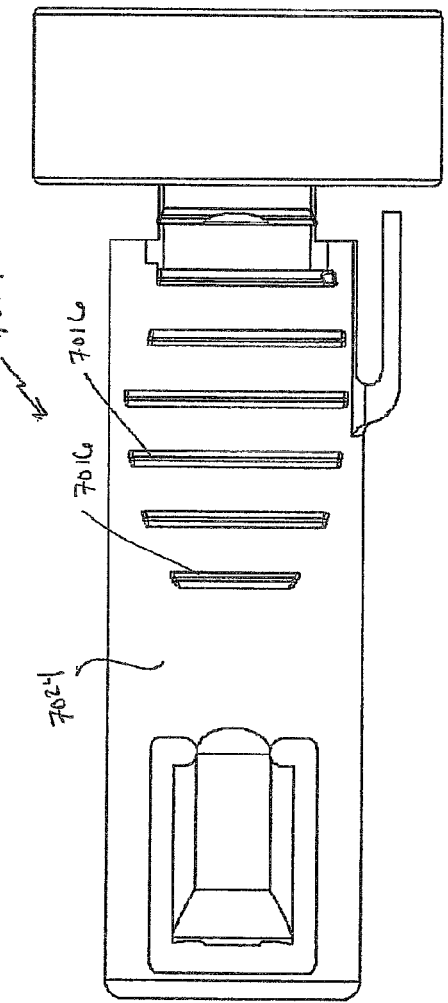

SAFETY BLOOD COLLECTION ASSEMBLY WITH INDICATOR

CROSS REFERENCE TO RELATED APPLICATIONS

The present application claims priority to U.S. patent application Ser. No. 12/044,469 filed Mar. 7, 2008, which claims priority to U.S. Provisional Application Ser. No. 60/941,870 filed Jun. 4, 2007, and U.S. Provisional Application Ser. No. 60/893,519 filed Mar. 7, 2007, the entire disclosure of each application is herein incorporated by reference.

BACKGROUND OF THE INVENTION

1. Field of the Invention

The present invention relates generally to shieldable safety needle assemblies and, more particularly, to needle assemblies having a housing, a needle cannula, and a shield restrainably engaged with a portion of the housing.

2. Description of Related Art

Typical needle assemblies include a needle cannula having a proximal end, a pointed distal end with a puncture tip, and a lumen extending therebetween. A thermoplastic hub is often mounted securely to the needle cannula at a location spaced apart from the distal end. The hub is typically provided with external threads or other surface configurations for mounting the needle cannula to another structure. Some needle assemblies are used for drawing a specimen, such as a sample of blood or other bodily fluid, from a patient.

A needle assembly that is used to draw a sample of blood or other bodily fluid is typically used in association with a housing. Needle cannulae used in association with these assemblies typically have pointed proximal and distal ends, and the needle hub is mounted to a location between the opposed ends of the needle cannula. The housing typically includes a substantially tubular sidewall with a widely opened proximal end, and a partly closed distal end. The hub of the prior art needle assembly can be engaged with the partly closed distal end of the needle holder. Thus, the pointed proximal end of the needle cannula projects into the needle holder for engagement with an evacuated tube, while the pointed distal end of the needle cannula projects distally beyond the needle holder for puncturing the patient's skin.

The needle assembly is often used with a specimen collection tube for drawing a sample of blood or other bodily fluid from a patient. The specimen collection tube typically includes a closed end, an open end, and a sidewall extending therebetween. The tube is typically evacuated, and the open end is sealed by a septum that retains the vacuum within the tube. The evacuated tube is dimensioned to be slid into the open proximal end of the needle holder. Sufficient sliding of the evacuated tube into the needle holder causes the proximal point of the needle cannula to pierce the septum of the evacuated tube. Thus, the needle cannula can be placed in communication with the interior of the evacuated tube.

The combined needle assembly and evacuated tube is employed by initially urging the pointed distal end of the needle cannula into a blood vessel of a patient. Once the targeted blood vessel has been accessed, the evacuated tube is urged into the needle holder such that the proximal point of the needle cannula pierces the septum of the tube. Low pressure conditions within the evacuated tube, as well as the patient's own vasculature pressure, generate a flow of blood from the patient through the needle cannula and into the evacuated tube. The evacuated tube may be removed from the needle holder after a sufficient quantity of blood has been collected. One or more additional evacuated tubes may similarly be urged into the open end of the needle holder for drawing one or more additional samples of blood to be analyzed. The needle cannula is then withdrawn from the patient after a sufficient volume of blood has been collected for the required analytical procedure. In order to reduce the risk of an accidental needle stick, or contact that could transmit pathogens from the patient to the medical practitioner, the needle cannula must be properly shielded after contact with the patient.

Many types of devices are available for shielding a used needle cannula. Example shielding devices include those disclosed in U.S. Pat. Nos. 5,348,544; 5,242,417; 6,592,556; 6,635,032; and 7,001,363, the entire disclosures of which are herein incorporated by reference. Most shielded needle assemblies are effective at performing their primary function, i.e., shielding a used needle cannula. However, many medical practitioners consider the available shieldable needle assemblies cumbersome. Additionally, in some cases, practitioners may be rushing and forget to operate the safety shield. Other situations arise where the patient moves suddenly or unexpectedly. Thus, the needle cannula may inadvertently be pulled out of the vein and exposed with no time for the phlebotomist to initiate safety shielding.

Another problem with many prior art blood collection devices relates to the time required to assure venous entry. In particular, blood will begin to flow through the cannula upon entry of the intravenous or distal end of the cannula into the vein. However, air present in the cannula, and in the multiple sample sleeve that covers the non-patient end of the cannula, will resist the flow of blood into and through the cannula. In response, the medical practitioner will typically urge an evacuated tube into the needle holder once the practitioner is reasonably sure that the vein has been entered. The rubber stopper at the end of the evacuated tube will deform the multiple sample sleeve over the non-patient end of the cannula and will permit the non-patient end of the cannula to enter the evacuated tube. The pressure differential between the evacuated tube and the cannula will cause the blood to flow into the evacuated tube. In conventional needle assemblies, this often provides the first visual assurance that the vein has been accessed properly.

However, there are many instances in which a medical practitioner will properly access a vein with the distal end of the needle cannula, but will mistakenly believe that the vein has not been entered. Hence, the practitioner will make a second attempt to access the vein. This adds to the discomfort for the patient, extends the time required to carry out a blood collection procedure, and increases the risk for accidental contact between the medical practitioner and a cannula that has been exposed to the patient's blood. Additionally, in some instances a passive shielding mechanism will be activated when the cannula is withdrawn from the patient, thereby making the needle cannula unusable and requiring the medical practitioner to obtain a new needle assembly.

SUMMARY OF THE INVENTION

A need continues to exist for safety needle assemblies incorporating at least one or both a visual flash indicator and a safety shield that can be transitioned from a retracted position in which the tip of a needle cannula is exposed, to an extended position in which the tip of the needle cannula is shielded, which minimizes the risk of exposure to medical personnel, is convenient to use, and is cost-effective.

In one embodiment of the present invention, a needle assembly includes a housing having a distal end, and a proximal end engageable with a specimen collection container. The housing includes a cannula extending distally from the housing, with the cannula having a patient end. A cannula shield is removably engaged with a portion of the housing, and is capable of shielding at least the patient end of the cannula. The cannula shield includes a safety shield engagement. The needle assembly further includes a pivoting safety shield engaged with a portion of the housing and transitionable from a retracted position in which the patient end of the cannula is exposed, to an extended position in which the patient end of the cannula is shielded by at least a portion of the safety shield. The safety shield includes at least one locking tab releasably engageable with the safety shield engagement, with the locking tab fixedly engageable with a portion of the housing in the extended position.

In one configuration, the pivoting safety shield is transitionable from a restrained position in which the locking tab is engaged with the safety shield engagement, to the retracted position. Removal of the cannula shield from the housing allows for transition of the pivoting safety shield from the retracted position to the extended position. Optionally, the housing may further include a flash indicator, and the cannula interior may be provided in fluid communication with the flash indicator. The flash indicator may be visible in the retracted position, and the pivoting safety shield may be disposed over the patient end of the cannula and the locking tab may engage at least a portion of the flash indicator in the extended position. Alternatively, the housing may further include a flash indicator, with the cannula interior in fluid communication with the flash indicator, with the flash indicator visible in the retracted position, and wherein the pivoting safety shield is disposed over the patient end of the cannula and the locking tab engages a portion of the housing distal to the flash indicator in the extended position.

In yet another configuration, the housing may include a forward hub portion and a rear hub portion connectable with the forward hub portion and defining a flash indicator therebetween. Optionally, the safety shield engagement is a ridge projecting dorsally from an outer surface of the cannula shield. The safety shield engagement may also extend substantially longitudinally along the cannula shield. The ridge may include a beveled edge and the locking tab may include an engagement surface corresponding to the beveled edge to provide a resistance interference therebetween. Alternatively, the locking tab may include a beveled edge and the ridge may include an engagement surface corresponding to the beveled edge to provide a resistance interference therebetween.

In yet a further configuration, at least a portion of the ridge is engageable with at least a portion of the locking tab in a detent arrangement to restrain the pivoting safety shield with the cannula shield. The detent arrangement may be adapted to resist disengagement until a force is imparted to the pivoting safety shield in a manner capable of moving the pivoting safety shield from the restrained position to the retracted position. The detent arrangement resists unintentional removal of the cannula shield from the housing. Release of the detent arrangement allows the pivoting safety shield to pivot from a restrained position to the retracted position.

In another embodiment of the present invention, a needle assembly includes a housing, having a distal end, and a proximal end, and a cannula extending distally from the housing. The cannula includes a patient end. The assembly also includes a pivoting safety shield fixedly engaged with a portion of the housing. The safety shield is transitionable over the cannula from a retracted position in which the patient end is exposed, to an extended position in which the patient end is shielded by at least a portion of the safety shield. The assembly also includes a cannula shield releaseably engaged with a portion of the housing and shielding at least the patient end of the cannula. The cannula shield includes a safety shield engagement, and the pivoting safety shield is releaseably engaged with the safety shield engagement, wherein removal of the cannula shield from the housing allows for transition of the safety shield from the retracted position to the extended position.

Optionally, the safety shield engagement is a ridge projecting dorsally from an outer surface of the cannula shield and extending along at least a portion of a longitudinal axis of the cannula shield. The pivoting safety shield may further include at least one locking tab adapted to releaseably engage the ridge. The ridge may include a beveled edge and the locking tab may include an engagement surface corresponding to the beveled edge to provide a resistance interference therebetween. At least a portion of the ridge is engageable with at least a portion of the locking tab in a detent arrangement to restrain the pivoting safety shield with the cannula shield. The detent arrangement may be adapted to resist disengagement until a force is imparted to the pivoting safety shield in a manner capable of moving the pivoting safety shield from the restrained position to the retracted position. The detent arrangement may prevent unintentional removal of the cannula shield from the housing, and disengagement of the detent arrangement enables removal of the cannula shield from the housing. Release of the detent arrangement allows the pivoting safety shield to pivot from a restrained position to the retracted position. In a further configuration, the housing includes a flash indicator, and the cannula interior is provided in fluid communication with the flash indicator.

In yet another embodiment of the present invention, a needle assembly includes a housing having a distal end and a proximal end, and a cannula extending distally from the housing. The cannula includes a patient end. The assembly also includes a cannula shield removably engaged with a portion of the housing, and including a locking tab receiving structure. The assembly also includes a pivoting safety shield engaged with a portion of the housing, transitionable from a retracted position in which the patient end of the cannula is exposed, to an extended position in which the patient end of the cannula is shielded by at least a portion of the safety shield. The safety shield includes at least one locking tab, wherein the locking tab receiving structure is adapted to receive the locking tab when the pivoting safety shield is in a restrained position.

The locking tab may extend from an internal wall of the pivoting safety shield. Optionally, the pivoting safety shield is pivotable about a hinge. When the cannula shield is removed from the needle assembly, the safety shield is capable of lockingly engaging at least one of the cannula or housing when the safety shield is in the extended position. In another configuration, when the pivoting safety shield is in the restrained position, the locking tab and locking tab receiving structure resist disengagement until a force is imparted to the pivoting safety shield in a manner capable of moving the safety shield from the restrained position to the retracted position.

In a further embodiment of the present invention, a blood collection assembly includes a first sub-assembly and a second sub-assembly, wherein the first sub-assembly includes a first portion for press-fit engagement with the second sub-assembly, and the second sub-assembly includes a corresponding second portion for press-fit engagement with the first sub-assembly. The first sub-assembly includes a hub having a flash indicator, the hub having a distal end and a proximal end engageable with a specimen collection container. The first sub-assembly also includes a cannula extending between a patient end and a non-patient end, defining a cannula interior, with the patient end of the cannula projecting at least partially from the distal end of the hub. The cannula interior is in fluid communication with the flash indicator. The first sub-assembly also includes a cannula shield removably engaged with the distal end of the hub and shielding at least the patient end of the cannula. The first sub-assembly further includes a pivoting safety shield fixedly engaged with a portion of the hub, transitionable from a retracted position in which the patient end is exposed, to an extended position in which the patient end is shielded by at least a portion of the safety shield. The second sub-assembly includes a specimen collection container holder having an interior through which a specimen collection container may be engaged with the proximal end of the hub.

Optionally, the cannula shield includes a safety shield engagement, and the safety shield comprises at least one locking tab releasably engageable with the safety shield engagement. The safety shield engagement may be a ridge projecting upwardly from an outer surface of the cannula shield and extending along at least a portion of a longitudinal axis of the cannula shield. At least a portion of the ridge may be engageable with at least a portion of the locking tab in a detent arrangement to restrain the safety shield with the cannula shield. Release of the detent arrangement may allow the safety shield to pivot from a restrained position to the retracted position. Removal of the cannula shield from the housing may allow for transition of the safety shield from the retracted position to the extended position.

In another configuration, the locking tab is releasably engagable with the safety shield engagement in a restrained position and fixedly engageable with a portion of the housing in the extended position. Engagement of the first portion and the second portion may include deflection of at least one of the first portion and the second portion to provide an interference therebetween. In another configuration, the first portion and the second portion may include a two-stage press-fit engagement. Engagement of the first portion and the second portion may include a first deflection of at least a portion of at least one of the first portion and the second portion to provide an interference therebetween, and a second deflection of at least a portion of at least one of the first portion and the second portion to provide a second interference therebetween. At least a portion of the first portion and at least a portion of the second portion may also include corresponding mating surfaces for threaded engagement therebetween. The press-fit engagement of the first portion of the first sub-assembly and the second portion of the second sub-assembly may prevent disengagement of the first sub-assembly from the second sub-assembly upon engagement of a specimen collection container with the proximal end of the hub.

DESCRIPTION OF THE DRAWINGS

FIG. 5 is a side view of the needle assembly of FIG. 1 having a safety shield in the retracted position.

FIG. 6 is a side view of the needle assembly of FIG. 2 having a safety shield in the extended position.

FIG. 7 is a side cross-sectional view of the needle assembly of FIG. 1 having a safety shield in the retracted position.

FIG. 8 is a side cross-sectional view of the needle assembly of FIG. 2 having a safety shield in the extended position.

FIG. 9 is a top cross-sectional view of the needle assembly of FIG. 1 having a safety shield in the retracted position and showing a locking mechanism in accordance with an embodiment of the present invention.

FIG. 10 is a top cross-sectional view of the needle assembly of FIG. 2 having a safety shield in the extended position and showing a locking mechanism.

FIG. 15A is a cross-sectional view of a needle assembly having a flash chamber used in connection with a blood collection assembly in yet a further embodiment.

FIG. 15B is an enlarged sectional view of a portion of the needle assembly of FIG. 15A.

FIG. 20 is a side cross-sectional view of the needle assembly of FIG. 16 having a safety shield in the retracted position and with a needle cover.

FIG. 21 is a side cross-sectional view of the needle assembly of FIG. 17 with the needle cover removed and having a safety shield in the extended position.

FIG. 22 is a top cross-sectional view of the needle assembly of FIG. 16 having a safety shield in the retracted position with a needle cover and showing a locking mechanism in accordance with an embodiment of the present invention.

FIG. 23 is a top cross-sectional view of the needle assembly of FIG. 17 with the needle cover removed and having a safety shield in the extended position and showing a locking mechanism.

FIG. 24 is a perspective view of the needle assembly of the present invention, with the safety shield removed for illustration purposes and including a needle cover in accordance with an embodiment of the present invention.

FIG. 25 is a cross-sectional view of the needle assembly of FIG. 24.

FIG. 29 is a perspective view of a needle assembly having a safety shield in the retracted position in accordance with a further embodiment of the present invention.

FIG. 30 is a perspective view of the needle assembly of FIG. 29 having a safety shield in the extended position.

FIG. 31 is a side view of the needle assembly of FIG. 29 having a safety shield in the retracted position.

FIG. 32 is a side view of the needle assembly of FIG. 30 having a safety shield in the extended position.

FIG. 33 is a top-down cross-sectional view of the needle assembly of FIG. 29 having a safety shield in the retracted position.

FIG. 34 is a top-down cross-sectional view of the needle assembly of FIG. 30 having a safety shield in the extended position.

FIG. 39 is a perspective view of a needle assembly with a push button activator having a removable cannula guard covering a safety shield in the retracted position in accordance with an embodiment of the present invention.

FIG. 40 is a perspective view of the needle assembly of FIG. 39 having the removable cannula guard removed showing the safety shield in the extended position.

FIG. 45 is a top view of the needle assembly of FIG. 39.

FIG. 46 is a top view of the needle assembly of FIG. 40.

FIG. 47 is a cross-sectional view of the needle assembly of FIG. 39.

FIG. 48 is a cross-sectional view of the needle assembly of FIG. 40.

FIG. 56 is an alternative exploded perspective view of a needle assembly in accordance with an embodiment of the present invention FIG. 57 is a partially assembled perspective view of the needle assembly of FIG. 56.

FIG. 58 is a partially assembled perspective view of the needle assembly of FIG. 56.

FIG. 59 is a perspective view of a needle assembly having a distal needle shield, and proximal needle shield in accordance with an embodiment of the present invention.

FIG. 60 is a top view of the hub assembly, distal needle shield, and proximal needle shield of FIG. 59.

FIG. 63 is a cross-sectional view of the side view of FIG. 62.

FIG. 64 is a perspective view of the needle assembly of FIG. 59 engaged with a specimen collection container holder in accordance with an embodiment of the present invention.

FIG. 67 is a perspective view of a needle assembly having a safety shield in the retracted position and including a glide mechanism in accordance with an embodiment of the present invention.

FIG. 68 is a perspective view of the needle assembly of FIG. 67 having a safety shield in the extended position.

FIG. 69 is a side view of the needle assembly of FIG. 67 having a safety shield in the retracted position.

FIG. 70 is a side view of the needle assembly of FIG. 68 having a safety shield in the extended position.

FIG. 71 is a cross-sectional view of the needle assembly of FIG. 69 having a safety shield in the retracted position.

FIG. 72 is a cross-sectional view of the needle assembly of FIG. 70 having a safety shield in the extended position.

FIG. 75 is a top view of the needle assembly of FIG. 73 in the assembled and retracted position.

FIG. 76 is a cross-sectional top view of the needle assembly of FIG. 75 in the retracted position.

FIG. 77 is a cross-sectional side view of the needle assembly of FIG. 73 in the assembled and retracted position.

FIG. 78 is a side view of the needle assembly of FIG. 77 in the retracted position.

FIG. 79 is a bottom view of the needle assembly of FIG. 73 in the assembled and retracted position.

FIG. 80 is a front view of the assembled needle assembly of FIG. 73.

FIG. 81 is a rear view of the needle assembly of FIG. 80.

FIG. 84 is a cross-sectional side view of the needle assembly of FIG. 77 in the extended position.

FIG. 85 is a side view of the needle assembly of FIG. 78 in the extended position.

FIG. 94 is a perspective view of a needle assembly having a hinged safety shield and a needle guard shield in accordance with an embodiment of the present invention.

FIG. 95 is a side view of the needle assembly of FIG. 94.

FIG. 96 is a top view of the needle assembly of FIG. 94.

FIG. 97 is a cross-sectional side view of the needle assembly of FIG. 94.

FIG. 103 is a side view of the needle assembly of FIG. 102.

FIG. 104 is a cross-sectional view of the needle assembly of FIG. 102.

FIG. 109 is a side view of the needle assembly of FIG. 108.

FIG. 110 is a top view of the needle assembly of FIG. 108.

FIG. 116 is a perspective view of the needle assembly of FIG. 108 in the extended position.

FIG. 117 is a top view of the needle assembly of FIG. 116 in the extended position.

FIG. 118 is a cross-sectional side view of the needle assembly of FIG. 116.

FIG. 121 is a rear view of the needle assembly of FIG. 116.

FIG. 122 is a sectional perspective view of an alternative hinged safety shield shown in the extended position in accordance with an embodiment of the present invention.

FIG. 123 is a perspective view of a needle assembly having a pierceable seal prior to use with a sample container in accordance with an embodiment of the present invention.

FIG. 124 is a perspective view of the needle assembly of FIG. 123 in use.

FIG. 125 is a perspective view of the needle assembly of FIG. 124 having the container removed from the pierceable seal after use.

FIG. 126 is a perspective view of a base portion of the housing of a needle assembly in accordance with an embodiment of the present invention.

FIG. 127 is a side view of the base portion of FIG. 126.

FIG. 128 is a perspective view of a hub portion of the housing of a needle assembly in accordance with an embodiment of the present invention.

FIG. 129 is a side view of the hub portion of FIG. 128.

FIG. 130 is a perspective view of an assembled housing of a needle assembly including the base portion of FIG. 126 and the hub portion of FIG. 128.

FIG. 131 is a side view of the assembled housing of FIG. 130.

FIG. 132 is an exploded perspective view of a needle assembly including a cannula shield and a pivoting safety shield in accordance with an embodiment of the present invention.

Figure 132:
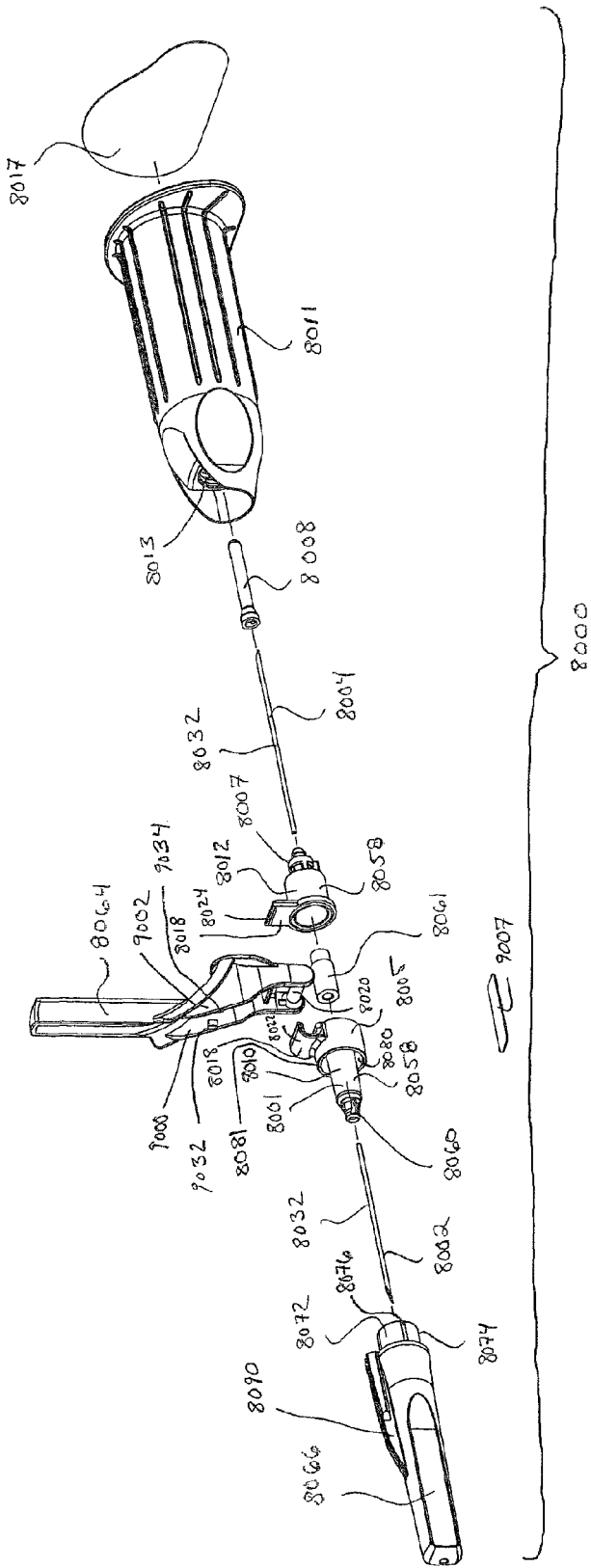
Figure 133:
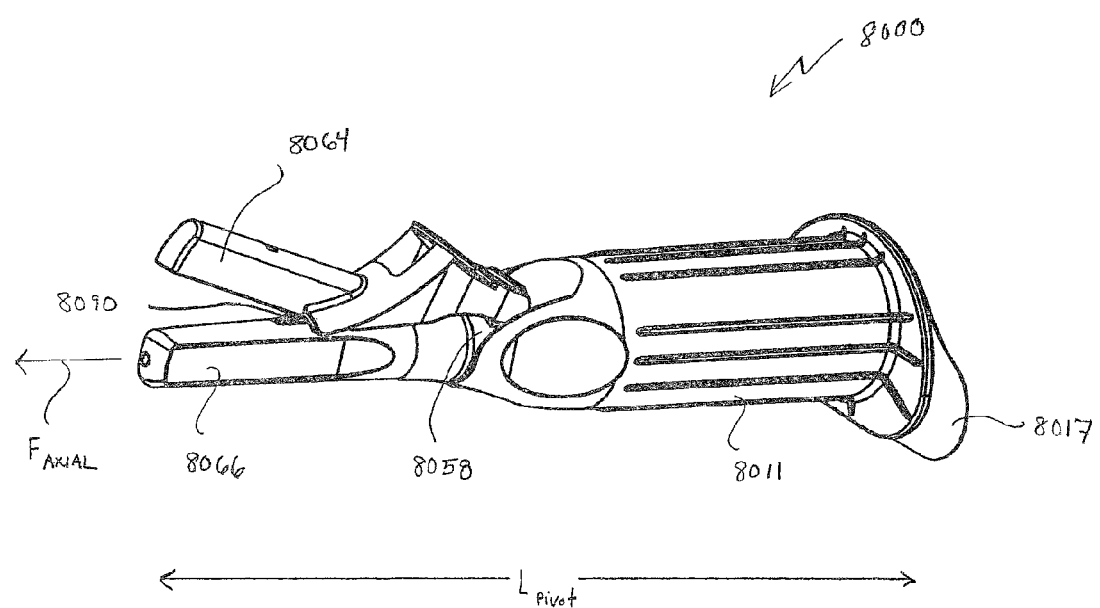

FIG. 133 is an assembled perspective view of the needle assembly of FIG. 132 including the cannula shield and the safety shield in the restrained position.

Figure 134:
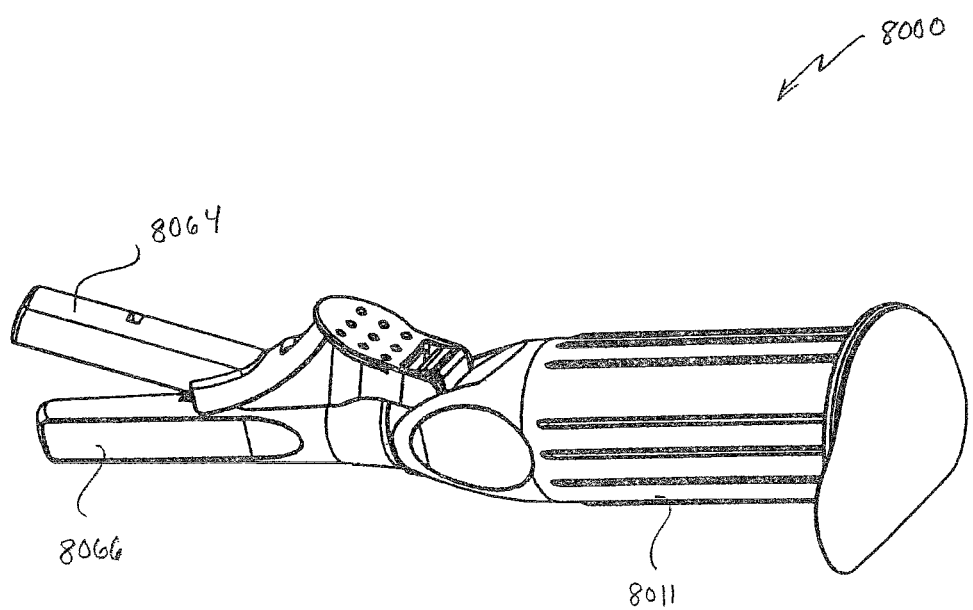

FIG. 134 is an alternative perspective view of the needle assembly of FIG. 133 including the safety shield in the restrained position.

Figure 135:
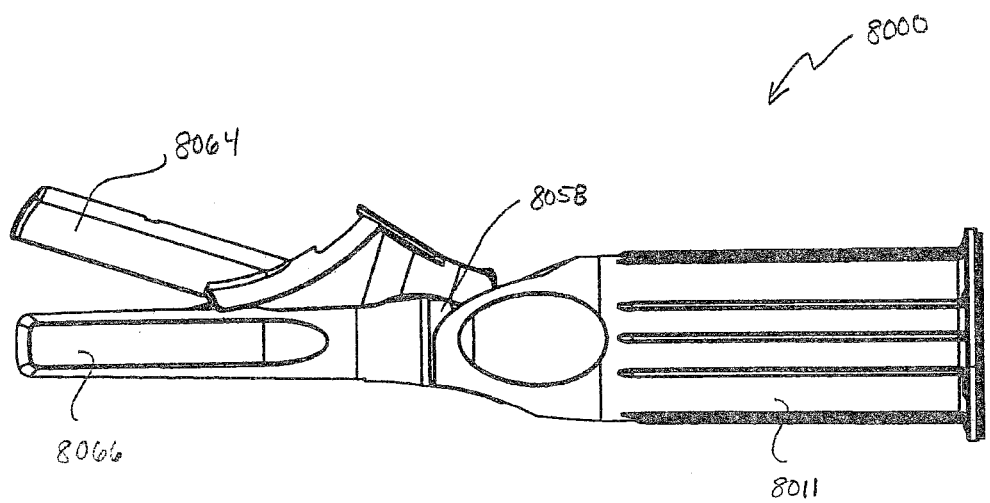

FIG. 135 is a side view of the needle assembly of FIG. 133.

Figure 136:
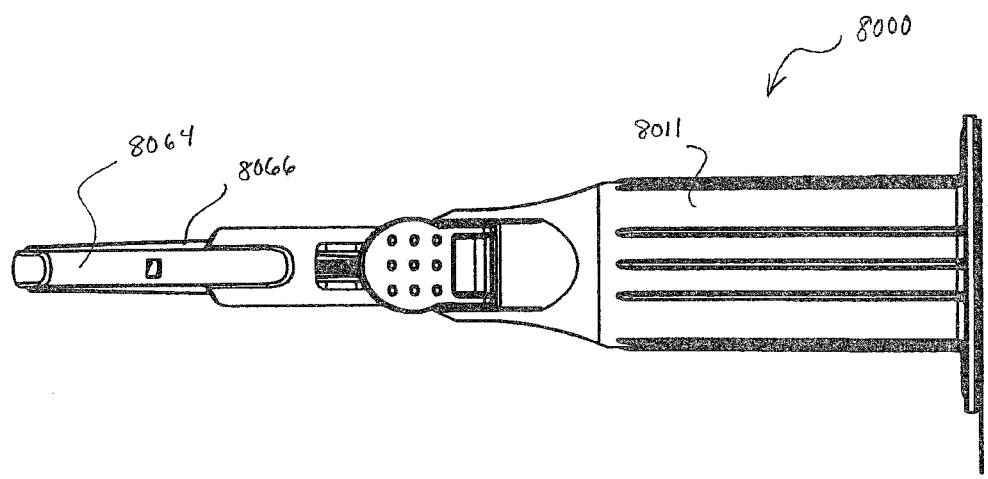

FIG. 136 is a top view of the needle assembly of FIG. 133.

Figure 137:
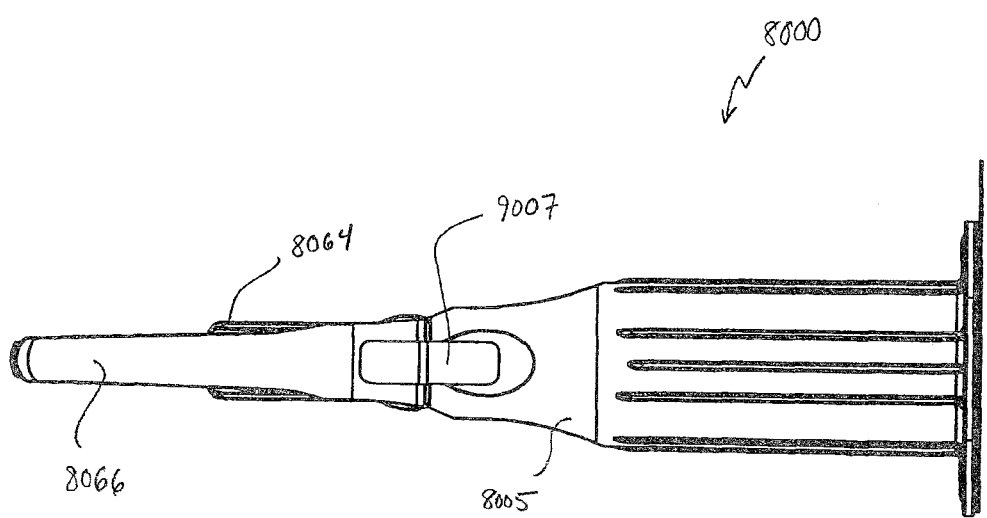

FIG. 137 is a bottom view of the needle assembly of FIG. 133.

Figure 138:
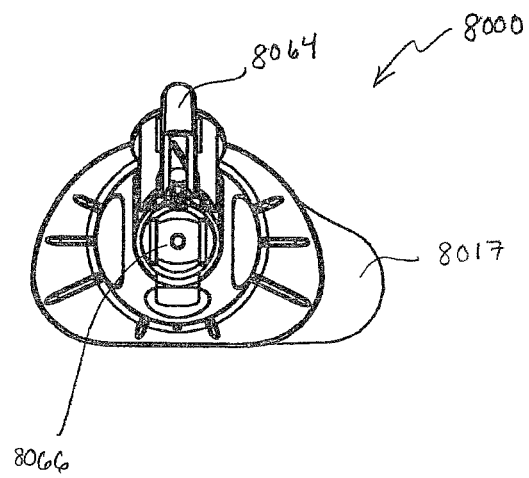

FIG. 138 is a front view of the needle assembly of FIG. 133.

Figure 139:
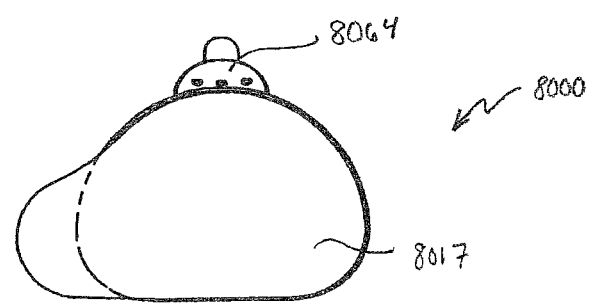

FIG. 139 is a rear view of the needle assembly of FIG. 133.

Figure 140:
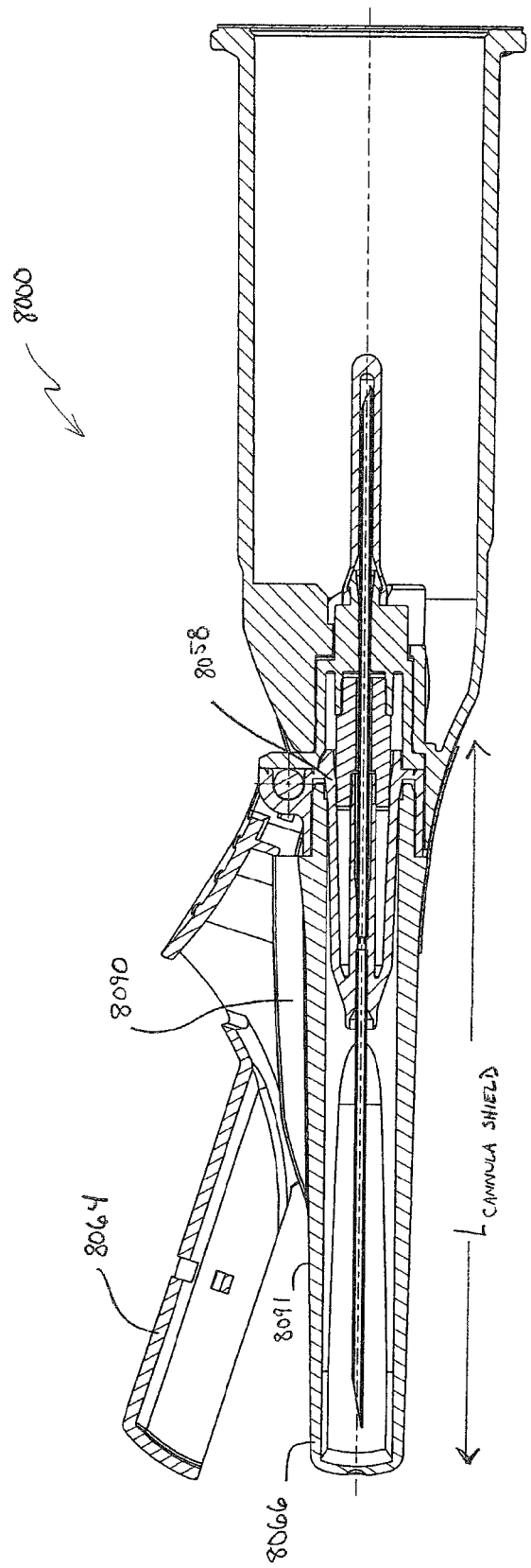

FIG. 140 is a cross-sectional side view of the needle assembly of FIG. 135.

Figure 141:
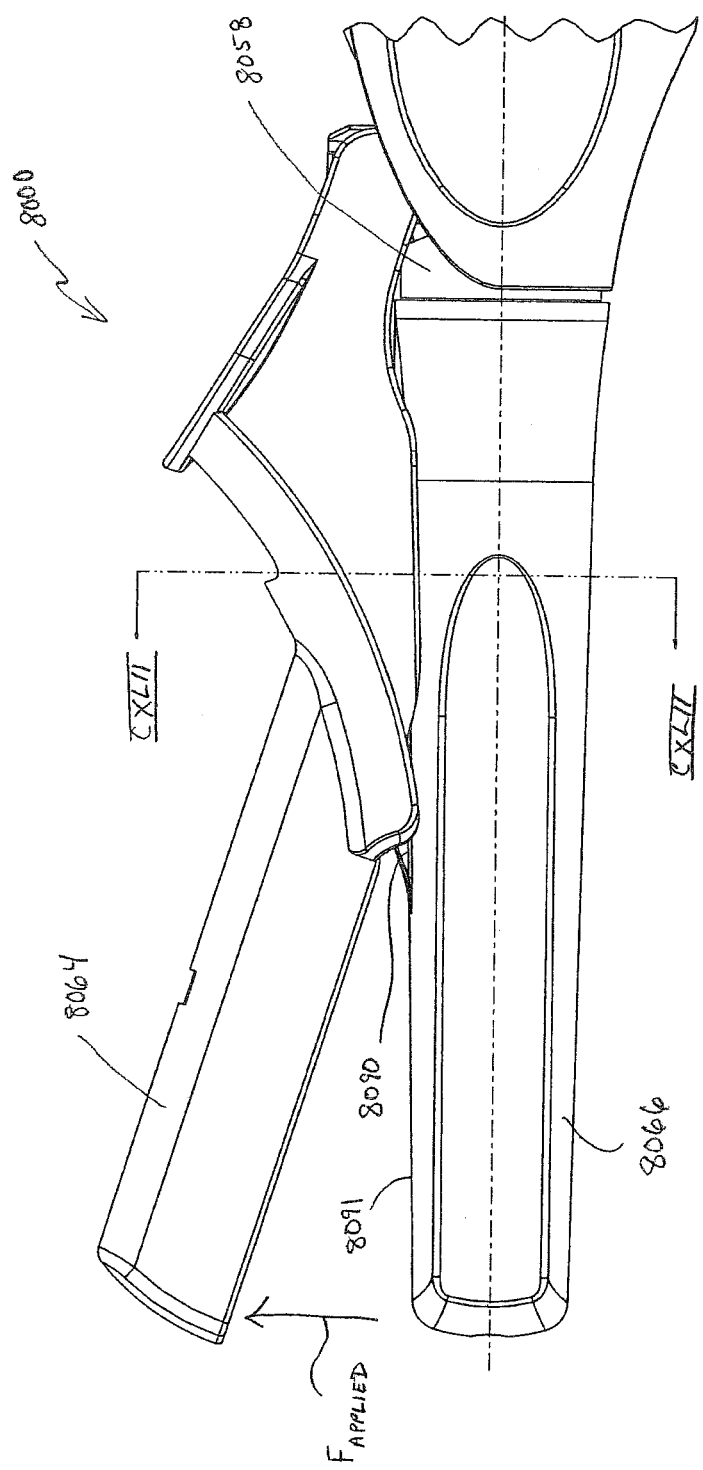

FIG. 141 is a sectional side view of a needle assembly having a cannula shield and a pivoting safety shield in the restrained position in accordance with an embodiment of the present invention.

Figure 142:
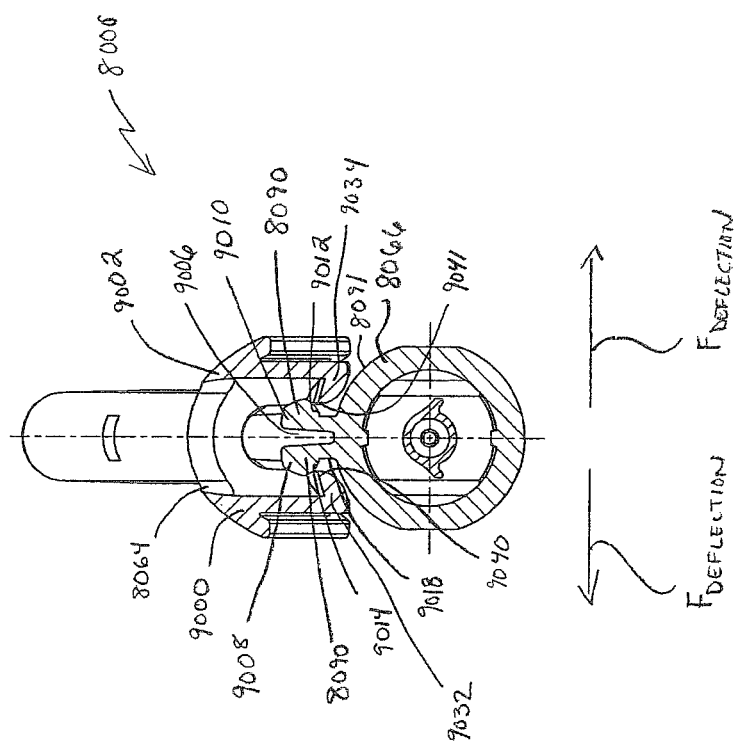

FIG. 142 is a cross-sectional view of FIG. 141 taken along line CXLII-CXLII.

Figure 143:
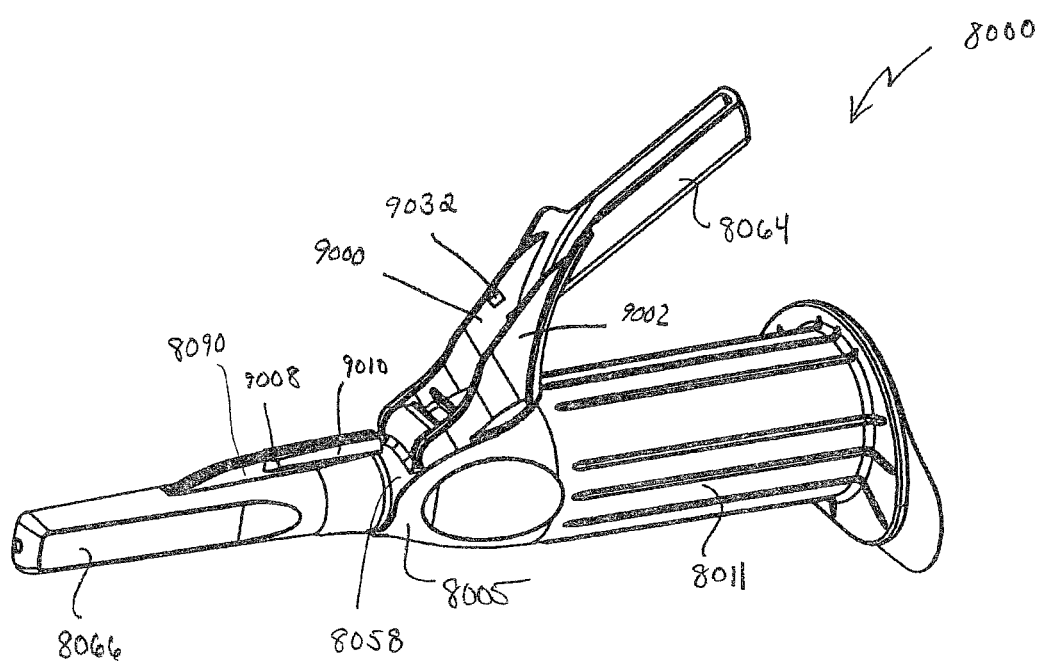

FIG. 143 is a perspective view of the needle assembly of FIG. 133 including the cannula shield and the safety shield in the retracted position.

Figure 144:
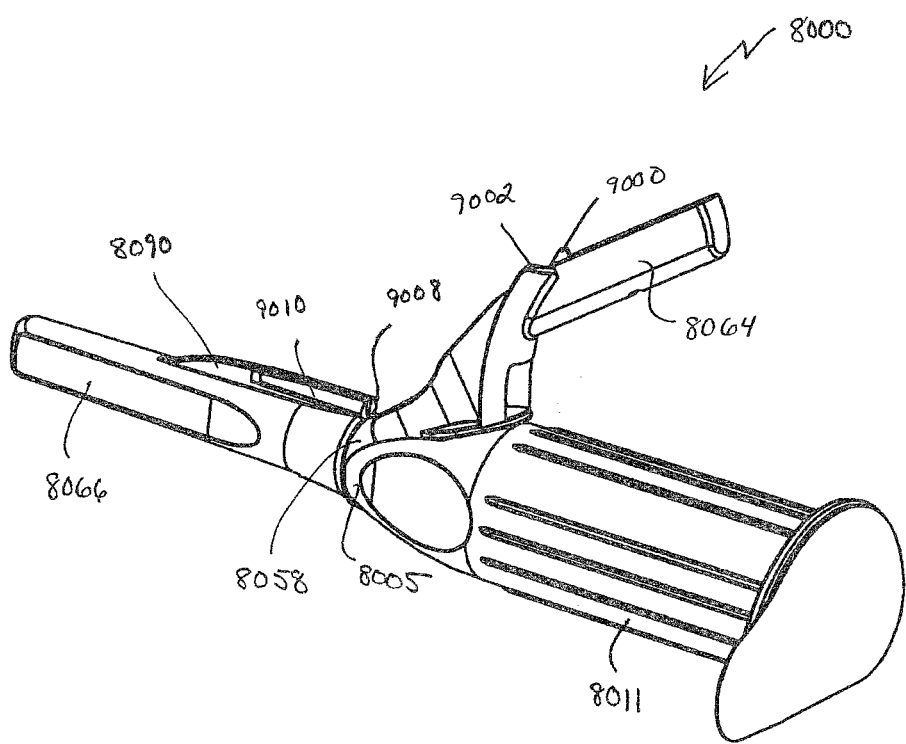

FIG. 144 is an alternative perspective view of the needle assembly of FIG. 143 including the safety shield in the retracted position.

Figure 145:
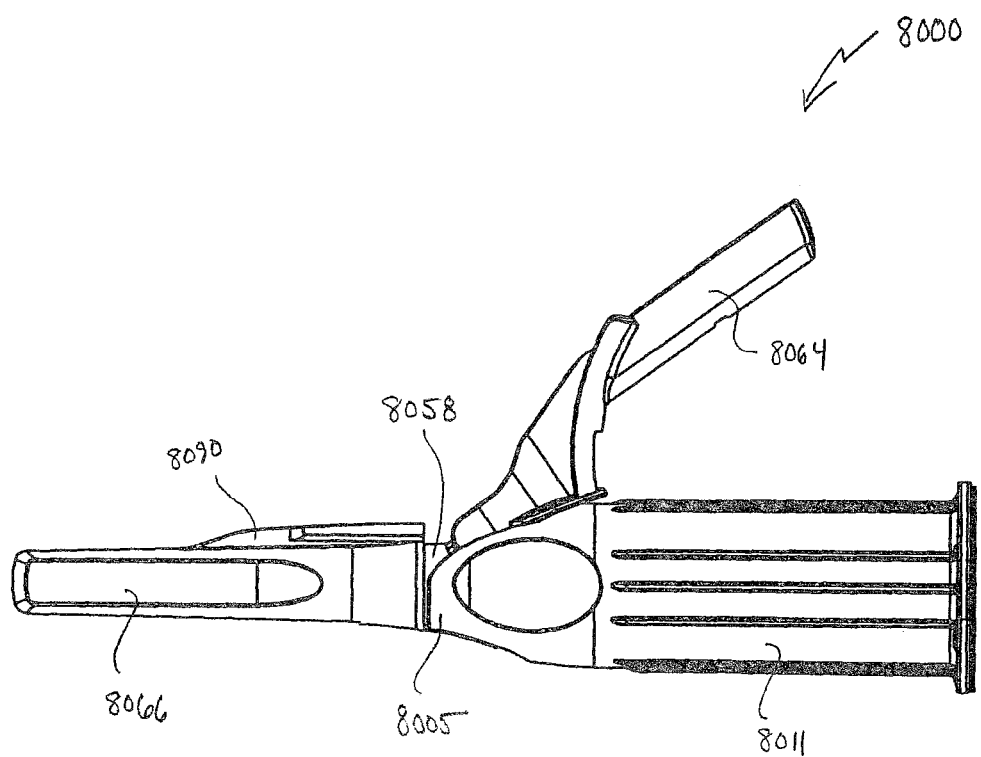

FIG. 145 is a side view of the needle assembly of FIG. 143.

Figure 146:
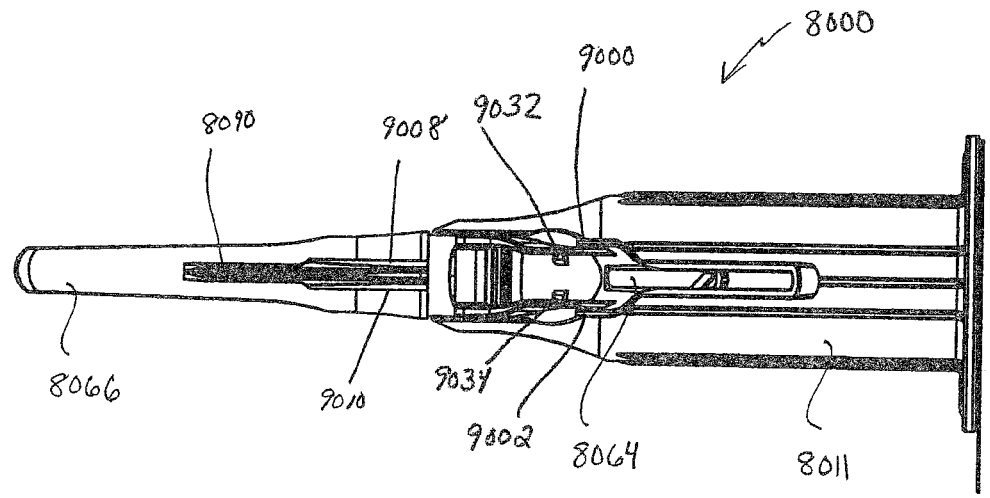

FIG. 146 is a top view of the needle assembly of FIG. 143.

Figure 147:
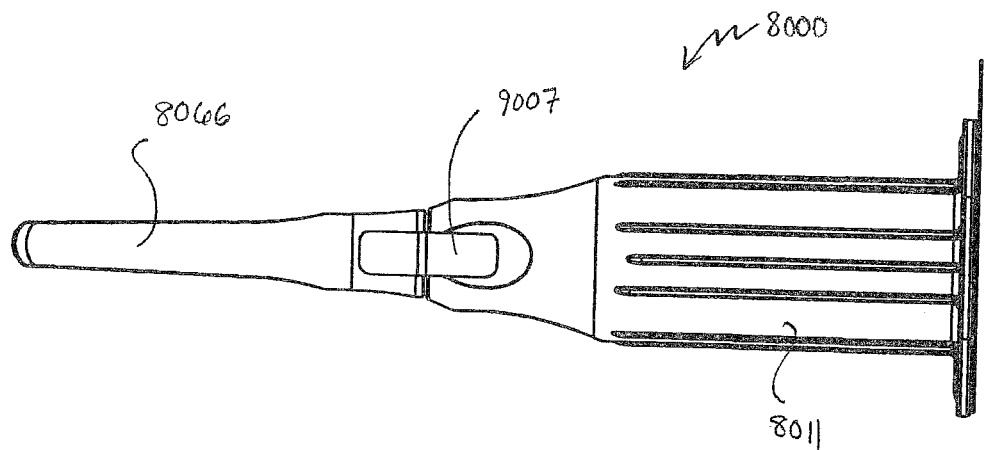

FIG. 147 is a bottom view of the needle assembly of FIG. 143.

Figure 148:
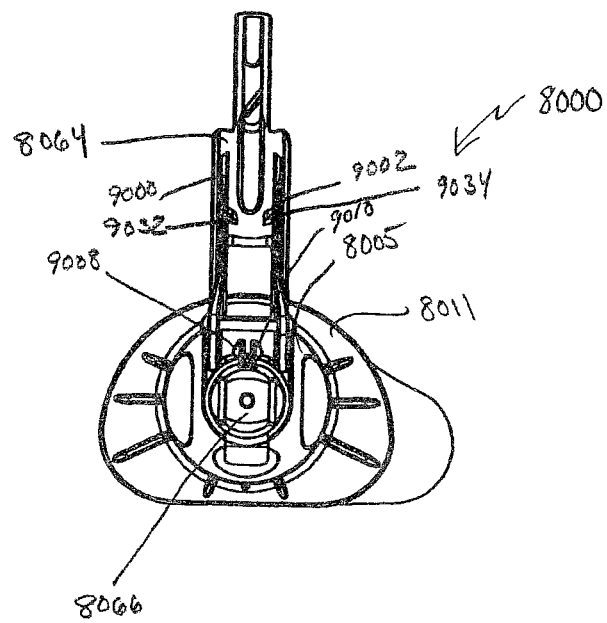

FIG. 148 is a front view of the needle assembly of FIG. 143.

Figure 149:
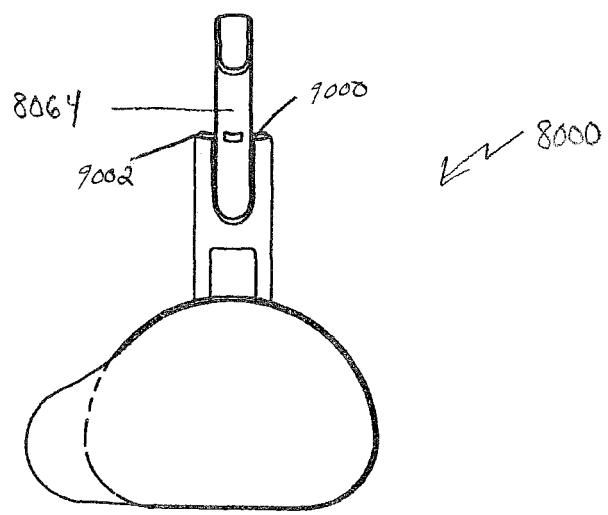

FIG. 149 is a rear view of the needle assembly of FIG. 143.

Figure 150:
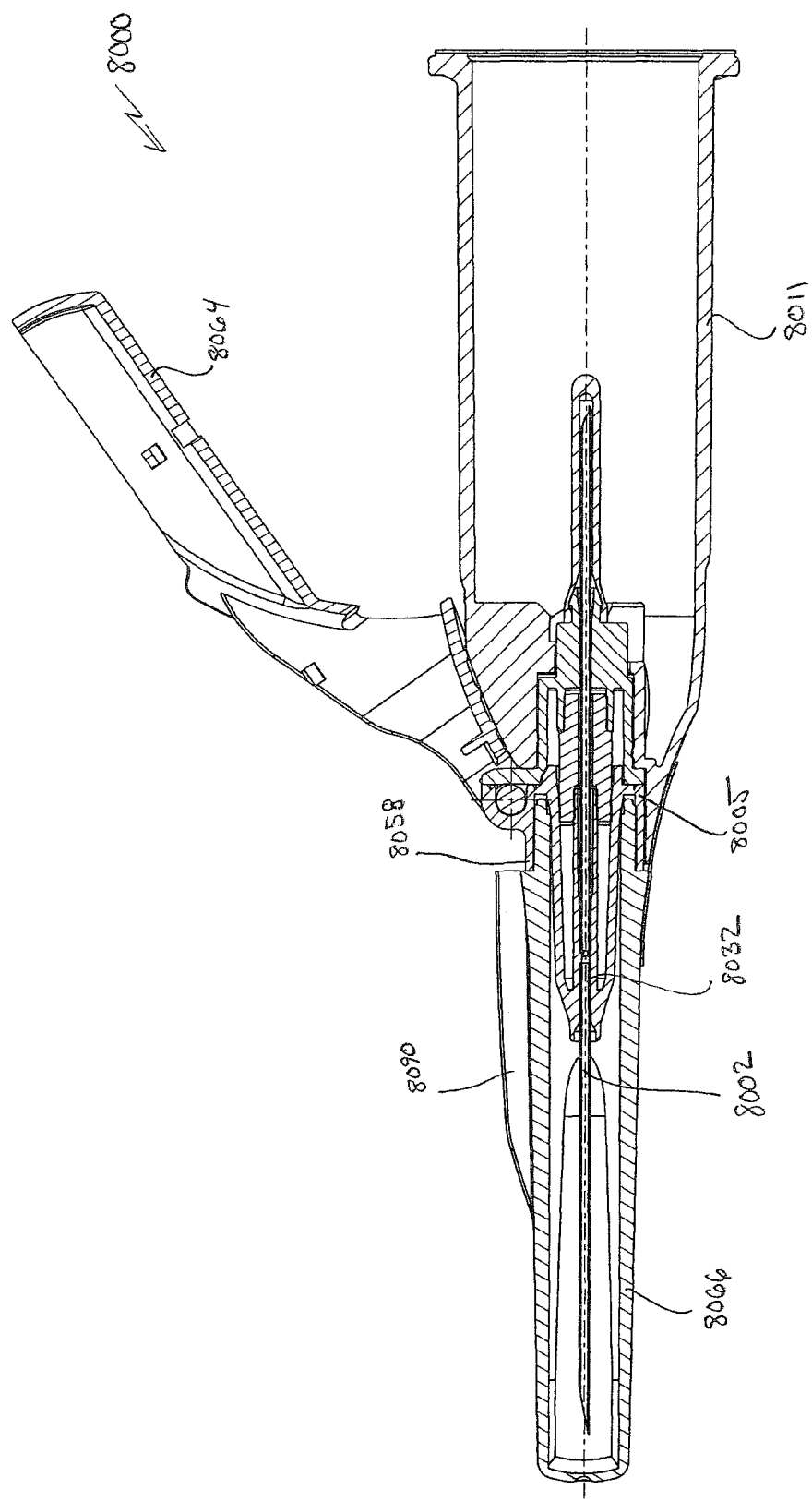

FIG. 150 is a cross-sectional side view of the needle assembly of FIG. 143.

Figure 151:
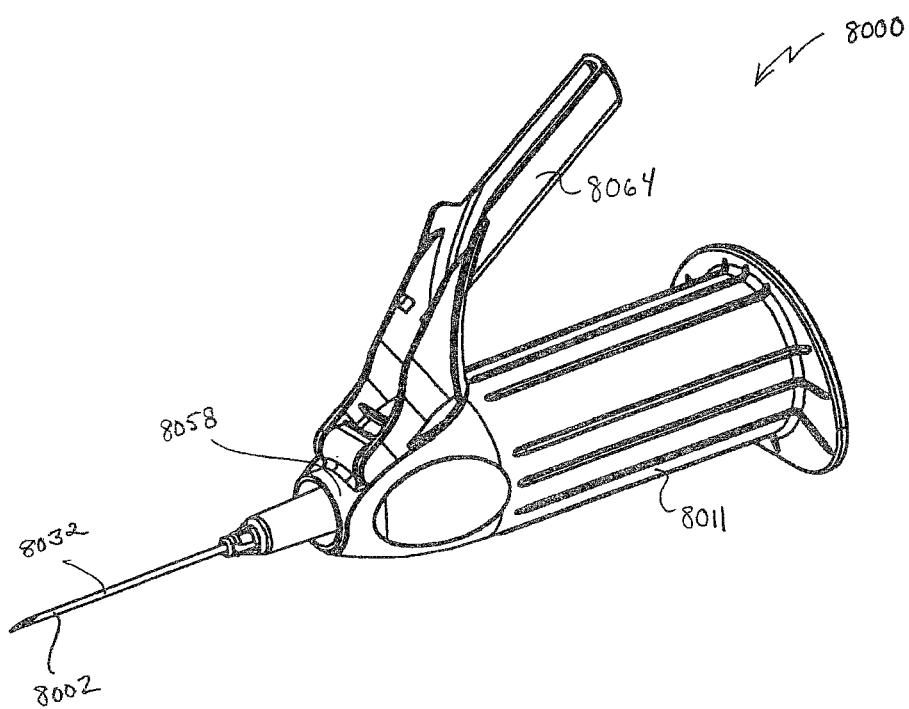

FIG. 151 is a perspective view of the needle assembly of FIG. 143 having the cannula shield removed and showing the safety shield in the retracted position.

Figure 152:
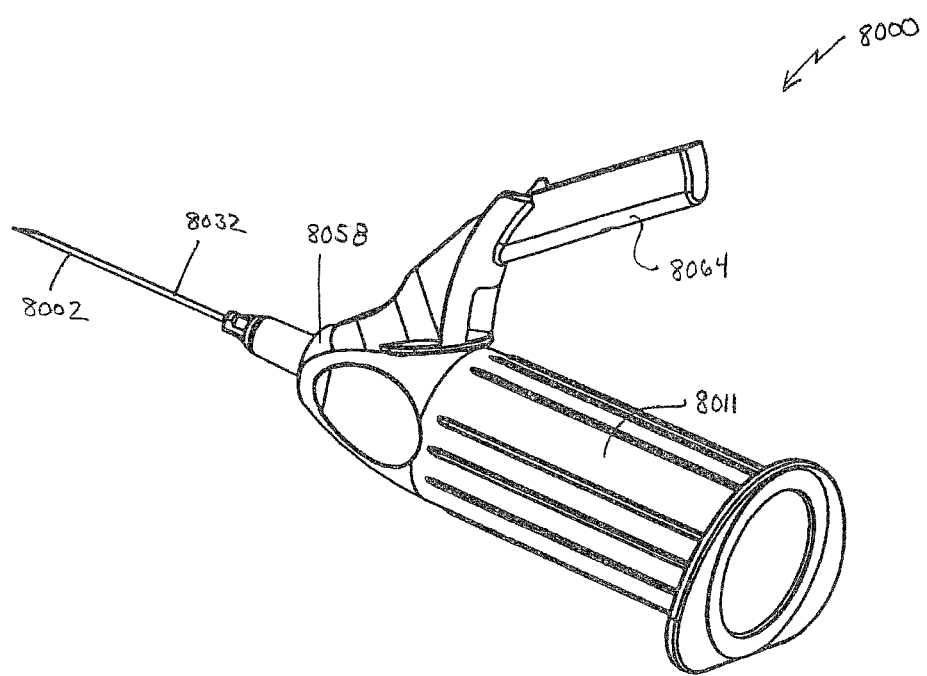

FIG. 152 is an alternative perspective view of the needle assembly of FIG. 151 having the cannula shield removed and showing the safety shield in the retracted position.

Figure 153:
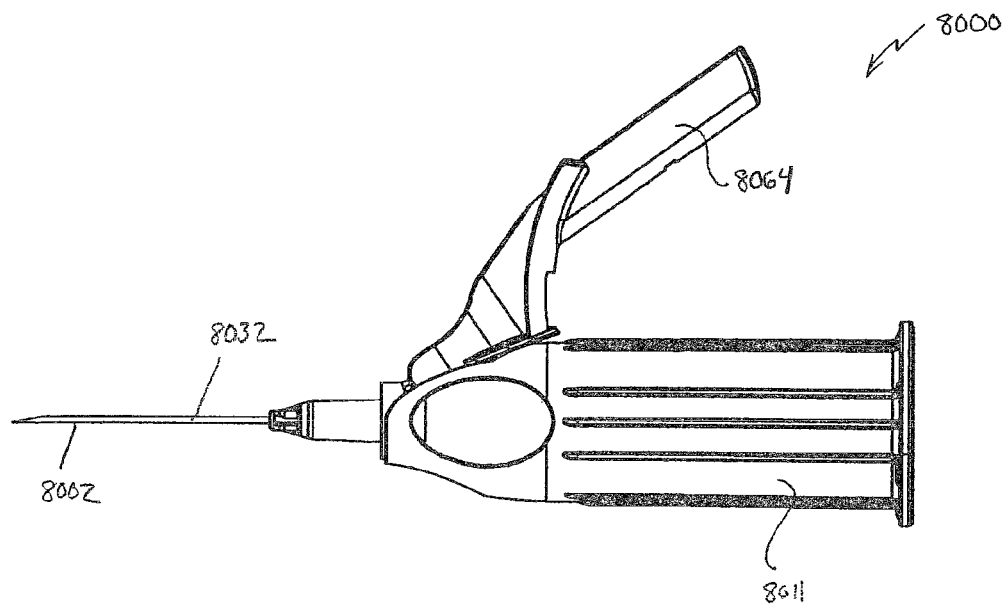

FIG. 153 is a side view of the needle assembly of FIG. 151.

Figure 154:
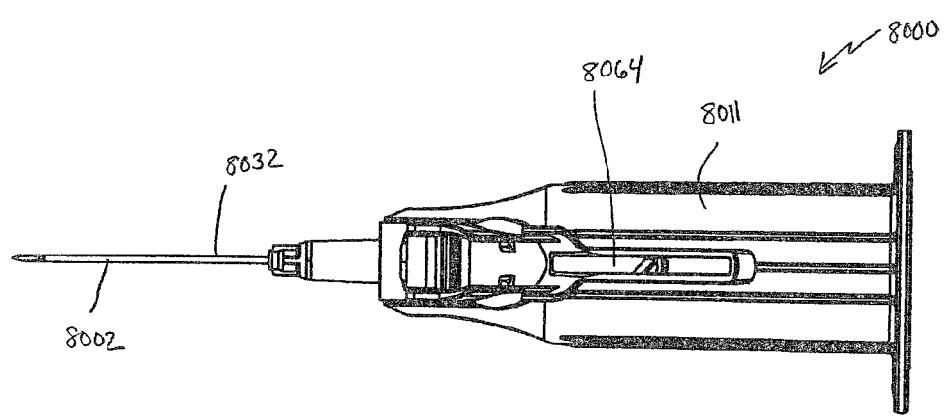

FIG. 154 is a top view of the needle assembly of FIG. 151.

Figure 155:
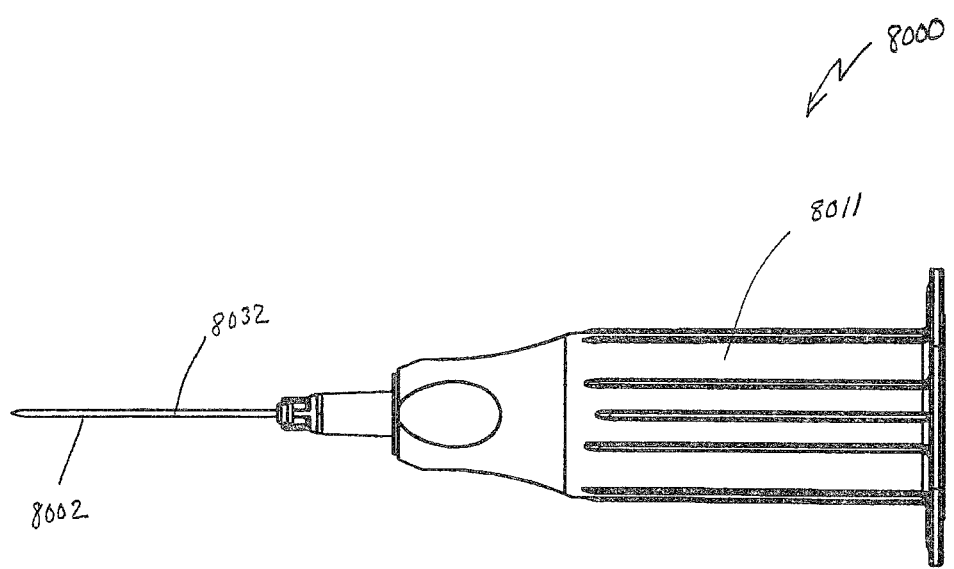

FIG. 155 is a bottom view of the needle assembly of FIG. 151.

Figure 156:
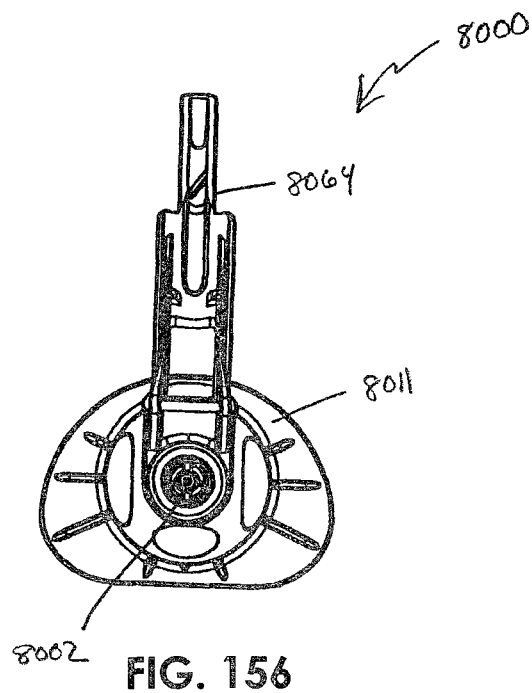

FIG. 156 is a front view of the needle assembly of FIG. 151.

Figure 157:
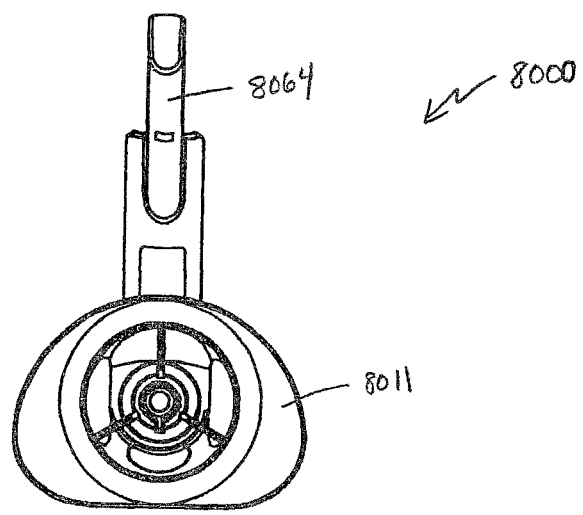

FIG. 157 is a rear view of the needle assembly of FIG. 151.

Figure 158:
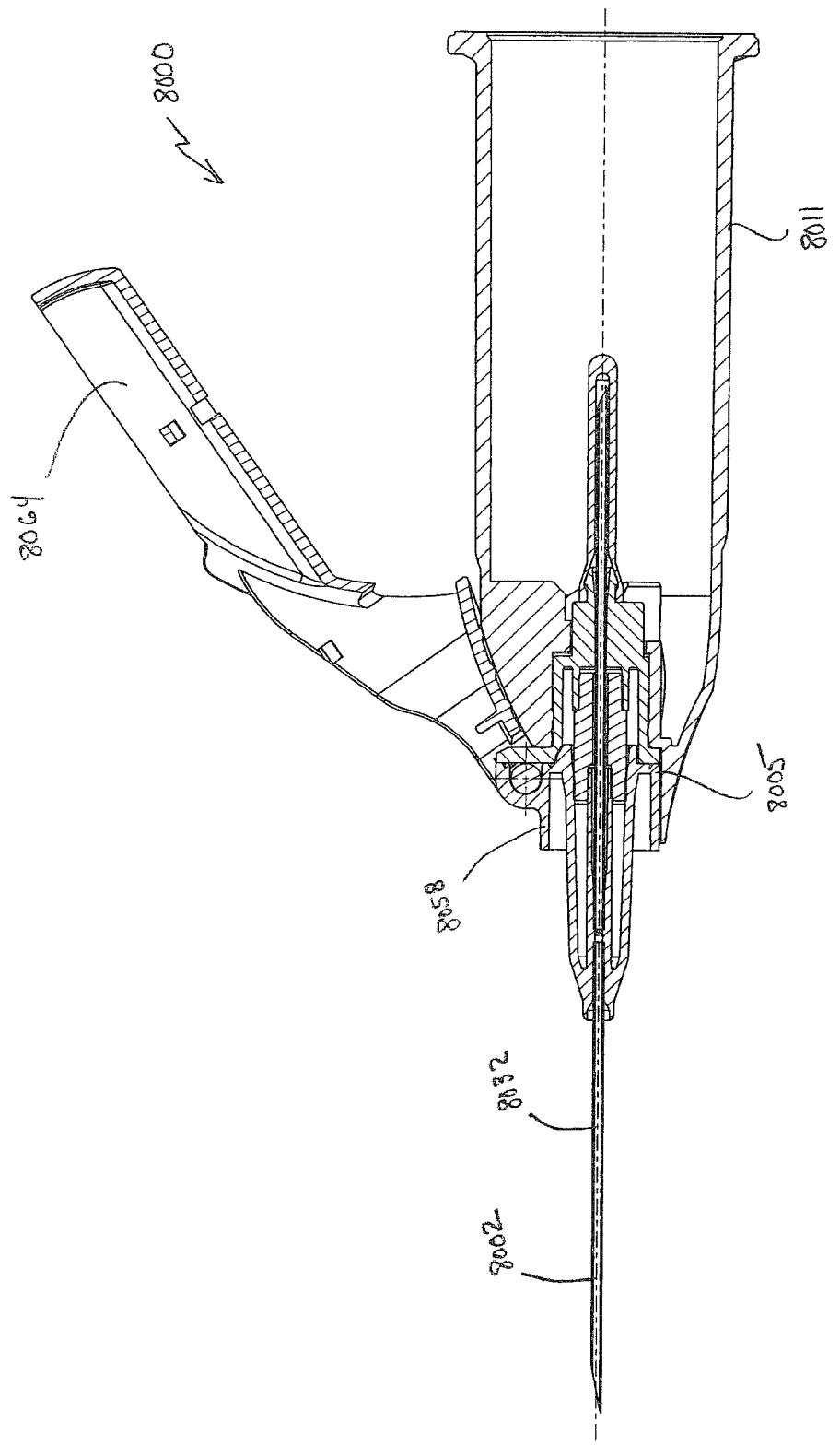

FIG. 158 is a cross-sectional side view of the needle assembly of FIG. 151.

Figure 159:
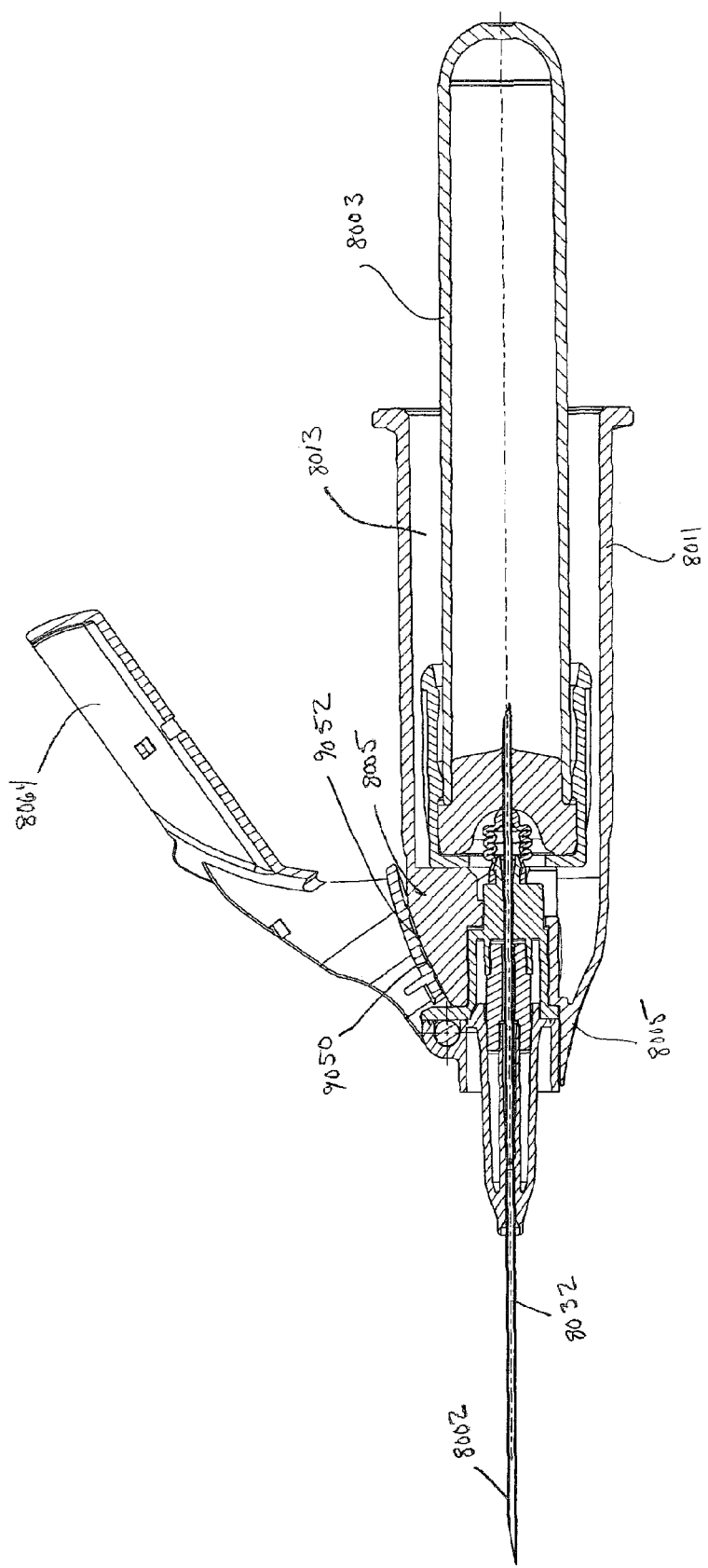

FIG. 159 is a cross-sectional side view of the needle assembly of FIG. 151 having a specimen collection container engaged therewith.

Figure 160:
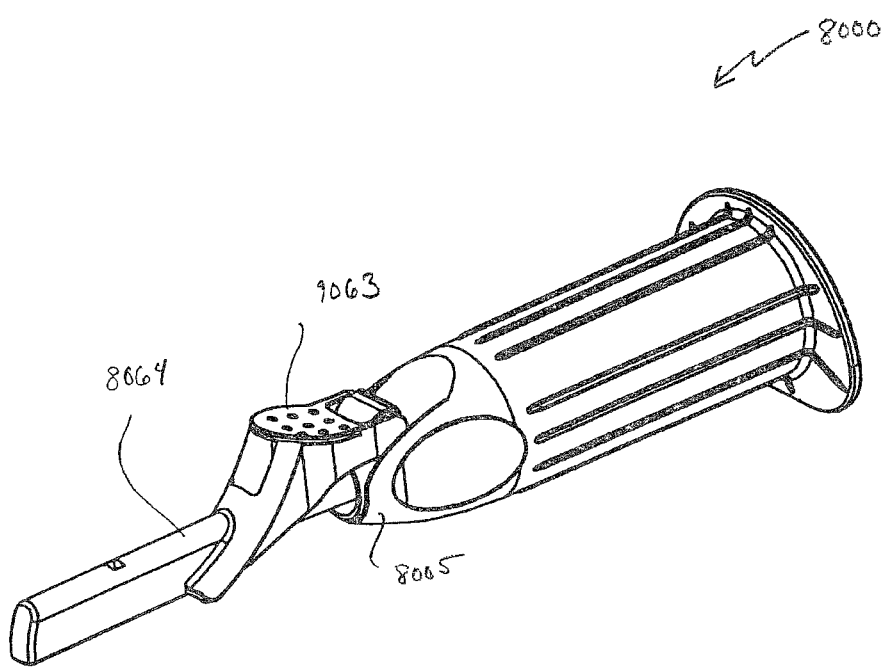

FIG. 160 is a perspective view of the needle assembly of FIG. 151 showing the safety shield in the extended position.

Figure 161:
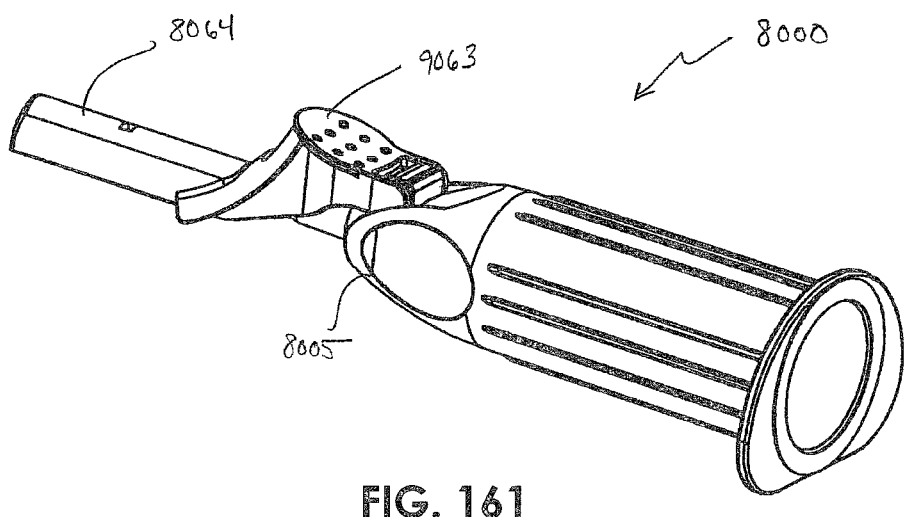

FIG. 161 is an alternative perspective view of the needle assembly of FIG. 160 showing the safety shield in the extended position.

Figure 162:
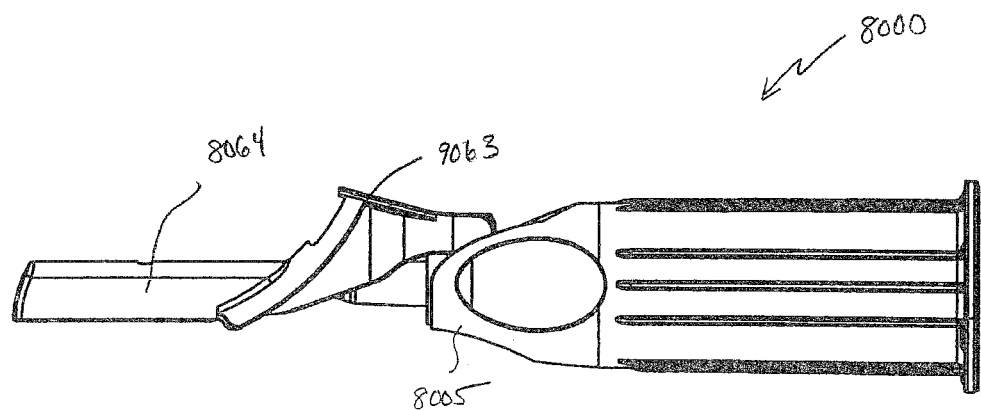

FIG. 162 is a side view of the needle assembly of FIG. 160.

Figure 163:
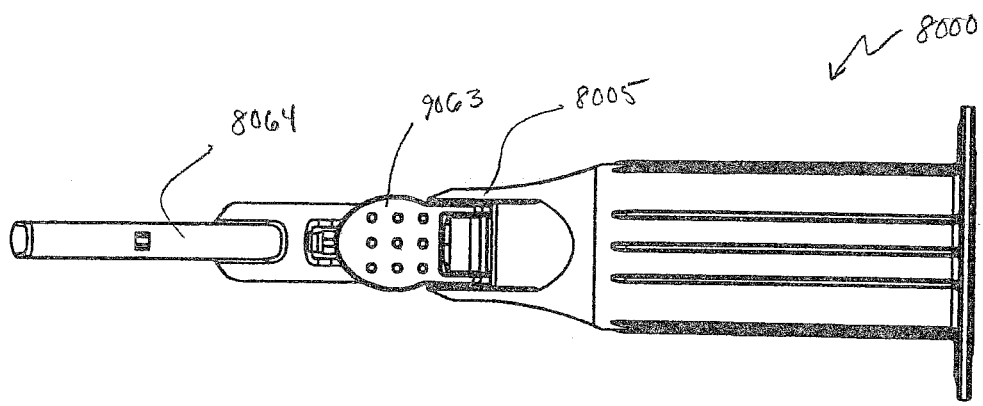

FIG. 163 is a top view of the needle assembly of FIG. 160.

Figure 164:
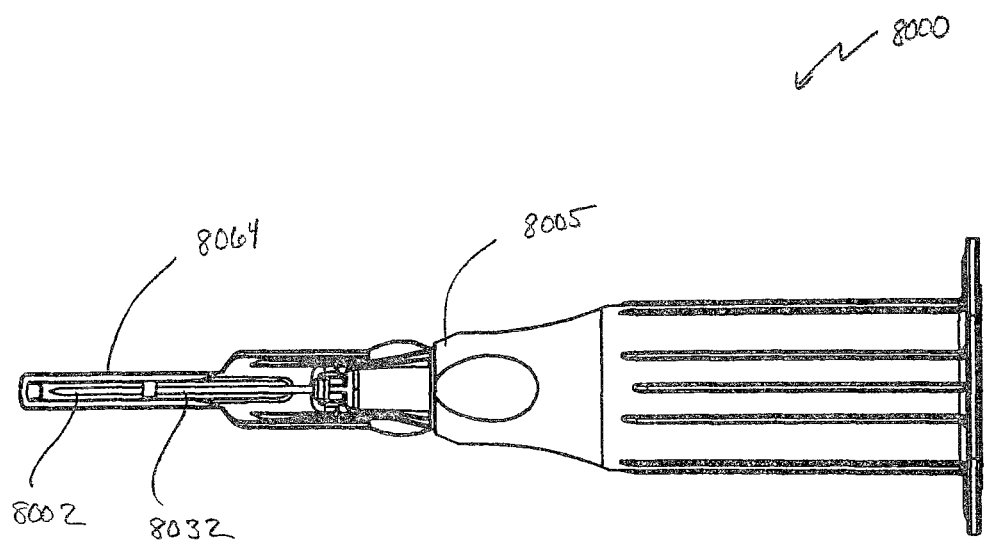

FIG. 164 is a bottom view of the needle assembly of FIG. 160.

Figure 165:
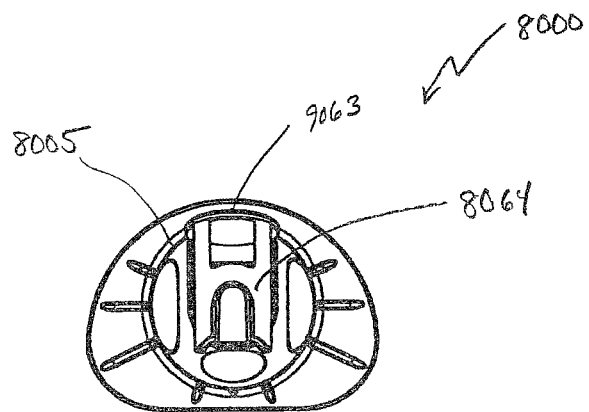

FIG. 165 is a front view of the needle assembly of FIG. 160.

Figure 166:
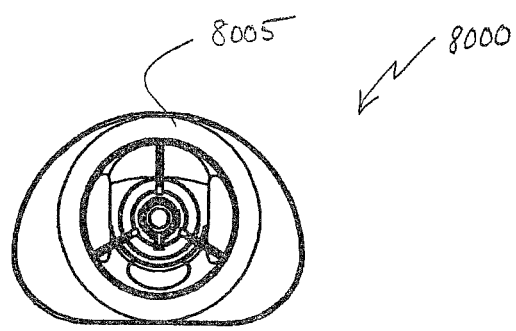

FIG. 166 is a rear view of the needle assembly of FIG. 160.

Figure 167:
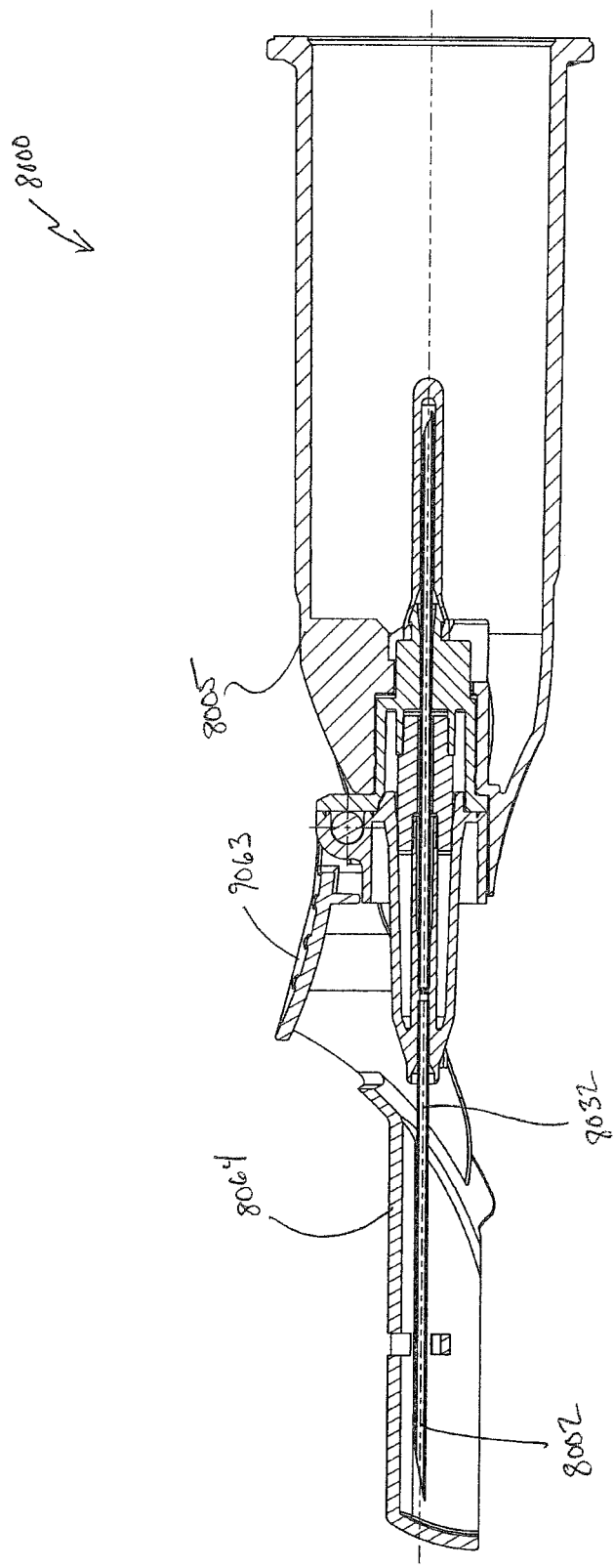

FIG. 167 is a cross-sectional side view of the needle assembly of FIG. 160.

Figure 168:
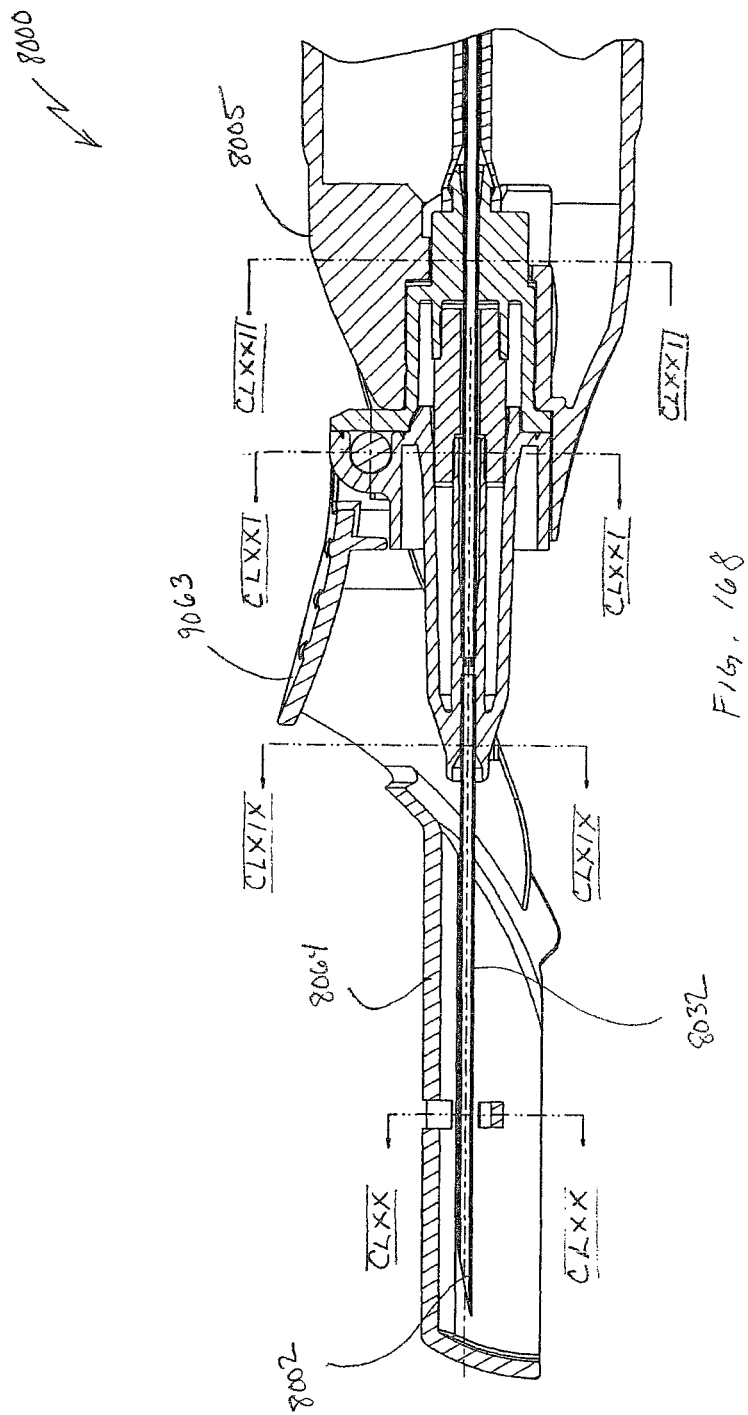

FIG. 168 is a cross-sectional side view of a needle assembly having a pivoting safety shield in the extended position in accordance with an embodiment of the present invention.

Figure 169:
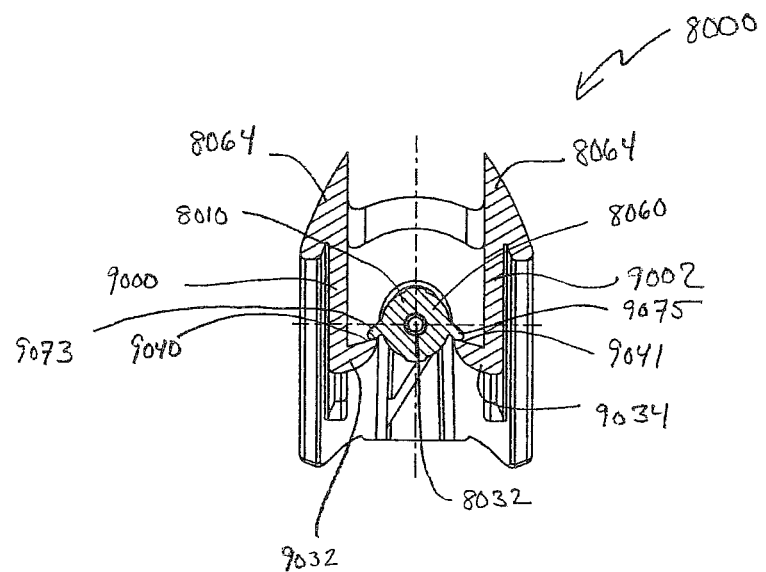

FIG. 169 is a cross-sectional view of FIG. 168 taken along line CLXIX-CLXIX.

Figure 170:
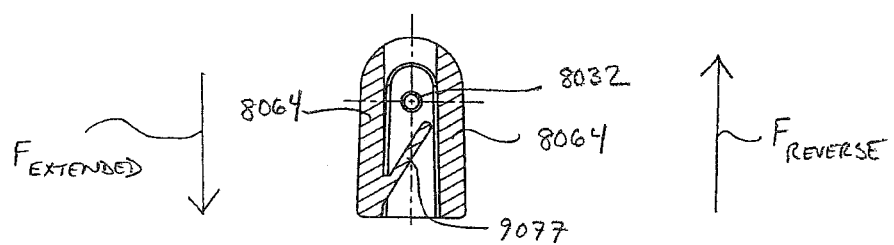

FIG. 170 is a cross-sectional view of FIG. 168 taken along line CLXX-CLXX.

Figure 171:
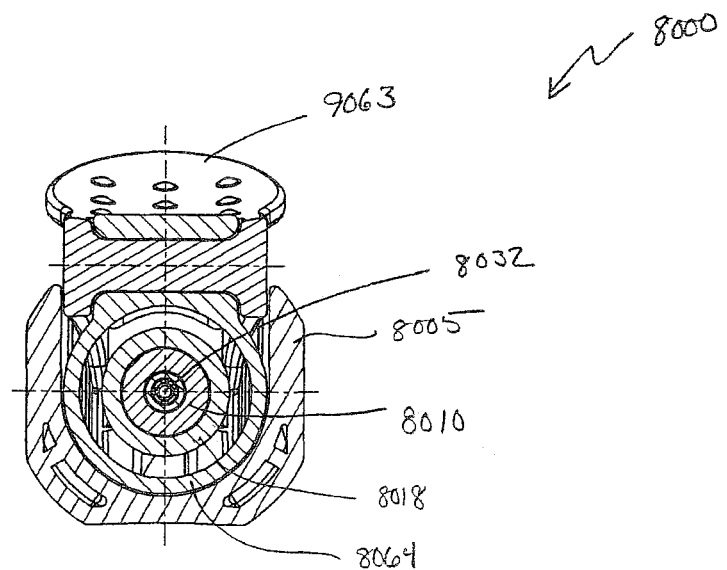

FIG. 171 is a cross-sectional view of FIG. 168 taken along line CLXXI-CLXXI.

Figure 172:
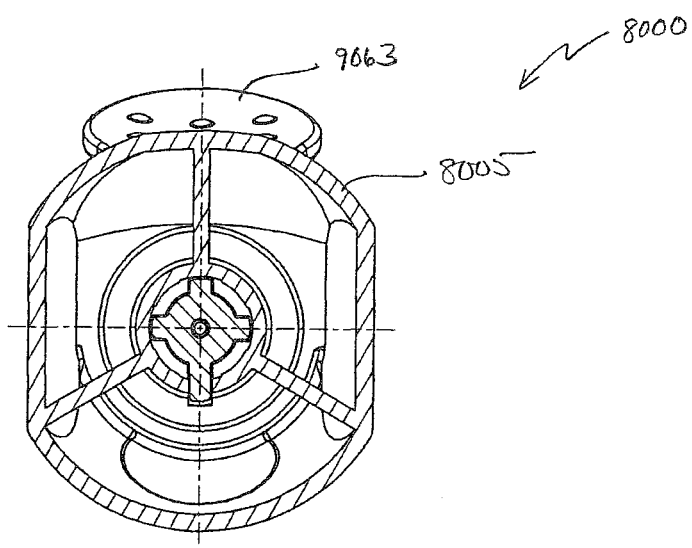

FIG. 172 is a cross-sectional view of FIG. 168 taken along line CLXXII-CLXXII.

Figure 172A:
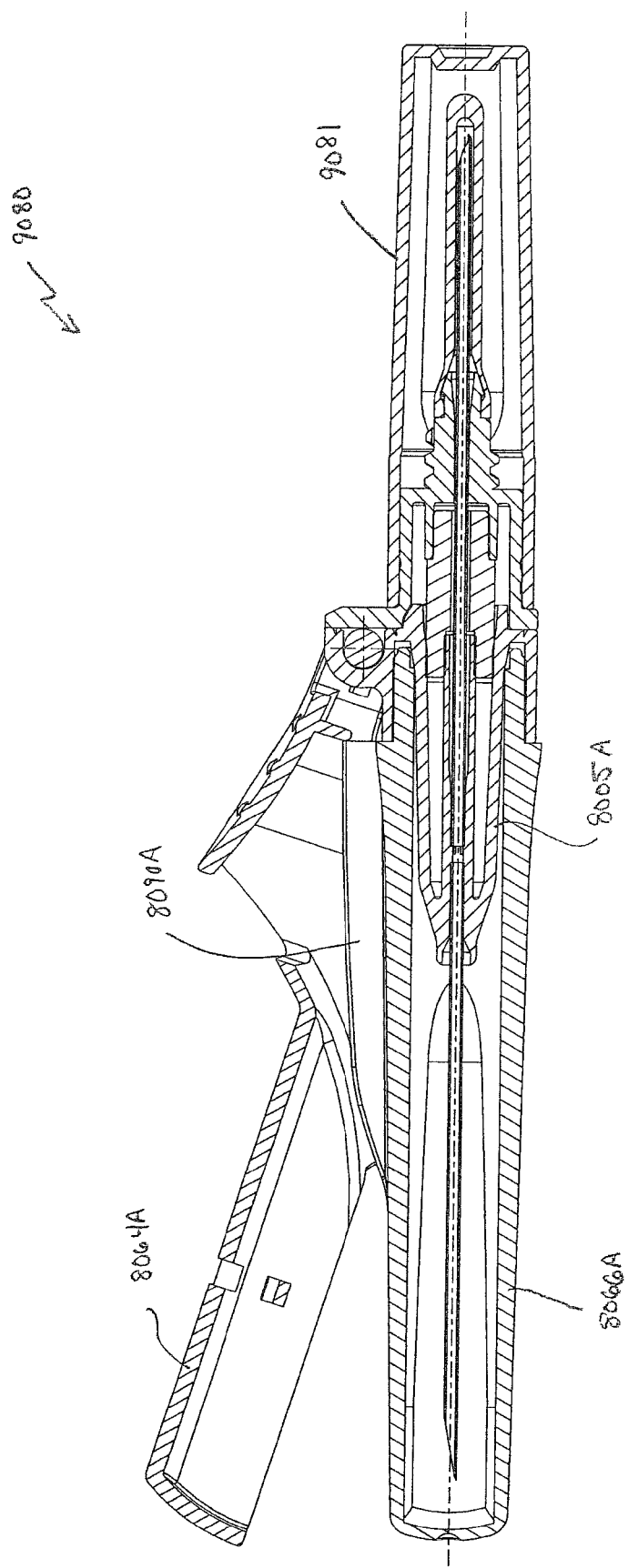

FIG. 172A is a cross-sectional side view of a needle assembly having a non-patient cannula shield, including the safety shield in the restrained position in accordance with an embodiment of the present invention.

Figure 172B:
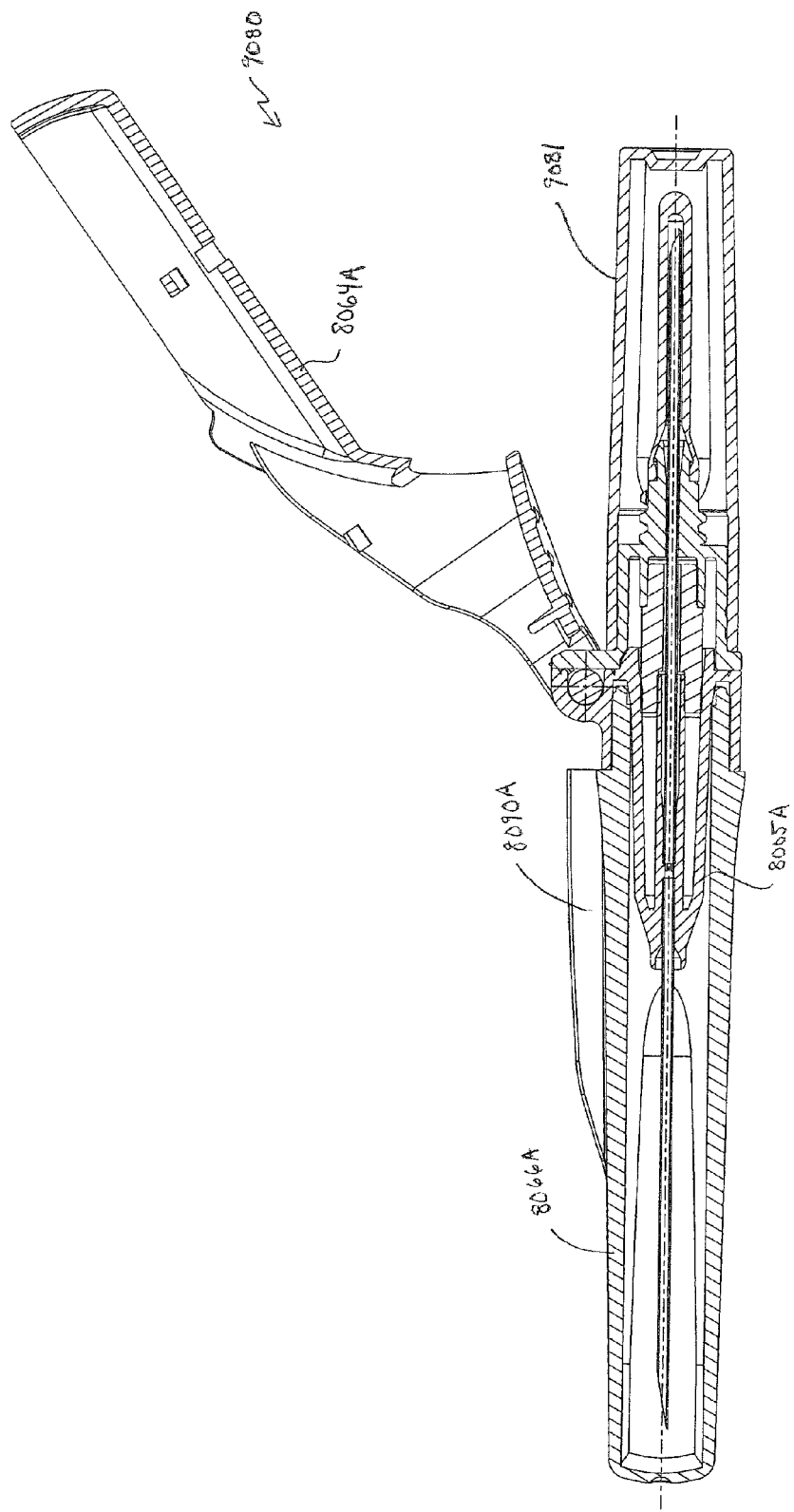

FIG. 172B is a cross-sectional side view of the needle assembly of FIG. 172A, showing the safety shield in the retracted position.

Figure 173:
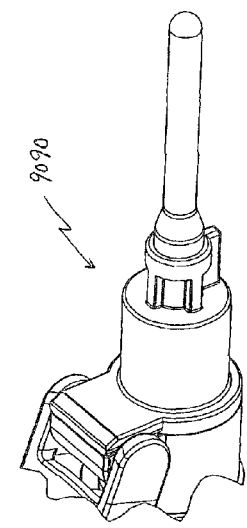

FIG. 173 is a sectional perspective view of a first sub-assembly of a needle assembly in accordance with an embodiment of the present invention.

Figure 174:
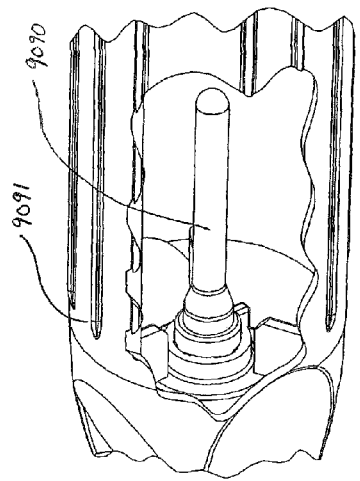

FIG. 174 is a sectional perspective view of the first sub-assembly of FIG. 173 engaged with a second sub-assembly.

Figure 175:
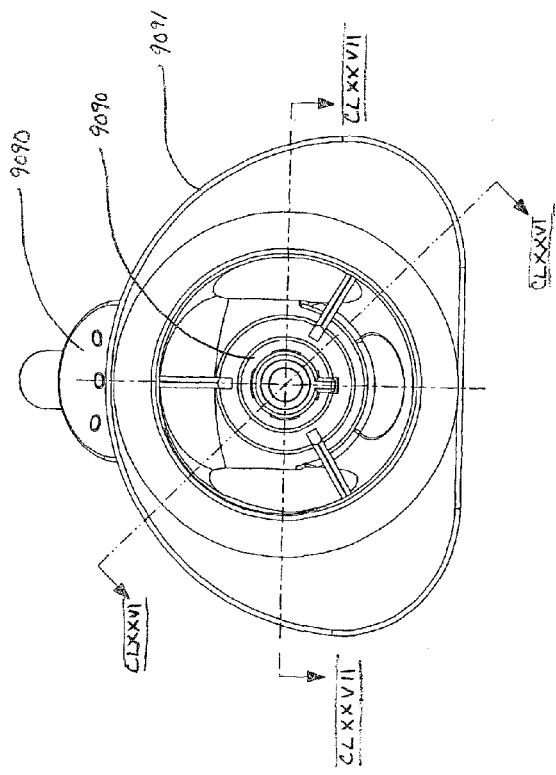

FIG. 175 is a rear view of the first sub-assembly engaged with the second sub-assembly of FIG. 174.

Figure 176:
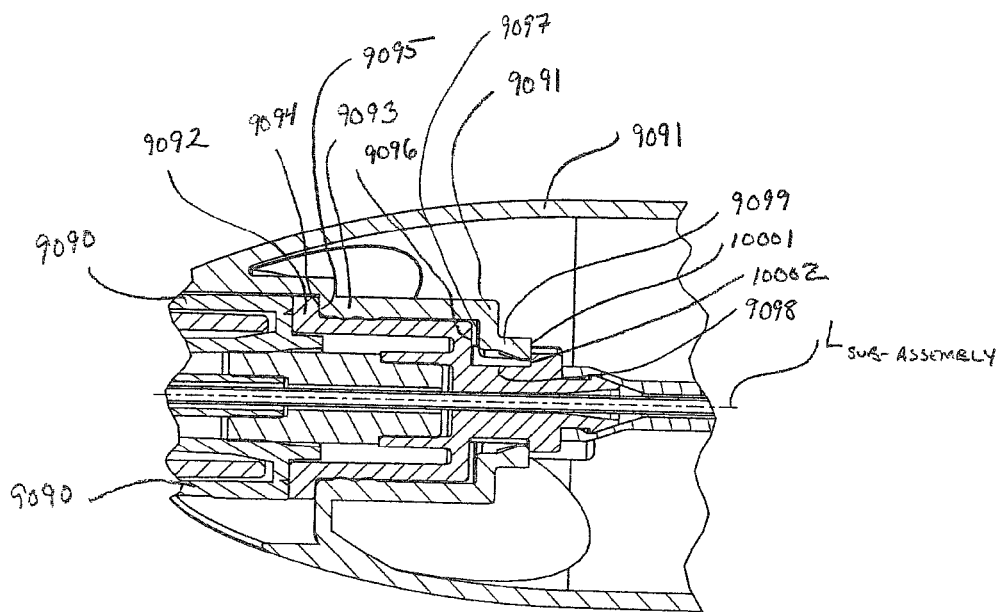

FIG. 176 is a sectional cross-sectional view of FIG. 175 taken along line CLXXVI-CLXXVI.

Figure 177:
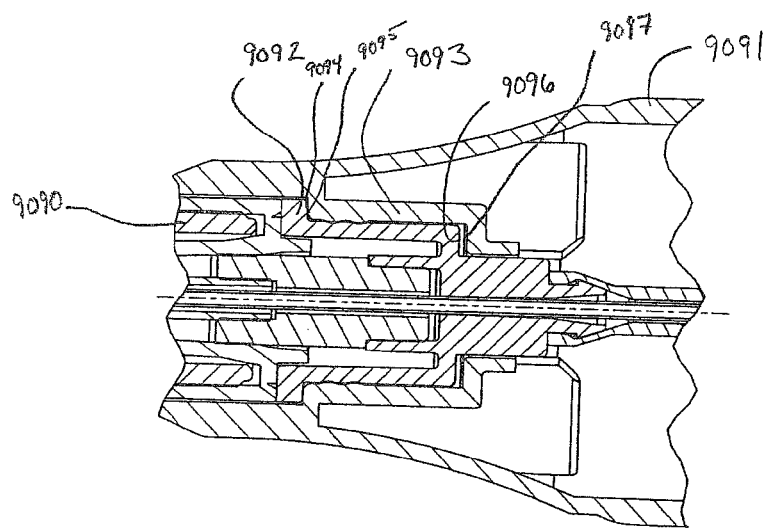

FIG. 177 is a sectional cross-sectional view of FIG. 175 taken along line CLXXVII-CLXXVII.

Figure 178:
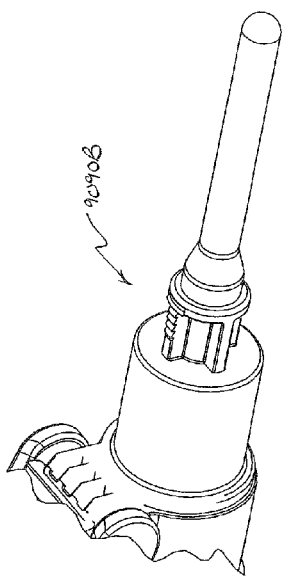

FIG. 178 is a sectional perspective view of a first sub-assembly of a needle assembly in accordance with an alternative embodiment of the present invention.

Figure 179:
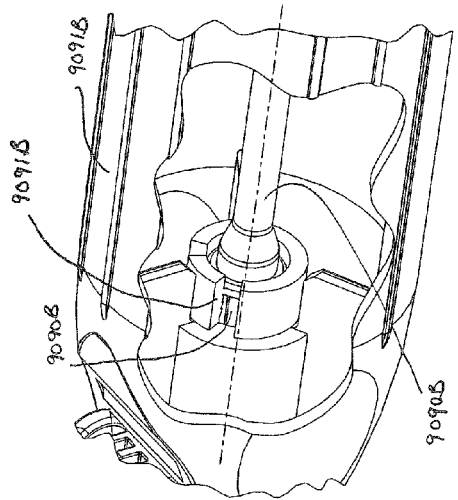

FIG. 179 is a sectional perspective view of the first sub-assembly of FIG. 178 engaged with a second sub-assembly.

Figure 180:
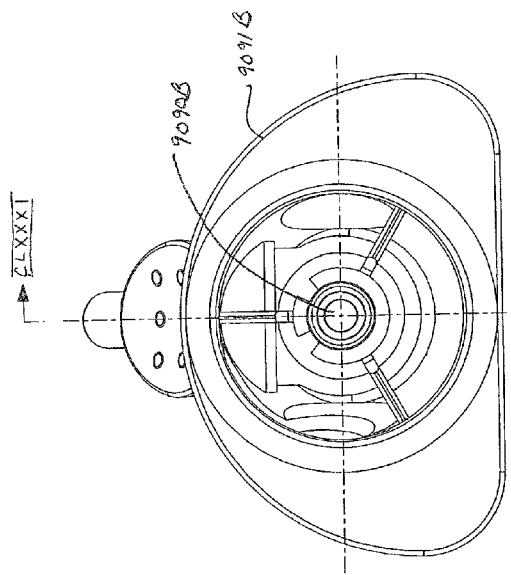

FIG. 180 is a rear view of the first sub-assembly engaged with the second sub-assembly of FIG. 179.

Figure 181:
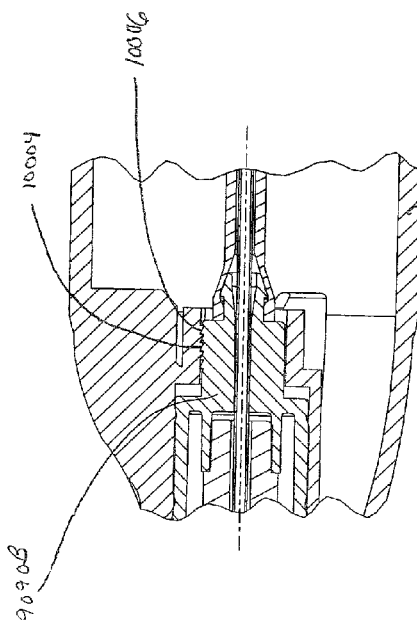

FIG. 181 is a sectional cross-sectional view of FIG. 180 taken along line CLXXXI-CLXXXI.

Figure 182:
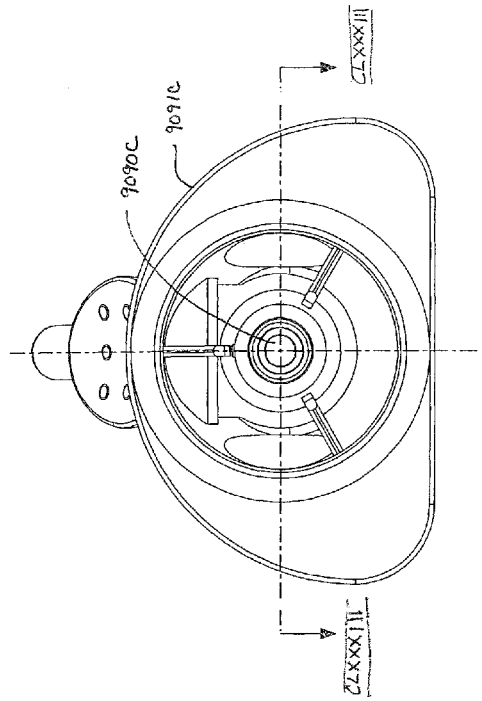

FIG. 182 is a rear view of a first sub-assembly engaged with a second sub-assembly in accordance with an alternative embodiment of the present invention.

Figure 183:
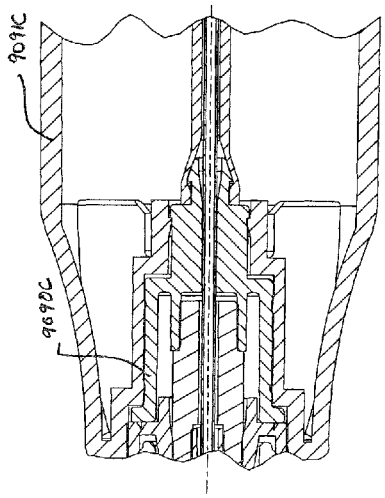

FIG. 183 is a sectional cross-sectional view of FIG. 182 taken along line CLXXXIII-CLXXXII.

Figure 184:
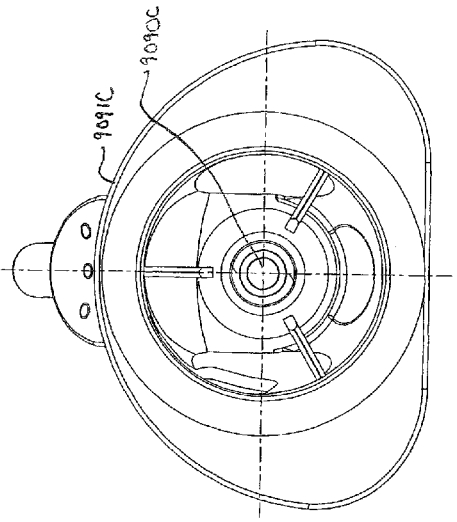

FIG. 184 is a rear view of a first sub-assembly engaged with a second sub-assembly in accordance with an alternative embodiment of the present invention.

Figure 185:
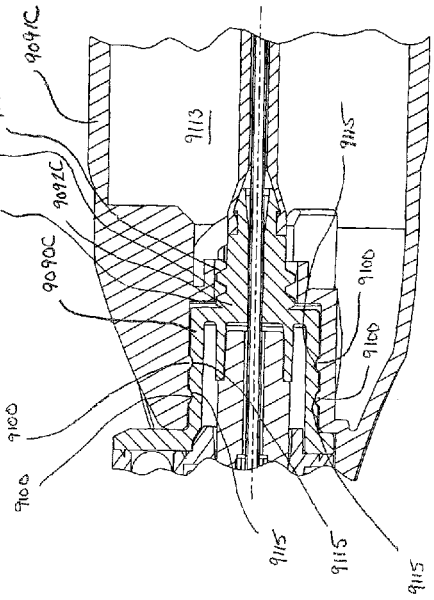

FIG. 185 is a sectional cross-sectional view of FIG. 184 taken along line CLXXXV-CLXXXV.

DETAILED DESCRIPTION

In general, the needle assembly of the present invention allows for access of a patient's vasculature by a needle cannula, visual indication of vasculature access, and subsequent safety shielding of the needle cannula to protect medical practitioners.

In one embodiment of the present invention, a needle assembly 30 is provided, as generally shown in FIGS. 1-10. The needle assembly 30 generally includes a housing 32 having a flash chamber 38 integral therewith, a cannula 34 associated with the housing 32, and a safety shield 36 adapted to transition from a retracted position, shown in FIG. 1, to an extended position, shown in FIG. 2, for safety shielding of the cannula 34 during and/or after use of the needle assembly 30. The needle assembly 30 is shown in the retracted position ready for use in a specimen collection procedure, such as a blood collection procedure, in FIG. 1, and after use in the extended position shielding the cannula in FIG. 2.

With particular reference to FIGS. 7-10, the needle assembly 30 includes a cannula 34 having a distal patient end 40 and a proximal non-patient end 42. It will be noted that the term "distal" as used herein, refers generally to the forward end of the needle assembly 30 that is adapted to puncture the skin of a patient and access the patient's vasculature, while the term "proximal" refers generally to the rear end of the needle assembly 30 that is engageable with a specimen collection container (shown in FIG. 123). The cannula 34 includes a sidewall 48 extending between the patient end 40 and the non-patient end 42 and defining a cannula interior 50. In one embodiment, the cannula 34 may include at least two distinct needles, such as a distal patient needle 52 and a proximal non-patient needle 54, both of which define a common central lumen within the cannula interior 50. In a further embodiment, the distal patient needle 52 is aligned substantially along a common axis with the proximal non-patient needle 54 and separated from the proximal non-patient needle 54 by a break 56. The proximal non-patient end 42 of the cannula 34 is provided for puncturing a specimen collection container (shown in FIG. 123). In one embodiment, the proximal non-patient end 42 of the cannula 34 may be covered by a pierceable elastomeric multiple sample sleeve 60. The distal patient end 40 may have a bevel for allowing easier penetration of a patient's skin.

The cannula 34 of the needle assembly may be at least partially supported by a portion of the housing 32. In one embodiment, the housing 32 may be a hub 64 for supporting a portion of the cannula 34. For example, proximal non-patient needle 54 and distal patient needle 52 may be affixed or otherwise adhered within a central opening 66 of the hub 64, with a break 56 present between proximal non-patient needle 54 and the distal patient needle 52. In another configuration, the hub 64 may be formed of separate elements. For example, a proximal or rear hub portion 68 may be connected with or affixed to a forward hub portion 70, thereby forming the hub 64 as a unitary structure, with the cannula 34 extending therethrough.

Figure 123:
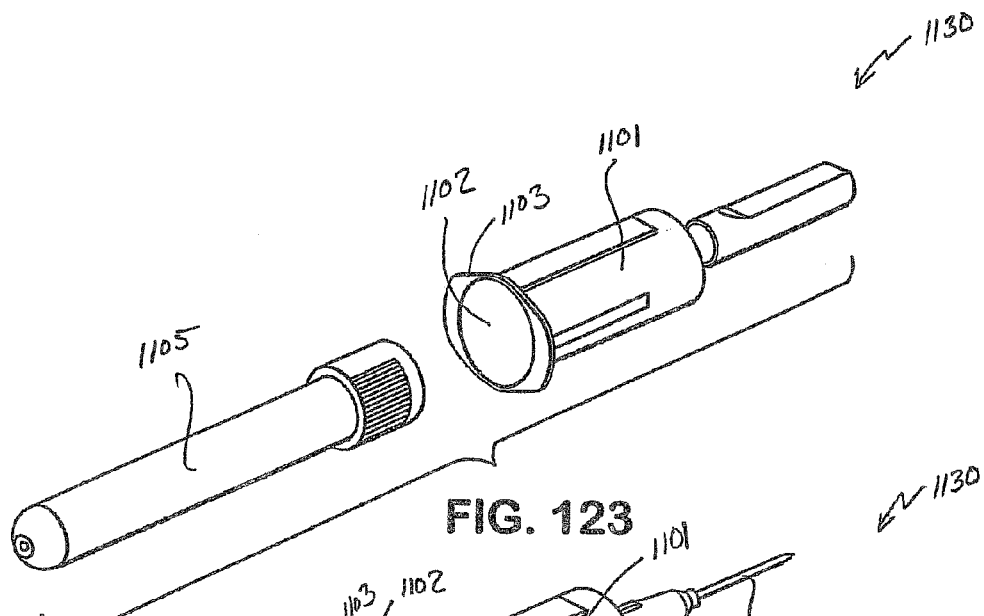

As shown in FIGS. 1-2 and 5-10, the housing 32 may have a distal end 74 and a proximal end 72 engageable with a specimen collection container (shown in FIG. 123). As used herein, the phrase "engageable with a specimen collection container" means that a specimen collection container may be attached to or affixed with a portion of the proximal end 72 of the housing 32, or that a specimen collection container may be passed within or disposed over or about a portion of the proximal end 72 of the housing 32 and secured to another portion of the housing 32. In one embodiment, the proximal end 72 of the needle assembly 30 may define a specimen collection container receiving port 76, adapted to receive a specimen collection container (shown in FIG. 123) therewith.

In another embodiment, the needle assembly 30 is a specimen collection assembly, such as a blood collection assembly, in which the housing 32 of the needle assembly 30 includes a specimen collection container holder 78 adjacent the proximal end 72 of the needle assembly 30. The specimen collection container holder 78 includes a proximal end 80, a distal end 82, and a tubular sidewall 84 extending therebetween. In one embodiment, the specimen collection container holder 78 may include a second tubular sidewall 86 circumferentially disposed about the tubular sidewall 84. The proximal end 80 of the specimen collection container holder 78 may be substantially open at opening 88 and may be adapted to receive a specimen collection container (shown in FIG. 123) therein. The proximal end 80 may also have a radially aligned flange 90 to facilitate manipulation of the needle assembly 30. The flange 90 may be non-circular to prevent the needle assembly 30 from rolling, or for other purposes such as communicating to the user the intended orientation of the needle assembly 30.

The specimen collection container holder 78 is adapted to accommodate at least a portion of the cannula 34 in a mating relationship. For example, the distal end 82 of the specimen collection container holder 78 may include an engagement portion 92 to which a portion of the cannula 34, such as the non-patient end 42 is mounted through a portion of the hub 64. In particular, the distal end 82 of the specimen collection container holder 78 may include an engagement portion 92 having a mating structure, such as a threaded engagement, adapted to receive the rear hub portion 68 of the hub 64. In one embodiment, the engagement portion 92 can include threads 94 for engagement with corresponding threads 96 of the rear hub portion 68 of hub 64. Other mating relationships are also contemplated herein, such as mating male and female luer assembly components. The hub 64 may be also adhesively affixed to the engagement portion 92 of the specimen collection container holder 78. In another embodiment, the hub 64 may be press-fit or snapped into the specimen collection container holder 78. Alternatively, hub 64 may be integrally formed with the distal end 82 of the specimen collection container holder 78, providing a mechanism for direct attachment of the cannula 34 to the specimen collection container holder 78. In certain embodiments, the cannula 34 is joined with a portion of the specimen collection container holder 78 by the manufacturer so that the device is ready for fast and convenient use by the medical practitioner.

In certain configurations, the patient end 40 of the cannula 34 projects at least partially from the distal end 74 of the housing 32, and the non-patient end 42 extends in a substantially proximal direction from the patient end 40. In another embodiment, the distal patient needle 52 projects at least partially from the distal end 74 of the housing 32, and the proximal non-patient needle 54 extends in a substantially proximal direction from the patient needle.

At least a portion of the housing 32, including the hub 64, the specimen collection container holder 78, and the second tubular sidewall 86, includes a flash chamber 98. As used herein, the term "flash chamber" includes a cavity into which a specimen, such as blood, from a patient may pass, and through which the presence of the specimen within the cavity may be visibly detected by a medical practitioner. The flash chamber 98 may be integrally formed with a portion of the housing 32 or, alternatively, may be separately formed and subsequently engaged with a portion of the housing 32. In one embodiment, the cannula interior 50 is in fluid communication with the flash chamber 98. In a further embodiment, the sidewall 48 of the cannula may define an opening extending between the cannula interior 50 and the flash chamber 98 to permit the flow of a specimen, such as blood, from the cannula 34 to the flash chamber 98. In another embodiment, the cannula 34 includes a distal patient needle 52 in fluid communication with the flash chamber 98, and a proximal non-patient needle 54 in fluid communication with the flash chamber 98. Accordingly, when the distal patient needle 52 is provided access with a patient's vasculature, blood may flow from the patient through the distal patient needle 52 and into the flash chamber 98. When the proximal non-patient needle 54 is engaged with an evacuated specimen collection container (not shown), blood may flow from the flash chamber 98 and through the proximal non-patient needle.

In one embodiment, the hub 64 may include an interior 100 between a portion of the rear hub portion 68 and a portion of the forward hub portion 70. A flash chamber 98 may be formed within at least a portion of the interior 100 of the hub 64. In one configuration, the hub 64, or at least a portion of the hub 64, such as the forward hub portion 70, may be constructed from a transparent or translucent material, such as a polymeric material or resin. Alternatively, a flash chamber 98 may be integrally formed within another portion of the housing 32, such as integrally formed with the specimen collection container holder 78, or within a portion of a secondary tubular sidewall 86.

In use, blood flow from a patient through the cannula 34 will enter the flash chamber 98 through the opening 88 in the cannula 34, thereby partially filling the flash chamber 98 with blood. The flash chamber 98 provides a visual mechanism for recognition of venous access to a medical practitioner. Example flashback indicators are described, for example, in United States Patent Publication No. 2005/0004524, the entire disclosure of which is herein incorporated by reference.

The needle assembly 30 further includes a safety shield 36, which provides a mechanism to shield the cannula 34, and in particular the puncture tip at the patient end 40, after use thereof. At least a portion of the safety shield 36 is restrainably engaged with a portion of the housing 32 and transitionable from a retracted position, as shown in FIGS. 1, 5, 7, and 9, to an extended position, as shown in FIGS. 2, 6, 8, and 10. The safety shield 36 may be transitionable from the retracted position to the extended position over a portion of the cannula 34. In one embodiment, the safety shield 36 is axially transitionable over the cannula 34. In a further embodiment, the safety shield 36 is axially transitionable over the cannula 34 from a retracted position, in which at least the puncture tip of the patient end 40 of the cannula 34 is exposed, such as for accessing a patient, to an extended position, in which at least the puncture tip of the patient end 40 of the cannula 34 is shielded by at least a portion of the safety shield 36. As used herein, the phrase "shielded by at least a portion of the safety shield" means that accidental contact with the puncture tip at the patient end 40 of the cannula 34 is prevented by the position of at least a portion of the safety shield in shielding orientation with respect to the patient end 40 of the cannula 34. In one embodiment, the safety shield 36 at least partially surrounds or encompasses the patient end 40 of the cannula 34 in the extended position.

Figure 2:
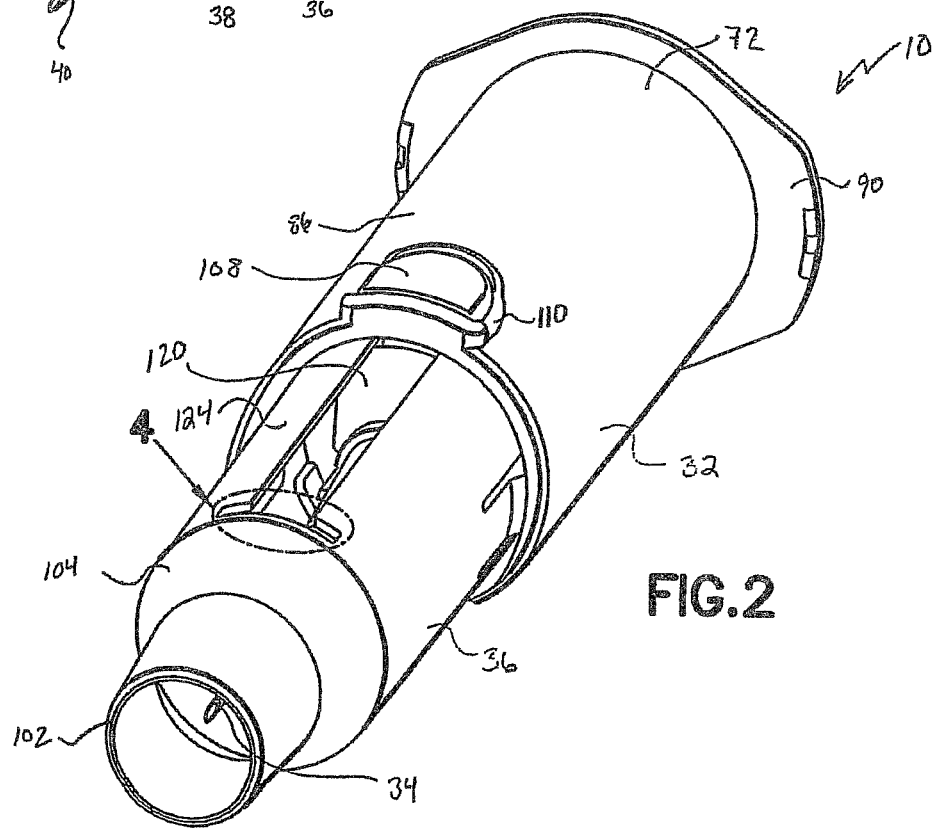
FIG. 2 is a perspective view of the needle assembly of FIG. 1 having a safety shield in the extended position.

In one embodiment, as shown specifically in FIGS. 5-10, the shield 36 may be disposed within an interior portion 106 of the housing 32, such as between the sidewall 84 and the second sidewall 86 of the housing 32, in the retracted position. For example, the safety shield 36 may be disposed between a sidewall 84 forming a portion of the specimen collection container holder 78 and a second sidewall 86 disposed about the sidewall 84. The safety shield 36 may have any suitable dimensions and configuration such that it is adapted to shield the puncture tip of the patient end 40 of the cannula 34 when the safety shield 36 is actuated to extend to the extended position, as shown in FIG. 2. In one embodiment, transition of the safety shield 36 from the retracted position to the extended position may be initiated once the puncture tip of the patient end 40 of the cannula 34 has been removed from the patient. In another embodiment, transition of the safety shield 36 from the retracted position to the extended position, may be initiated while the cannula 34 is in communication with the body of a patient, such as while the patient end 40 of the cannula 34 is in fluid communication with the vasculature of a patient. Accordingly, the safety shield 36 may be deployed over the cannula 34 while the cannula 34 is accessing the interior of the patient's blood vessel (not shown), or after the cannula 34 has been removed from the patient. If the transition of the safety shield 36 from the retracted position to the extended position occurs while the cannula 34 is accessing the interior of a patient's blood vessel, the distal portion 102 of the safety shield 36 will contact the patient's skin.

In one embodiment, the shield 36 includes a shielding portion 104 which is axially moveable in the direction of the longitudinal axis A of the cannula 34, shown in FIG. 5, from the retracted position to the extended position. The shielding portion 104 may be restrainably engaged within the interior portion 106 of the housing 32 in the retracted position, and the shielding portion 104 may extend from the interior portion 106 of the housing 32 in the extended position. In one embodiment, axial transition of the shield 36 from the retracted position to the extended position transitions the shielding portion 104 from within the interior portion 106 of the housing 32 to a location at least partially exterior to the housing 32 substantially along the longitudinal axis A of the cannula 34. In another embodiment, the interior portion 106 of the housing 32 may be circumferentially disposed about the specimen collection container holder 78 or specimen collection container receiving port 76. In yet another embodiment, the interior portion 106 of the housing 32 is co-axial with the specimen collection container holder 78 or specimen collection container receiving port 76. As used herein, the term "co-axial" includes orientations in which the interior portion 106 and the specimen collection container holder 78 or specimen collection container receiving port 76 are each disposed about the longitudinal axis A of the cannula 34. In a further embodiment, the safety shield 36 is disposed about at least a portion of the cannula 34, and transition of the safety shield 36 from the retracted position to the extended position telescopes the safety shield 36 over a portion of the cannula 34. Optionally, the safety shield 36 may be substantially circumferentially disposed about at least a portion of the cannula 34. It is also contemplated herein that the safety shield 36 may include a single telescoping portion, such as shielding portion 104, or may include multiple circumferentially disposed nesting segments that are each transitionable over the cannula 34.

Figure 3:
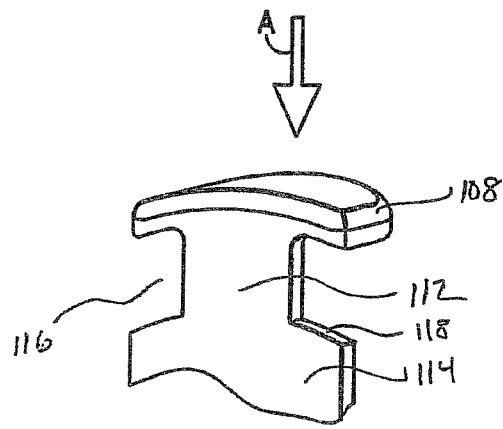
FIG. 3 is an enlarged perspective view of the push button element of a needle assembly in accordance with an embodiment of the invention.
Figure 4:
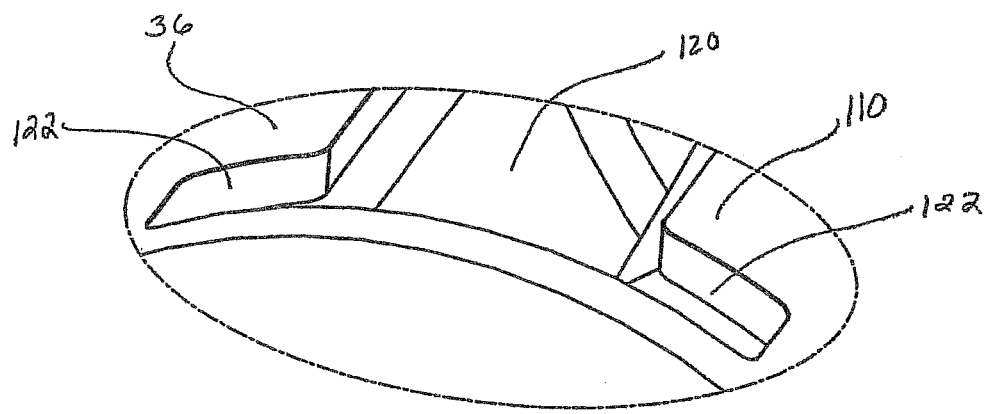
FIG. 4 is an enlarged perspective view taken from section 4 of FIG. 2, showing the channel of the safety shield in accordance with an embodiment of the invention.
Figure 11:
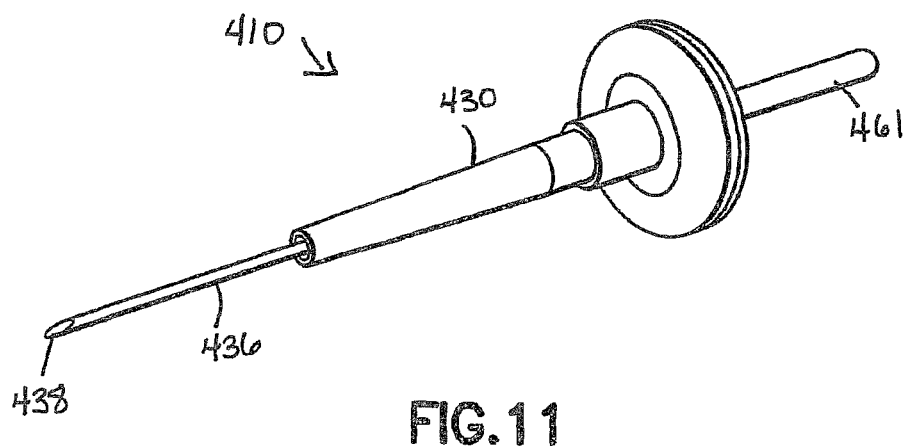
FIG. 11 is a perspective view of a needle assembly having a flash chamber in accordance with a further embodiment of the present invention.
Figure 12:
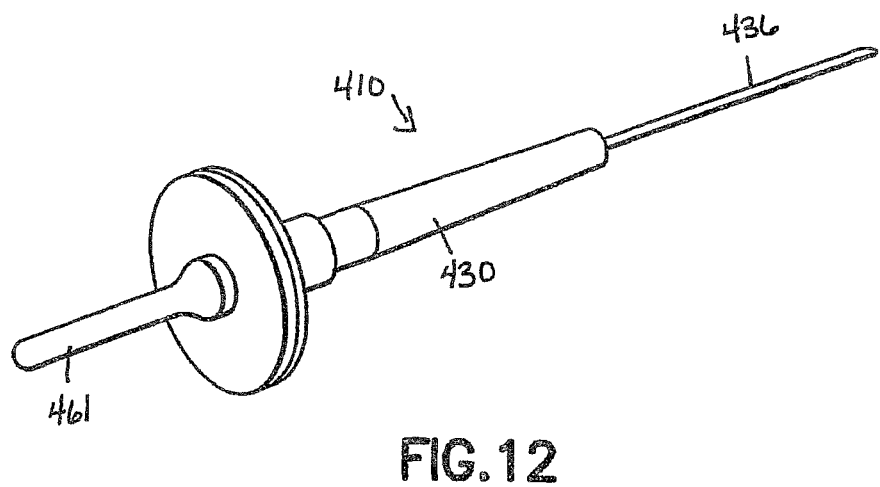
FIG. 12 is a rear perspective view of the needle assembly having a flash chamber of FIG. 11.

The safety shield 36 may be deployed by a release member 108, such as a push button, transitionable from a first position to a second position. The release member 108 may be deployable through an exterior surface 110 of the safety shield 36 and housing 32. In one embodiment, the release member 108 may actuate the transition of the safety shield 36 from the retracted position to the extended position. In another embodiment, the release member 108 may initiate an activator to transition the safety shield 36 from the retracted position to the extended position. In the embodiment depicted in FIGS. 1-10, the release member 108 includes a member 112, such as an arm, oriented in a substantially perpendicular orientation with respect to the transition axis T of the safety shield 36, shown in FIG. 6. As used herein, the phrase "transition axis" includes the orientation of the shield during transition from the retracted position to the extended position. In certain embodiments, the transition axis is aligned with the longitudinal axis A of the cannula 34. The member 112 may be connected to a restraining portion 114, such as an enlarged body, creating a passage region 116, such as a narrowed neck, as shown in FIG. 3. In one embodiment, the passage region 116 defines a non-enclosed region, such as an indentation or a cut-away portion. The restraining portion 114 of the release member 112 further includes a shoulder 118 adjacent the passage region 116. Further, as shown in FIG. 3, safety shield 36 includes an elongated channel 120 extending through the shield 36, with an enlarged opening adjacent the forward or distal end thereof, creating a stop surface shoulder 122 adjacent the forward edge of the channel 120. In one embodiment, the elongated channel 120 extends longitudinally through the shield 36 along a top surface thereof.

Figure 1:
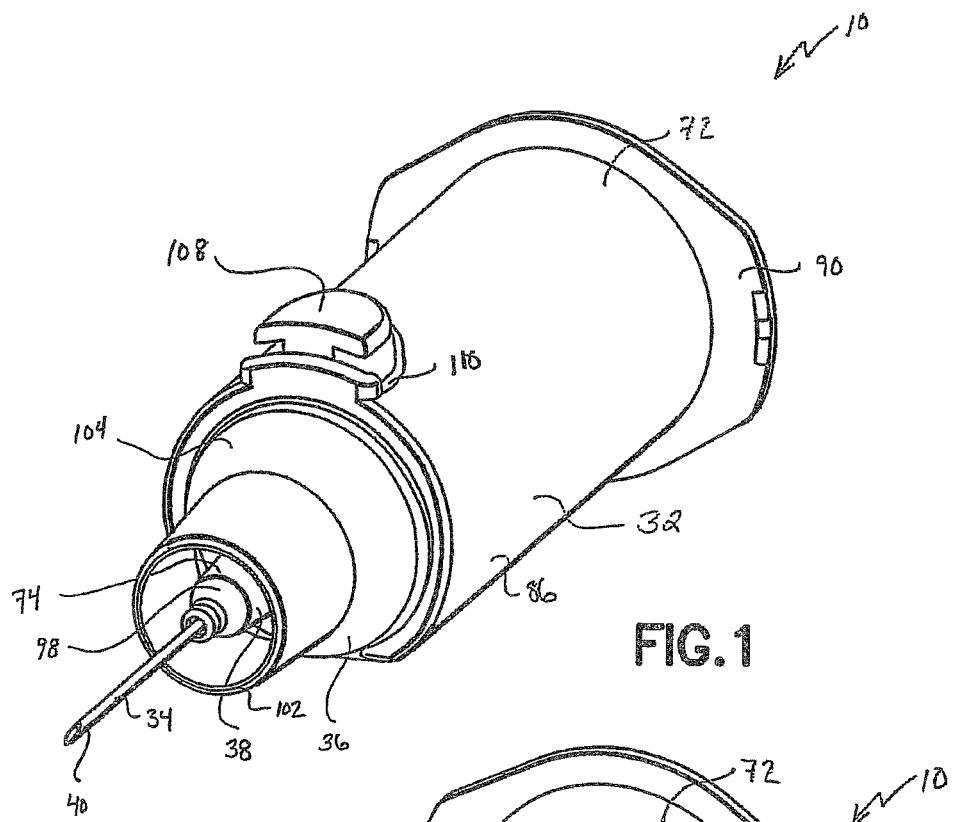
FIG. 1 is a perspective view of a needle assembly having a safety shield in the retracted position in accordance with an embodiment of the present invention.

With the safety shield 36 in the retracted position as shown in FIG. 1, the release member 108 is in a first position, with the restraining portion 114 extending into the shield 36, and with the stop surface shoulder 122 in an abutting engagement with the shoulder 118 of the release member 108, thereby preventing movement of the safety shield 36 in a forward or distal direction. When release member 108, such as a push button, is transitioned from the first position, such as depressed in the direction of arrow A in FIG. 3, the restraining portion 114 moves in a substantially downward orientation with respect to safety shield 36, thereby releasing the abutting engagement between stop surface shoulder 122 and the shoulder 118. As such, the sidewall 124 of the safety shield 36 adjacent elongated channel 120 can guide through the passage region 116 of the release member 108 unobstructed, thereby permitting safety shield 36 to transition from the retracted position shown in FIG. 1 to the extended position shown in FIG. 2. Accordingly, the restraining portion 114 of the release member 108 engages a stop surface shoulder 122 of the shield 36 in the restrained position, and the stop surface shoulder 122 of the shield 36 passes through the passage region 116 of the release member 108 upon transition of the release member from a first position to a second position and transition of the shield 36 from the restrained position to the extended position.

In one embodiment, the safety shield 36 may be biased toward the extended position by a spring 126 disposed between a portion of the safety shield 36 and a portion of the housing 32. The safety shield 36 may be biased toward the extended position by the spring 126 when the shield 36 is in the retracted position. In one embodiment, the spring 126 may be disposed between a proximal portion 128 of the safety shield 36 and a proximal end 72 of the housing 32. In another embodiment, as shown in FIGS. 7-10, the spring 126 may be disposed between the sidewall 84 of the housing 32 and the second sidewall 86. Upon transition of the release member 108 from the first position to the second position, the abutting engagement between the stop surface shoulder 122 and the shoulder 118, shown in FIG. 3, is released and the spring 126 biases the safety shield 32 to the extended position thereby safely shielding the cannula 32.

As shown in FIGS. 9-10, the safety shield 36 may further be provided with a barrier mechanism 130 structured to prevent the safety shield 36 from transitioning from the extended position to the retracted position once the safety shield 36 has been transitioned from the retracted position to the extended position. Accordingly, the barrier mechanism 130 prevents re-entry of the shield 36 into the housing 32 and exposure of cannula 34 after it has been shielded. In the embodiment, at least one of the distal end 74 of the housing 32 and the proximal portion 128 of the shield 36 include a barrier mechanism 130. In another embodiment, both the distal end 74 of the housing 32 and the proximal portion 128 of the shield 36 include a barrier mechanism 130.

The barrier mechanism 130 may include a restraint 132 and a break 134. The break 134 may include a slanted distal portion 136 and a proximal portion 138 having a plane substantially perpendicular to a portion of the safety shield 36. The break 134 is sized to allow passage beyond the restraint 132 included within the distal end 74 of the housing 32 when the safety shield 36 is transitioned from the restrained position to the extended position. The proximal portion 138 of the break 134 is also dimensioned to restrain the safety shield 36 against the restraint 132 to resist passage of the safety shield 36 past the restraint 132 once the shield 36 is transitioned from the retracted position to the extended position. In another embodiment, the release member 108 may be at least partially restrained by a portion of the shield 36, such that the shield 36 cannot be reset after transitioning from the retracted position to the extended position.

As shown in FIGS. 1, 5, 7, and 10, the flash chamber 98 is at least partially visible to a medical practitioner when the safety shield 36 is in the retracted position. In one embodiment, at least a portion of the flash chamber 98 extends beyond the distal portion 102 of the safety shield 32 in the retracted position. In another embodiment, at least a portion of the flash chamber 98 is visible through at least a portion of the shield 36 in the retracted position. In another embodiment, at least a portion of the shield 36 through which the flash chamber 98 is visible made of a translucent or transparent material.

As shown in FIGS. 11-15B, an alternative flash chamber, such as described in United States Publication No. 2006/0036219, filed Aug. 16, 2004, and U.S. application Ser. No. 12/044,354, filed Mar. 7, 2008, the entire disclosure of each of which is herein incorporated by reference, may be employed within the present invention.

In addition to conventional flash chambers which may include a vent mechanism in communication with an external environment surrounding the needle assembly, it is also contemplated herein that a needle assembly may include a flash chamber having a vent plug which seals upon flow of blood into the flashback chamber, thereby inhibiting any pressurized air that may build up within the chamber, from moving in a reverse direction toward the inlet of the cannula. As shown in FIGS. 11-15B, it is also contemplated herein that a similar vent plug may be positioned within the housing at a location such that the vent plug divides the housing into two chambers having sizes and dimensions to establish predetermined volumes thereto. Moreover, the porous vent remains porous to blood and does not seal upon contact with blood. Desirably, the blood does not contact the vent plug at the initial flash indication, but such sealing occurs at a later point during use of the assembly, as will be described in more detail herein.

For example, as shown in FIGS. 11-14, a porous vent is positioned within the housing at a location such that the vent divides the housing into two chambers having sizes and dimensions to establish predetermined volumes thereto, so that the blood does not contact the porous vent for at the initial flash indication, but such contact occurs at a later point during use of the assembly, as will be described in more detail herein.

As shown in FIGS. 11-14, needle assembly 410 includes a housing 412 having a fluid inlet end or first end 414 and a fluid outlet end or second end 416. Needle assembly 410 includes exterior wall 418 defining the housing interior. Exterior wall 418 extends generally longitudinally at the first end 414 forming an elongate longitudinal first portion 419 having a first diameter. At second end 416, exterior wall 418 forms a second portion 421 that has a second diameter that is generally larger than the first diameter of the first portion 419. Accordingly, housing 412 may form a structure having a generally T-shaped cross-section. The exterior wall 418 at second end 416 may be a separate element 428 that is attachable to main body portion 430 forming housing 412, thereby assisting in manufacture and assembly of needle assembly 410. First portion 419 and second portion 421 may be arranged relative to each other in a variety of arrangements, so long as they are capable of functioning for transport of air therebetween as discussed herein.

Needle assembly 410 further includes a fluid inlet cannula 436 extending from first end 414 of housing 412. Fluid inlet cannula 436 includes an exterior end 439 that defines a sharpened bevel at patient puncture tip 438, and extends within first end 414 of housing 412, and may be fixedly mounted therein. Fluid inlet cannula 436 is characterized further by a substantially cylindrical lumen extending between the ends and communicating with the interior of housing 412.

Figure 13:
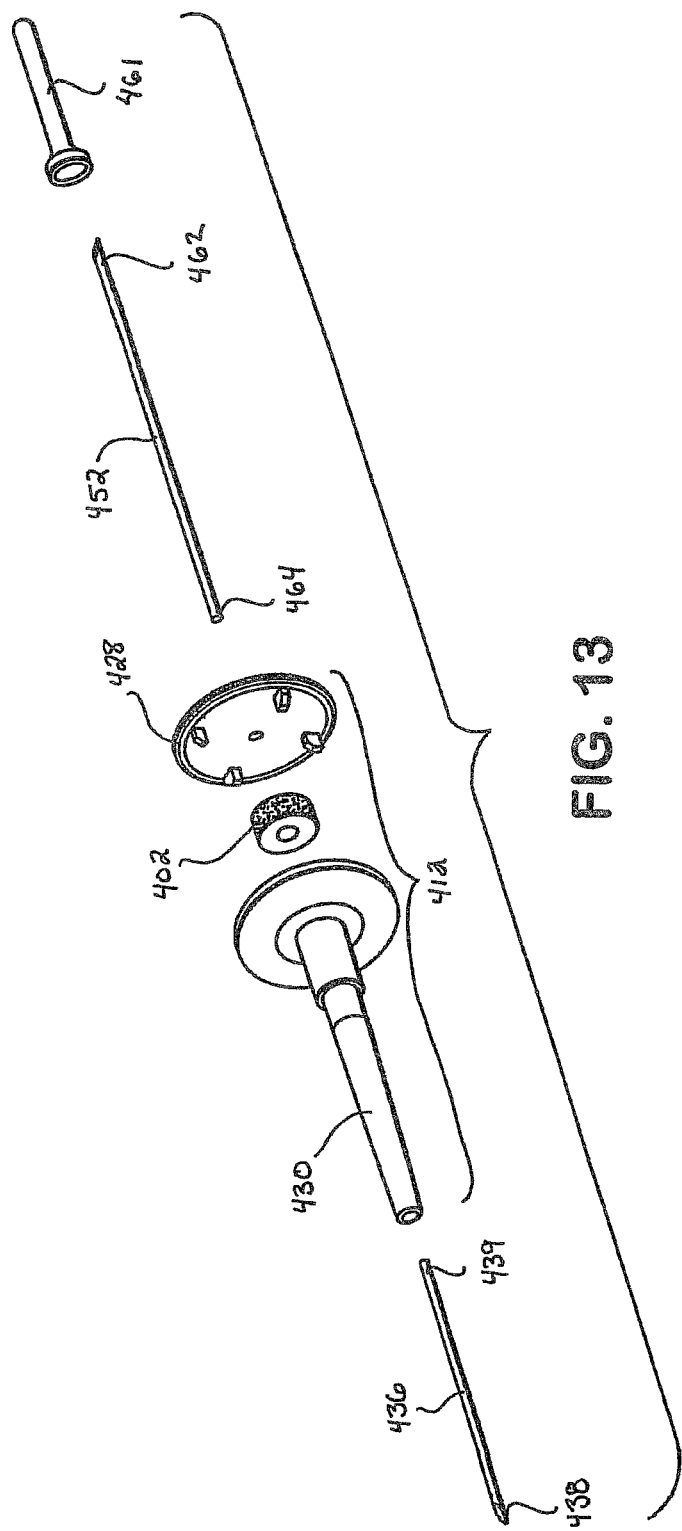
FIG. 13 is an exploded view of the needle assembly having a flash chamber of FIG. 11.

Needle assembly 410 also includes a non-patient puncture tip extending from second end 414 of housing 412. As seen in FIG. 13, this may be accomplished by providing needle assembly 410 with a second cannula in the form of fluid outlet cannula 452. In particular, the end of fluid outlet cannula 452 may define a sharpened bevel forming non-patient puncture tip 462. Fluid outlet cannula 452 extends within second end 416 of housing 412, and may be fixedly mounted therein. Fluid outlet cannula 452 is characterized further by a substantially cylindrical lumen communicating with the interior of housing 412. Fluid outlet cannula 452 is mounted within housing 412 so that an interior end 464 passes substantially coaxially therein such that fluid outlet cannula 452 substantially aligns axially with the interior end of inlet cannula 436. Desirably, this is achieved by mounting fluid outlet cannula 452 at a location adjacent second end 416 of housing 412, such that the interior end 464 of fluid outlet cannula 452 extends within housing 412 to a location adjacent the interior end 439 of inlet cannula 436. Additionally, the interior end 464 of fluid outlet cannula 452 is spaced only a small distance from the interior end 439 of inlet cannula 436, thereby forming an axial gap therebetween for flow of blood into flash chamber 426 about fluid outlet cannula 452. The distance between the interior end 464 of fluid outlet cannula 452 and the interior end 439 of inlet cannula 436 forming the axial gap is sufficient to provide for flow of blood into the flash chamber 426 based upon the patient's blood pressure after venipuncture. In certain embodiments, an axial gap that is less than 0.5 mm may result in a flashback that is inconsistent.

Figure 14A:
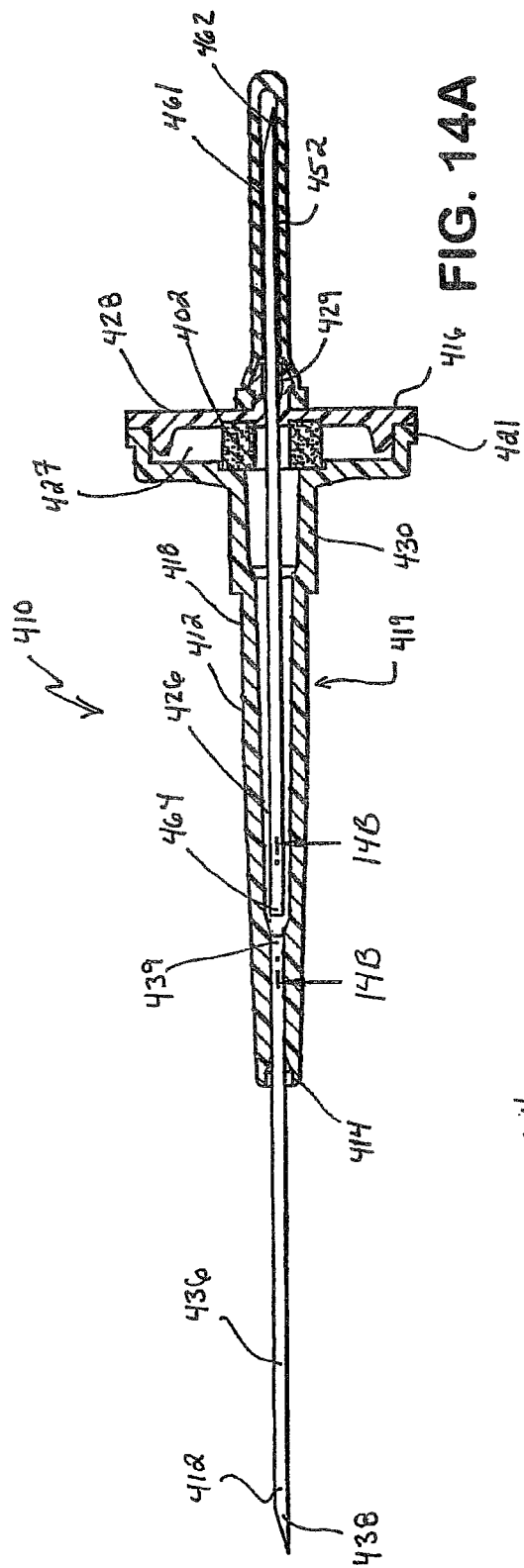
FIG. 14A is a cross-sectional view of the needle assembly having a flash chamber of FIG. 11.
Figure 14B:
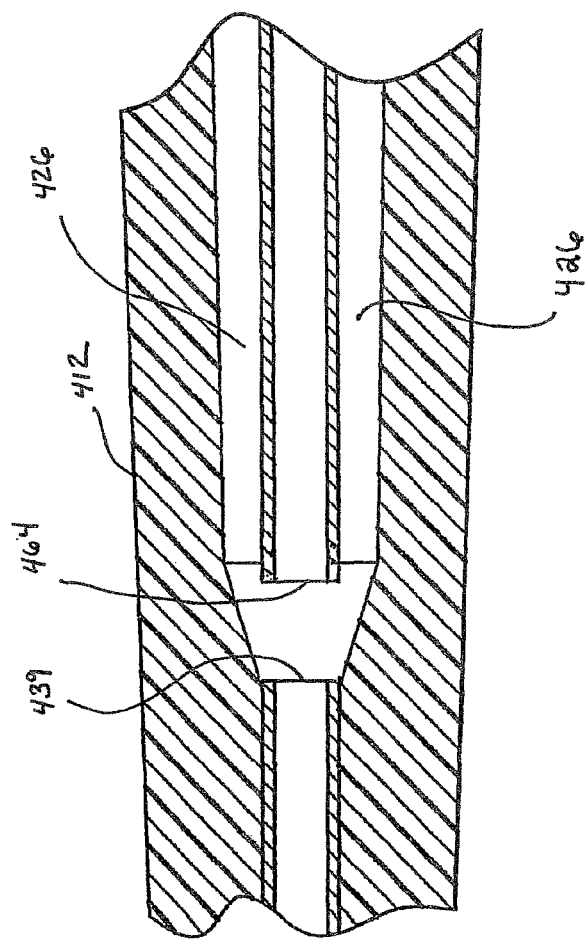
FIG. 14B is an enlarged cross-sectional view of a portion of the needle assembly of FIG. 14A.

As seen in FIG. 14B, fluid inlet cannula 436 and fluid outlet cannula 452 are positioned and dimensioned within housing 412 so as to achieve both desirable flow of blood through assembly 410 and to achieve effective flashback indication. In particular, wall 418 of housing 412 is dimensioned to provide a radial gap around fluid outlet cannula 452 of about 0.2 mm at an area surrounding the internal end 464 thereof. This gap achieves a substantially laminar blood flow within flashback chamber 426 and prevents blood hemolysis. Additionally, the small radial gap between the inner surface of wall 418 and fluid outlet cannula 452 at the area surrounding the internal end 464 enables a drop of blood to be spread thinly across the radial gap in flashback chamber 426 to provide a magnified flashback indication with a very small volume of blood. Thus, an easily visualized flashback indication is achieved quickly at the first appearance of blood within flashback chamber 426. It is contemplated herein that internal end 464 of outlet cannula 452 may be partially supported within housing 412, so long as blood flow into flashback chamber 426 is achieved about the internal end 464.

In an alternate arrangement, a single cannula is provided. Such an arrangement is depicted in the embodiment of FIGS. 15A-15B (shown in connection with a blood collection assembly as will be described in more detail herein). In such an arrangement, the fluid inlet cannula and the fluid outlet cannula represent one single cannula 470, having a patient puncture tip 438 a non-patient puncture tip 462, and a lumen 442 extending therethrough, and with the body of the cannula 470 being fixedly attached to a portion of the housing 412 and passing entirely through housing 412. A portion of cannula 470 extending through housing 412 includes one or more openings such as slot or aperture 444 to provide communication between lumen 442 and flashback chamber 436 within housing 412. In the embodiment shown in FIGS. 15A-15B, two separate apertures 444 are shown on opposing sides of cannula 470, although it is contemplated that any number of openings or apertures 444 can be included to provide for blood flow into the flash chamber 436.

Returning to the embodiment of FIGS. 11-14, needle assembly 410 further includes a sealable sleeve 461 mounted to fluid outlet end 416 of housing 412. This may be accomplished by providing a mounting protrusion 429 at second end 416 of housing 412, such as on element 428, with sealable sleeve 461 representing an elastomeric element that can be frictionally fit or otherwise affixed over protrusion 429. Sealable sleeve 461 covers non-patient puncture tip 462 at the exterior end of fluid outlet cannula 452 when sealable sleeve 461 is in an unbiased condition. However, sealable sleeve 461 can be collapsed in response to pressure exerted by the stopper of an evacuated tube for urging exterior end 460 of fluid outlet cannula 452 through both sealable sleeve 461 and the stopper of an evacuated tube, as known in the art.

The embodiment of FIGS. 11-14 further includes a porous vent 402 positioned within the interior of housing 412. Porous vent 402 is positioned within housing 412 to divide housing 412 into two distinct chambers, namely a first chamber represented by flashback chamber 426 and a second chamber represented by secondary chamber 427. Porous vent 402 may be constructed of a suitable material as described above with respect to vent plug 900, albeit without the hydrophilic material that swells on contact. In this manner, porous vent 402 is adapted to vent air therethrough, and represents a porous structure including a plurality of pores that allow for passage of blood therethrough. As discussed in more detail herein, during use of needle assembly 410, the internal pores within porous vent 402 at least partially fill with blood due to the negative pressure established within secondary chamber 427.

Such filled pores in combination with the negative pressure within secondary chamber 427 prevent air flow between the secondary chamber 427 and the flashback chamber 426, and provide for fluid resistance of the blood through porous vent 402, as will be described in further detail.

Desirably, porous vent 402 is positioned within the interior of housing 412 between first portion 419 and second portion 421. In this manner, first portion 419 of housing 412 essentially defines the flashback chamber 426, and second portion 421 of housing 412 essentially defines the secondary chamber 427. Alternatively, porous vent 402 may be positioned within the interior of housing 412 at a location spanning the transition between the first diameter of first portion 419 and the second diameter of second portion 421, as shown in the embodiment of FIGS. 15A and 15B. In any event, porous vent 402 is generally a cylindrically shaped member with a central opening therein axially encircling a portion of the cannula, particularly fluid outlet cannula 452.

The interior volume of housing 412 is defined by the sum of the volumes of flashback chamber 426 and secondary chamber 427 as well as the volume represented by the pores of porous vent 402. Such interior volume is configured so as to provide for certain attributes to the needle assembly 410, in particular with respect to the ability of the secondary chamber 427 to be at least partially evacuated of a portion of air therein to establish a negative pressure therein upon application of an evacuated tube to needle assembly 410 during use thereof. Such negative pressure within secondary chamber 427 draws blood through the pores of porous vent 402 based on when blood contacts porous vent 402 and partially fills the pores thereof. In a particular embodiment of the invention, the overall interior volume of housing 412 may be from about 300 mm³ to about 400 mm³. Such a volume is particularly useful for the intended use of needle assembly 410 for conventional venipuncture for drawing a blood sample from a patient using a needle cannula having a conventional gauge for venipuncture as is known in the art. With such an internal volume, porous vent 402 is desirably positioned within housing interior so as to define flashback chamber 426 as having a volume that represents from about 5 percent to about 20 percent of the total overall volume of housing 412, desirably from about 7 percent to about 12 percent of the total overall volume of housing 412, including the volume of secondary chamber 427 and the volume of the pores within porous vent 402. Such a ratio of the flashback chamber 426 to the total overall volume of the housing 412 assures that flashback chamber 426 has sufficient volume to properly visualize the initial flash, and desirably while preventing blood from fully contacting the porous vent 402 at initial venipuncture, based on the initial build-up of pressure within secondary chamber 427 caused by venous pressure forcing the blood into flashback chamber 426. Such volume ratios are effective for the intended use as described in further detail herein, wherein blood flowing into flashback chamber 426 upon initial venipuncture does not contact porous vent 402, and wherein at least a portion of the air is drawn out from secondary chamber 427 based upon application of an evacuated blood collection tube to the needle assembly 410. In this manner, secondary chamber 427 can effectively draw blood from within flashback chamber 426 and from within fluid inlet cannula 436 toward secondary chamber 427, such as into and through porous vent 402, when patient puncture tip 438 is removed from the patient and is exposed to the external environment. In one particular embodiment, the total interior volume of the housing 412 is about 380 mm³, with the flashback chamber 426 having a volume of about 30 mm³, the secondary chamber 427 having a volume of about 300 mm³, and the pores of the porous vent 402 representing a volume of about 50 mm³.

Needle assembly 410 may be assembled as follows. Fluid inlet cannula 436 is positioned through first end 414 of housing 412 such that the open interior end 439 is positioned within an interior portion of housing 412 at first portion 419 and patient puncture tip 438 extends externally of first end 414. Fluid outlet cannula 452 is positioned within housing 412 through the opposite end, such that open internal end 464 is positioned within an interior portion of housing 412 at first portion 419 adjacent interior end 439 of fluid inlet cannula 436, with a slight gap therebetween, and with non-patient puncture tip extending externally of second end 416. Fluid inlet cannula 436 and fluid outlet cannula 452 may be affixed therein in any known manner, desirably through a medical grade adhesive.

In alternate embodiments including only a single cannula 470, such cannula 470 is affixed within housing 412 such that opening 472 is positioned within the interior of housing 412 at first portion 419, with patient puncture tip 438 extending externally of first end 414 and non-patient puncture tip 462 extending externally of second end 416.

Porous vent 402 is then inserted within housing 412 and positioned over fluid outlet cannula 452 (or over the single cannula 470), and element 428 is thereafter affixed to the second end 416, enclosing the interior of housing 412. Sealable sleeve 461 is then affixed over protrusion 429. As such, the interior of housing 412 is closed from the external environment, with the sole path for fluid communication between the interior of housing 412 and the external environment being provided through the patient puncture tip 438.

Needle assembly 410 assembled as such can be used in connection with a blood collection tube holder 403, as depicted in the embodiment shown in FIGS. 15A-15B.

In use, needle assembly 410 may be provided with collection tube holder 403 attached thereto. Patient puncture tip 438 is inserted through the skin of a patient and into the patient's vasculature, desirably into a vein. Upon venipuncture, a closed environment is achieved within housing 412, since housing 412 is an entirely closed structure, and since sealable sleeve 461 closes off the only outlet of housing 412 (i.e., fluid outlet cannula 452). The patient's blood pressure causes blood to flow through patient puncture tip 438, into fluid inlet cannula 436, and out interior end 439 (or through opening 472 in the embodiment of FIGS. 15A-15B), into flashback chamber 426 surrounding interior end 464 of fluid outlet cannula 452. The transparent or translucent nature of housing 412 permits visualization of the blood within flashback chamber 426, providing an indication that venipuncture is achieved.

Since the interior of housing 412 is a closed environment, the flow of blood into flashback chamber 426 causes air to be trapped within the housing interior, including within flashback chamber 426, porous vent 402 and secondary chamber 427, as well as within fluid outlet cannula 452, causing such trapped air to be slightly pressurized therein. Flashback chamber 426 and secondary chamber 427 are configured through their size and dimensions such that the volumes thereof permit blood to flow into flashback chamber 426 at this initial venipucture, but the build up of air pressure within the pores of porous vent 402 and within secondary chamber 427 prevents blood from fully contacting porous vent 402, and desirably prevents blood from even partially contacting porous vent 402 at the initial venipuncture.

After such initial venipuncture and flash visualization, a sample collection container having a negative pressure therein, such as an evacuated blood collection tube (not shown) as is commonly known in the art, is inserted within the tube holder 403. The stopper (not shown) of such evacuated container contacts and displaces sealable sleeve 461, causing non-patient puncture tip 462 to puncture through sealable sleeve 461 and through the stopper of the evacuated container. At this point, fluid communication is established between the non-patient puncture tip 462 and the interior of the evacuated collection container. The negative pressure within the evacuated collection container draws the blood that has collected within flashback chamber 426 into fluid outlet cannula 452 and into the evacuated collection container. Along with the blood within flashback chamber 426, the negative pressure within the evacuated collection container will also draw at least a portion of the air out of the flashback chamber 426 and out of the secondary chamber 427 through the pores of the porous vent 402, toward and into the evacuated collection container. In addition, the close proximity and alignment of fluid outlet cannula 452 and fluid inlet cannula 426 causes blood to be drawn from fluid inlet cannula 436 and from the patient, simultaneously with such air being drawn from the flashback chamber 426 and secondary chamber 427.

Such drawing of air reduces the pressure within the flashback chamber 426 and the secondary chamber 427, establishing a negative pressure therein with respect to the patient's blood stream and with respect to the external environment. This negative pressure that has been established within the interior of housing 412, and specifically within flashback chamber 426 and secondary chamber 427, draws additional blood from within fluid inlet cannula 436 and from the patient into flashback chamber 426, with the blood contacting porous vent 402. With such blood filling flashback chamber 426, the blood fully contacts the surface of porous vent 402 that extends within flashback chamber 426, and begins to fill the pores of porous vent 402. Such filling of the pores of porous vent 402 that are directly at the interface of porous vent 402 and flashback chamber 426 closes off the porous vent 402 from airflow therethrough but does not fully act as a seal, in that the blood does not cause the material of the porous vent 402 to swell or close off to air flow, but instead merely physically fills the voids within the porous vent 402. Moreover, since a portion of the air within secondary chamber 427 has been drawn out form secondary chamber 427, the secondary chamber 427 represents a closed chamber with a negative pressure therein relative to the external environment. Secondary chamber 427 will therefore continue to have a drawing effect on the blood within the pores of porous vent 402 and within flashback chamber 426 through the pores of porous vent 402 toward secondary chamber 427, without releasing any air from the secondary chamber 427 in the opposite direction due to the pores of porous vent 402 at the interface of the flashback chamber 426 being filled with blood, thereby effectively preventing air flow through porous vent 402 due to the filled pores. The draw created by negative pressure within secondary chamber 427 has a fluid resistance based on the blood filling the pores of porous vent 402 and based on the tortuous path created by the pores of the porous vent 402, and therefore is a gradual draw with reduced fluid movement.

At this point, the evacuated collection container and the secondary chamber 427 are both at a negative pressure with respect to the external environment (and with respect to the patient's bloodstream), and therefore both effect a draw from the fluid inlet cannula 436. This effect may essentially establish an equilibrium within the flashback chamber 426, such that the blood contained within the flashback chamber 426 is not drawn toward or into either the secondary chamber 427 through the pores of porous vent 402 or into the evacuated collection container (through the fluid inlet cannula 436), but instead essentially remains within flashback chamber 426 in a steady state. The negative pressure of the evacuated collection container draws blood directly from the patient through fluid inlet cannula 436, due to the close proximity and alignment of fluid outlet cannula 452 and fluid inlet cannula 436, as well as due to the equilibrium established within flashback chamber 426 (based on the opposite draw forces between the evacuated collection container and the evacuated secondary chamber 427). The continual draw of blood into the evacuated collection container gradually causes the pressure within the collection container to increase.

Once the evacuated collection container is filled with the desired amount of blood, the container is removed from the non-patient puncture tip 462, thereby releasing the fluid communication between the non-patient puncture tip 462 and the evacuated collection container, with sealable sleeve 461 then covering and closing off non-patient puncture tip 462. Absent such draw from the negative pressure of the evacuated collection tube, the negative pressure within the secondary chamber 427 effects a slight draw on the blood within flashback chamber 426 through the pores of porous vent 402. Such draw, however, is very slow and gradual, due to the tortuous path of blood flow through the pores of porous vent 402.

Additional evacuated collection containers can thereafter be inserted into tube holder 403 and used for sample collection through non-patient puncture tip 462 as described above, by placing a second evacuated collection container within the holder 403 and establishing fluid communication between the non-patient puncture tip 462 and the interior of the evacuated collection container by puncturing the stopper, as discussed. In such further sampling, the evacuated collection container and the secondary chamber 427 are both at a negative pressure, and therefore both effect a draw from the fluid inlet cannula 436. As above, this effect essentially establishes an equilibrium within the flashback chamber 426, thereby preventing the blood contained within the flashback chamber 426 from being drawn toward or into the secondary chamber 427 (through the porous vent 402). The negative pressure of the evacuated collection container draws blood directly from the patient through fluid inlet cannula 436 as discussed above, due to the close proximity and alignment of fluid outlet cannula 452 and fluid inlet cannula 426. Once any such additional evacuated collection containers are filled with the desired amount of blood, the container is removed from the non-patient puncture tip 462, thereby releasing the fluid communication between the non-patient puncture tip 462 and the evacuated collection container, with sealable sleeve 461 then covering and closing off non-patient puncture tip 462.

Once all of the desired blood samples have been drawn in this manner, patient puncture tip 438 is removed from the vasculature of the patient, thereby exposing the opening of patient puncture tip 438 to the external environment. Since the sole communication path between the housing interior and the external environment is through patient puncture tip 438, the negative pressure established within secondary chamber 427 relative to the external environment will affect a gradual draw on the blood contained within flash chamber 426 and within fluid inlet cannula 436 toward and through porous vent 402. Such drawing effect will move any blood contained within fluid inlet cannula 436 away from patient puncture tip 438, thereby preventing any blood from leaking from patient puncture tip 438 out of fluid inlet cannula 436. Such negative pressure within secondary chamber 427 may continue to have a gradual drawing effect through the porous vent 402 for a prolonged period of time after removal of patient puncture tip 438 from the patient, and may draw all of the remaining blood contained within fluid inlet cannula 436 and flashback chamber 426 through porous vent 402 and/or into secondary chamber 427. Needle assembly 410 can then be properly disposed of in a known manner. It is anticipated herein, that the flash chamber 426 described with reference to FIGS. 11-15B may be employed within any of the embodiments described elsewhere in the present application.

In yet another embodiment, FIGS. 16-28 depict an alternative configuration of a needle assembly 230 in accordance with the present invention. As shown, needle assembly 230 is similarly constructed to the needle assembly 30, described above with reference to FIGS. 1-10. Needle assembly 230 includes an alternate release member 208 and an optional removable cannula guard 216. Needle assembly 230 generally includes a cannula 234 associated with a housing 232, and a safety shield 236 adapted for safety shielding the cannula 234 during and/or after use of the device. As previously described, the housing 232 may include a hub 264, a specimen collection container receiving port 276 and/or a specimen collection container holder 278, and a second sidewall 286 at least partially surrounding a sidewall 284 of the specimen collection container holder 278. The hub 264 may be adapted for at least partially supporting the cannula 34, which includes a patient end 240 and a non-patient end 242, as previously described. The cannula 34 may also include a distal patient needle 252 and a separate proximal non-patient needle 254, as also previously described. The needle assembly 230 further includes a flash chamber 298 defined therein, as previously described.

As shown in FIGS. 16, 18, 20, and 21-25, the needle assembly 230 is shown in the retracted position with a removable cannula guard 216 associated with a portion of the housing 232 and generally shielding the cannula 234. The removable cannula guard 216 is engageable with a portion of the housing 232 and is removable prior to use of the needle assembly 230. The removable cannula guard 216 is provided to shield the cannula 234, in particular, the puncture tip of the patient end 240 of the cannula 234, prior to use in a specimen collection procedure. In one embodiment, the cannula guard 216 is configured to circumferentially surround the cannula 234. The cannula guard 216 has a proximal end 246 having an interior portion 248 sized to extend at least partially over a portion of the housing 232, such as an exterior surface 253 of the hub 264. In another embodiment, the removable cannula guard 216 has a proximal end 246 having an interior portion 248 sized to extend at least partially over the exterior surface 253 of the hub 264 and to extend within at least a portion of the interior 258 of the distal end 260 of the housing 232.

The removable cannula guard 216 may be removably mated to a portion of the hub 264 and/or the specimen collection container holder 278, such as by a frictional engagement or press-fit mechanism. Alternately, removable cannula guard 216 may be mated by a threaded engagement (not shown), in which threads (not shown) may be disposed on a portion of the hub 264, or specimen collection container holder 278, and/or removable cannula guard 216. In one embodiment, the proximal end 246 of the removable cannula guard 216 may have an area of increased thickness 266, as compared to the thickness of the remainder of the removable cannula shield 216, to provide additional support for mating engagement with the housing 232. In a further embodiment, the area of increased thickness 266 if provided is to provide additional support for mating engagement with the hub 264.

The removable cannula guard 216 may have any suitable dimensions and may be made of any suitable materials to allow the puncture tip of the patient end 240 of the cannula 234 to remain shielded prior to use and/or during transport. In one embodiment, the removable cannula guard 216 has sufficient strength to allow the needle assembly 230 to be packaged as a "hardpack" packaging configuration, as is conventionally known, without damage to the cannula 234 or needle assembly 230. An example removable cannula guard and an example hardpack packaging structures are disclosed, for example, in U.S. Pat. Nos. 6,997,913 and 6,984,223, the entire disclosure of each of which are herein incorporated by reference.

Prior to use, the removable cannula guard 216 is removed from the needle assembly 230, such as by applying force to disengage the frictional engagement or press-fit mechanism and/or unscrew the threaded engagement. Once the removable cannula guard 216 has been removed from the needle assembly 230, a medical practitioner can use the needle assembly 230 as previously described herein.

Figure 26:
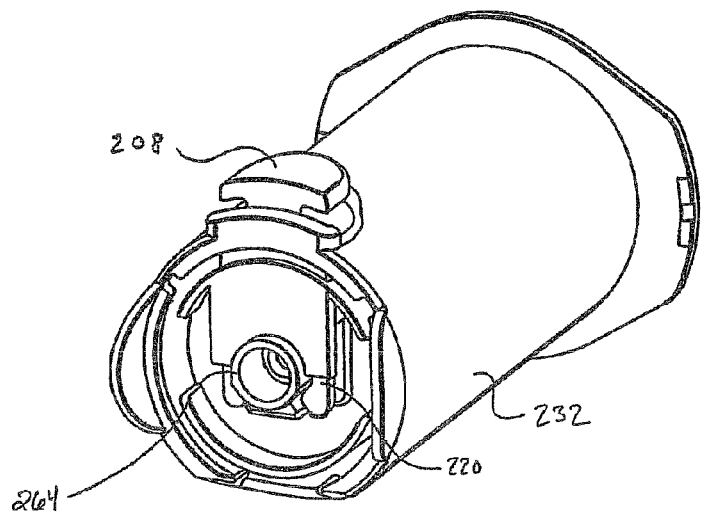
FIG. 26 is a perspective view of the holder portion of the needle assembly of an embodiment of the present invention having the push button in the unengaged retracted position.
Figure 27:
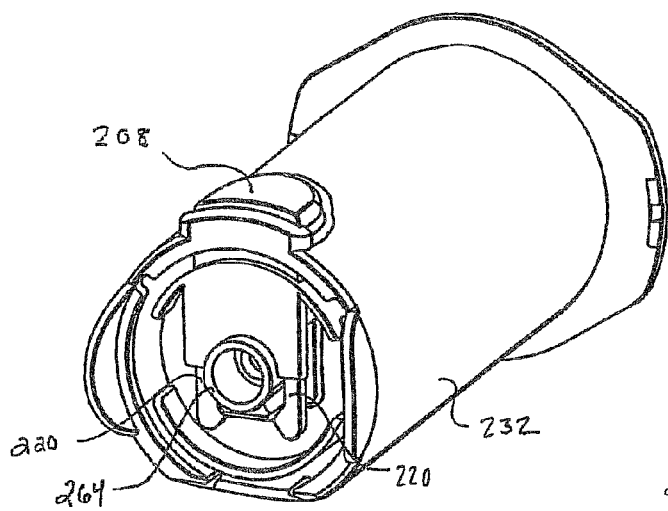
FIG. 27 is a perspective view of the holder shown in FIG. 26 having the push button in the engaged extended position.
Figure 28:
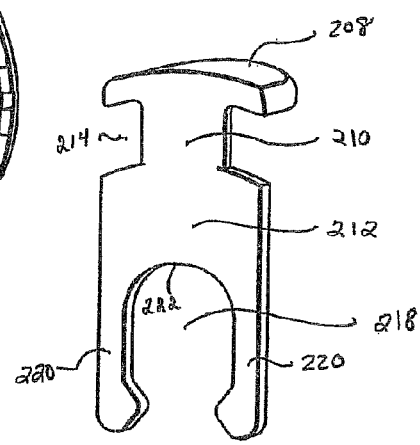
FIG. 28 is a perspective view of an embodiment of the push button in accordance with the present invention.

Further, as shown specifically in FIGS. 26-28, the needle assembly 230 may include an alternative release member 208, such as an alternative push button. In one embodiment, the release member 208 may actuate the transition of the safety shield 236 from the retracted position to the extended position. In another embodiment, the release member 208 may initiate an activator to transition the safety shield 236 from the retracted position to the extended position. In the embodiment depicted in FIGS. 26-28, the release member 208 includes a member 210 having a restraining portion 212 and a passage region 214, as previously described. The restraining portion 212 may also define an interior recess 218 defined at least in part by two depending arms 220. The interior recess 218 is dimensioned to accommodate at least a portion of the housing 232, such as a portion of the hub 264, therethrough. FIGS. 26-27 are partial perspective views of the needle assembly 230 having the shield and cannula removed therefrom to illustrate the mechanism of the release member 208. When the release member 208 is in a first position, as shown in FIG. 26, the rim 222 may be provided such that it does not engage a portion of the hub 264. When the release member 208 is transitioned to the second position, as shown in FIG. 27, both depending arms 220 are lowered and the rim 222 contacts a portion of the hub 264.

As shown in FIG. 26, when the release member 208 is in a first position, corresponding to the retracted position of the shield (shown in FIG. 16), the rim 222 of the interior recess 218 is separated from the hub 264 and restraining portions 224 of the depending arms 220 may contact at least a portion of the hub 264. The safety shield is prevented from transitioning from the restrained position to the extended position by the restraining portion 212, as similarly discussed herein in greater detail with reference to FIGS. 3-4. As shown in FIG. 27, when the release member 208 is deployed to the second position, corresponding to the extended position of the shield (shown in FIG. 17), the rim 222 engages at least a portion of the hub 264. The restraining portions 212 are advanced beyond the hub 264. Once the restraining portions 212 have advanced beyond the hub 264, the hub 264 prevents the release member 208 from being returned to its original state prior to activation, such as through a locking engagement with hub 264. Also shown in FIG. 17, the needle assembly 230 may include a plurality of ribs 238 to prevent rotation of the safety shield 236 with respect to the housing 232, such as with respect to the specimen collection container holder 278.

Figure 16:
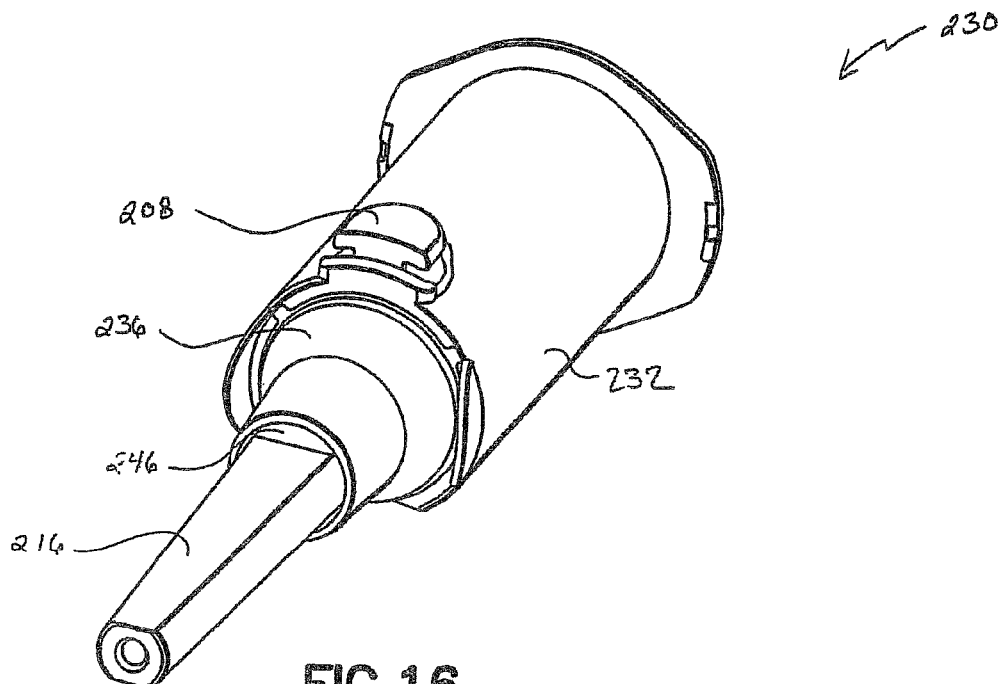
FIG. 16 is a perspective view of a needle assembly having a safety shield in the retracted position and a needle cover in accordance with an embodiment of the present invention.
Figure 17:
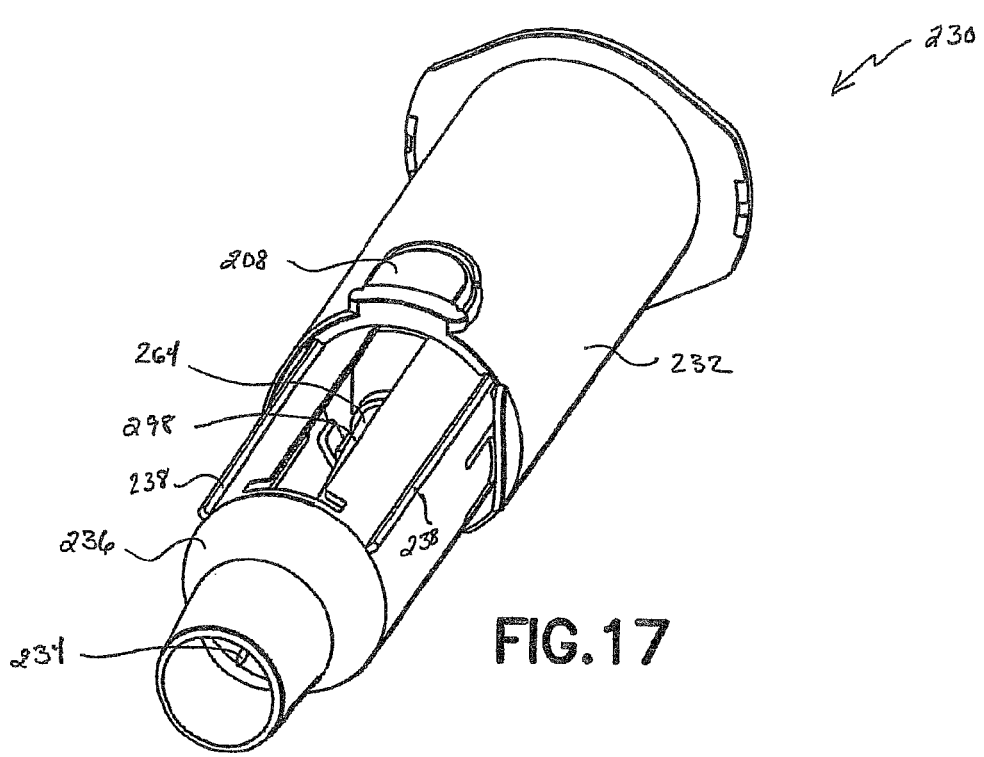
FIG. 17 is a perspective view of the needle assembly of FIG. 16 with the needle cover removed and having a safety shield in the extended position.
Figure 18:
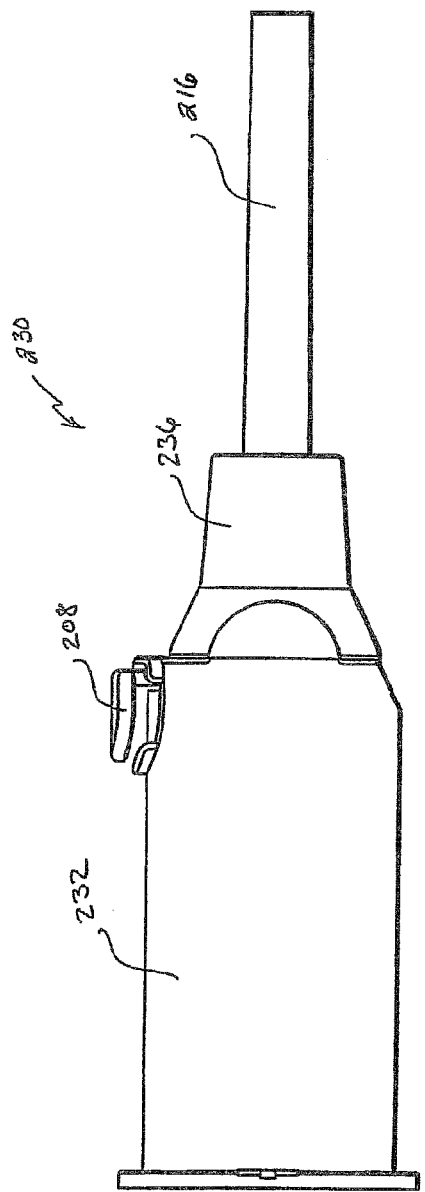
FIG. 18 is a side view of the needle assembly of FIG. 16 having a safety shield in the retracted position and with a needle cover.
Figure 19:
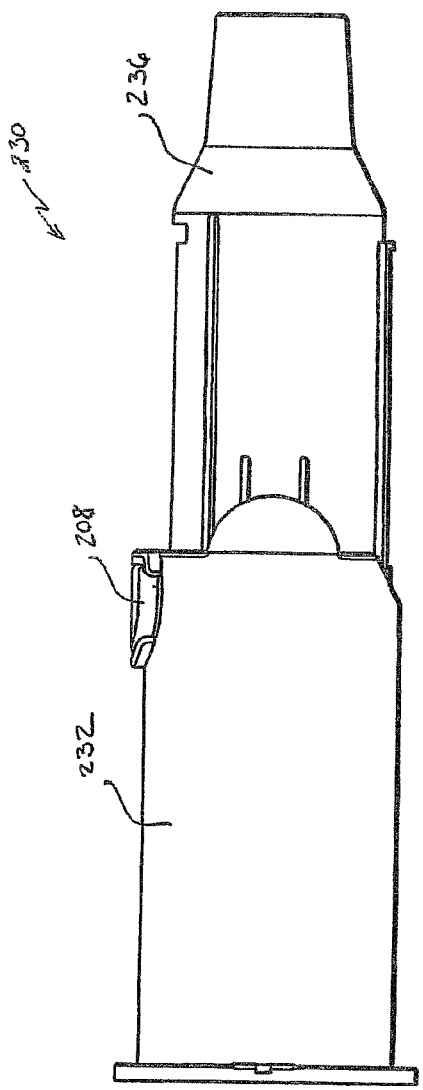
FIG. 19 is a side view of the needle assembly of FIG. 17 with the needle cover removed and having a safety shield in the extended position.

As shown in FIGS. 24-25, the removable cannula guard 216 may further include a portion in abutment with a portion of release member 208, thereby physically preventing deployment of the release member 208 until the removable cannula guard 216 is removed from the needle assembly 230. In one embodiment, the removable cannula guard 216 includes a tab 274 that extends at least partially within the interior recess 218 (shown in FIG. 28) of the release member 208, thereby preventing transition of the release member 208 from a first position, as shown in FIG. 16, to a second position, as shown in FIG. 17. Accordingly, accidental transition of the safety shield 236 from a retracted position to the extended position is prevented during transport or standard pre-use handling.

Moreover, as shown in FIGS. 22-23, a tamper-resistant flange 278 may be provided adjacent the distal end 260 of the housing 232, such as adjacent the distal end 282 of the second sidewall 286 to prevent the forced re-entry of the safety shield 236 into the housing 232 once the safety shield 236 has been transitioned from the retracted position to the extended position. In one embodiment, the flange 278 is attached to, or integral with, an exterior surface 284 of the second sidewall 286 at the distal end 282 and oriented to extend beyond the distal end 282 of the housing 232 in the distal direction. As shown in FIG. 23, when the needle assembly 230 is in the extended position, the flange 278 may shield a barrier mechanism 292, similar to the barrier mechanism previously described herein with reference to FIGS. 9-10. The barrier mechanism 292 is structured to prevent the re-entry of the safety shield 236 into the housing 232 once the safety shield 236 has been transitioned from the retracted position to the extended position. However, in certain configurations, it may be possible to insert a pry tool (not shown) between the safety shield 236 and a portion of the housing 232 thereby flexing the needle assembly 230 to a sufficient degree that abutting portions of the barrier mechanism 292 can become disengaged, thereby allowing re-entry of the safety shield 236 into the housing 232. In order to prevent insertion of such a pry tool, flange 278 may be provided to shield the distal end 260 of the housing 232 from tampering.

FIGS. 29-38 depict another embodiment of the present invention, in which a needle assembly 330 is similarly constructed as described above, with the exception of the configuration of the housing 332. Needle assembly 330 generally includes a cannula 334 associated with the housing 332, and a safety shield 336 adapted for safety shielding of the cannula 334 during and/or after use of the device. Needle assembly 330 further includes a hub 364 for supporting at least a portion of the cannula 334 and a flash chamber 398 as previously described.

In the embodiment shown in FIGS. 29-38, the housing 332 may include a first portion 344, with a second portion 346 connected to the first portion 344. The first portion 344 may be distal to the second portion 346 along the transition axis T (shown in FIG. 32) of the shield 336. In one embodiment, the first portion 344 and the second portion 346 are co-formed. In another embodiment, the first portion 344 and the second portion 346 are separately formed and subsequently assembled. In yet another embodiment, the first portion 344 and the secondary portion 346 may be secured together in a bayonet fashion. Alternatively, the first portion 344 and the secondary portion 346 may be adhered together through the use of conventional adhesives.

As shown in FIGS. 33-34, the cannula 334 may be positioned in part within the interior 350 of the secondary portion 346 and in part within the interior 352 of the first portion 344. In another embodiment, the non-patient end 342 of the cannula 334 may be positioned within the interior 350 of the secondary portion 346, and at least the puncture tip of the patient end 340 of the cannula 334 extending beyond the first portion 344. The hub 364 may be positioned within the interior 352 of the first portion 344, although in certain embodiments it may be desirable to position the hub 364 in part within the interior 350 of the secondary portion 346 and in part within the interior 352 of the first portion 344. In another embodiment, the secondary portion 346 may include a conventional specimen collection container holder 378. In yet another embodiment, a specimen collection container receiving port 380, engageable with a specimen collection container (shown in FIG. 123), is defined within the secondary portion 346.

The flash chamber 398 is visible to a medical practitioner when the safety shield 336 is in the retracted position, as shown in FIG. 29. Referring again to FIGS. 29-34, the housing 332, such as the first portion 344, may include a sidewall 358 having an observation window 360, shown in FIGS. 29-32, defined therein. In one embodiment, the observation window 360 includes an opening surrounded entirely by a sidewall 358. In another embodiment, the observation window 360 includes a cut-away portion of the housing 332. In another embodiment, the observation window 360 includes a translucent and/or transparent material within the opening. In yet another embodiment, the observation window 360 includes a cut-away portion that is at least partially open, i.e., the observation window 360 is not entirely surrounded by a sidewall 358 of the housing 332.

In accordance with an embodiment of the present invention, at least a portion of the flash chamber 398 is visible through the observation window 360 when the shield 336 is in the retracted position. In another embodiment, at least a portion of the first portion 344 of the housing 332 defines an observation window 360 and the flash chamber 398 is visible through the observation window 360 of the first portion 344 of the housing 332 when the shield is in the retracted position. In another embodiment, the safety shield 336 may be formed of a translucent and/or transparent material such that the flash chamber 398 is visible through both the observation window 360 and a portion of the safety shield 336. In another embodiment, both the safety shield 336 and the first portion 344 of the housing 332 are made of a transparent material or translucent material, such that the flash chamber 398 is visible through both structures. The first portion 344 and the safety shield 336 can be made of the same or different translucent and/or transparent materials. In another embodiment, the patient end 340 of the cannula 334 may include a bevel 338 and the position of the observation window 360 within the housing 332 corresponds to the orientation of the bevel 338, i.e., the orientation of the angled surface of the bevel 338. This may assist medical practitioners in properly orienting the cannula 334 within the patient without visually observing the patient end 340 of the cannula 334.

As shown in FIG. 33, the safety shield 336 may be disposed entirely within the first portion 344 of the housing 332 in the retracted position. In one embodiment, the safety shield 336 is adapted to at least partially surround, such as circumferentially surround, at least a portion of the cannula 334. In one embodiment, the safety shield 336 may be made of a substantially rigid material. In another embodiment, the safety shield 336 may be made of any substantially resilient deformable material having an elasticity sufficient that the safety shield 336 may be compressed and expanded without substantial damage thereof, such that it may be configured to fold against itself in an accordion folding arrangement.

As shown in FIGS. 33-34, a spring 368 may be biased between a portion of the safety shield 336 and a portion of first portion 344 of the housing 332. In one embodiment, the spring 368 is biased between a proximal portion 372 of the shield 336 and an inner surface 384 of the interior 352 of the first portion 344. In another embodiment, the spring 368 is biased between a proximal portion 372 of the shield 336 and a distal end 376 of the secondary portion 346. In yet another embodiment, the spring 368 is biased between a biasing portion 388 of the safety shield 336 and either of an inner surface 384 of the interior 352 of the first portion 344 and a distal end 376 of the secondary portion 346.

As shown in FIGS. 29-38, the safety shield 336 may be transitioned from the retracted position, shown in FIG. 29, to the extended position, shown in FIG. 30, by spring 368. During transition of the safety shield 336 from the retracted position to the extended position, spring 368 advances the safety shield 336 from a position within the first portion 344 of the housing 332 to a location distal from the distal portion 392 of the first portion 344. In this embodiment, the safety shield 336 is adapted to move between the retracted position, in which at least the puncture tip of the patient end 340 of the cannula 334 is exposed for accessing the patient, and the extended position in which the puncture tip of the patient end 340 is encompassed or otherwise safely shielded from exposure. The safety shield 336 may be at least partially deployed over the cannula 334 while the cannula 334 is accessing the interior of the patient's blood vessel (not shown), or after the cannula 334 has been removed from the patient. If the transition of the safety shield 336 from the retracted position to the extended position occurs while the cannula 334 is accessing the interior of a patient's blood vessel, the distal portion 394 of the safety shield 336 will contact the patient's skin.

In yet another embodiment, the needle assembly 330 may further include a barrier mechanism 396, similar to the barrier mechanisms previously described, to prevent the safety shield 336 from re-entering the housing 332 once the safety shield 336 has been transitioned from the retracted position to the extended position. Alternatively, as shown in FIGS. 33-34, the restraint 390 and break 386 are shown in opposite arrangement, such that the break 386 is incorporated within the housing 332, specifically the distal end 392 of the first portion 344, and the restraint 390 is incorporated within the safety shield 336 adjacent a proximal portion 372 of the shield 336.

Figure 35:
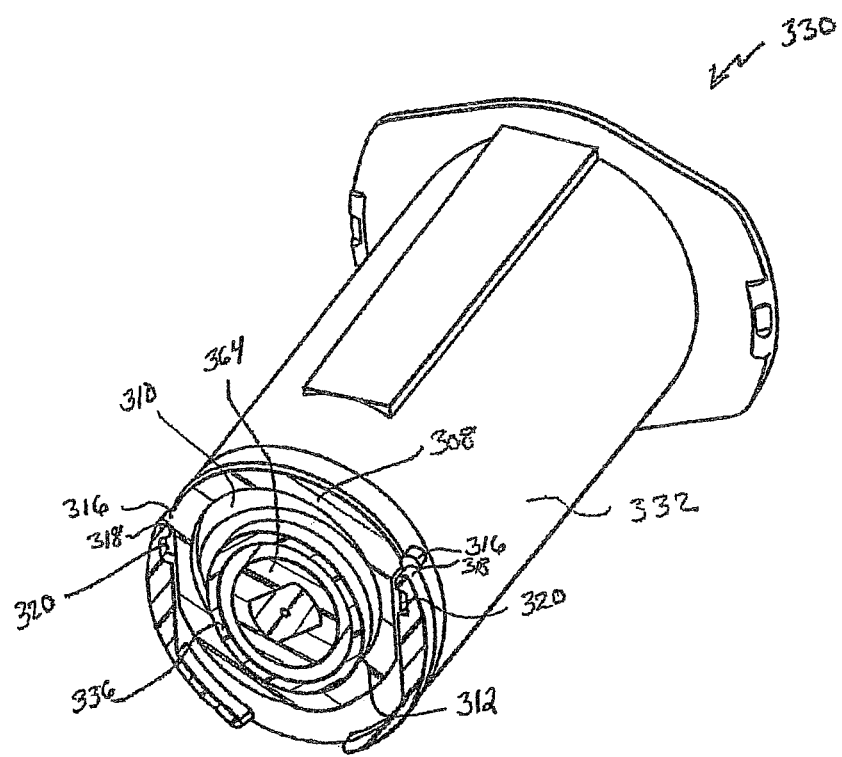
FIG. 35 is a perspective view of FIG. 29 showing the front-section of a portion of the needle holder.
Figure 36:
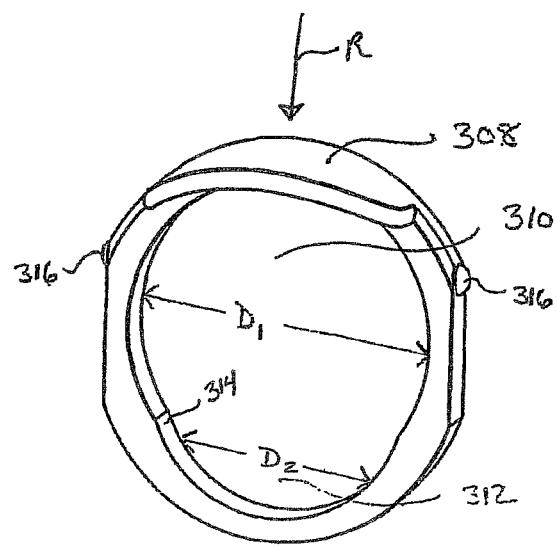
FIG. 36 is a perspective view of the push button of the needle assembly shown in FIG. 29.

As shown in FIGS. 29-36, a release member 308, such as a push button, may actuate the transition of the safety shield 336 from the retracted position to the extended position. In another embodiment, the release member 308 may initiate an activator to transition the safety shield 336 from the retracted position to the extended position. In the embodiment depicted in FIGS. 29-34, the release member 308 may operate in a substantially similar fashion to the release members previously described, however, the passage region 310 may define at least one substantially circular opening. As shown in FIG. 36, the restraining portion 312 of the release member 308 may also define a partially circular opening. FIG. 35 shows a cut away view of the needle assembly 330 with the release member 308 in the first position, corresponding to the shield 336 in the retracted position. As shown in FIG. 35, the restraining portion 312 is engaged with at least a portion of the safety shield 336, such that a shoulder 314 of the release member 308 prevents the safety shield 336 from transitioning to the extended position by the bias of the spring 368. In this configuration, the restraining portion 312 and the passage region 310 define continuous partially circular openings having different diameters. In one embodiment, the passage region 310 has a diameter $D_1$ and the restraining portion 312 has a diameter $D_2$, wherein $D_2$ is smaller than $D_1$. When the release member 308 is in the first position, the safety shield 336 is at least partially aligned with and restrained by the diameter of the opening of the restraining portion 312, thereby holding the safety shield 336 in the retracted position. When the release member 308 is transitioned to the second position, the restraining portion 312 is advanced below the safety shield 336 and the passage region 310, having an opening of increased diameter is aligned with the safety shield 336, thereby allowing the safety shield 336 to transition therethrough.

In one embodiment, the restraining portion 312 may be sized to circumferentially surround a portion of the housing 332, such as the hub 364. Optionally, the release member 308 may include a stabilizing feature for stabilizing the release member 308 in the first position and engaging a corresponding shoulder 318 of the housing 332, such as shown in FIGS. 29 and 35. In one embodiment, the stabilizing feature may include a detent protrusion 316, such as two detent protrusions 316, for engaging a corresponding shoulder 318 of the housing 332 and stabilizing the release member 308 in the first position. When the release member 308 is depressed in the direction shown by arrow R in FIGS. 29 and 36, the safety shield 336 is transitioned to the extended position, shown in FIG. 30. As the release member 308 is advanced in the direction shown by arrow R, the detent protrusions 316 are advanced in a downward direction and are received within a recess 320, shown in FIG. 35, within the housing 332. Due to the increased diameter of the passage region 310, as compared to the diameter of the restraining portion 312, and the presence of the detent protrusion 316 within the recess 320, the safety shield 336 is advanced through the passage region 310, thereby transitioning the safety shield 336 from the retracted position to the extended position.

Figure 37:
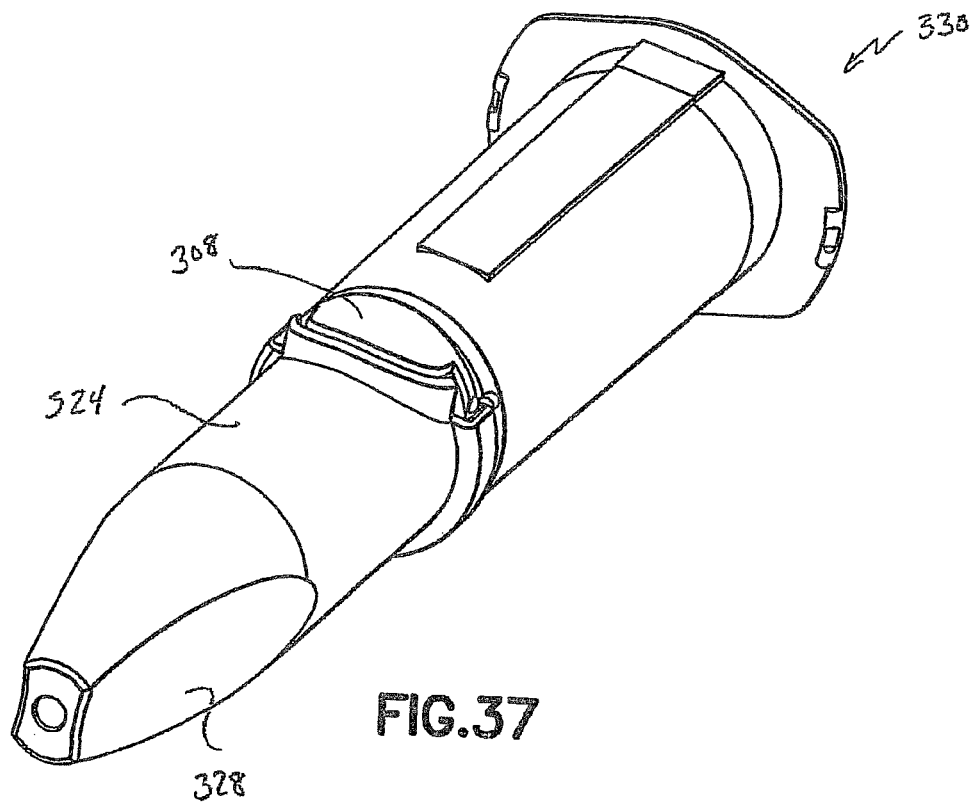
FIG. 37 is a perspective view of the needle assembly of FIG. 29 having a needle shield in accordance with an embodiment of the present invention.
Figure 38:
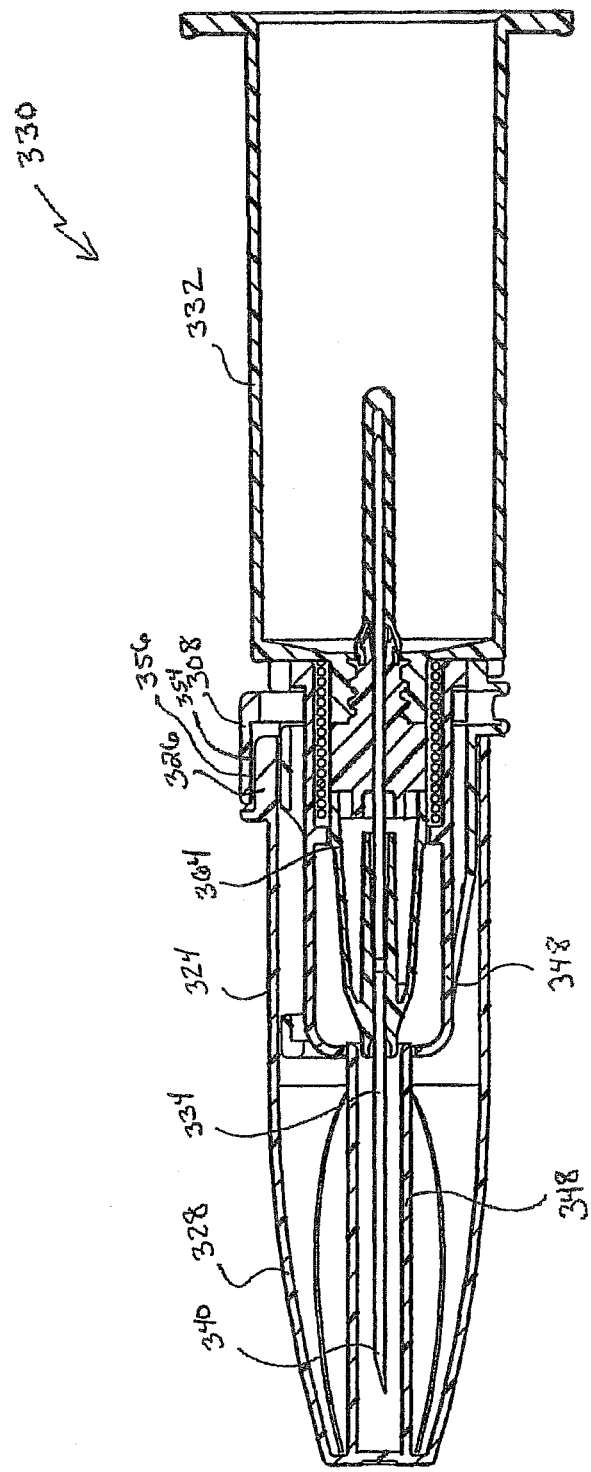
FIG. 38 is a cross-sectional view of the needle assembly shown in FIG. 29 having a removable cannula guard disposed thereon.
Figure 41:
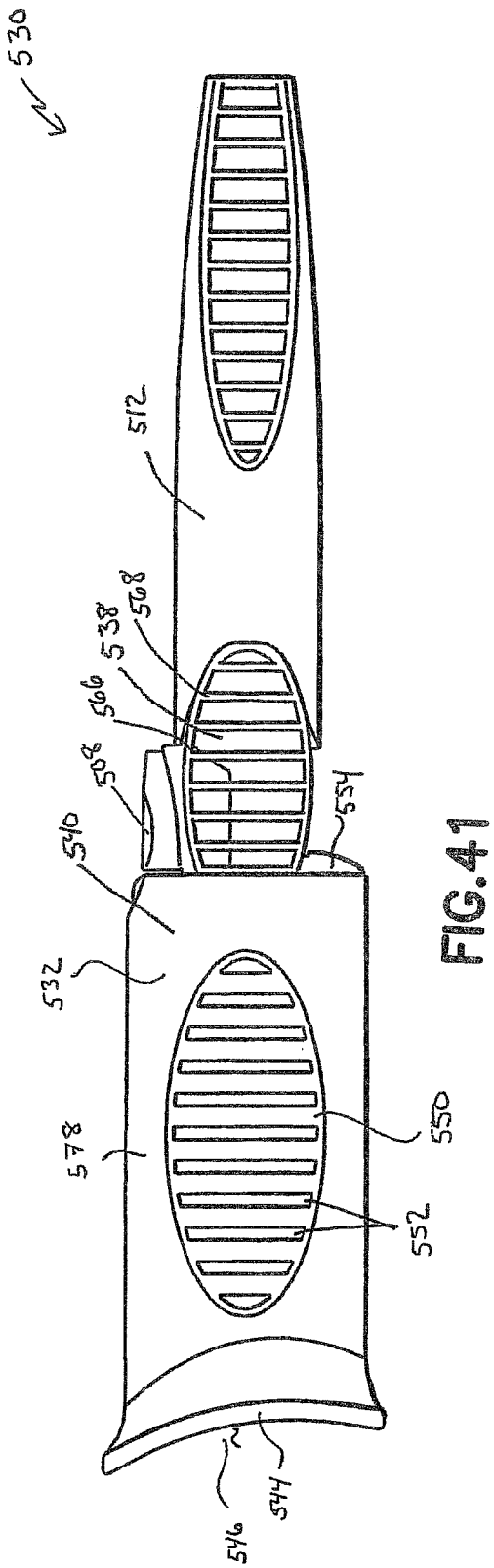
FIG. 41 is a side view of the needle assembly of FIG. 39.
Figure 42:
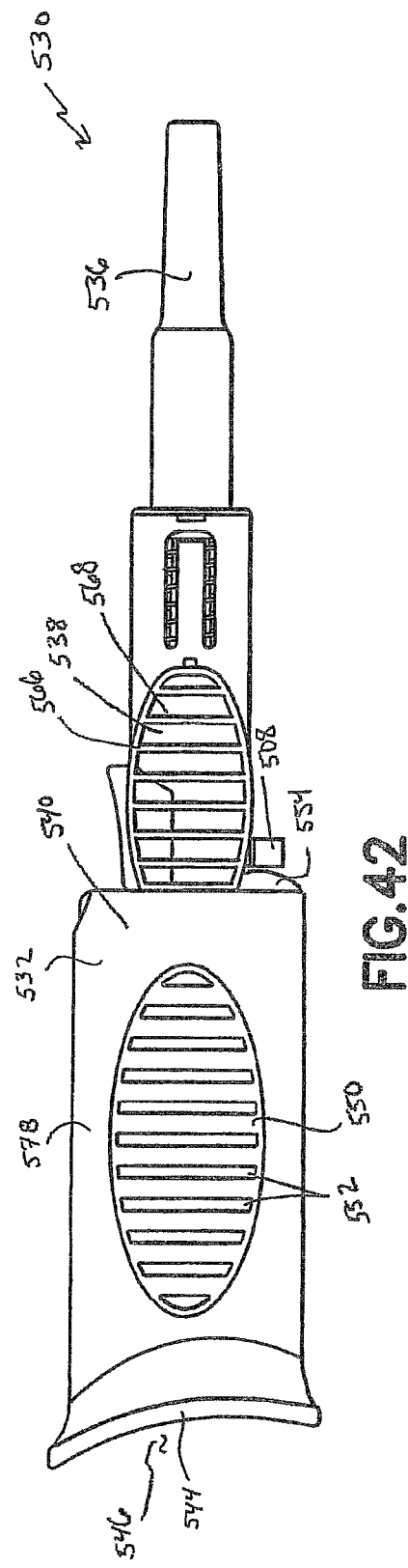
FIG. 42 is a side view of the needle assembly of FIG. 40.

Further, as shown in FIGS. 37-38, the needle assembly 330 may include a removable cannula guard 324 for surrounding the cannula 334, particularly the puncture tip of the patient end 340, prior to use. As previously described herein, the removable cannula guard 324 may include a tab portion 326 structured to prevent transition of the release member 308 from a first position to a second position. In this embodiment, the tab portion 326 includes an upper surface 354 structured to face a lower surface 356 of the release member 308 to provide an abutment or interference therebetween. Once a medical practitioner removes the removable cannula guard 324 from the needle assembly 330, the release member 308 may be deployed as described herein.

As shown in FIGS. 37-38, the removable cannula guard 324 may include a tapered portion 328 having a contour for allowing a medical practitioner to more easily grip the removable cannula guard 324 for removal from the needle assembly 330. In another embodiment, the removable cannula guard 324 may have a reinforcing tube 348 disposed within the interior of the removable cannula guard 324 and structured to at least partially surround the cannula 334. The reinforcing tube 348 may also include fastening means 362 for removeably securing the removable cannula guard 324 to the hub 364 of the needle assembly 330. In one embodiment, the fastening means 362 can include corresponding friction-fit or press-fit structures. In another embodiment, the fastening means 362 can include corresponding threaded structures for mating engagement allowing a medical practitioner to remove the removable cannula guard 324 from the needle assembly 330 by rotational movement of the removable cannula guard 324 with respect to the housing 332.

FIGS. 39-58 illustrate yet another embodiment of a needle assembly 530 of the present invention. FIGS. 39, 41, 43, 45, and 47 each illustrate the needle assembly 530 with a removable cannula guard 512 which must be removed prior to use of the needle assembly 530, as previously described. The removable cannula guard 512 may include a tab portion 512a structured to prevent depression of the release member 508.

In this embodiment, the tab portion 512a is designed to provide an abutment or interference between the release member 508 and the safety shield 536, as previously described.

The needle assembly 530 generally includes a cannula 534 associated with a portion of the housing 532, such as a hub 564 for supporting at least a portion of the cannula 534, and/or a specimen collection container holder 578. The needle assembly also generally includes a safety shield 536 adapted for safety shielding the cannula 534 during and/or after use of the needle assembly 530. The needle assembly 530 further includes a flash chamber 598 within at least a part of the housing 532, as previously described.

In one embodiment, the needle assembly 530 includes a first portion 538, with a secondary portion 540 connected to the first portion 538. The secondary portion 540 defines an interior 542 structured to receive the specimen collection container, such as an evacuated blood collection tube (not shown) therein. In one embodiment, the secondary portion 540 is a specimen collection container holder 578. In another embodiment, the secondary portion 540 is a blood collection container holder 578 and the needle assembly 530 is a blood collection assembly 530.

In one embodiment, the secondary portion 540 includes an arcuate proximal end 544. As shown specifically in FIGS. 41-42, the side portions of the arcuate proximal end 544 each define a generally concave proximal region 546 and, as shown specifically in FIGS. 43-44, the top and bottom portions of the arcuate proximal end 544 each define a generally convex proximal region 548 separated by the generally concave proximal regions 546 of the side portions. Optionally, the exterior surface 550 of the secondary portion 540 may include opposing ridged areas 552 for allowing a medical practitioner to easily grasp the secondary portion 540. In one embodiment, the opposing ridged areas 552 may be made of a tacky elastomeric material.

The distal end 554 of the secondary portion 540 may also include an engagement mechanism 556 for engaging the first portion 538. In one embodiment, the distal end 554 of the secondary portion 540 includes at least one recess 558, shown in FIGS. 47-48, for mating engagement with a protrusion 560 integral with the proximal end 562 of the first portion 538. The first portion 538 and the secondary portion 540 may be secured together by a press-fit locking mechanism, a threaded screw mechanism, a bayonet mechanism, or may be adhered together through the use of conventional adhesives. Optionally, the exterior surface 566 of the first portion 538 may also include opposing ridged areas 568 for allowing a medical practitioner to easily grasp the first portion 538. The cannula 534 may be positioned in part within the interior 42 of the secondary portion 540 and in part within the interior 570 of the first portion 538, as previously described.

Optionally, the secondary portion 540 of the present embodiment can include at least one tube preload indicator 572 for indicating to a medical practitioner the appropriate depth to which a specimen collection container, such as an evacuated blood tube, can be inserted without accessing the interior of the evacuated blood tube, such as by penetration of the cannula 534. Optionally, a portion of the cannula 534 may be protected by a pierceable sleeve 582 disposed about the proximal end of the cannula 534. In one embodiment, the preload indicator 572 may be a raised or recessed band disposed within the interior or exterior surface of the secondary portion 540, such as within an interior or exterior surface of the sidewall of the secondary portion 540. Alternatively, the preload indicator 572 can be a colored or textured band within the interior or exterior of the secondary portion 540. In another embodiment, the preload indicator 572 can be a continuous or segmented band. In this manner, an evacuated blood collection tube can be "pre-loaded" into the needle assembly 530 prior to use.

In one embodiment, the hub 564 at least partially supports the cannula 534, as previously described. The hub 564, including rear hub portion 574 and forward hub portion 576, is desirably molded from a transparent or translucent polymeric material or resin. As such, the hub 564, and in particular forward hub portion 576, defines a flash chamber 598. In one embodiment, the rear hub portion 574 engages the forward hub portion 576 through a portion of the secondary portion 540 of the housing 532 to form a sealed flash chamber 598. In this configuration, the flash chamber 598 can be formed by introduction of the rear hub portion 574 through the interior 542 of the secondary portion 540 for engagement with a portion of the forward hub portion 576 disposed within the interior 570 of the first portion 538. The housing 532 may include a forward hub portion 576 and a rear hub portion 574 connectable with the forward hub portion 576 and defining the flash chamber therebetween. In one embodiment, a protrusion 580 of the rear hub portion 574 extends through the secondary portion 540 of the housing 532 and matingly engages a corresponding recess within the forward hub portion 576. Accordingly, in one configuration, the rear hub portion 574 is connectable with the forward hub portion 576 through at least a portion of a specimen collection container holder 578, shown in FIG. 39. In another configuration, the rear hub portion 576 defines a specimen collection container receiving port 504 therein, shown in FIG. 55.

Figure 49:
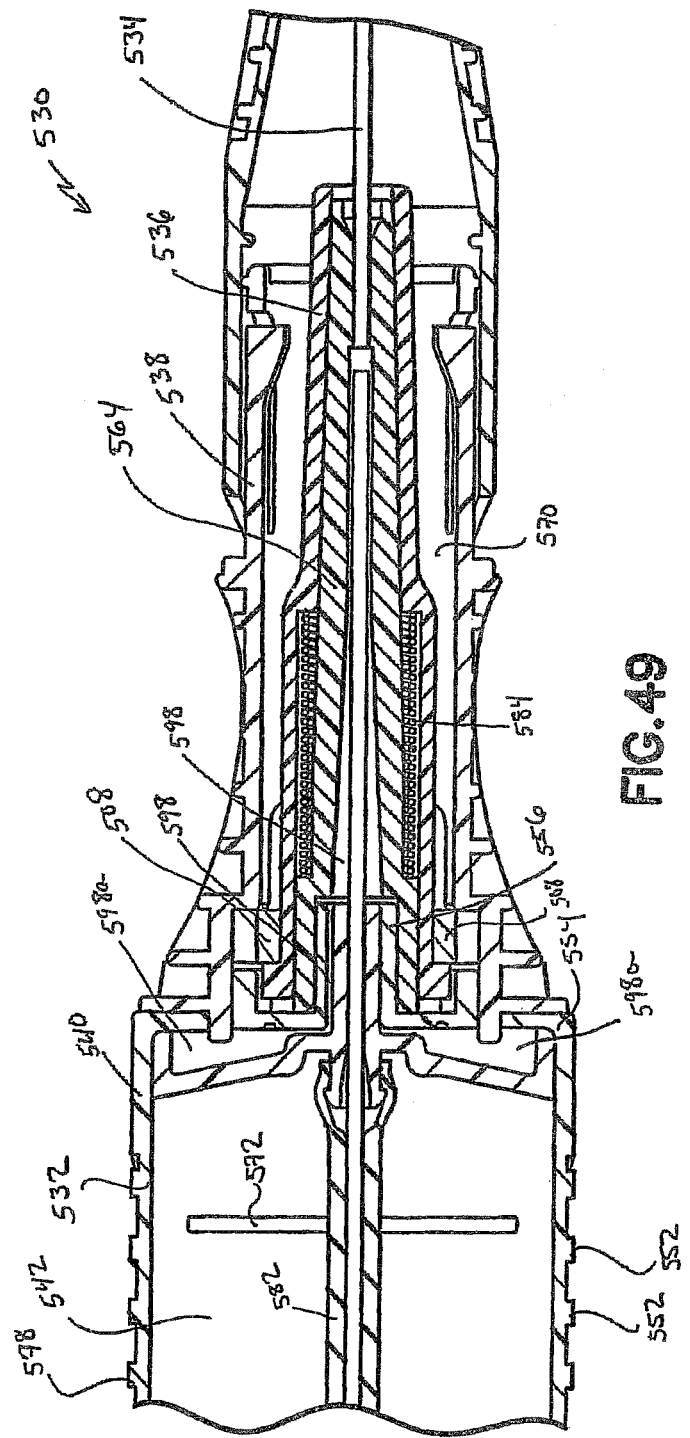
FIG. 49 is a close-up cross-section view of the needle assembly of FIG. 47.
Figure 50:
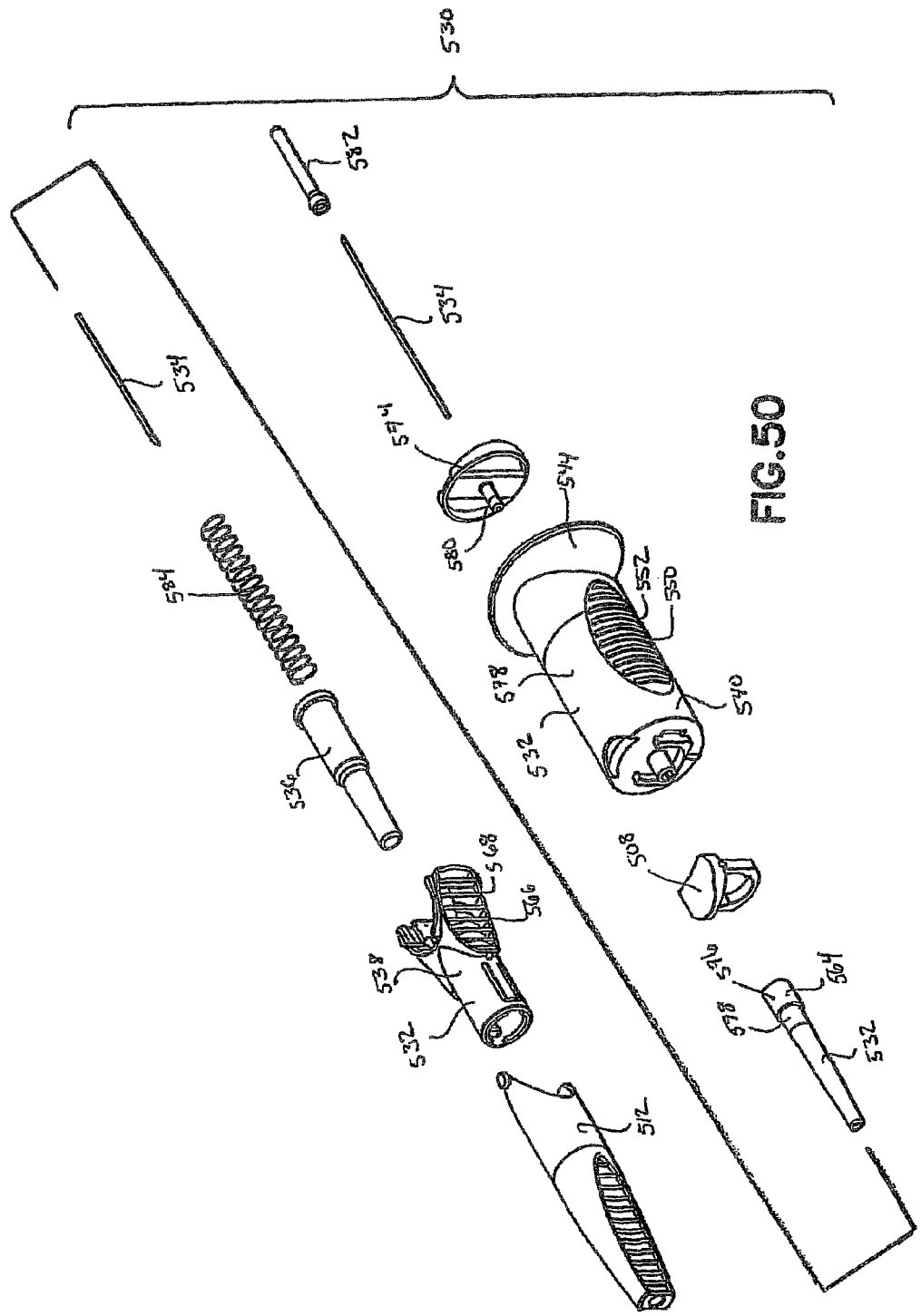
FIG. 50 is an exploded perspective view of the needle assembly of FIG. 39.

As shown in FIG. 49, in one embodiment at least a portion of the rear hub portion 574 is restrained within the interior 542 of the secondary portion 540, such that a portion of the flash chamber 598 may be formed within the secondary portion 540, such as within a blood collection tube holder. In another embodiment, the flash chamber 598 can be formed at least partially within the forward hub portion 576 and at least partially within rear hub portion 574. In this configuration, a slim profile of the needle assembly 530 can be maintained while increasing the volume of the interior of the flash chamber 598 visible to a medical practitioner when the safety shield 536 is in the retracted position.

As shown in FIG. 49, in one embodiment, the void 598a formed between the forward hub portion 538 and the rear hub portion 540 may allow for the compression of air therein, thereby creating sufficient pressure to force fluid, such as blood, entering the cannula 534 to be forced into the flash chamber 598. In one embodiment, the void 598a is sized to accommodate a sufficient volume of compressed air to force blood entering the cannula 534 into the flash chamber 598.

Transition of the safety shield from the retracted position, shown in FIG. 39 with the removable cannula guard 512 in place, to the extended position, shown in FIG. 40, may be effected as previously described. In one embodiment, a spring 584 disposed between a portion of the safety shield 536 and a portion of the housing 532 biases the safety shield 536 toward the extended position. In another embodiment, a release member 508, such as a push button, may actuate the transition of the safety shield 536 from the retracted position to the extended position, as previously described. Alternatively, the release member 508 may initiate an activator to transition the safety shield 536 from the retracted position to the extended position, also as previously described.

Figure 43:
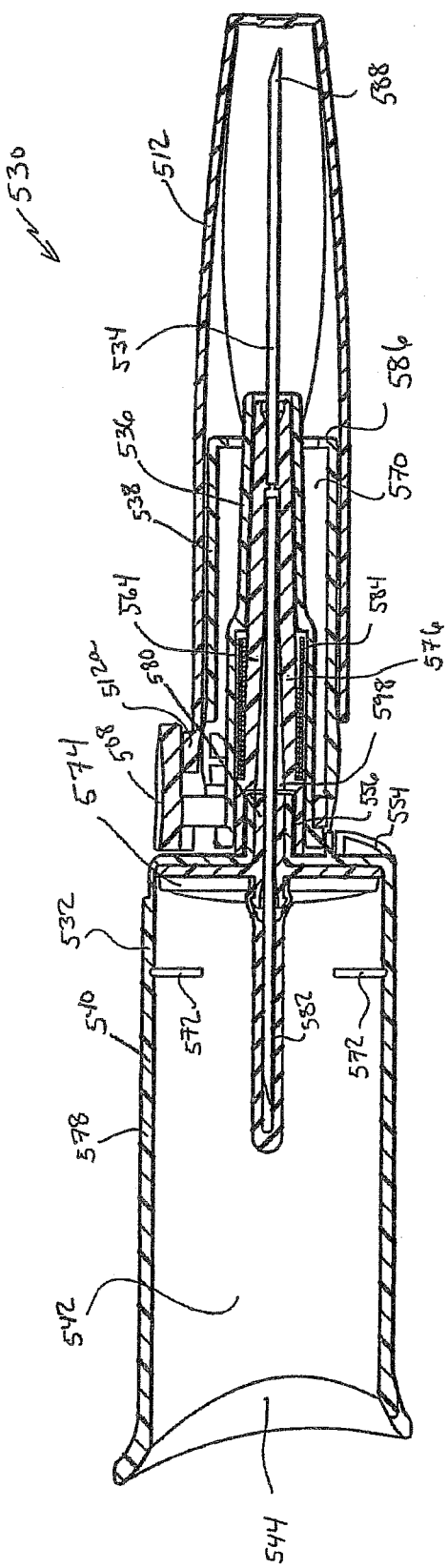
FIG. 43 is a cross-sectional view of the needle assembly of FIG. 39.
Figure 44:
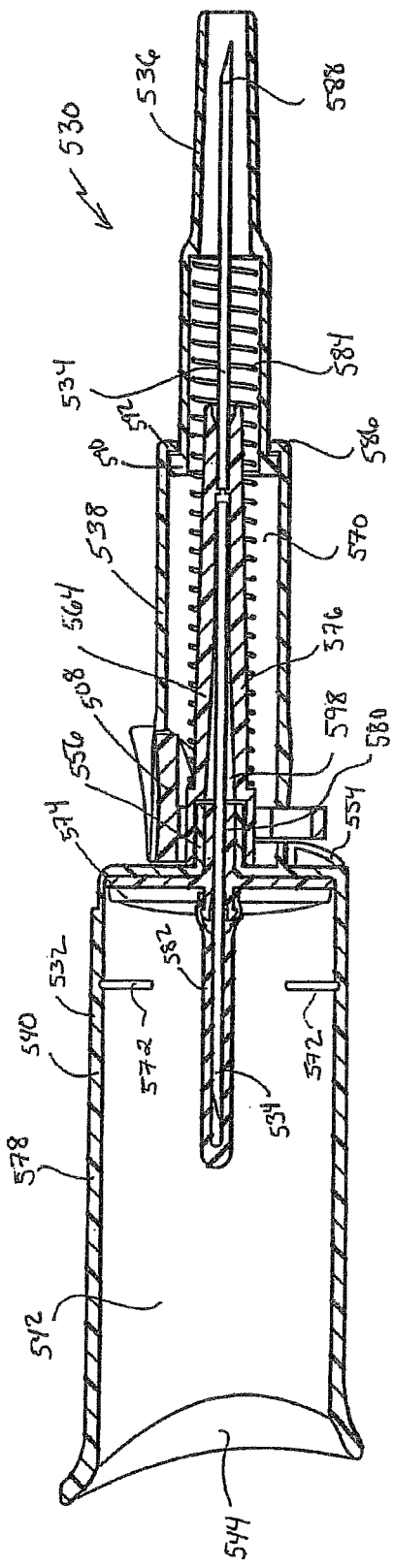
FIG. 44 is a cross-sectional view of the needle assembly of FIG. 40.

During transition of the safety shield 536 from the retracted position to the extended position, the spring 584 advances the safety shield 536 from a position at least partially within the first portion 538 of the housing 532 to a location distal from the distal region 586 of the first portion 538, as shown in FIGS. 43-44. In this embodiment, the safety shield 536 is adapted to move between the retracted position, in which at least the puncture tip of the patient end 588 of the cannula 534 is exposed for accessing the patient, and the extended position in which the puncture tip of the patient end 588 of the cannula 534 is encompassed or otherwise safely shielded from exposure. It is noted that although FIGS. 39, 41, 43, 45, and 47 each show the removable cannula guard 512 disposed over the cannula 534 in the retracted position, the removable cannula guard 512 is removed prior to use of the needle assembly 530, in which the cannula 534 is exposed.

As shown in FIG. 44, in the extended position, the safety shield 536 is retained within the distal region 586 of the first portion 538 by the engagement of proximal rim 590 of the safety shield 536 against distal restraint 592 of the first portion 538. As shown in FIG. 48, also in the extended position, the safety shield 536 is prevented from re-entering the first portion 538 of the housing 532, beyond the engagement at the distal region 586, by the engagement of the proximal rim 590 of the safety shield 536 and the barrier mechanism 594 of the first portion 538 of the housing 532.

As shown in FIG. 48, the barrier mechanism 594 may include a locking tab 596 that is deflectable upon transition of the safety shield 536 from the retracted to the extended position, but substantially resists deflection once the safety shield 536 is in the extended position. The locking tab 596 may include a tapered surface 528 which allows the safety shield 536 to advance thereover due to the applied force of spring 584 during transition from the retracted position to the extended position. The locking tab 596 may also include a stopped surface 526 to prevent the safety shield 536 from passing over the locking tab 596 once transition from the retracted position to the extended position has occurred. Therefore, the safety shield 536 of the needle assembly 530 remains locked in place over the cannula 534 once the safety shield 536 has been transitioned from the retracted position to the extended position.

Figure 51:
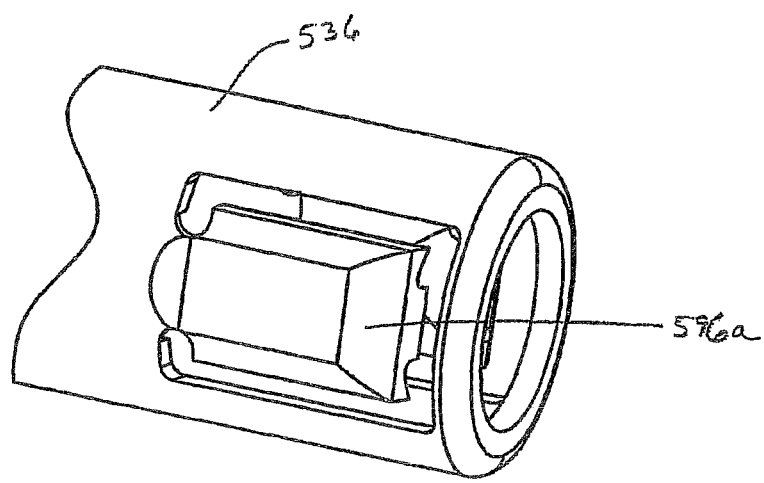
FIG. 51 is a partial perspective side view of a locking tab in accordance with an embodiment of the present invention.
Figure 52:
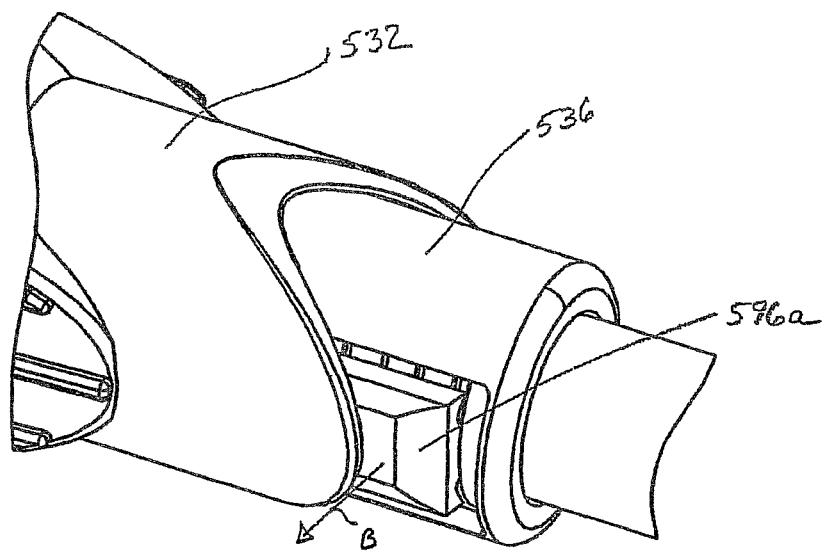
FIG. 52 is a partial perspective side view of the locking tab of FIG. 51 partially engaged with a housing in accordance with an embodiment of the present invention.

As shown in FIGS. 51-52, an alternative locking tab 596a may be included within the needle assembly 530. The locking tab 596a includes a similar geometry as described above, permitting transition of the safety shield 536 thereover by deflection when the shield 536 is transitioned from the retracted position to the extended position, and substantially resisting axial deflection once the shield 536 has been transitioned to the extended position. As shown in FIG. 52, a portion of the housing 532 may be disposed about the locking tab 596a to substantially resist deflection in the radial direction as shown by the arrow B in FIG. 52.

Figure 53:
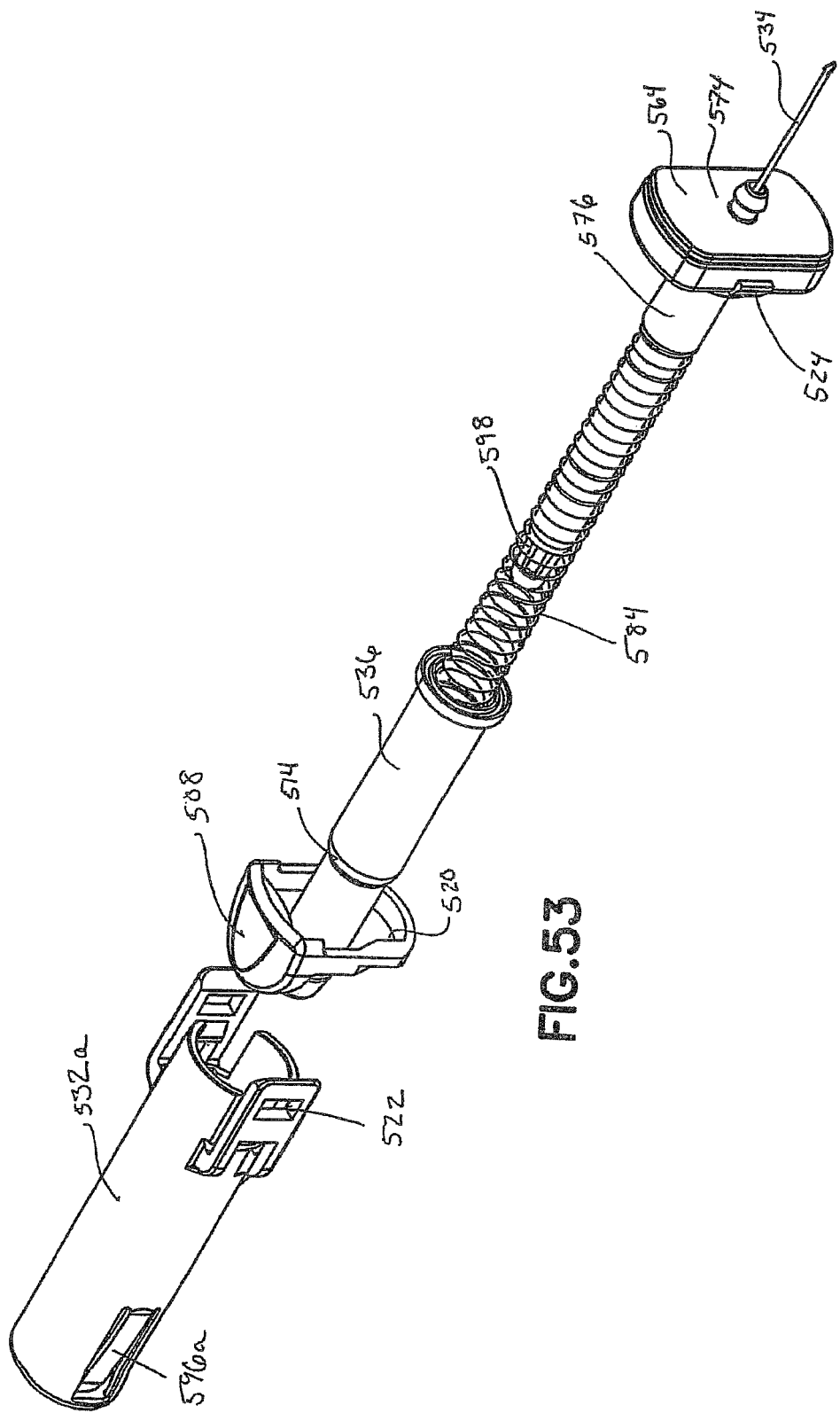
FIG. 53 is an exploded perspective view of a needle assembly in accordance with an embodiment of the present invention.
Figure 54:
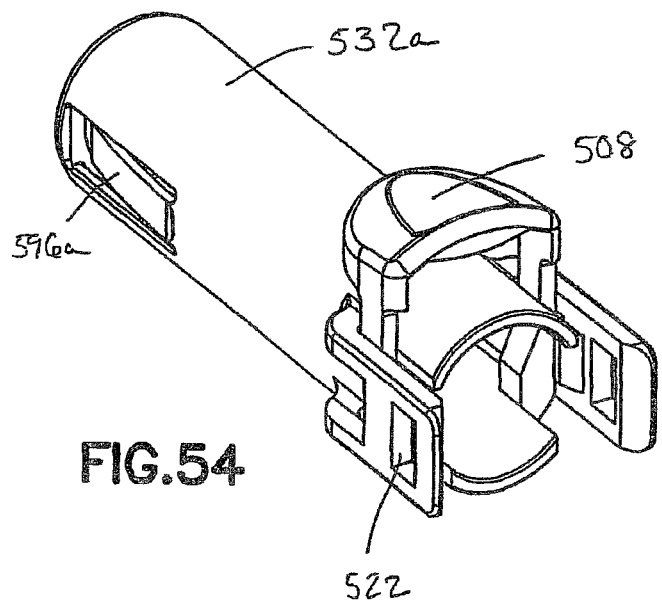
FIG. 54 is a partially assembled perspective view of the needle assembly of FIG. 53.
Figure 55:
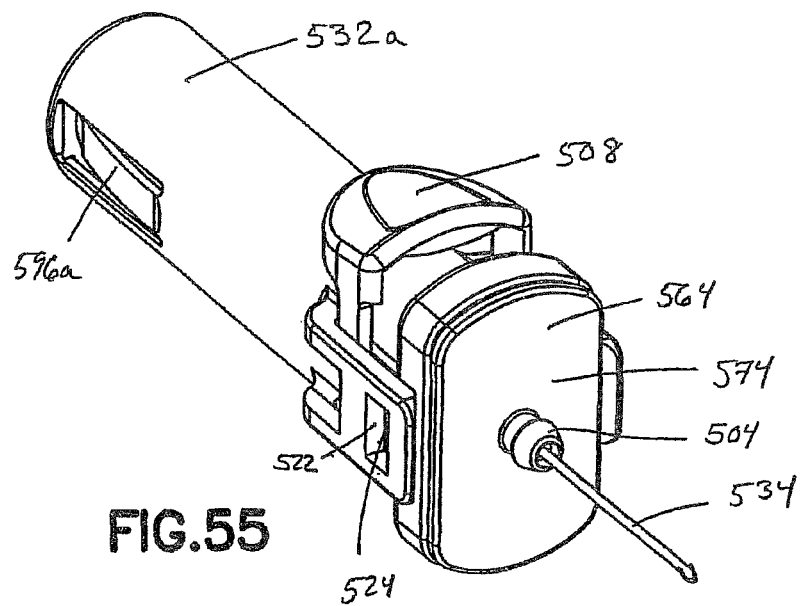
FIG. 55 is a partially assembled perspective view of the needle assembly of FIG. 53.
Figure 65:
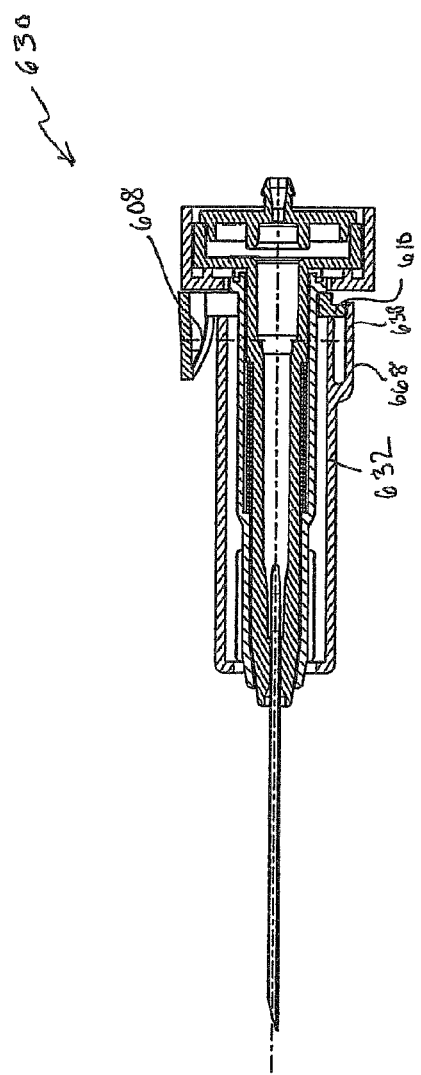
FIG. 65 is a cross-sectional side view of a needle assembly in the retracted position having an alternative locking mechanism in accordance with an embodiment of the present invention.
Figure 66:
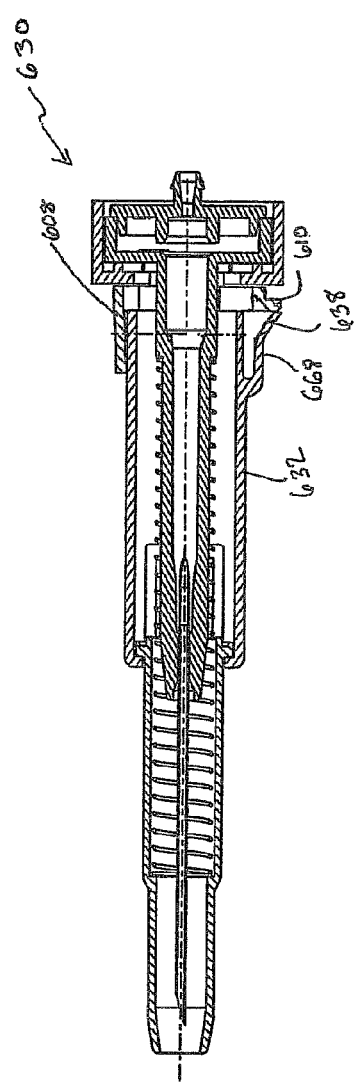
FIG. 66 is a cross-sectional side view of the needle assembly of FIG. 65 in the extended position.
Figure 73:
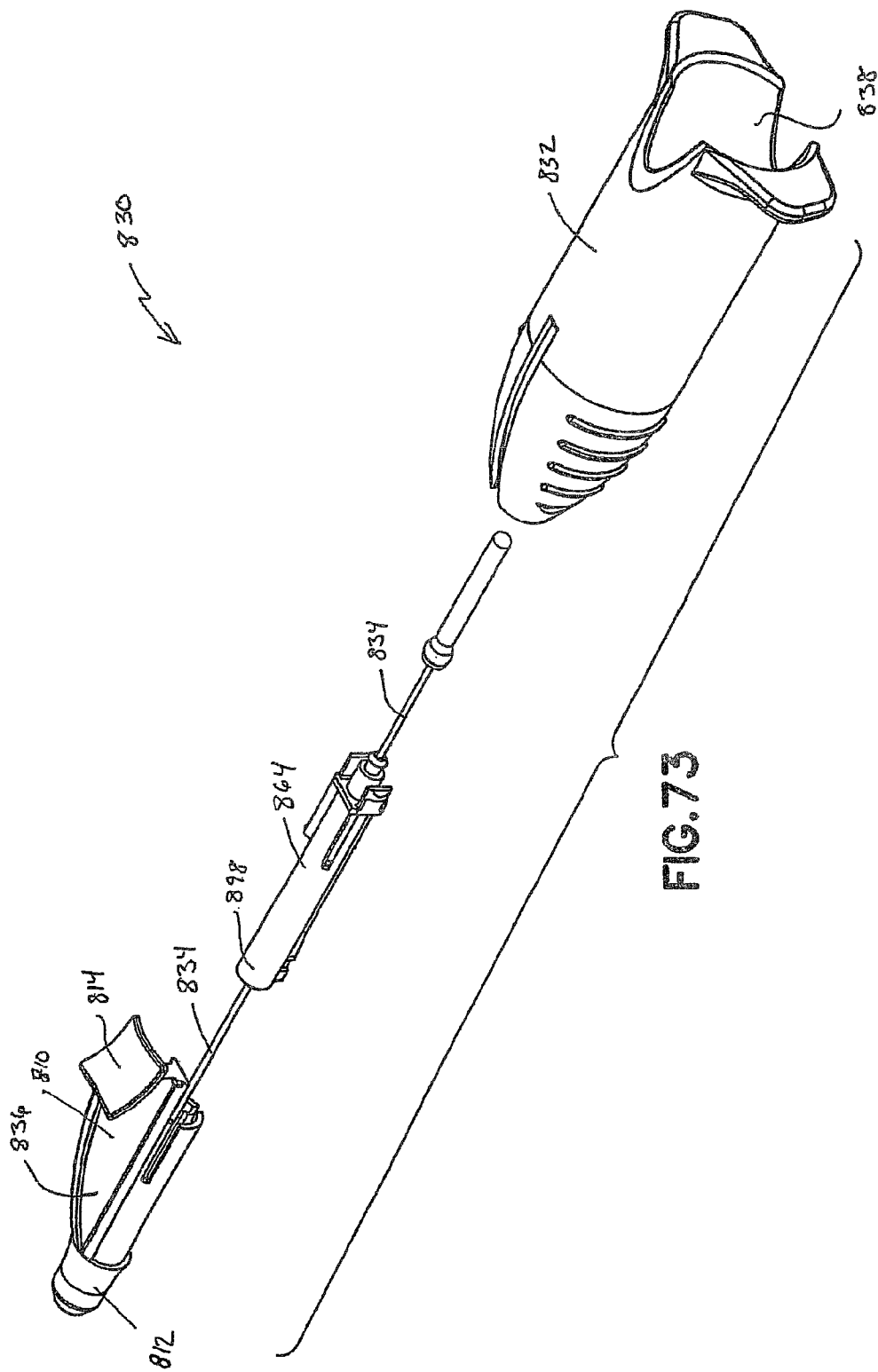
FIG. 73 is an exploded perspective view of a needle assembly with a glideable safety shield in accordance with an embodiment of the present invention.

As shown in FIGS. 53-55, during assembly of the present embodiment, the cannula 534 may be joined with the forward hub portion 576 and the rear hub portion 574 to form hub 564 having a flash chamber 598 therein, with the cannula 534 in fluid communication with the interior of the flash chamber 598. A spring 584 may be disposed between the forward hub portion 576 and a portion of the safety shield 536. The safety shield 536 may be inserted within an interior of a second housing portion 532a through a portion of the release member 508. As shown in FIG. 53, a portion of the housing 536 may include a joining mechanism 522 for engaging a corresponding tab 524 on the hub 564 to engage the hub 564 with a second housing portion 532a. As shown, locking tabs 596a may be provided within a distal end of the second housing portion 532a. When the hub 564 and the second housing portion 532a are joined, the shield 536 is biased toward the extended position by the spring 584. However, the release element 508 restrains the bias of the spring in the first position by engaging a shoulder 514 of the safety shield 536 and the restraining portion 520 of the release member 508. As shown in FIGS. 53-55, assembly of the release member 508 may be accomplished for a proximal or rearward direction, however, it is also contemplated herein that assembly may be directed from an upwardly direction, as shown in FIGS. 65-66, or from a distally or frontward direction.

As shown in FIG. 56, the hub 564 may be formed by engaging the forward hub portion 576 with the rear hub portion 574. The cannula 534 may be engaged with and partially supported by at least one of the forward hub portion 576 and the rear hub portion 574. A porous plug 510 may be disposed between the forward hub portion 576 and the rear hub portion 574 within the flash chamber 598 defined therebetween and in fluid communication with the cannula 534.

As shown in FIGS. 57-58, a needle assembly 530 may include a non-patient needle 516 (or the non-patient end of the cannula) having a pierceable sleeve 582 disposed thereover and may be aligned with the patient needle 518 through the flash chamber 598 defined within the hub 564. A spring 584 may be disposed between the forward hub portion 576 and a portion of the safety shield 536. The safety shield 536 may be inserted within an interior of a second housing portion 532a through a portion of the release member 508. The combined safety shield 536, second housing portion 532a, hub 564, and cannula 534 may be inserted within a third housing portion 532b, such as a specimen collection container holder or a blood collection tube holder.

It is anticipated herein that the hub 564, cannula 534, safety shield 536, and second housing portion 532a may be integrally provided within a third housing portion 532b, such as a blood collection tube holder. Alternatively, hub 564, cannula 534, safety shield 536, and second housing portion 532a may be provided as a non-integral arrangement in which the hub 564 may include a specimen collection container receiving port 504, shown in FIG. 55, adapted for later engagement with a specimen collection container.

As shown in FIGS. 59-63, the non-integrated needle assembly 630 is similarly structured to the embodiments described above. In one embodiment, the forward hub portion 674 and the rear hub portion 676 are joined, such as permanently joined, via a weld adjacent the outer circumference 678 of the hub 664. The flash chamber 698 may be formed between the forward hub portion 674 and the rear hub portion 676. In another embodiment, at least one of the forward hub portion 674 and the rear hub portion 676 are formed, such as molded, from a transparent or translucent polymeric material or resin. Accordingly, the flash chamber 698 may be visible to a medical practitioner through the hub 664.

A first housing portion 632a may be disposed about at least a portion of the forward hub portion 674 and the safety shield 636 and removable cannula guard 612 may be disposed about the patient end 640 of the cannula 634 and engaged with the first housing portion 632a, as previously described. A distal cannula guard 646 may be provided for at least partially surrounding the non-patient end 642 of the cannula 634, prior to use. The distal cannula guard 646 may engage at least a portion of the first housing portion 632a and can be removed therefrom upon application of typical manual pressure. Both the distal cannula guard 646 and the removable cannula guard 612 are provided to shield the non-patient end 642 of the cannula 634 (or non-patient needle) and the patient end 640 of the cannula 634 (or patient needle) from accidental contact with medical practitioners prior to initiation of a medical procedure.

Figure 61:
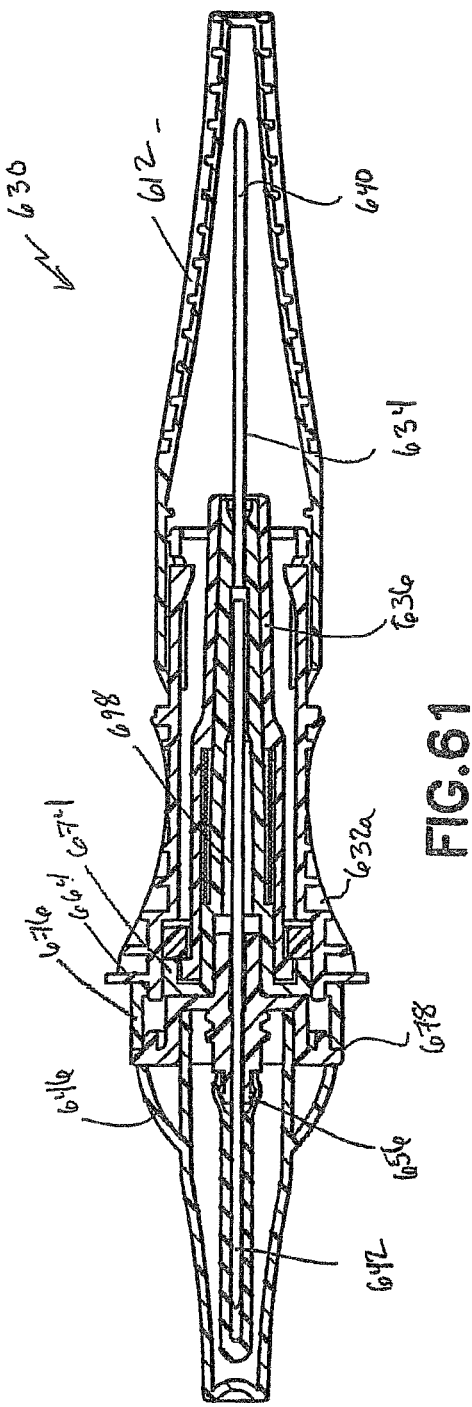
FIG. 61 is a cross-sectional top view of the needle assembly of FIG. 60.
Figure 62:
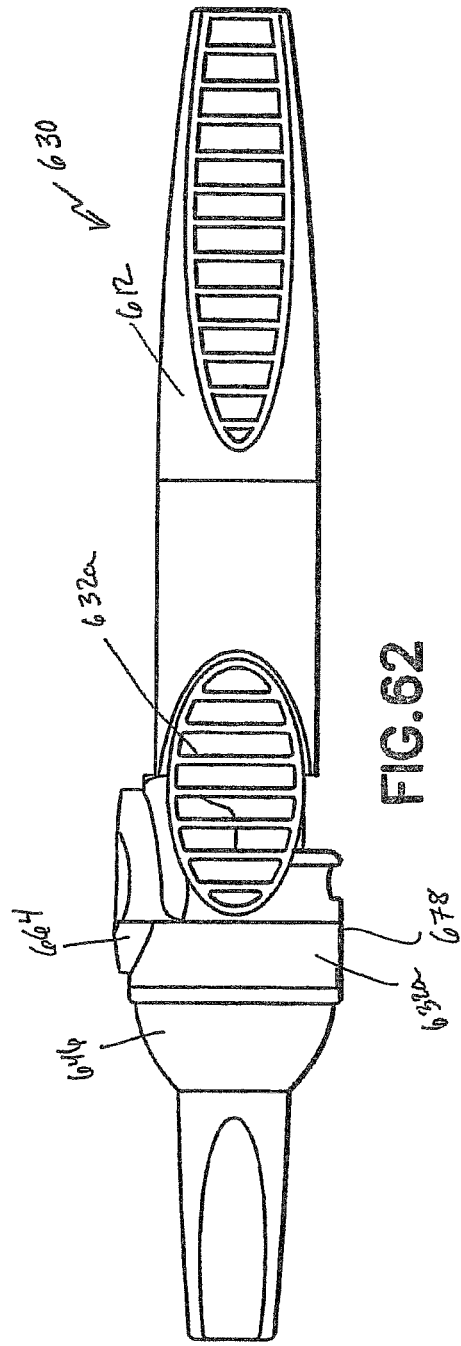
FIG. 62 is a side view of the needle assembly of FIG. 59.

The rear hub portion 676 further includes a specimen collection container engagement port 656, shown in FIGS. 61 and 63, which is engageable with a specimen collection container holder 652 (as shown in FIG. 64), such as a blood collection tube holder. In another embodiment, the specimen collection container engagement port 656 is directly engageable with a specimen collection container, such as an evacuated blood collection tube. It is further contemplated herein, that a flash chamber similar to the configuration shown in FIG. 49 with reference to 598, may be employed within the present design.

As shown in FIGS. 65-66, an additional mechanism 668 of the needle assembly 630 is shown. In this embodiment, the release member 608 is adapted to transition from a first position to a second position, as previously described. Release member 608 further includes a projection 610 which deforms at least a portion of the housing 632, such as tab portion 638 adjacent the release member 608, when the release member is transitioned from the first position to the second position. Deformation of the tab portion 638 of the housing 632 restrains the release member 608 in the second position, thereby preventing the release member 608 from returning to the first position.

FIGS. 67-72 depict another embodiment of the present invention, in which collection assembly 730, is similarly constructed to the above-described embodiments, with the exception of the configuration of safety shield 736 and the attachment of safety shield 736 to the housing 732. Needle assembly 730 generally includes a cannula 734, associated with the housing 732, such as supported by a hub 764, as previously described. A flash chamber 798 is associated with a portion of the housing 732, such as defined within the hub 764.

In the embodiment shown in FIGS. 67-72, the safety shield 736 may include a first portion 710, such as an arm portion, and a second portion 712, such as a shield portion, with the second portion 712 connected to the first portion 710. The first portion 710 is configured to slideably engage a portion of the housing 732 along the longitudinal axis L, shown in FIG. 71, of the cannula 734 when a medical practitioner applies typical manual force to the safety shield 736 substantially in the direction shown by arrow C. In one embodiment, the first portion 710 is configured to slideably engage, such as glide along, a glide mechanism 714 integral with the housing 732. In another embodiment, a portion of the housing 732 and a portion of the safety shield 736 define an engaging glide mechanism 714, wherein a portion of the safety shield 736 is axially transitionable with respect to a portion of the housing 732.

In one embodiment, the first portion 710 includes a protrusion 718 for slideably engaging a groove 720 recessed into a portion of the exterior surface 716 of the housing 732, thereby establishing a glide mechanism 714. In another embodiment, the first portion 710 includes a recess for slideably engaging a protrusion extending above the exterior surface 716 of the housing 732. The first portion 710 may include a grip region 722 for receiving the finger of a medical practitioner to aid in the advancement of the safety shield 736 from the retracted position, shown in FIG. 67, to the extended position, shown in FIG. 68 along the glide mechanism 714.

The second portion 712 of the safety shield 736 is adapted to at least partially surround, such as circumferentially surround, a portion of the hub 764 disposed at least partially within the housing 732 when the shield 736 is in the retracted position, such that the flash chamber 798 defined therein, is at least partially visible to a medical practitioner when the safety shield 736 is in the retracted position. In one embodiment, at least a portion of the flash chamber 798 is visible to a medical practitioner through an observation window 724 or cutaway portion within the second portion 712 of the safety shield 736.

In another embodiment, the second portion 712 of the safety shield 736 may be constructed of a transparent material and/or translucent material, such that the flash chamber 798 may be visible therethrough.

In this embodiment, the safety shield 736 is adapted to move between a retracted position, as shown in FIG. 67, in which at least the puncture tip of the patient end 740 of the cannula 734 is exposed for accessing the patient, and an extended position, shown in FIG. 68, in which the puncture tip of the cannula 734 is encompassed or otherwise safely shielded from exposure. The second portion 712 of the safety shield 736 is adapted to at least partially surround, such as circumferentially surround, at least a portion of the cannula 734 in the extended position. In another embodiment, the patient end 740 of the cannula 734 is at least partially surrounded by the second portion 712 of the safety shield in the extended position.

The safety shield 736 may be deployed over the cannula 734 while the cannula 734 is accessing the interior of the patient's blood vessel (not shown), or after the cannula 734 has been removed from the patient. If the transition of the safety shield 736 from the retracted position to the extended position occurs while the cannula 734 is accessing the interior of a patient's blood vessel, the distal portion 744 of the safety shield 736, such as of the second portion 712 of the safety shield 736, will contact the patient's skin. In one embodiment, the safety shield 736 includes a detent mechanism to temporarily restrain the safety shield 736 in a retracted position and a locking mechanism 750 adapted to maintain the safety shield 736 in the extended position after it is moved thereto. As shown in FIG. 71, the first portion 710 of the safety shield 736 may include a locking mechanism 750 which is deflected or otherwise radially biased against a portion of the housing 732, such as by a portion of the first portion 710, when the safety shield 736 is in the retracted position. As shown in FIG. 72, once the safety shield 736 is transitioned to the extended position, the locking mechanism 750 is advanced, such as longitudinally advanced along the longitudinal axis L of the cannula 734 until contact with the housing 732 is disrupted. At this point, the radially biasing forces maintaining the locking mechanism 750 in a substantially parallel orientation with respect to the cannula 734 are released, and the locking mechanism swings toward the cannula 734, as shown by arrow D, to engage a distal end of the housing 732. Once the locking mechanism 750 is engaged with the distal end of the housing 732, retraction of the safety shield 736 from the extended position to the retracted position is prevented.

An alternative needle assembly 830 having a glideable safety shield 836 is shown and described with reference to FIGS. 73-86. In this configuration, the needle assembly 830 generally includes a cannula 834 associated with a portion of the housing 832, and a safety shield 836 adapted for safety shielding of the cannula 834 during and/or after use of the device. A proximal portion 838 of the interior of housing 832 may be configured to receive an evacuated blood collection tube (not shown) therein and may include an interior ridge 840, as shown in FIG. 76, for limiting the advancement of the evacuated blood collection tube through the proximal portion 838 of the housing 832.

The cannula 834, may include a distal patient needle 44 (or a patient end of a single cannula) and a proximal non-patient needle 46 (or a non-patient end of a single cannula). The proximal non-patient needle 46 may be provided for puncturing of an evacuated blood collection tube (not shown). Distal patient needle 44 may be beveled to define a puncture tip for puncturing the skin of a patient and accessing the patient's vasculature. The cannula 834 is supported by at least a portion of the housing 832, such as a hub portion 864. A flash chamber 898 may be defined within the hub 864 as previously described. In one embodiment, the hub 864 and the cannula 834 can be integrally formed with the remainder of the housing 832. Alternatively, the hub 864 and/or the cannula 834 can be separately formed and subsequently assembled.

In the embodiment shown in FIGS. 73-86, the safety shield 836 may include a first portion 810, such as an arm portion, and a second portion 812, such as a shield portion. The first portion 810 and the second portion 812 are connected. The first portion 810 may include a grip portion 814 for receiving the finger of a medical practitioner to aid in the advancement of the safety shield 836 from the retracted position in which the patient end 44 is exposed, shown in FIGS. 75-79, to the extended position in which the patient end 44 is shielded, shown in FIGS. 82-86.

The safety shield 836 is configured to slideably engage a portion of the hub 864 along a glide mechanism 816 established by the interface of an upper surface 820 of the hub 864 and a lower surface 818 of the safety shield 836, such as a lower surface of the second portion 812 of the safety shield 836. The interface of the upper surface 820 and the lower surface 818 may be provided as a frictional slide between the two surfaces. Alternatively, the upper surface 820 may be provided with a protrusion (not shown), as previously described, for receipt within a corresponding groove (not shown), as previously discussed, within a portion of the lower surface 818. Alternatively, the upper surface 820 may be provided with a groove (not shown) for receipt of a protrusion (not shown) extending from a portion of the lower surface 818.

Figure 74:
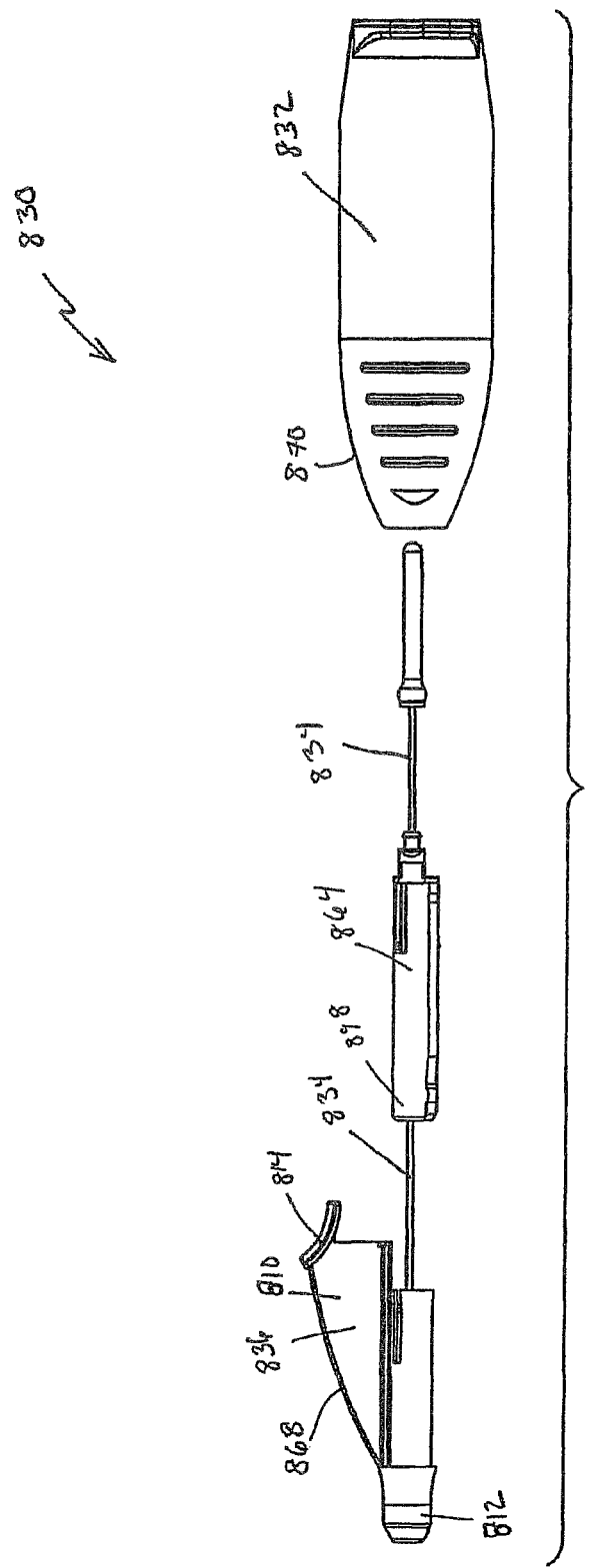
FIG. 74 is an exploded perspective view of the needle assembly of FIG. 73.
Figure 82:
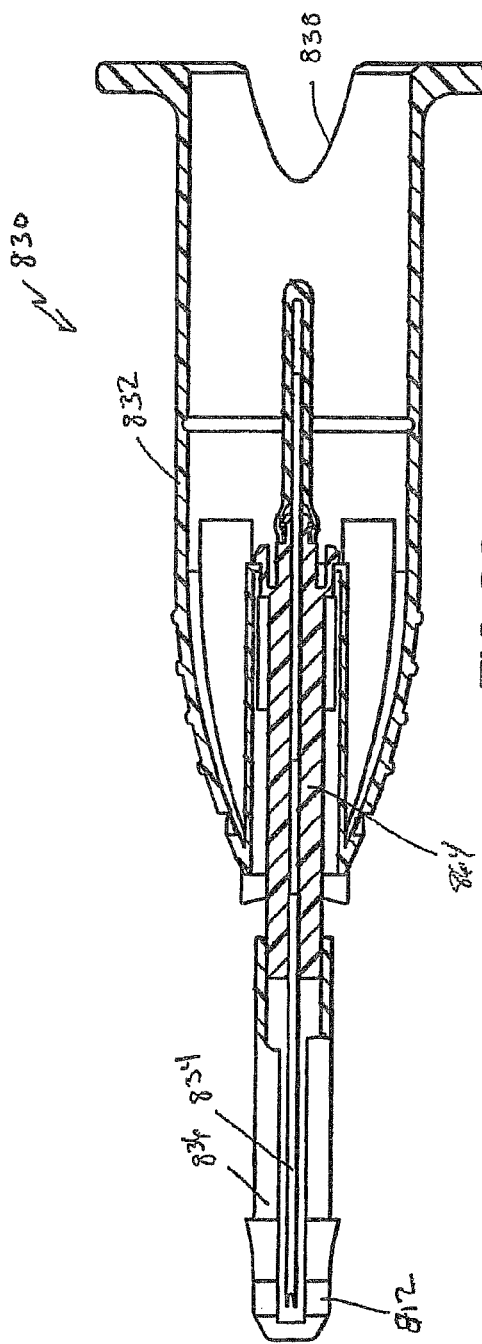
FIG. 82 is a cross-sectional top view of the needle assembly of FIG. 76 in the extended position.
Figure 83:
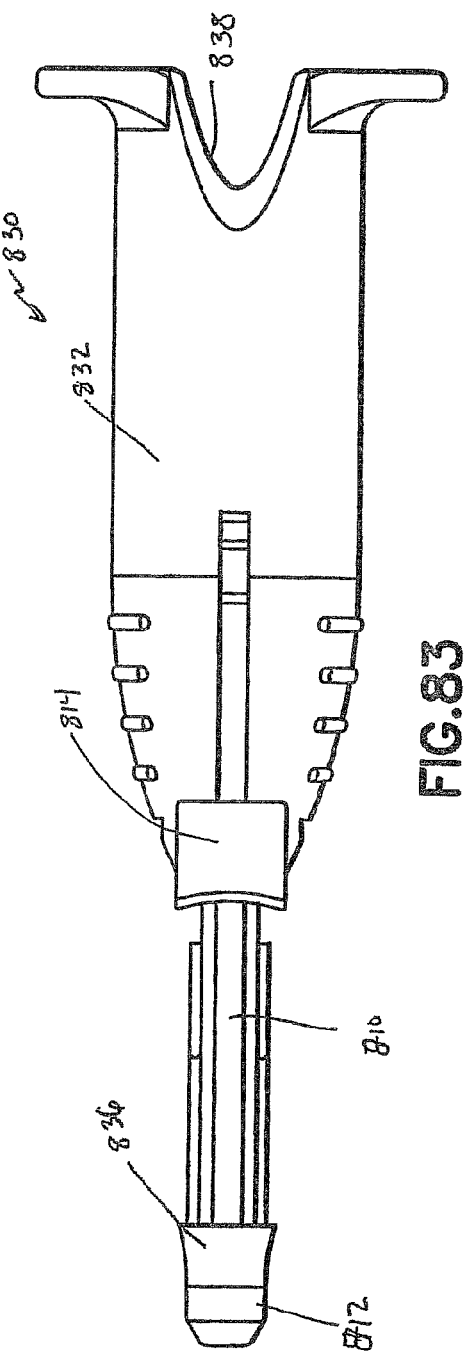
FIG. 83 is a top view of the needle assembly of FIG. 82 in the extended position.

In one embodiment, the first portion 810 of the shield 836 may slideably engage a portion of the hub 864 along the longitudinal axis T (shown in FIG. 75) of the cannula 834. As shown in FIG. 77, the first portion 810 of the shield 836 may have a first end 850 which slideably engages a portion of the hub 864, such that the lower surface 818 of the shield 836 slideably engaged the upper surface 820 of the hub 864. The first portion 810 of the shield 836 may also have a second end 852, shown in FIGS. 77-78, extending at least partially through a portion of the housing 832. In another embodiment, the second end 852 of the first portion 810 may extend at least partially through a portion of the outer surface 856 of the housing 832. In yet another embodiment, as shown in FIG. 75, the second end 852 of the first portion 810 extends at least partially through a groove 858 defined in the outer surface 856 of the housing 832. The groove 858 may extend within the housing 832 substantially along the longitudinal axis T of the cannula 834. The first portion 810 of the shield 836 may slide within the groove 858 as the shield 836 is transitioned from the retracted position to the extended position. In another embodiment, as shown in FIG. 74, the first portion 810 may have a contoured surface 868 that substantially corresponds to a distal contoured surface 870 of the housing 832.

The second portion 812 of the safety shield 836 is adapted to at least partially surround, such as circumferentially surround, at least a portion of the hub 864 in the retracted position. In one embodiment, the second portion 812 is disposed about a portion of the cannula 834 and axially aligned with a portion of the first portion 810 to transition about the cannula 834 from the retracted position to the extended position.

The safety shield 836 may also be prevented from unintentional advancement from the housing 832, prior to initiation by a medical practitioner, by the resistance engagement of a portion of the shield 836 with a portion of the housing 832 and/or hub 864. Upon application of force by a medical practitioner to the grip portion 814 in the direction shown by arrow R in FIG. 77, the safety shield 836 is advanced in a distal direction along the longitudinal axis T, shown in FIG. 75, from the housing 832.

Figure 86:
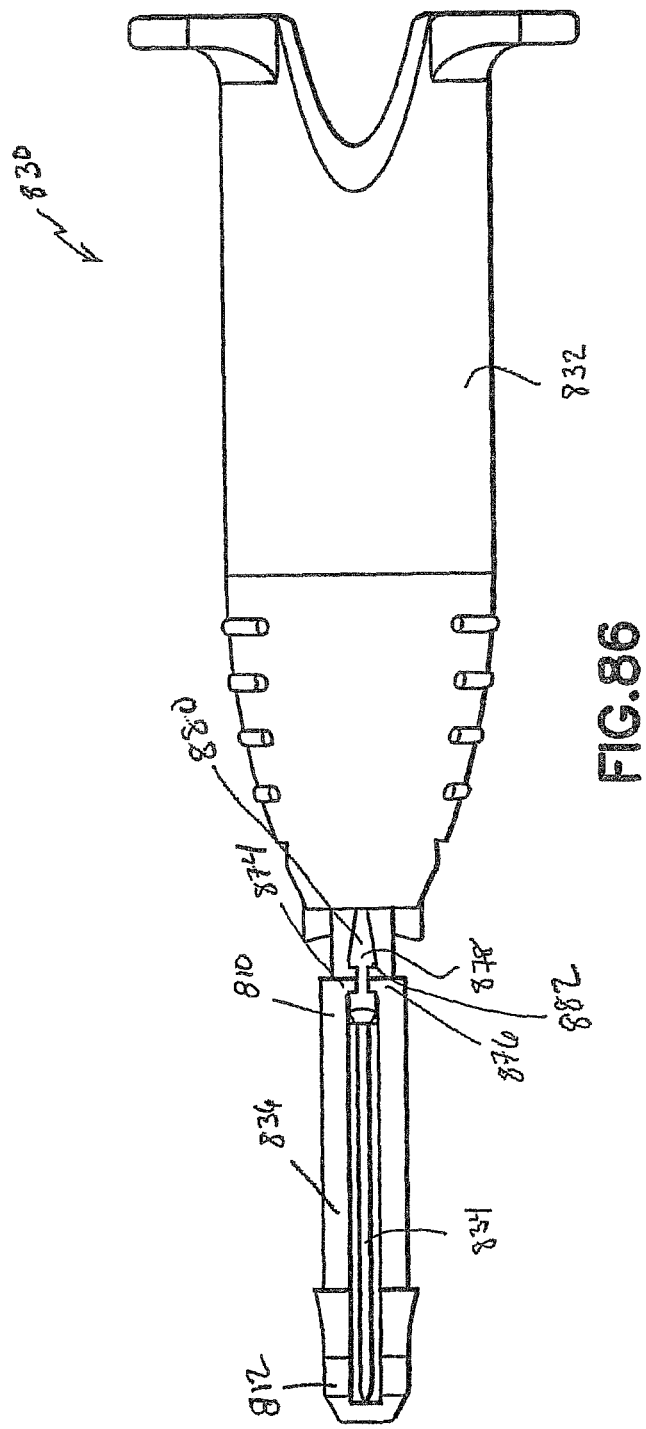
FIG. 86 is a bottom view of the needle assembly of FIG. 79 in the extended position.

With reference to FIGS. 79 and 86, the safety shield 836 may include restraining means 874 for preventing transition of the shield 836 from the extended position to the retracted position, once the shield 836 has been transitioned from the retracted position to the extended position. During transition of the safety shield 836 from the retracted position to the extended position, a proximal protrusion 876 of the safety shield 836 is advanced through a restraint notch 878 within the housing 832 and/or hub 864, such as within the glide mechanism 816.

The restraint notch 878 may include a triangular portion 880 structured to allow the proximal protrusion 876 of the safety shield 836 to easily pass therethough, and a restraining surface 882 structured to prevent re-entry of the proximal protrusion 876 of the safety shield 836 once the transition of the safety shield 836 from the retracted position to the extended position has occurred. In this manner, once the safety shield 836 has shielded the patient end 844 of the cannula 834, the safety shield 836 may not re-enter the housing 832.

In one embodiment, the flash chamber 898 is at least partially visible to a medical practitioner when the safety shield 836 is in the retracted position. Accordingly, a portion of the shield 836, such as the second portion 812, may be constructed of a transparent material and/or translucent material, such that the flash chamber 898 may be visible therethrough.

FIGS. 87-91 depict another embodiment of the present invention, in which collection assembly 930 is constructed as similarly described above, with the exception of the configuration of safety shield 936 and the attachment of safety shield 936 to the housing 932. Needle assembly 930 generally includes cannula 934 associated with the housing 932, and a safety shield 936 adapted for safety shielding of the cannula 934 during and/or after use of the device. Needle assembly 930 further includes a hub 964 for supporting the cannula 934 and defining a flash chamber 998, as previously described, therein.

In the embodiment shown in FIGS. 87-91, a safety shield 936 includes a depending arm 940 attached to the exterior surface 942 of the housing 932. The depending arm 940 may include a plurality of extendable segments 948, such as first extendable segment 944 connected to second extendable segment 950. In one embodiment, the first extendable segment 940 may be pivotally or hingedly connected, such as by a pivot 956, to the base portion 952 of the depending arm 940, allowing the first extendable segment 944 to articulate with respect to the base portion 952. In another embodiment, the second extendable segment 950 may be pivotally or hingedly connected, such as by a pivot 956, to the first extendable segment 944, allowing the second extendable segment 950 to articulate with respect to the first extendable segment 944.

In one embodiment, the depending arm 940 of the shield 936 is oriented on a first side of the cannula 934. In another embodiment, the shield 936 includes a second depending arm 970, as similarly described, oriented on a second side of the cannula 934, with the second side being substantially opposite the first side. In a further embodiment, the depending arm 940 and the second depending arm 970 may be connected, such as by a union 972. In another embodiment, the depending arm 940 and the second depending arm 970 may be connected by at least one pivot 956. In a further embodiment, a pivot 956 may provide for an articulation of less than 180 degrees.

Figure 87:
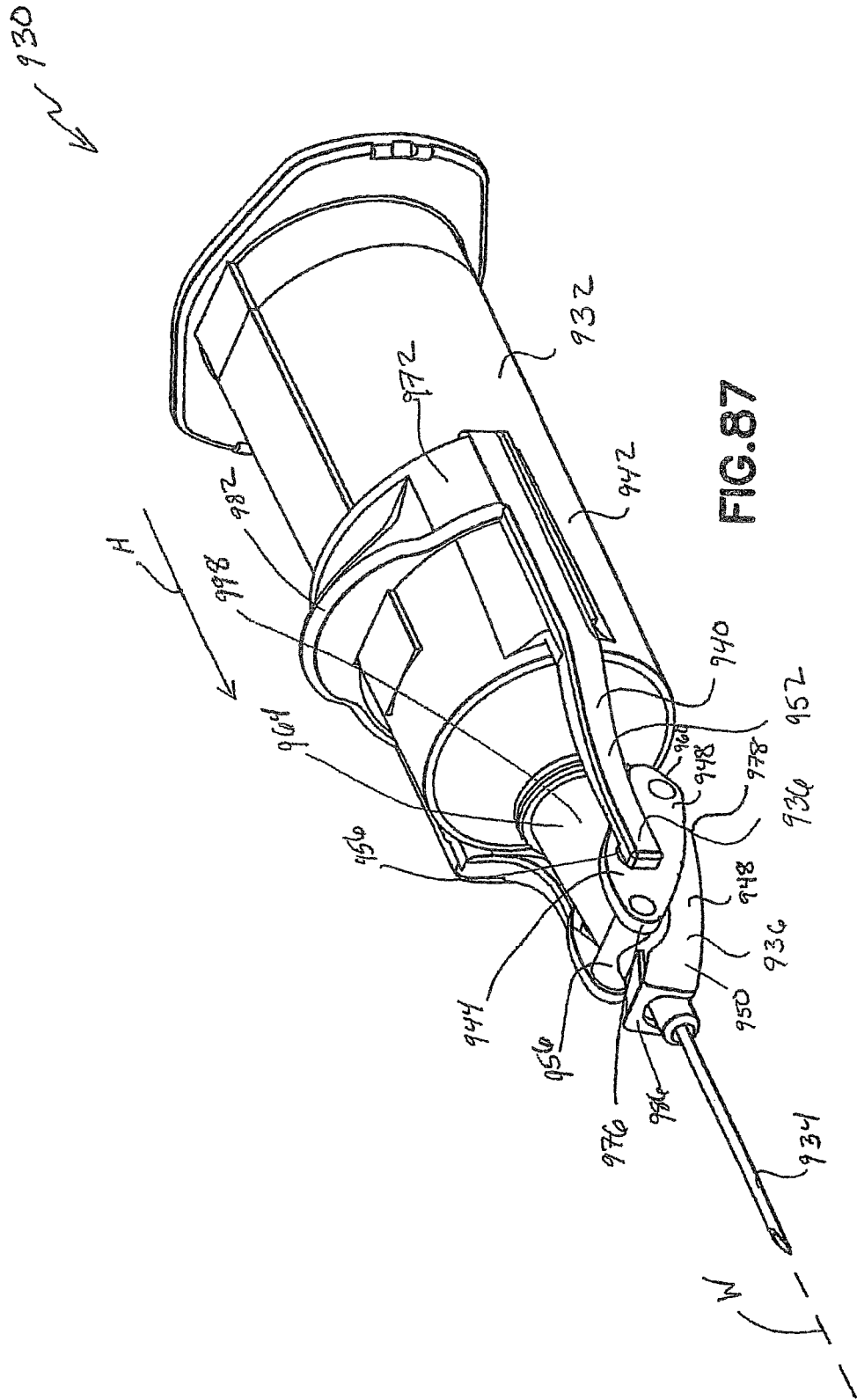
FIG. 87 is a perspective view of a needle assembly having an articulating hinge safety shield in the retracted position in accordance with an embodiment of the present invention.

In one embodiment, the orientation of the depending arm 940 and the second depending arm 970 provides for the flash chamber 998 to be easily viewed when the shield is in the retracted position. In the retracted position, as shown in FIG. 87, the extendable segments 948 are oriented in a substantially lateral orientation, such that a distal alignment end 976 of the first extendable segment 944 is spaced apart from a proximal alignment end 978 of the second extendable segment 950. In one embodiment, the distal alignment end 976 of the first extendable segment 944 is offset or positioned within a distinct longitudinal plane from the proximal alignment end 978 of the second extendable segment 950 in the lateral orientation. In a further embodiment, at least one of the distal alignment end 976 of the first extendable segment 944 and the proximal alignment end 978 of the second extendable segment 950 are offset from the transition axis W of the shield 936 in the lateral orientation.

Figure 88:
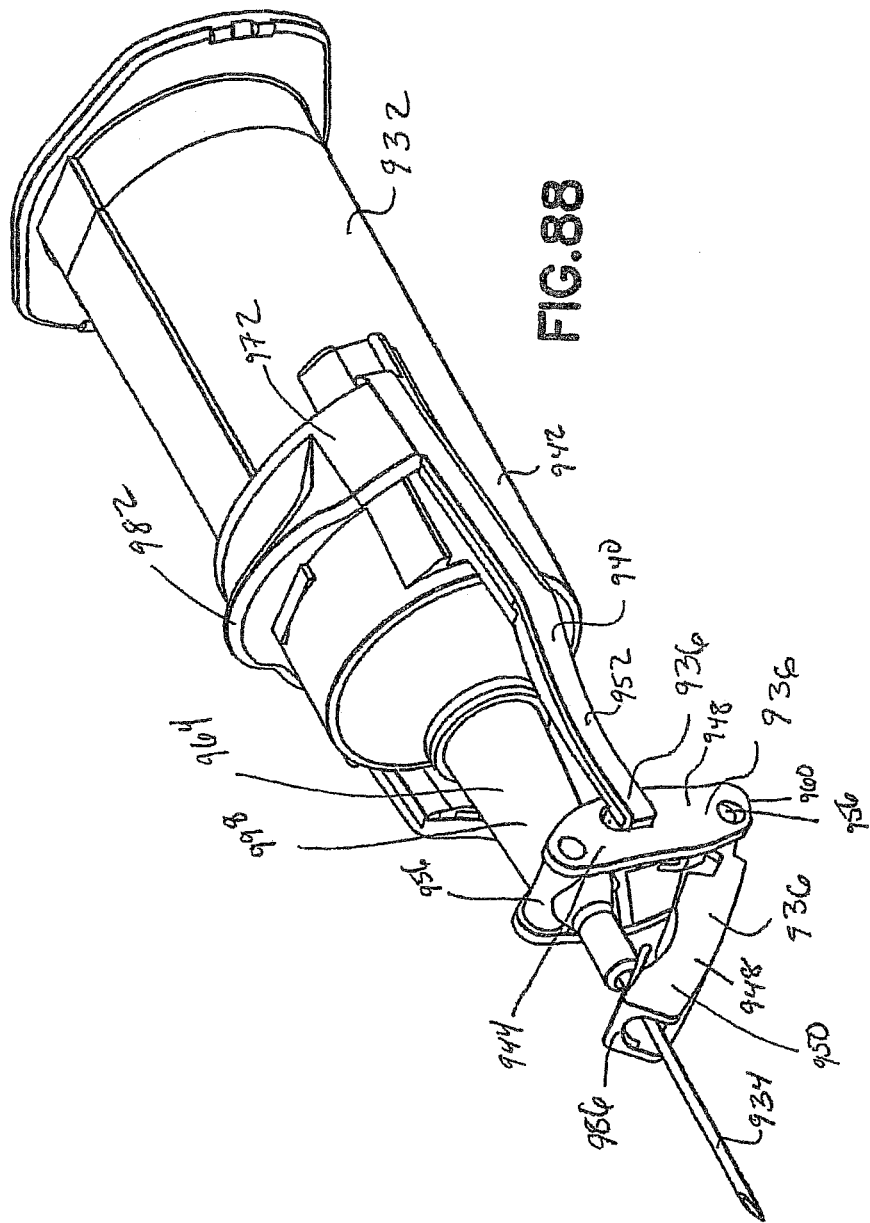
FIGS. 88-90 are perspective views of the needle assembly of FIG. 87 having an articulating hinge safety shield shown in various stages of partial extension.
Figure 89:
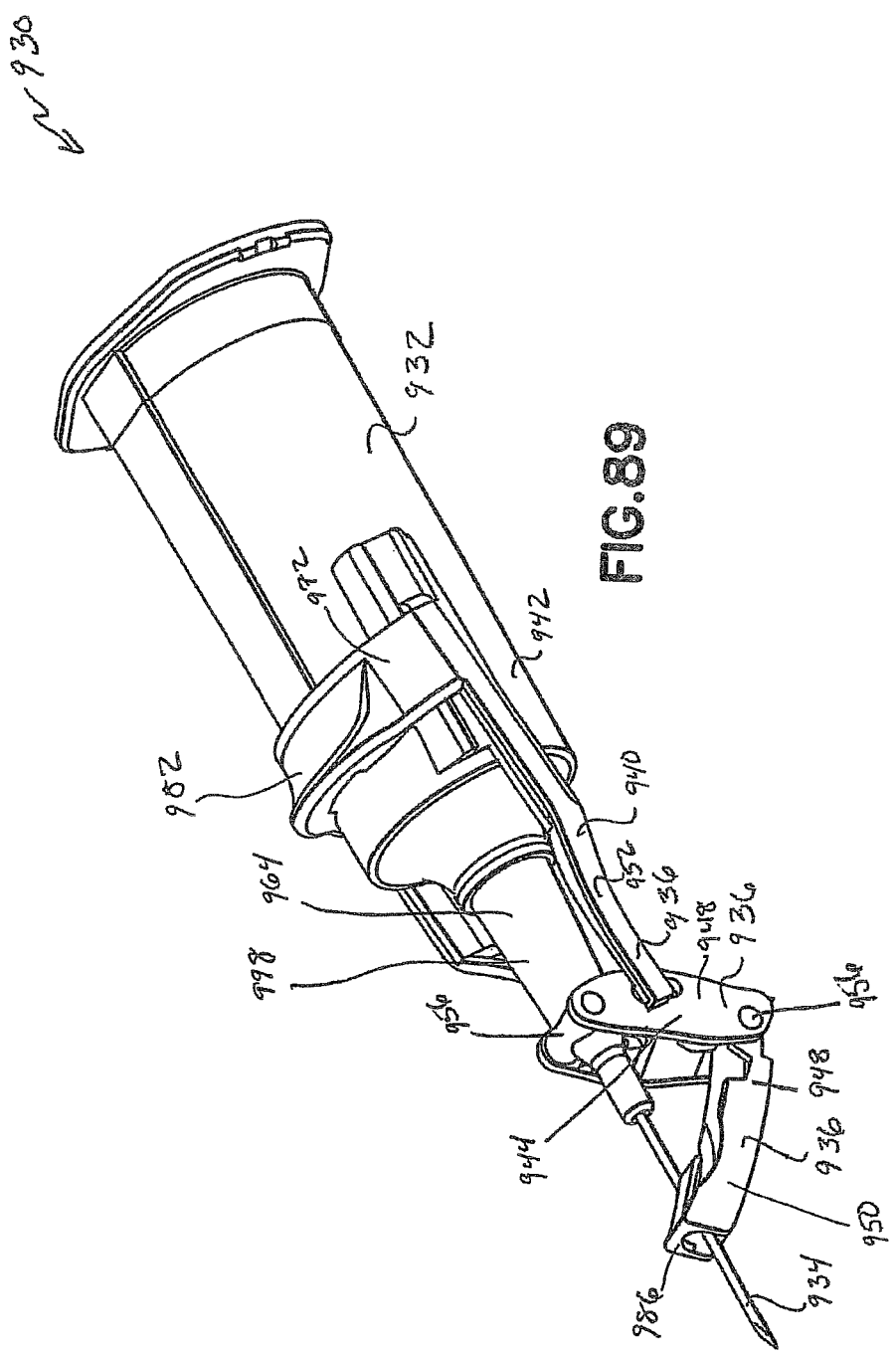
Figure 90:
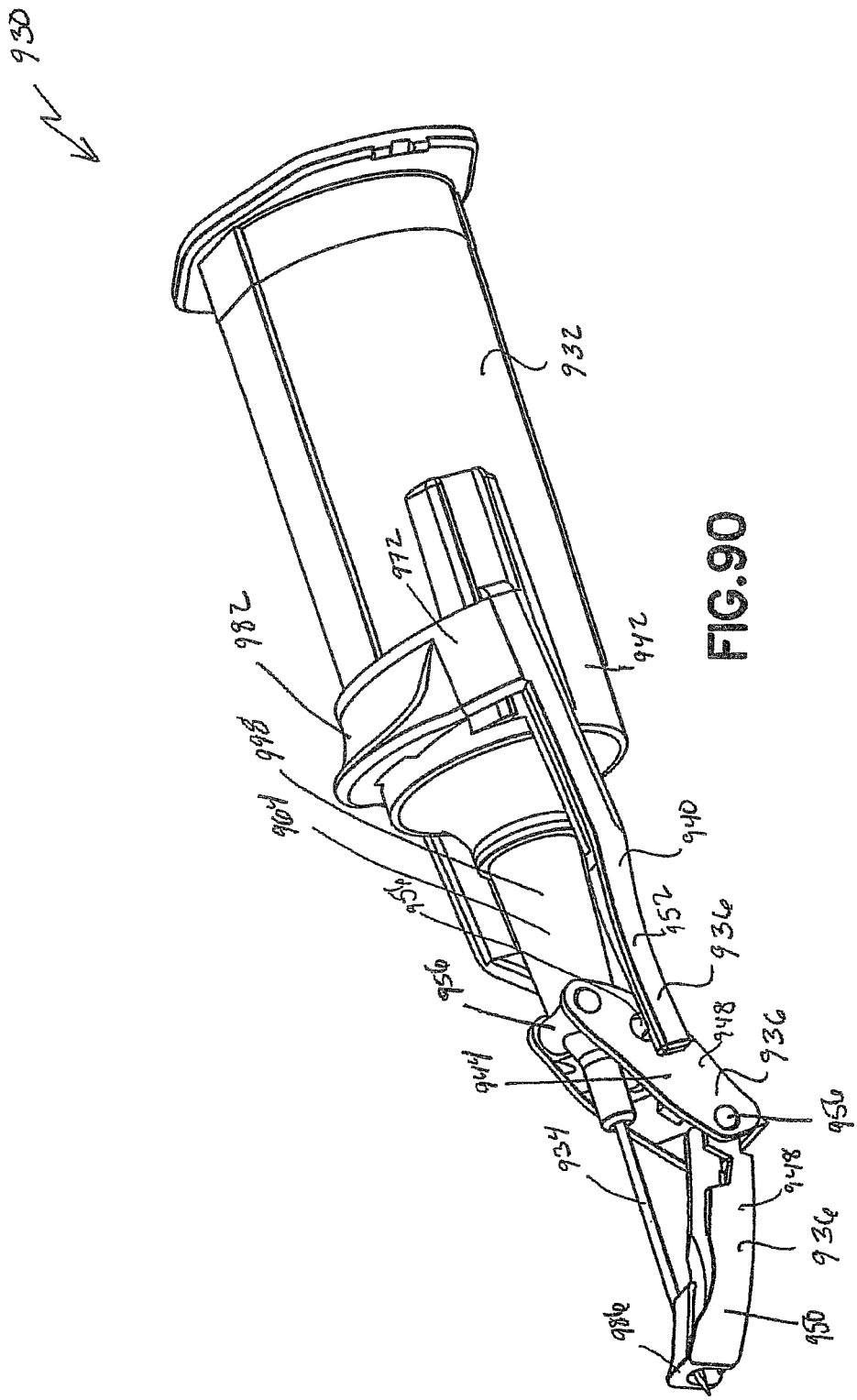

The safety shield 936 may be transitioned from the retracted position to the extended position by the application of manually applied force to the release member 982 in the direction as shown by arrow H, shown in FIG. 87. In the partially extended position, as shown in FIG. 88, the forward urging of the base portion 952 initiates the first extendable segment 944 to articulate about the pivot 956 until a proximal end 960 reaches the apex position (shown in FIG. 88). As shown in FIG. 89, movement of the first extendable segment 944 advances the second extendable segment 950 through pivot 956. Such movement may be accomplished by continued forward movement of release member 982 in the direction of arrow H, shown in FIG. 87, which causes movement of the base portion 952, which in turn articulates the first extendable segment 944. Alternatively, the extendable segments 948 may be constructed of a material having resiliency, so as to effect automatic movement once the first extendable segment 944 reaches an apex, thereby creating a mechanism for automatic continued movement. In order to accommodate this motion, the free end 986 of the second extendable segment 950 is advanced along the transition axis W, shown in FIG. 87.

Figure 91:
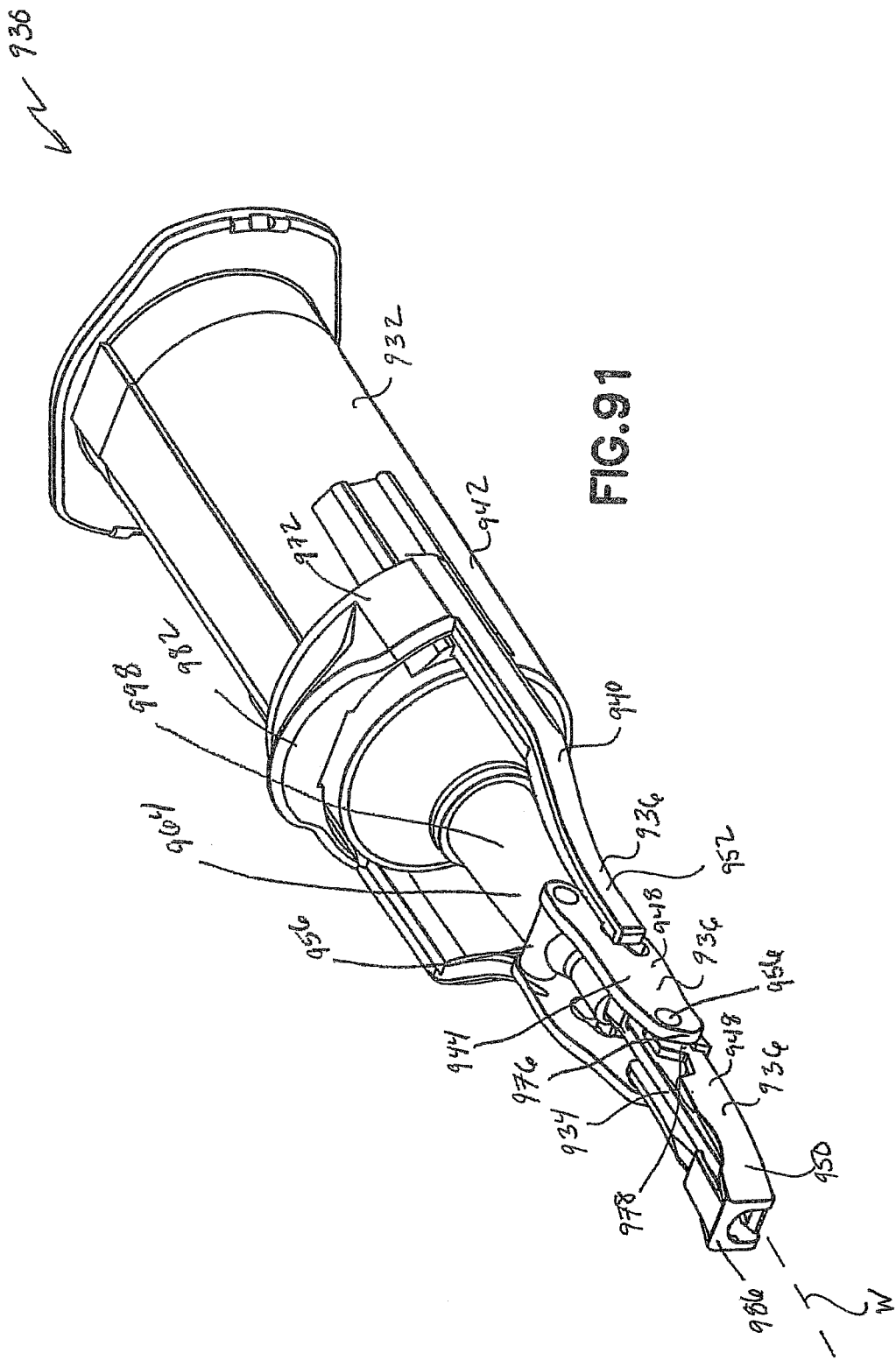
FIG. 91 is a perspective view of the needle assembly of FIG. 87 having an articulating hinge safety shield in the fully extended position.

In the fully extended position, as shown in FIG. 91, the first extendable segment 944 and the second extendable segment 950 are oriented in a substantially parallel orientation with respect to each other along substantially the same longitudinal plane as the cannula 934 in shielding orientation of the cannula 934. In the fully extended position the extendable segments 948 are substantially longitudinally oriented, such that a distal alignment end 976 of the first extendable segment 944 is substantially adjacent the proximal alignment end 978 of the second extendable segment 950. In one embodiment, the distal alignment end 976 of the first extendable segment 944 contacts the proximal alignment end 978 of the second extendable segment 950 along the same longitudinal plane W, as shown in FIG. 91.

The safety shield 936, specifically the first extendable segment 944 and the second extendable segment 950, may have any suitable dimensions and configuration such that they are adapted to shield the cannula 934, and in particular the puncture tip thereof, when the safety shield 936 is in the extended position. The safety shield 936 may be deployed over the cannula 934 while the cannula 934 is accessing the interior of the patient's blood vessel (not shown), or after the cannula 934 has been removed from the patient. A locking mechanism, as similarly described herein, may further be employed to prevent transition of the shield 936 from the extended position to the retracted position once the shield 936 has been transitioned from the retracted position to the extended position.

In one embodiment, the flash chamber 998 may be visible to medical practitioners in both the retracted position and the extended position, as well as in the partly extended position. In another embodiment, transition of the safety shield 936 from the retracted position to the extended position is accomplished without obstructing the view of the flash chamber 998. In this configuration, articulation of the safety shield 936 occurs remotely from the viewpath of the flash chamber 998. For example, the pivots 956 may be positioned on the bottom portion of needle assembly 930, so as not to obstruct a direct top-line view of the flash chamber 998 by a medical practitioner.

Figure 92:
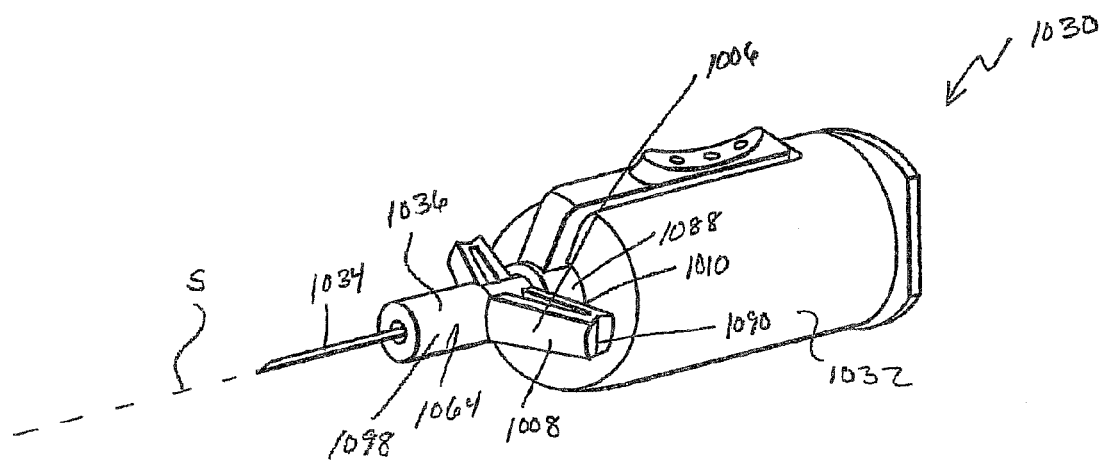
FIG. 92 is a perspective view of a needle assembly having a butterfly hinged safety shield in the retracted position in accordance with an embodiment of the present invention.
Figure 93:
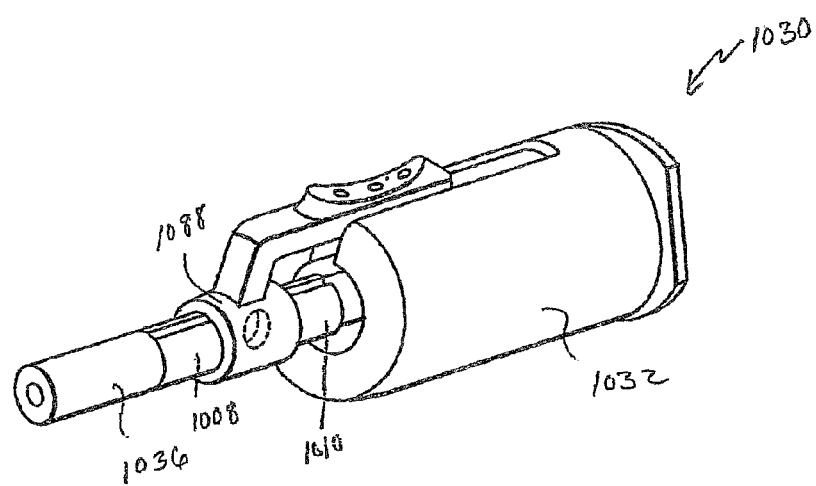
FIG. 93 is a perspective view of the needle assembly of FIG. 92 having a butterfly hinged safety shield shown in the extended position.
Figure 98:
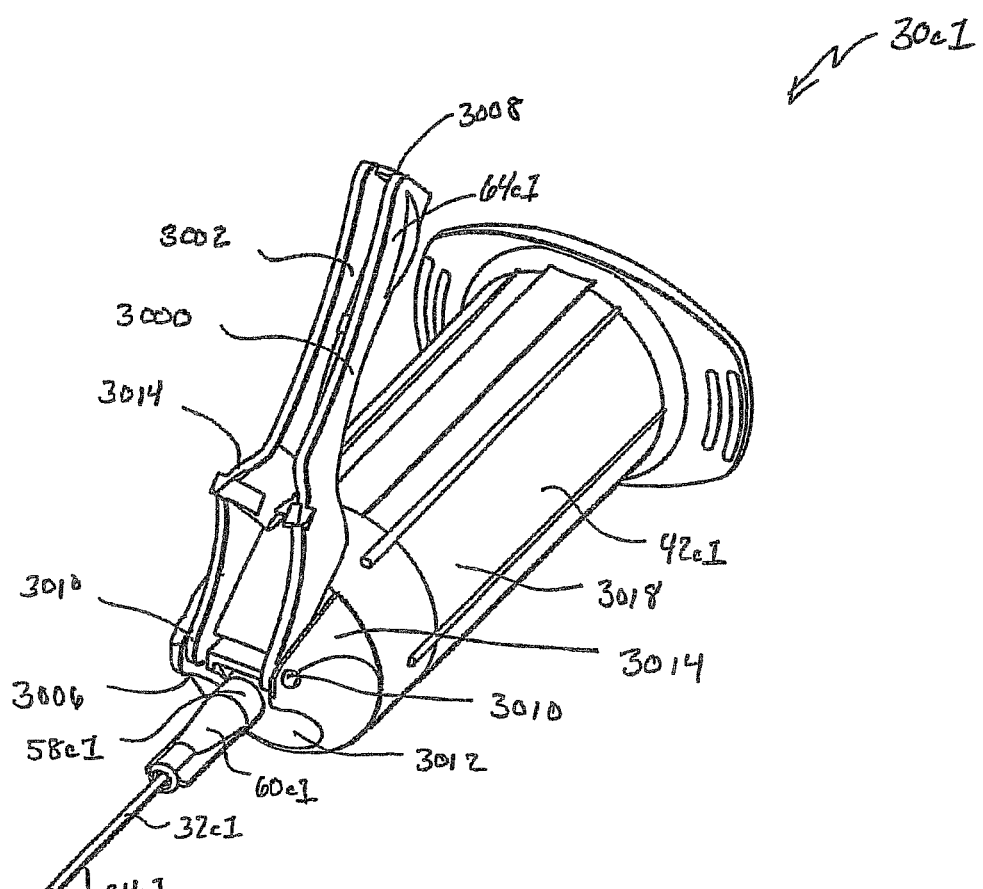
FIG. 98 is a perspective view of the needle assembly of FIG. 94 having the needle guard shield removed and in the retracted position.
Figure 99:
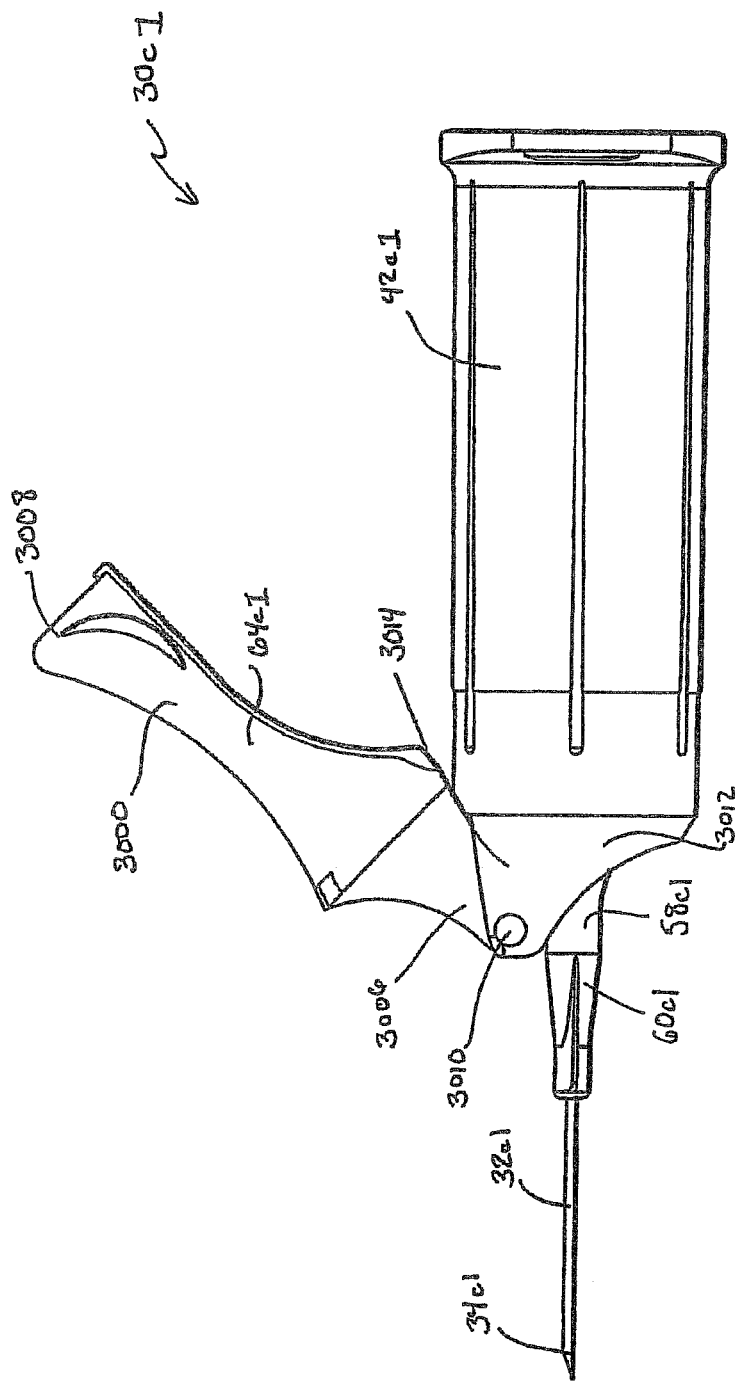
FIG. 99 is a side view of the needle assembly of FIG. 98.
Figure 100:
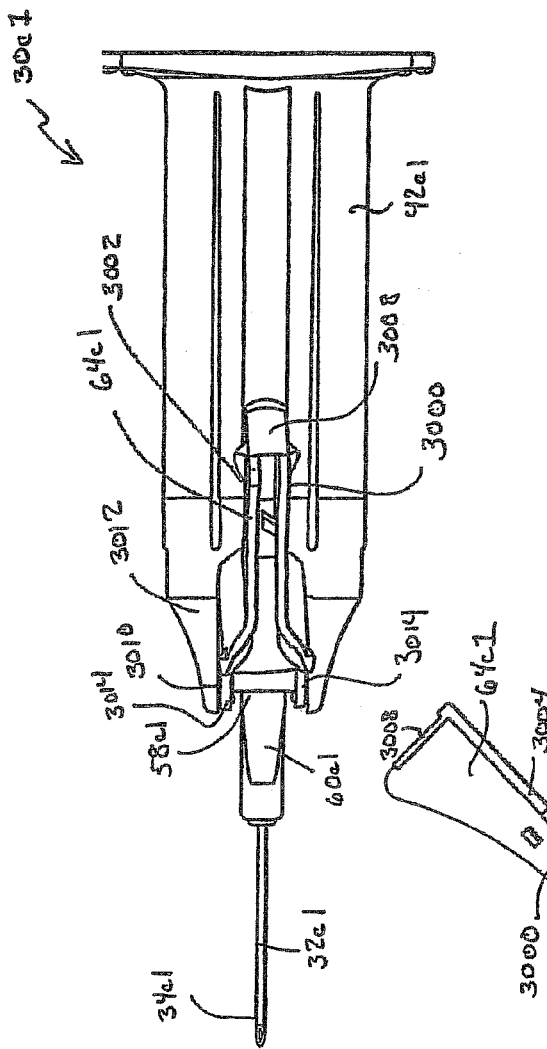
FIG. 100 is a top view of the needle assembly of FIG. 98.
Figure 101:
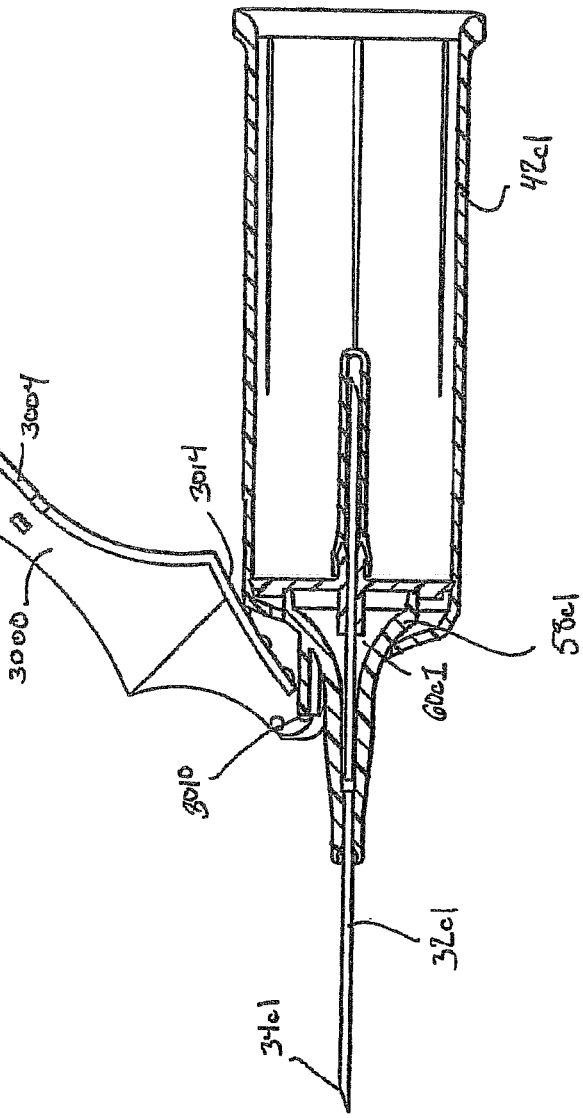
FIG. 101 is a cross-sectional side view of the needle assembly of FIG. 98.

FIGS. 92-93 depict another embodiment of the present invention, in which needle assembly 1030 is similarly as described above, with the exception of the configuration of safety shield 1036 and the attachment of safety shield 1036 to the housing 1032. Needle assembly 1030 generally includes a cannula 1034 associated with the housing 1032, and a safety shield 1036 adapted for safety shielding of the cannula 1034 during and/or after use of the device. Needle assembly 1030 further includes a hub 1064 for supporting the cannula 1034 and defining a flash chamber 1098 therein, as previously described. At least a portion of the hub 1064 and the flash chamber 1098 are visible through a portion of the safety shield 1036 in the retracted position.

In one embodiment, the shield 1036 includes a depending arm 1006 transitionable from a first position, shown in FIG. 92, in which the depending arm 1006 is substantially perpendicular to the longitudinal axis S of the cannula 1034 (shown in FIG. 92), to a second position, shown in FIG. 93, in which the depending arm is substantially oriented along the longitudinal axis S of the cannula 1034. In one embodiment, the depending arm 1006 may include a first portion 1008 and a second portion 1010 pivotally or hingedly connected therebetween.

A portion of the shield 1036 is adapted to at least partially surround, such as circumferentially surround, at least a portion of the tip of the cannula 1034 in the extended position shown in FIG. 93. In one embodiment, the flash chamber 1098 is at least partially visible to a medical practitioner when the safety shield 1036 is in the retracted position. In the retracted position, the first portion 1008 and the second portion 1010 are oriented in a substantially perpendicular orientation with respect to the axis of the cannula 1034, and substantially parallel to each other in the extended position. The shield may further include a circular portion 1088 disposed circumferentially about a portion of the cannula 1034. In one embodiment, once the first portion 1008 and the second portion 1010 are aligned in substantially parallel orientation, the circular portion 1088 may be advanced over the depending arm 1006, such as over the hinge 1090 connecting the first portion 1008 and the second portion 1010, thereby locking the hinge 1090 in place.

In another embodiment, shown in FIGS. 94-106, another alternative hinged assembly embodiment of the present invention is shown. Needle assembly 30c1 generally includes needle structure 32c1 associated with needle holder 42c1, and a safety shield 64c1 adapted for safety shielding of the needle structure 32c1 after use of the device. Needle assembly 30c1 further includes a hub 58c1 for supporting the needle structure 32c1 and a flashback indicator 60c1 defined therein, as previously described.

In the embodiment shown in FIGS. 94-106, the safety shield 64c1 may include a first depending arm 3000 and a second depending arm 3002 substantially parallel to the first depending arm 3000. The first depending arm 3000 and the second depending arm 3002 are connected together by a connection surface 3004 that is substantially perpendicular to the first depending arm 3000 and the second depending arm 3002. The safety shield 64c1 has a proximal end 3006 adjacent the needle holder 42c1 and a distal end 3008 opposed from the proximal end 3006. At least a portion of the proximal end 3006 of the safety shield 64c1 is pivotally connected to the needle holder 42c1. Preferably, the proximal end 3006 of the safety shield 64c1 is connected to the needle holder 42c1 by two opposing pivots 3010. In a further embodiment, the safety shield 64c1 is pivotally connected to the front cone 3012 of the needle holder 42c1 by pivots 3010 extending through opposing attachment arms 3014 connected to the front cone 3012 and oriented along the longitudinal axis of the needle holder 42c1.

Figure 102:
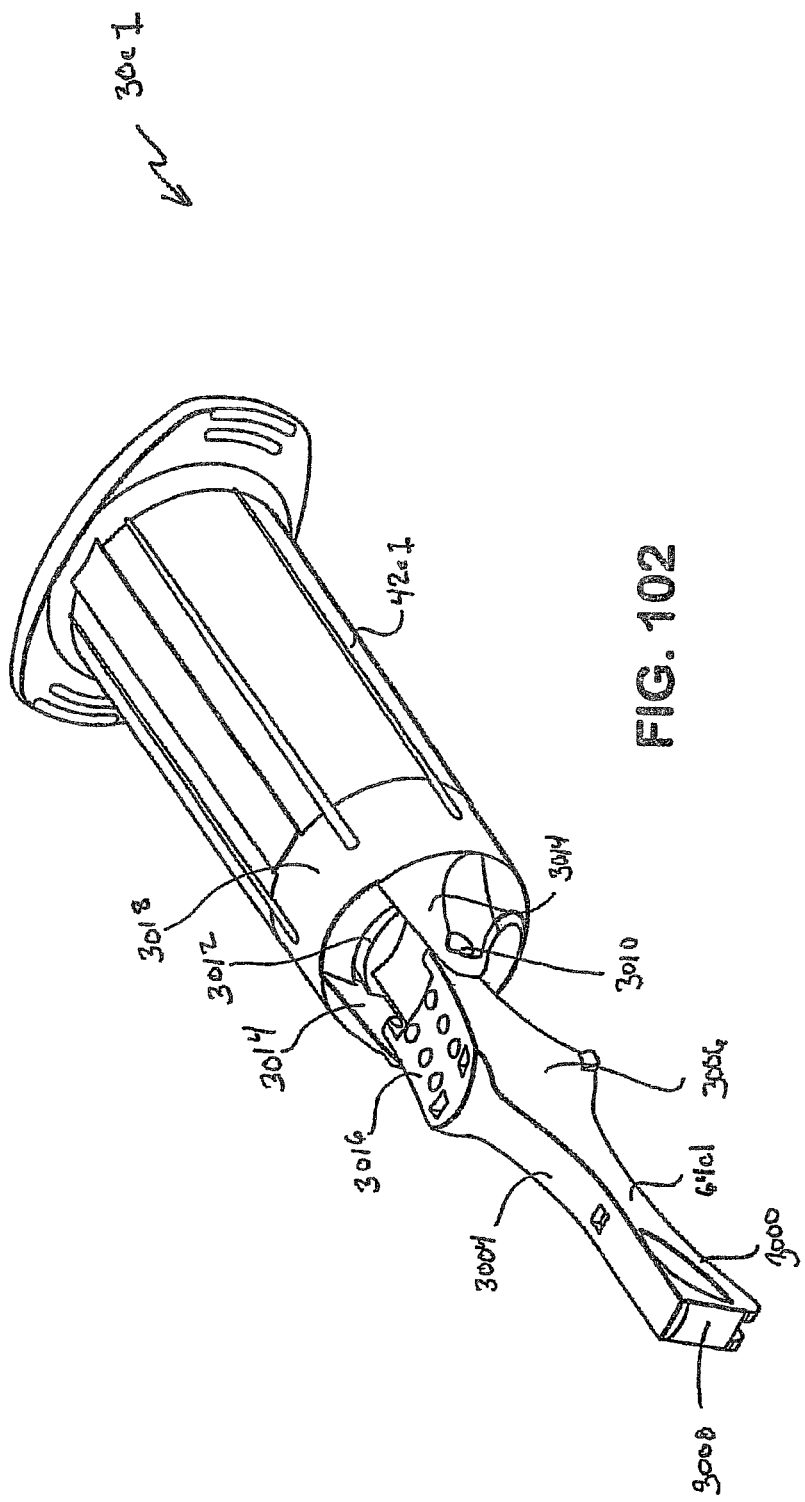
FIG. 102 is a perspective view of the needle assembly of FIG. 98 in the extended position.

The pivot(s) 3010 allow the safety shield 64c1 to transitionally pivot in a rotational manner with respect to the needle holder 42c1 from a retracted position, as shown in FIGS. 98-101 to an extended position, as shown in FIGS. 102-104. In one embodiment, the safety shield 64c1 may also include a shield engaging area 3016 within the connection surface 3004 adjacent the proximal end 3006 having a contour substantially corresponding to the contour of the exterior surface 3018 of the needle holder 42c1 and/or the exterior surface 3018 of the front cone 3012. In this configuration, the shield engaging area 3016 may rest against a portion of the needle holder 42c1 in the retracted position.

As shown in FIG. 97, the hub 58c1 may include a front hub portion 3026 and a rear hub portion 3028 joined to the first hub portion 3026. The front hub portion 3026 may have a substantially conical shape disposed about the flashback indicator 60c1. In one embodiment, at least a portion of the front hub portion 3026 extends distally beyond the front cone 3012 of the needle holder 42c1. In another embodiment, at least a portion of the front hub portion 3026 has a contour that corresponds to a contour of the front cone 3012 of the needle holder 42c1. The rear hub portion 3028 of the hub 58c1 may include a disk structure dimensioned to contact an interior perimeter of the needle holder 42c1 to prevent advancement of an evacuated blood collection tube (not shown) therebeyond. At least a portion of the needle structure 32c1 may extend through the front hub portion 3026 and the rear hub portion 3028 of the hub 58c1. Although the hub 58c1 may be provided within the collection assembly as an integral element, in an alternative configuration, the hub 58c1, including the front hub portion 3026 and the rear hub portion 3028, as well as the needle structure 32c1 may be separately formed and subsequently assembled within the collection assembly 30c1.

In one embodiment, the needle assembly 30c1 may be provided with a removable IV needle shield 3020 covering at least a portion of the needle structure 32c1, such as covering at least a portion of the distal needle portion 34c1. In one embodiment, as shown in FIG. 97, the needle shield 3020 can be sized to extend over at least a portion of the front hub portion 3026 of the hub 58c1, the front cone 3012 of the needle holder 42c1, the flashback indicator 60c1, and/or the hub 58c1. The needle shield 3020 can be removed from the needle assembly 30c1 prior to use by typical manual applied pressure.

Referring again to FIG. 97, in another embodiment the needle shield 3020 can be provided with a raised protrusion 3022 disposed on the exterior surface 3024 of the needle shield 3020. In one embodiment, the raised protrusion 3022 is circumferentially disposed about the needle shield 3020. In another embodiment, the raised protrusion 3022 corresponds to a notch 3030 within the safety shield 64c1 such that the needle shield 3020 cannot be accidentally released from the needle assembly 30c1 until the safety shield 64c1 is positioned in the retracted position, as shown in FIGS. 98-101.

The safety shield 64c1 can be sized to have any dimensions suitable to allow the safety shield 64c1 to be pivoted away from the needle structure 32c1 in the retracted position, as shown in FIGS. 98-101, to allow a medical practitioner to engage the needle structure 32c1 with a patient, and to pivot toward and shield the needle structure 32c1, specifically the tip of the distal needle portion 34c1 in the extended position, as shown in FIGS. 102-104. In one embodiment, the safety shield 64c1 may be pivoted away from the axis of the needle structure 32c1 to a sufficient angle to allow a medical practitioner to view the flashback indicator 60c1 and/or hub 58c1 in the retracted position. In another embodiment, the safety shield 64c1 is made of a transparent and/or translucent material to allow a medical practitioner to view the flashback indicator 60c1 and/or hub 58c1 therethrough.

Figure 105:
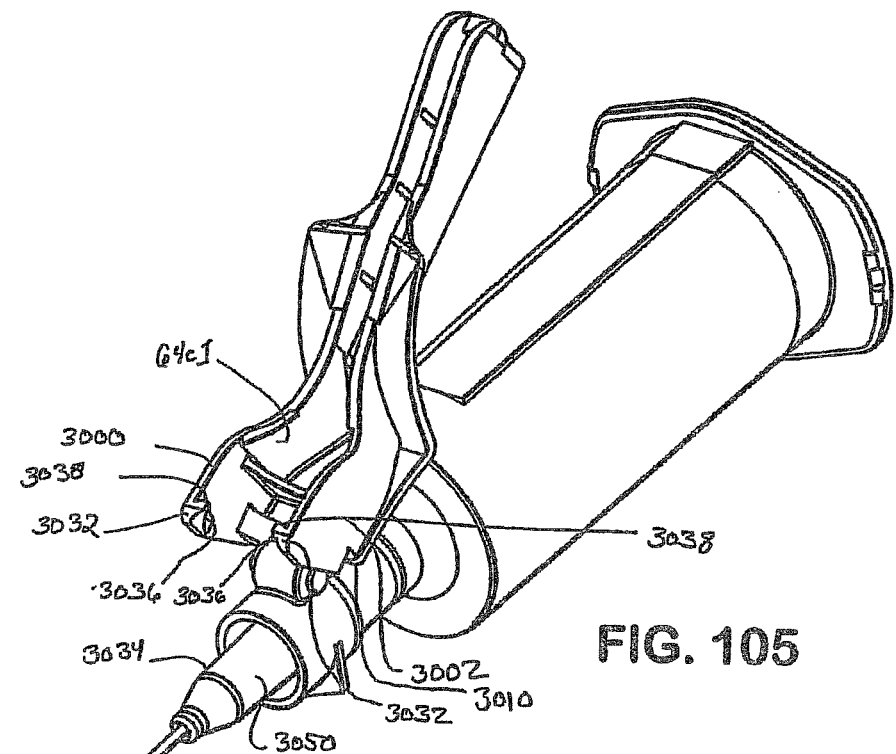
FIG. 105 is a perspective view of the engagement of the safety shield and the front hub portion in accordance with an embodiment of the present invention.
Figure 106:
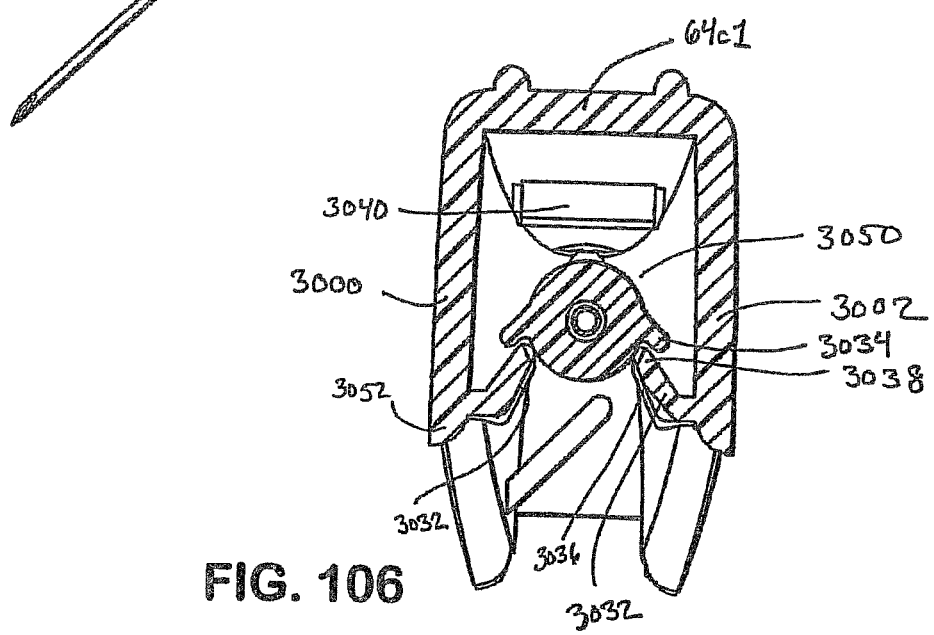
FIG. 106 is a close-up sectional perspective view of the engagement between the safety shield and the front hub portion in accordance with an embodiment of the present invention.
Figure 107:
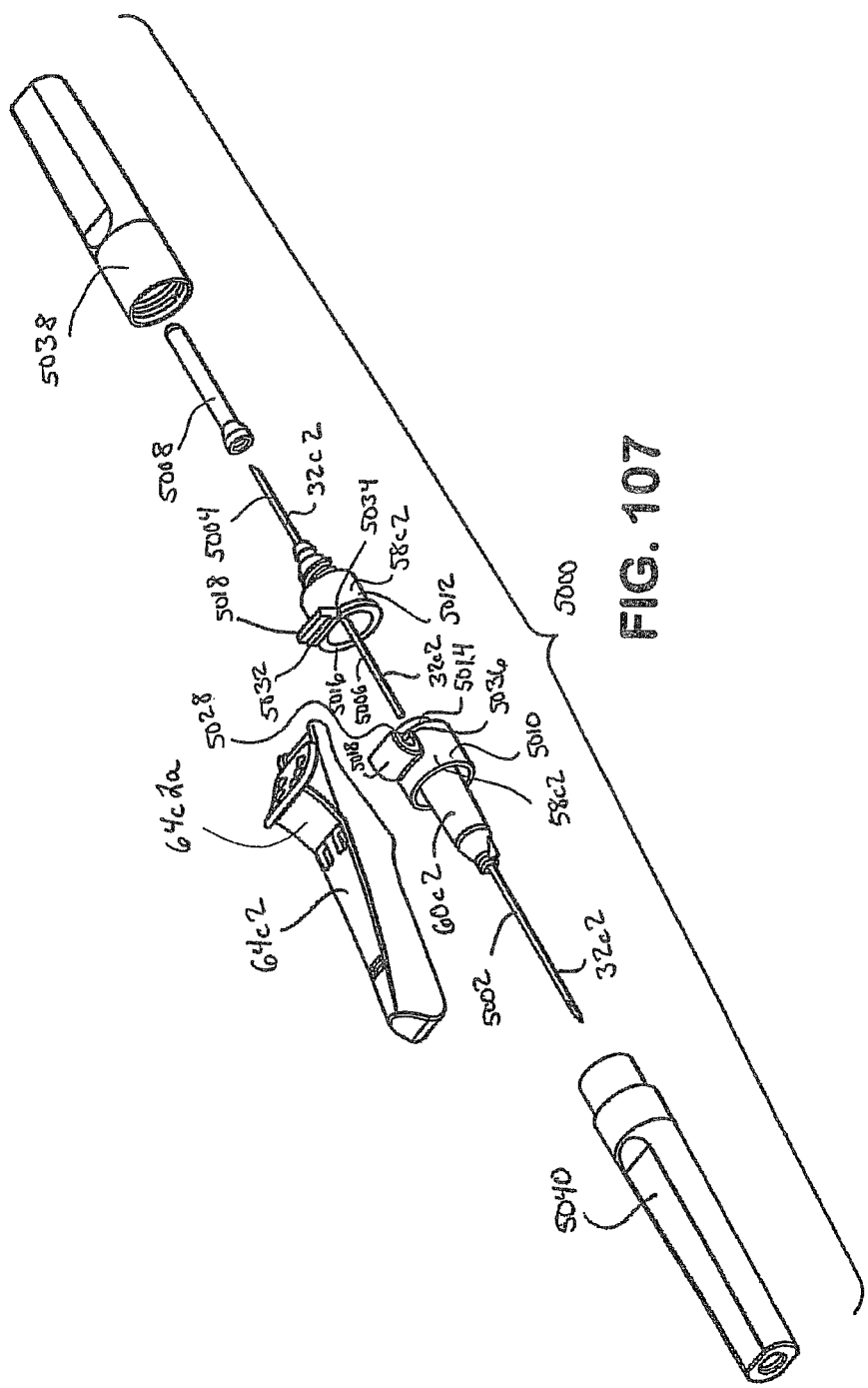
FIG. 107 is an exploded perspective view of a needle assembly having a hinged safety shield in accordance with an embodiment of the present invention.
Figure 108:
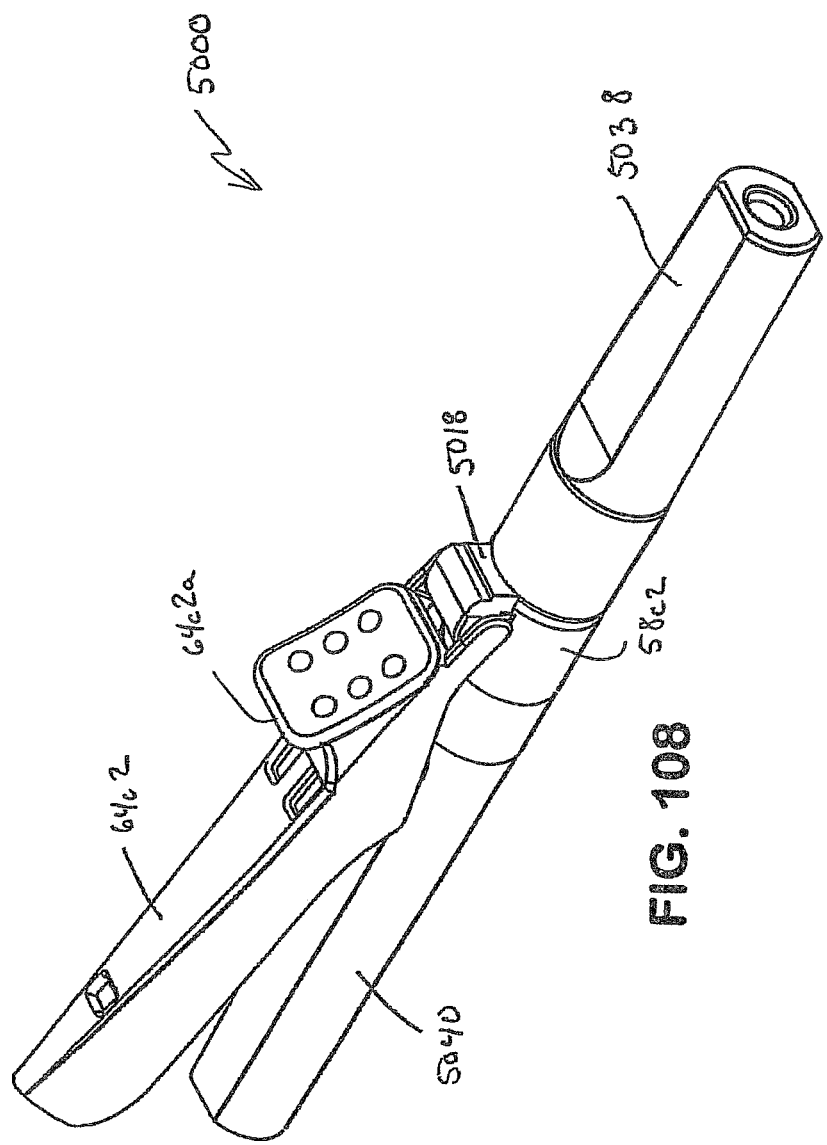
FIG. 108 is an assembled perspective view of the needle assembly of FIG. 107 in the retracted position.
Figure 111:
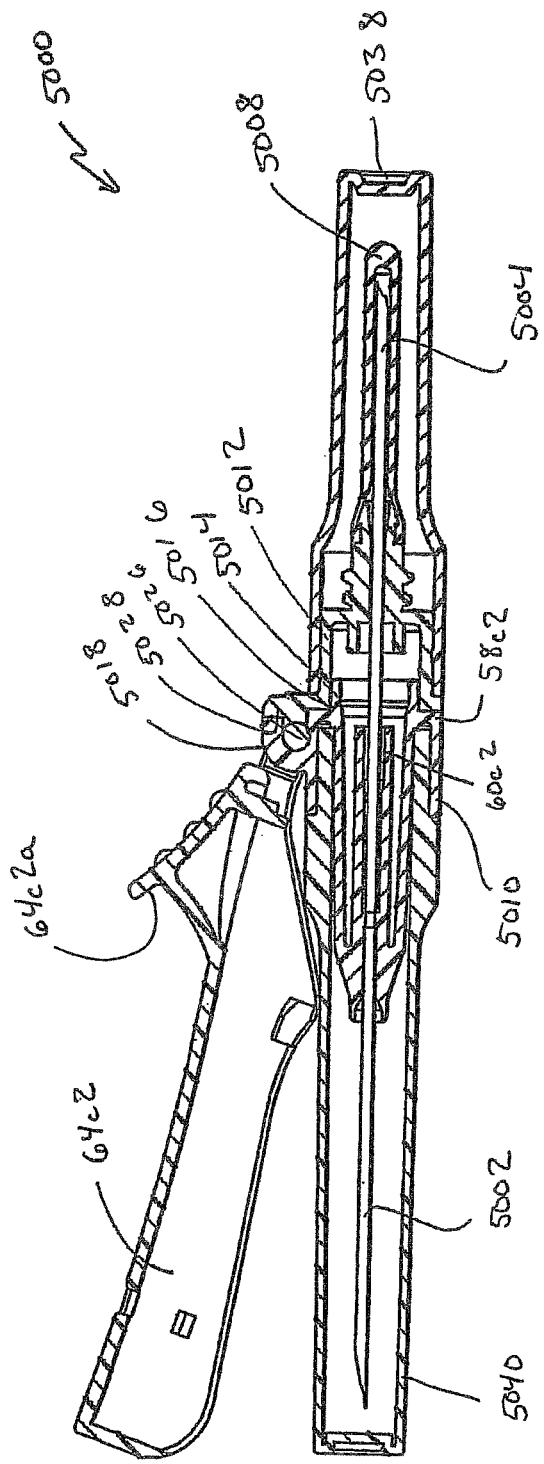
FIG. 111 is a cross-sectional side view of the needle assembly of FIG. 108.
Figure 112:
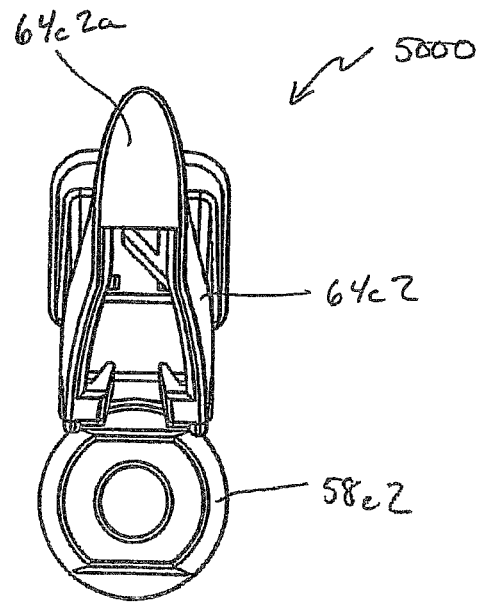
FIG. 112 is a front view of the needle assembly of FIG. 108.
Figure 113:
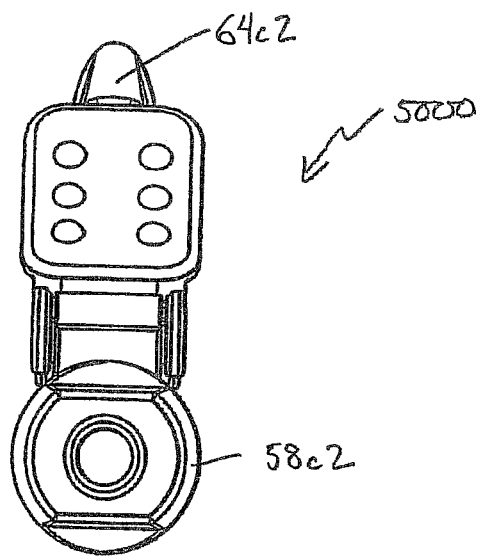
FIG. 113 is a rear view of the needle assembly of FIG. 108.

Once the distal needle portion 34c1 has been removed from the patient, the needle assembly 30c1 may be transitioned from the retracted position to the extended position. In one embodiment, the first depending arm 3000 and the second depending arm 3002 of the safety shield 64c1 may be constructed to form a press-fit lock with at least a portion of the front hub portion 3026, the front cone 3012 and/or the needle holder 42c1. This prevents the safety shield 64c1 from re-transitioning to the retracted position once the initial transition from the retracted position to the extended position has occurred. As shown in FIGS. 105-106, the first depending arm 3000 and the second depending arm 3002 may each include an inwardly angled restraint 3032 disposed adjacent the pivot 3010 at the proximal end 3006 of the safety shield 64c1. The angled restraint 3032 includes a sloped surface 3036 and a restraining surface 3038. The front hub portion 3026 may also include a plurality of ledges 3034 for engaging the angled restraints 3032. In one embodiment, when the safety shield 64c1 of the needle assembly 30c1 is transitioned from the retracted position to the extended position, the angled restraint 3032 of the safety shield 64c1 engages the ledge(s) 3034 of the front hub portion 3026. Specifically, the restraining surface 3038 engages the ledge(s) 3034 and prevents subsequent movement of the safety shield 64c1. In one embodiment, the ledge(s) 3034 are positioned on the distal end 3050 of the hub 58c1. In another embodiment, the angled restraint(s) 3032 are positioned on the safety shield 64c1 at a location distal from the pivot(s) 3010 for correspondingly engaging the ledge(s) 3034 on the distal end 3050 of the hub 58c1. Alternatively, the front cone 3012 may also include a plurality of ledges 3034a for engaging the angled restraint 3032 of the safety shield 64c1. In yet another embodiment, the angled restraint(s) 3032 are positioned on the superior side 3052 of the safety shield 64c1 and may extend in a direction proximal from the pivot(s) 3010. Accordingly, the engagement of the safety shield 64c1 and the hub 58c1 may occur at the superior side 3052 (bottom side), of the needle assembly 30c1. Transition of the angled restraint 3032 over the ledge(s) 3034 can be effectuated with typical manual pressure. As shown in FIG. 106, the safety shield 64c1 may optionally include a biasing element 3040 for further securing the front hub portion 3026 within the safety shield 64c1. Thus, the locking structure of the safety shield 64c1 engages at least a portion of the flash chamber, defined within the hub 58c1. In one embodiment, the locking structure of the safety shield 64c1 engages at least a portion of the housing, such as the hub 58c1, at a location distal to the flash chamber.

FIGS. 107-121 depict yet another alternative hinged assembly embodiment of the present invention. A needle assembly 5000, as shown in FIGS. 107-113, generally includes a needle structure 32c2, associated with a hub 58c2, and a safety shield 64c2 connected to the hub 58c2 and adapted for safety shielding of the needle structure 32c2 after use of the device. In one embodiment, the needle assembly 5000 may incorporate features of other known needle assemblies having hinged safety shields, such as those disclosed in United States Patent Publication No. 2005/0187493, the entire disclosure of which is hereby incorporated by reference.

The needle structure 32bc2 may include a distal needle portion 5002 and a proximal needle portion 5004. Distal needle portion 5002 and proximal needle portion 5004 may be separate needles, both of which represent needle cannulae defining central lumen 5006 extending therethrough. The proximal needle portion 5004 represents a non-patient end of the needle structure 32bc2, which is provided for puncturing of an evacuated blood collection tube (not shown). The proximal needle portion 5004 may be covered by an elastomeric multiple sample sleeve 5008 that can be pierced by a pointed end of proximal needle portion 5004 of the needle structure 32c2. Distal needle portion 5002 represents a patient end of the needle structure 32c2, and may be beveled to define a puncture tip for puncturing the skin of a patient and accessing the vasculature of the patient.

The hub 58c2 may include a front hub portion 5010 and a rear hub portion 5012 and is capable of supporting the needle structure 32c2 therethrough. In one embodiment, the distal needle portion 5002 may be integral with the front hub portion 5010 and the proximal needle portion 5004 may be integral with the rear hub portion 5012. The front hub portion 5010 and the rear hub portion 5012 are structured to matingly engage. The front hub portion 5010 may include a protrusion 5014, such as a raised annular ring, for engaging a corresponding recess 5016 integral to the rear hub portion 5012. In another embodiment, the front hub portion 5010 and the rear hub portion 5012 may be joined together via an adhesive or weld. Once assembled, the hub 58c2 defines a flashback indicator 60c2 therein, as previously described.

The hub 58c2 may further include a collar 5018 for surrounding at least a portion of the safety shield 64c2, such as a pivot 5020 of the safety shield 64c2, as previously described herein. In one embodiment, the front hub portion 5010 includes a first collar portion 5022 and the rear hub portion 5012 includes a second collar portion 5024. The first collar portion 5022 may include a generally c-shaped region 5028 for accommodating an attachment bearing 5026 of the safety shield 64c2, shown in FIGS. 112 and 114, therein. The attachment bearing 5026 may be integral with the safety shield 64c2. The attachment bearing 5026 may also be integral with a portion of the hub 58c2, such as the first collar portion 5022 and/or the second collar portion 5024. Alternatively, the attachment bearing 5026 may be separately provided and subsequently assembled with the safety shield 64c2 and/or the hub 58c2. The attachment bearing 5026 can extend between a first depending arm 5044 and a second depending arm 5046 of the safety shield 64c2, as shown in FIG. 115. The second collar portion 5024 may include a cap region 5030 having an interior surface 5032 substantially corresponding to the attachment bearing 5026 of the safety shield 64c2. The first collar portion 5022 may include a protrusion 5034 for engaging a corresponding recess 5036 integral to the second collar portion 5024. Accordingly, in one embodiment, the engagement of the front hub portion 5010 with the rear hub portion 5012 also engages the first collar portion 5022 with the second collar portion 5024. In another embodiment, the collar 5018 is positioned substantially on a top surface of the hub 58c2 to allow the safety shield 64c2 to likewise be connected to the top surface of the hub 58c2.

Referring again to FIGS. 107-113, a proximal IV needle shield 5038 and a distal IV needle shield 5040 can be respectively provided over the proximal needle portion 5004 and the distal needle portion 5002 prior to use, as described herein.

During use, the proximal IV needle shield 5038 can be removed from the proximal needle portion 5004 and the needle holder 42c2, shown in FIGS. 115-121, can be inserted over the proximal needle portion 5004 and engaged with at least a portion of the hub 58c2. In one embodiment, the needle holder 42c2 is engaged with a portion of the rear hub portion 5012.

Figure 114:
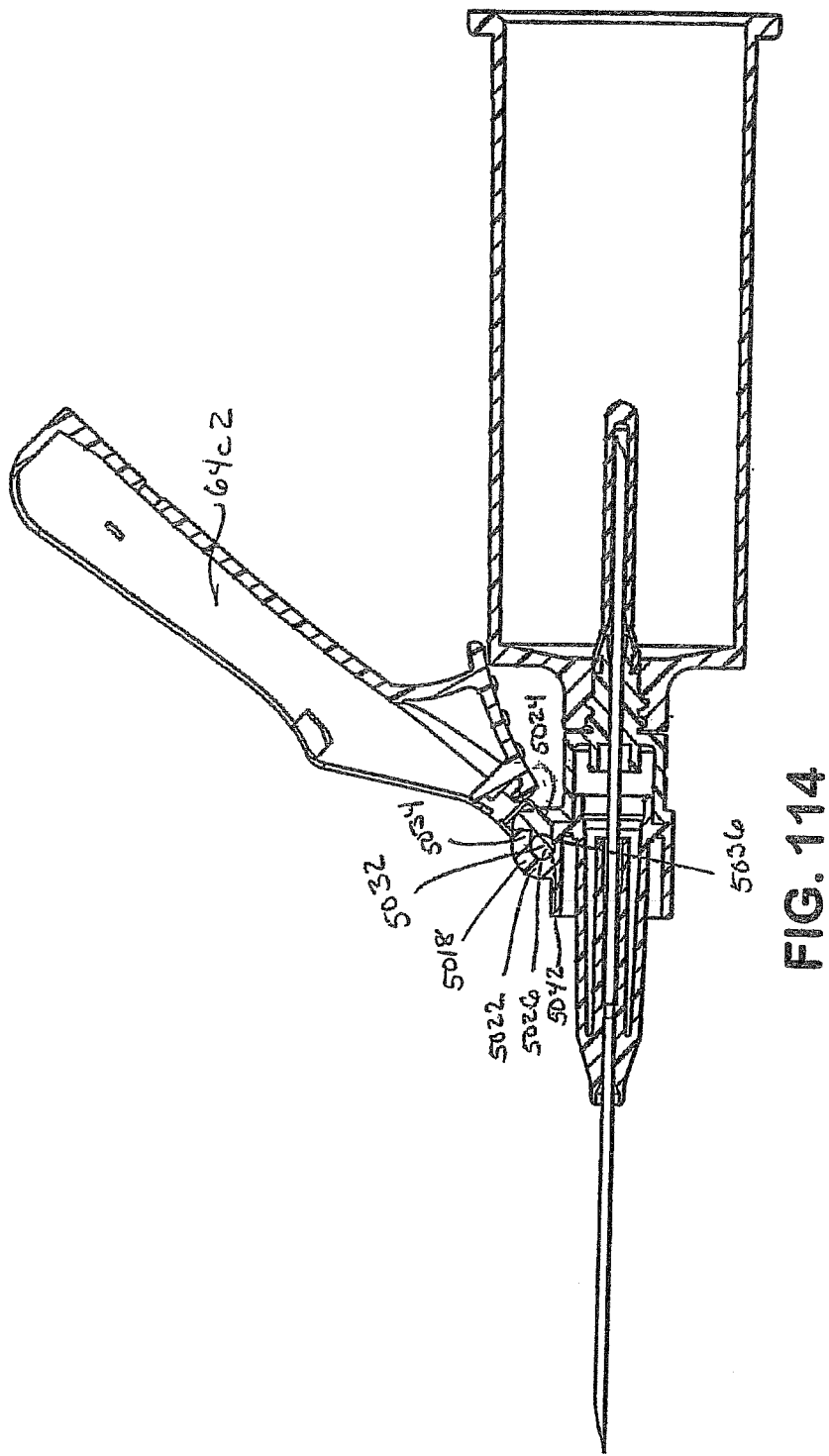
FIG. 114 is a cross-sectional side view of the needle assembly of FIG. 108.
Figure 115:
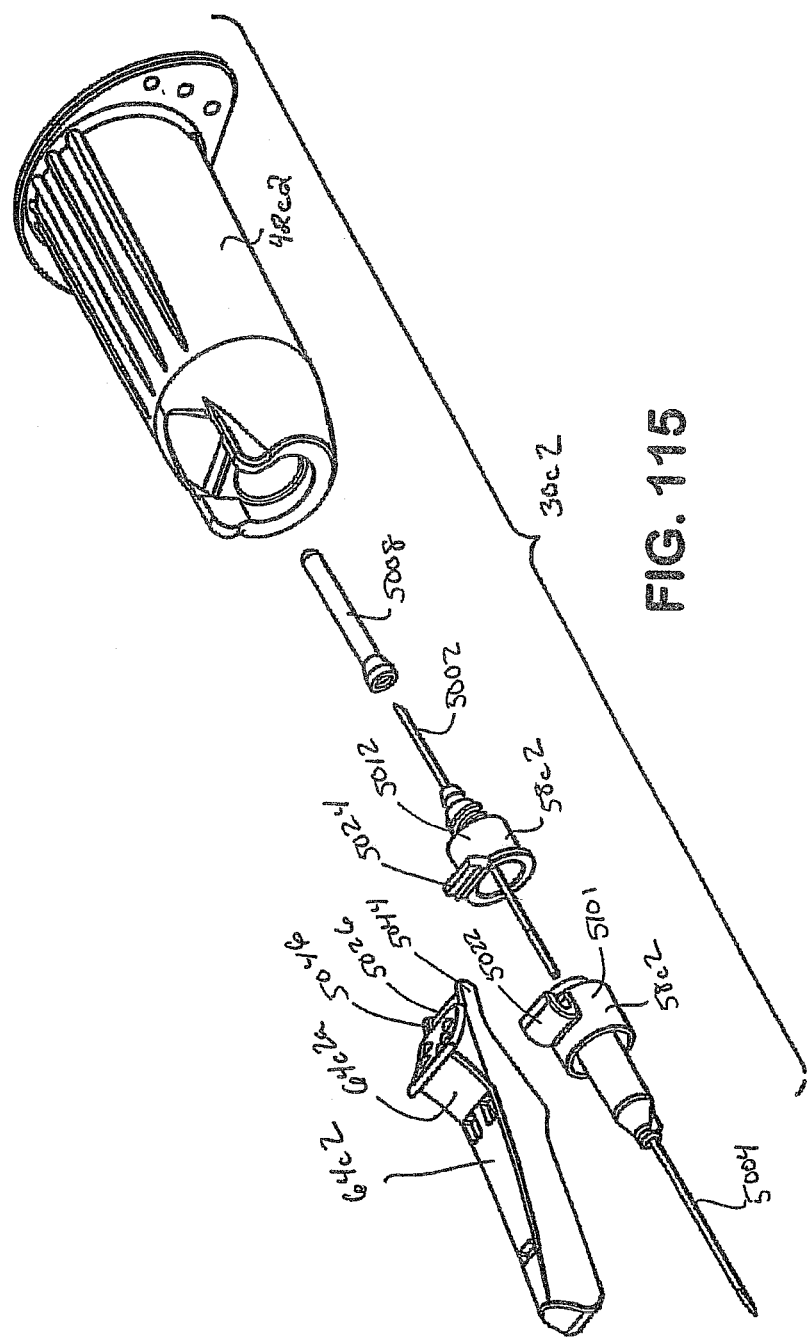
FIG. 115 is an alternative exploded view of a needle assembly having a hinged safety shield in accordance with an embodiment of the present invention.
Figure 119:
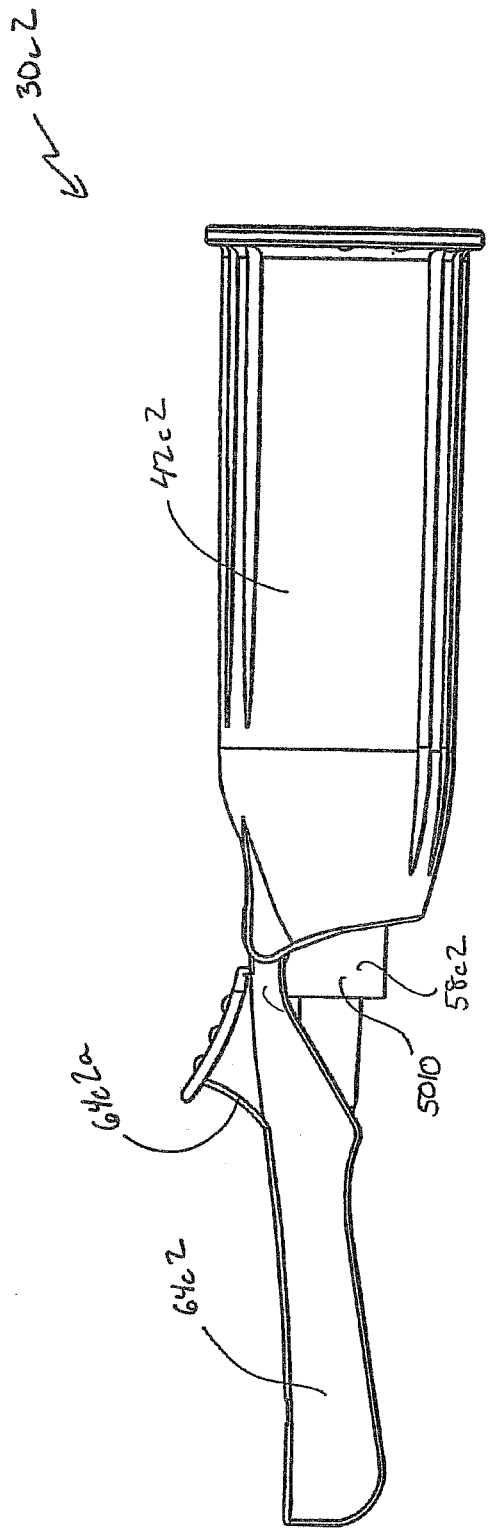
FIG. 119 is a side view of the needle assembly of FIG. 116 in the extended position.
Figure 120:
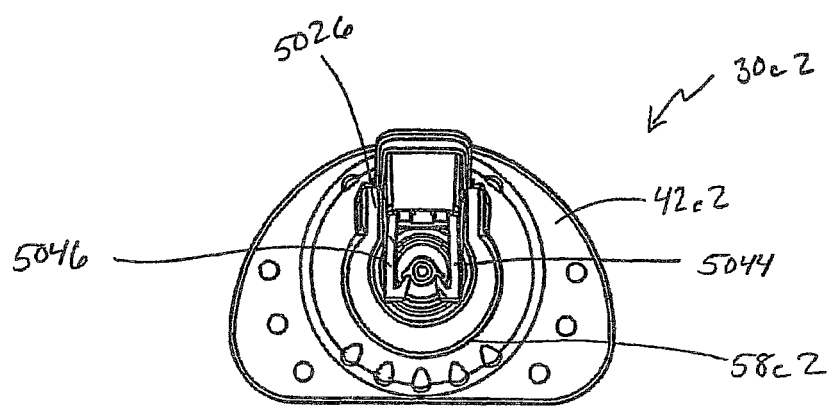
FIG. 120 is a front view of the needle assembly of FIG. 116.
Figure 121:
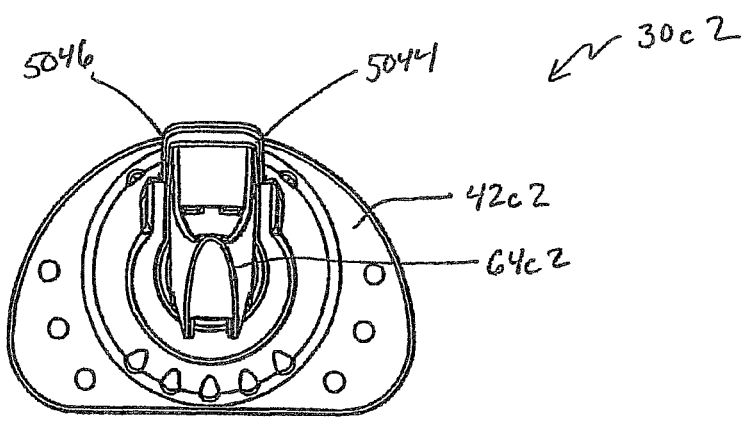

In another embodiment, shown in FIG. 114, the attachment bearing 5026 of the safety shield 64c2 may include a notch 5042 for retaining the safety shield 64c2 within a specified location. For example, the notch 5042 may frictionally retain the safety shield 64c2 within the collar 5018 at a specified angle in the retracted position. This allows a medical practitioner to position the safety shield 64c2 at a desired angle during a medical procedure without attending to accidental closure or slippage of the safety shield 64c2.

As shown in FIGS. 115-121, the needle assembly 30c2 can be transitioned from the retracted position, shown in FIG. 114, in which the distal needle portion 5002 is unshielded for the purpose of accessing a patient, to the extended position, in which the distal needle portion 5002 is safety shielded from exposure, as described herein. With reference to FIGS. 107-121, in another embodiment, the safety shield 64c2 may include a thumb press-region 64c2a for enabling a medical practitioner to pivot the safety shield 64c2 to engage a portion of the proximal IV shield 5038 prior to puncturing the skin of a patient. In one embodiment, the thumb press-region 64c2a extends at least partially beyond the safety shield 64c2 to enable the medical practitioner to easily contact the thumb-press region 64c2a with a single finger or thumb.

Figure 122:
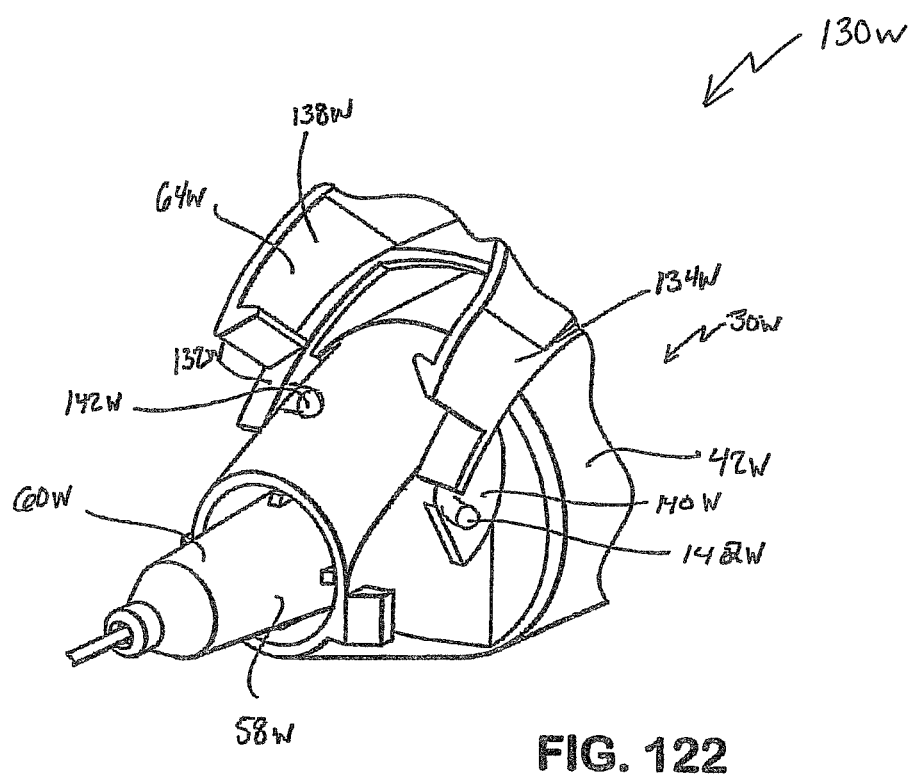

In an alternative embodiment, as shown in FIG. 122, a collection assembly 130w, may include a safety shield 64w may include a first end 138w having a first depending arm 132w and a second depending arm 134w substantially parallel to the first depending arm 132w. The first depending arm 132w and the second depending arm 134w may be connected together. The first depending arm 132w and the second depending arm 134w may have substantially the same area. The safety shield 64w has an end 140w that is connected to the needle holder 42w by at least one pivot 142w. Preferably, the end 140w of the safety shield 64w is connected to the needle holder 42w by two pivots 142w. Example pivoting mechanisms are described in United States Patent Publication No. 2005/187,493, the entire content of which is herein incorporated by reference.

In one embodiment, the pivot 142w may include a protrusion integrally formed with the second end 140w of the safety shield 64w and a corresponding recess defined in the distal end of the needle holder 42w. In another embodiment, the pivot 142w may include a recess defined within the second end 140w of the safety shield 64w and a corresponding recess defined within the distal end of the needle holder 42w. In yet another embodiment, a first pivot 142w can be disposed on a first side of the distal end of the needle holder 42w and a second pivot 142w can be disposed on a second side of the distal end of the needle holder 42w, the first and second sides of the needle holder 42w being substantially opposite each other. The pivot(s) 142w allow the safety shield 64w to pivot in a rotational manner with respect to the needle holder 42w from a retracted position, as shown in FIG. 122 to an extended position, as previously described.

Figure 124:
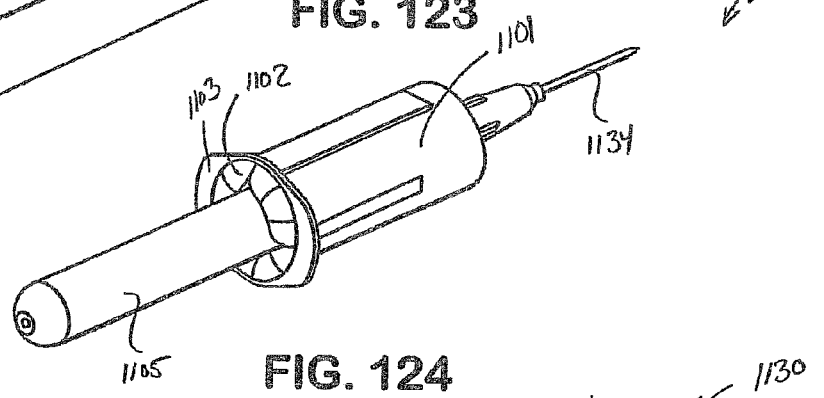
Figure 125:
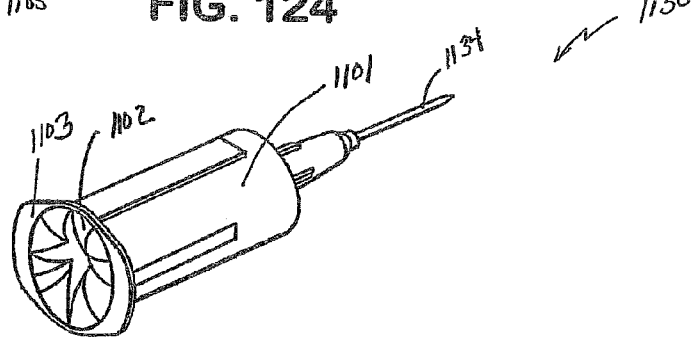

In yet another embodiment of the invention, shown in FIGS. 123-125, the needle assembly 1130 includes a specimen collection container holder 1101 having a pierceable or punctureable shield 1102 disposed over the proximal end 1103 of the specimen collection container holder 1101 to provide a sterile environment within the interior of the specimen collection container holder 1101 prior to use. In one embodiment, the pierceable or punctureable shield 1102 is made of a paper, polymeric, and/or thin metal film having perforated sections therein which may be pierced by standard manually applied pressure. In use, a medical practitioner may insert any conventionally known specimen collection container 1105, such as a blood collection tube, into the proximal end 1103 of the specimen collection container holder 1101 through the pierceable or punctureable shield 1102.

The needle assembly 1130 may then be used in any manner as previously described herein to perform a medical procedure and/or shield a cannula 1134 after use. After use, the pierceable or punctureable shield 1102 may remain attached to the specimen collection container holder 1101 to provide a clear indication of use of the needle assembly 1130. Accordingly, a needle assembly 1130 including a pierceable or punctureable shield 1102 provides a clear tamper and/or use indicator to a medical practitioner. The pierceable or punctureable shield 1102 described herein is suitable for use with any of the above-described collection assemblies. It is further contemplated that a separate, removable liner (not shown) may be affixed, such as through a removable adhesive, over the outer surface of shield 1102. Such a removable liner provides further sterility and barrier protection prior to the use. In addition, the pierceable or punctureable shield 1102 may be applied to the proximal end 1103 of the specimen collection container holder 1101 as a prepackaged device with the need for additional external packaging.

Figures 126, 127:
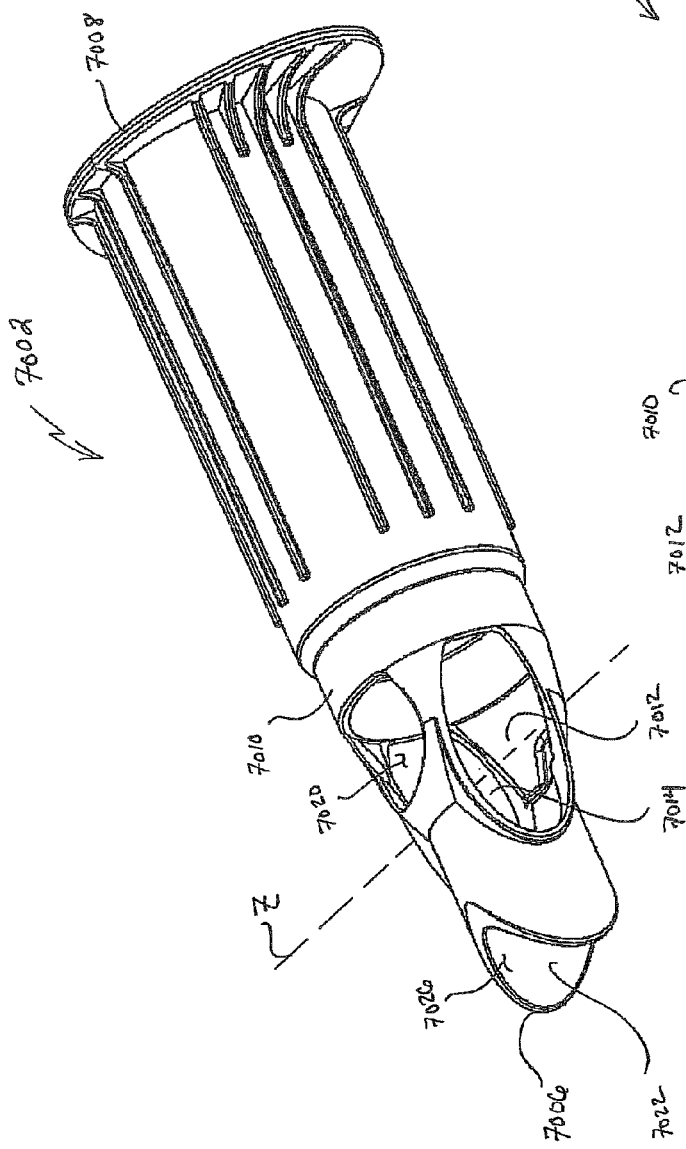
Figure 130:
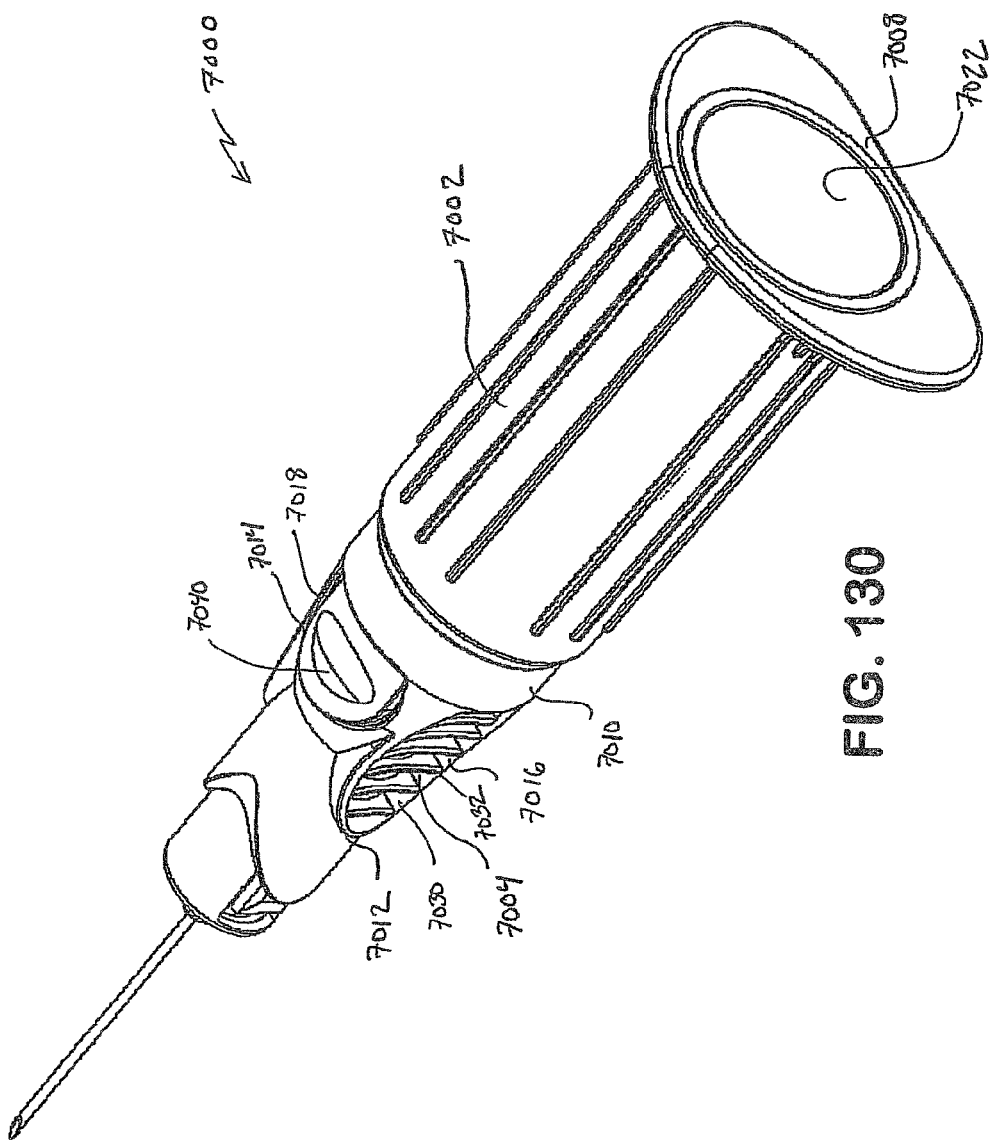
Figure 131:
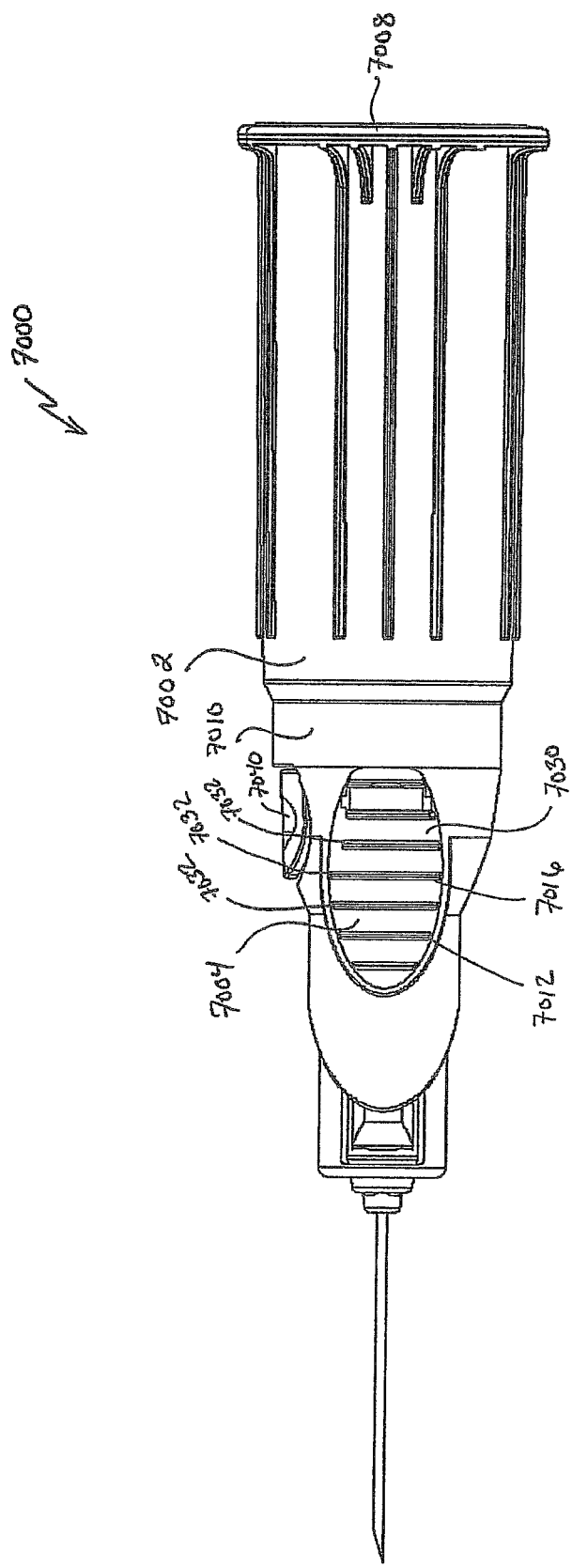

FIGS. 126-131 illustrate yet a further embodiment of the present invention in which the housing 7000 of a needle assembly, shown in FIGS. 130-131, as previously described herein, includes a base portion 7002, shown in FIGS. 126-127, and a hub portion 7004, shown in FIGS. 128-129, engageable with the base portion 7002. Referring to FIGS. 126-127, the base portion 7002 has a distal end 7006 and a proximal end 7008 with a sidewall 7010 extending therebetween. In one embodiment, the sidewall 7010 defines at least one opening 7012 through which a first portion 7016 of the hub 7004, shown in FIG. 128, may be received. In another embodiment, the opening 7012 is adapted to allow a first portion 7016 of the hub 7004, to pass from an interior 7022 of the base portion 7002 through the sidewall 7010 to a position external to the interior 7022 of the base portion 7002. In another embodiment, the sidewall 7010 defines a second opening 7014 through which a second portion 7018 of the hub 7004, shown in FIG. 128, may be received. In yet another embodiment, the first opening 7012 of the base portion 7002 may be aligned in a substantially opposed orientation with respect to the second opening 7014, such that the first opening 7012 and the second opening 7014 are aligned along a common through-axis Z, as shown in FIG. 126. In a further embodiment, the sidewall 7010 of the base portion 7002 may include a release member opening 7020 through which a release member 7040, shown in FIGS. 130-131 and as previously described, may be received.

As shown in FIGS. 128-129, the hub 7004 may include a first portion 7016 extending in a substantially radial orientation from a body portion 7024 of the hub 7004. In another embodiment, the hub 7004 may include a second portion 7018 extending in a substantially radial orientation from the body portion 7024 of the hub 7004 and aligned in a substantially opposed orientation with respect to the first portion 7016, such that the first portion 7016 and the second portion 7018 are aligned at least partially along a common axis Y, as shown in FIG. 128. In another embodiment, the common axis Y of the hub portion 7004 may be alignable with the through-axis Z of the base portion 7002, shown in FIG. 126.

As shown in FIGS. 130-131, the hub portion 7004 may be at least partially insertable within the base portion 7002 such that the first portion 7016 of the hub 7004 extends at least partially through the opening 7012 defined within the sidewall 7010 of the base portion 7002. In another embodiment, the hub portion 7004 may be at least partially insertable within the base portion 7002 such that the first portion 7016 of the hub portion 7004 extends at least partially through the opening 7012 defined within the sidewall 7010 of the base portion 7002, and the second portion 7018 of the hub extends at least partially through the second opening 7014 defined within the sidewall 7010 of the base portion 7002. In yet another embodiment, the hub portion 7004 may be insertable into the interior 7022 of the base portion 7002 through the proximal end 7008. In yet another embodiment, at least one of the first portion 7016 and the second portion 7018 are deflectable against an interior wall 7026 of the interior 7022 of the base portion, such as adjacent the proximal end 7008 during insertion of the hub portion 7004 into the base portion 7002. In yet a further embodiment, at least one of the first portion 7016 and the second portion 7018 include a gripable region 7030 enabling a user to easily contact the housing 7000 when the hub portion 7004 is disposed within the base portion 7002. In one embodiment, the gripable region 7030 includes a plurality of ribs 7032.

FIGS. 132-139 depict yet another embodiment of the present invention, in which a needle assembly 8000, such as a blood collection assembly, having a pivoting safety shield 8064 and a removable cannula shield 8066 engaged with a housing 8005 is generally shown in the restricted position. As shown specifically in FIG. 132, needle assembly 8000 generally includes a cannula structure 8032, associated with a hub 8058 with the pivoting safety shield 8064 connected to the hub 8058 and adapted for safety shielding of the cannula structure 8032 after use of the device. The cannula structure 8032 may include a distal needle portion 8002 and a proximal needle portion 8004. Distal needle portion 8002 and proximal needle portion 8004 may be separate needles, both of which represent needle cannula defining a cannula interior and central lumen extending therethrough. Alternatively, distal needle portion 8002 and proximal needle portion 8004 may be one needle with or without an opening between the ends. The proximal needle portion 8004 represents a non-patient end of the cannula structure 8032, which is provided for puncturing of an evacuated specimen collection container 8003, such as shown in FIG. 164. The proximal needle portion 8004 may be covered by an elastomeric multiple sample sleeve 8008 that can be pierced by a pointed end of proximal needle portion 8004 of the cannula structure 8032. Distal needle portion 8002 represents a patient end of the cannula structure 8032, and may be beveled to define a puncture tip for puncturing the skin of a patient and accessing the vasculature of the patient. The patient end of the distal needle portion 8002 projects at least partially from the distal end 8001 of the housing 8005 opposite the proximal end 8007 of the housing 8005 which is engageable with a specimen collection container 8003.

In one embodiment, the housing 8005 includes a hub 8058 which includes a distal front hub portion 8010 and a proximal rear hub portion 8012 and is capable of supporting the cannula structure 8032 therethrough. In one embodiment, the distal needle portion 8002 may be integral with the front hub portion 8010 and the proximal needle portion 8004 may be integral with the rear hub portion 8012. The front hub portion 8010 and the rear hub portion 8012 are structured to matingly engage. At least one of the front hub portion 8010 and the rear hub portion 8012 may include a protrusion, such as a raised annular ring for engaging a corresponding recess integral to the other of the front hub portion 8010 and the rear hub portion 8012. In another embodiment, the front hub portion 8010 and the rear hub portion 8012 may be joined together via an adhesive or weld. Once assembled, the hub 8058 defines a flashback indicator 8060 therein, as previously described. The hub 8058 may also include a porous vent 8061 as also previously described.

The hub 8058 may further include a collar 8018 for surrounding at least a portion of the safety shield 8064, such as an attachment bearing 8020 of the safety shield 8064, as previously described herein. In one embodiment, the front hub portion 8010 includes a first collar portion 8022 and the rear hub portion 8012 includes a second collar portion 8024. The first collar portion 8022 may include a generally c-shaped region for accommodating the attachment bearing 8020 of the safety shield 8064 therein. In one embodiment, the first collar portion 8022 may include a chamfered portion adjacent the c-shaped region for further restraining the attachment bearing 8020 therein. The attachment bearing 8020 may be integral with the safety shield 8064. The attachment bearing 8020 may also be integral with a portion of the hub 8058, such as the first collar portion 8022 and/or the second collar portion 8024. Alternatively, the attachment bearing 8020 may be separately provided and subsequently assembled with the safety shield 8064 and/or the hub 8058. The second collar portion 8024 may include an interior surface substantially corresponding to the attachment bearing 8020 of the safety shield 8064, such that when the first collar portion 8022 and the second collar portion 8024 are joined, the safety shield 8064 is fixedly engaged with the housing 8005 and capable of pivoting with respect to the housing 8005. In one embodiment, the safety shield 8064 is capable of pivoting substantially along the longitudinal axis $L_{Pivot}$ of the housing 8005, as shown in FIG. 133.

Referring again to FIG. 132, it is contemplated herein that the needle assembly 8000 may include an integrated specimen collection container holder 8011. The specimen collection container holder 8011 may define an interior 8013 through which a specimen collection container 8003, shown in FIG. 164, may be engaged with the proximal end of the rear hub portion 8012. Optionally, the proximal end of the specimen collection container holder 8011 may be provided with a cover 8017 for maintaining sterility within the interior 8013 of the specimen collection container holder 8011 prior to use, as previously described. Alternatively, although the needle assembly 8000 is depicted as engaged with a specimen collection container holder 8011, it is anticipated herein that the proximal end of the needle assembly 8000 may be provided without a specimen collection container holder 8011 engaged therewith. Specifically, the proximal needle portion 8004 of the cannula structure 8032 may be covered with a proximal needle cover, such as shown and described herein with reference to FIGS. 107-113.

Referring again to FIG. 132, prior to use of the needle assembly 8000, the distal needle portion 8002 of the cannula structure 8032 is covered with a cannula shield 8066. The cannula shield 8066 is adapted to removably engage a portion of the housing 8005, such as the hub 8058, and to shield at least the patient end of the distal needle portion 8002 of the cannula structure 8032. In one embodiment, a proximal portion 8072 of the cannula shield 8066 is adapted to engage the distal front hub portion 8010. The proximal portion 8072 of the cannula shield 8066 may include an attachment protrusion 8074, having a plurality of attachment ridges 8076 extending outwardly from the attachment protrusion 8074, adapted to engage a receiving recess 8080 of the distal front hub portion 8010 to secure the cannula shield 8066 to the hub 8058. In this configuration, a frictional interference fit is created between the attachment protrusion 8074 and the receiving recess 8080. In a further configuration, the attachment ridges 8076 may be adapted to slightly deform against the inner surface 8081 of the receiving recess 8080 to increase the frictional interference between the cannula shield 8066 and the hub 8058.

Referring yet again to FIG. 132, the cannula shield 8066 further includes a safety shield engagement 8090, such as a locking tab receiving structure. The safety shield engagement 8090 is adapted for releaseably engaging at least a portion of the safety shield 8064 in the restrained position, as shown in FIGS. 133-142, prior to use of the needle assembly 8000. In this embodiment, a portion of the cannula shield 8066 and a portion of the safety shield 8064 are engaged to releaseably lock the cannula shield 8066 to the needle assembly 8000 to prevent accidental removal of the cannula shield 8066 from the needle assembly 8000 prior to use. Accordingly, in addition to the frictional interference between the cannula shield 8066 and the hub 8058, the releaseable engagement between the cannula shield 8066 and the safety shield 8064 provides an additional locking mechanism to prevent accidental removal of the cannula shield 8066 from the needle assembly 8000. In prior needle assemblies, changes in temperature and other environmental factors could weaken the frictional resistance between protective cover structures and the base assembly causing unintentional release of a protective cover. In the present invention, the releaseable engagement between the cannula shield 8066 and the safety shield 8064 provides additional mechanical locking mechanism for further restraining the cannula shield 8066 with the needle assembly 8000 prior to use.

As shown in FIGS. 133-142, when the needle assembly 8000 is in the restrained position, the cannula shield 8066 is engaged with the safety shield 8064. In this configuration, environmental factors such as changes in temperature or typically manually applied axial force $F_{Axial}$, as shown in FIG. 133, on the cannula shield 8066 will not disengage the cannula shield 8066 from the needle assembly 8000.

As shown in FIG. 137, an optional sterility label 9007 can be applied between a portion of the cannula shield 8066 and the housing 8005 to evidence that the cannula shield 8066 has not been removed from the needle assembly 8000 prior to use.

As shown specifically in FIGS. 140-142, the safety shield engagement 8090 may be a ridge projecting dorsally from an outer surface 8091 of the cannula shield 8066, such as in a generally upwardly direction. The safety shield engagement 8090 may extend along at least a portion of a longitudinal axis of the cannula shield $L_{CannulaShield}$, as shown in FIG. 140. As shown in FIG. 142, the ridge may include a first ridge portion 9008 and a second ridge portion 9010 separated by a divided region 9006. In a further configuration, the first ridge portion 9008 and the second ridge portion 9010 may include corresponding beveled edge portions 9012, 9014 disposed to opposingly face the outer surface 8091 and separated from the outer surface 8091 by a neck region 9018.

Referring again to FIGS. 140-142, the safety shield 8064 may be provided with a first depending arm 9000 and a second depending arm 9002, constructed to form a press-fit lock with at least a portion of the cannula shield 8066. In one configuration, the first depending arm 9000 includes a first locking tab 9032, and the second depending arm 9002 includes a second locking tab 9034, with each of the first locking tab 9032 and the second locking tab 9034 adapted to releaseably engage the safety shield engagement 8090. In a further configuration, the first locking tab 9032 releaseably engages the first ridge portion 9008 and the second locking tab 9034 releaseably engages the second ridge portion 9010. Each of the first locking tab 9032 and the second locking tab 9034 may have an engagement surface 9040, 9041 corresponding to the beveled edge portions 9012, 9014 to provide a resistance interference therebetween. In a further configuration, the engagement surface 9040, 9041 may have an upwardly angled slope and/or an opposingly corresponding beveled edge to increase the interference resistance when engaged with the first ridge portion 9008 and the second ridge portion 9010.

The engagement of the safety shield engagement 8090 of the cannula shield 8066 and the locking tab 9032, 9034 of the safety shield 8064 are provided in a detent arrangement to releasably restrain the safety shield 8064 with the cannula shield 8066. The detent arrangement prevents unintentional removal of the cannula shield 8066 from the housing 8005 of the needle assembly 8000. The detent arrangement is adapted to resist disengagement until an intentionally upwardly directed force is imparted to the safety shield 8064 in a direction opposite the cannula shield 8066, as shown in FIG. 141 by the arrow $F_{Applied}$. The intentionally upwardly directed force may be imparted by typically manually pressure applied by a medical practitioner. As such a force is applied, the first locking tab 9032 and the second locking tab 9034 of the safety shield 8064 are deflected laterally in opposing directions, as shown by arrows $F_{Deflection}$ in FIG. 142. Once the first locking tab 9032 and the second locking tab 9034 are deflected laterally, the engagement of the first locking tab 9032 with the first ridge portion 9008 and the engagement of the second locking tab 9034 with the second ridge portion 9010 are released and detent arrangement of the cannula shield 8066 with the safety shield 8064 is disengaged.

Once the safety shield 8064 is transitioned from the restrained position, shown in FIGS. 133-142, to the retracted position, shown in FIGS. 143-150, the detent arrangement between the safety shield 8064 and the cannula shield 8066 has been disengaged. Disengagement of the detent arrangement allows a medical practitioner to subsequently remove the cannula shield 8066 from the needle assembly 8000 by applying manual force along the longitudinal axis of the cannula shield $L_{Cannula\ Shield}$, as shown in FIG. 140. Removal of the cannula shield 8066 from the needle assembly 8000 causes the sterility label 9007, shown in FIG. 147, to break, thereby evidencing exposure of the distal needle portion 8002 of the cannula structure 8032, shown in FIG. 150

Once the needle assembly 8000 is transitioned to the retracted position and the cannula shield 8066, shown engaged with the needle assembly 8000 in FIGS. 143-150, is removed, the distal needle portion 8002 of the needle assembly 8000 is exposed and ready for use by a medical practitioner to contact the vasculature of a patient, as shown in FIGS. 151-158. As used herein, the term "retracted position" means the position in which the safety shield 8064 is pivoted away from the patient end of the distal needle portion 8002 of the cannula structure 8032. Once the safety shield 8064 is transitioned to the retracted position and the cannula shield 8066, shown in FIGS. 132-142, is removed, the flashback indicator 8060 defined within the hub 8058 may be visible to a medical practitioner, as previously described herein, for providing visual evidence of contact between the distal needle portion 8002 of the cannula structure 8032 and the patient's vasculature. As shown in FIG. 159, a specimen collection container 8003 may be inserted into the interior 8013 of the specimen collection container holder 8011 of the needle assembly 8000 during use of the needle assembly in a vasculature access medical procedure. As also shown in FIG. 159, the exterior profile 9050 of the safety shield 8064 and the exterior profile 9052 of the housing 8005 may have a substantially corresponding profile to provide enhanced user stability.

Once the needle assembly 8000, in particular the distal needle portion 8002 of the cannula structure 8032 has been removed from contact with the patient, the safety shield 8064 may be transitioned to the extended position, as shown in FIGS. 160-172. The safety shield 8064 is transitionable over the distal needle portion 8002 of the cannula structure 8032 from a retracted position in which the patient directed distal needle portion 8002 is exposed, to an extended position in which the patient directed distal needle portion 8002 is shielded by at least a portion of the safety shield 8064. It is noted that transition of the safety shield 8064 from the retracted position to the extended position is possible only after the cannula shield 8066 shown in FIGS. 132-151, has been removed from the needle assembly 8000. Accordingly, removal of the cannula shield 8066 from the housing 8005 allows for transition of the safety shield 8064 from the retracted position, shown in FIGS. 143-159, to the extended position, shown in FIGS. 160-172. It is further noted that transition from the extended position to the retracted position does not automatically occur once the cannula shield 8066 is removed from the needle assembly 8000, but rather a medical practitioner must apply a downwardly directed force on a portion of the safety shield 8064, such as the thumb-press region 9063, to transition to safety shield 8064 from the retracted position to the extended position, as previously described.

As shown specifically in FIGS. 167-168, once the safety shield 8064 is transitioned to the extended position, the first locking tab 9032 of the first depending arm 9000 and the second locking tab 9034 of the second depending arm 9002 engage with and lock to at least a portion of the housing 8005, such as the front hub portion 8010, as previously described. Specifically, the engagement surface 9040 of the first locking tab 9032, and the engagement surface 9041 of the second locking tab 9034, may each engage a portion of the housing 8005 to fixedly and substantially non-removably secure the safety shield 8064 over the distal needle portion 8002.

As shown in FIG. 169, the engagement surface 9040 of the first locking tab 9032 of the first depending arm 9000 of the safety shield 8064 engages a first ledge 9073 of the front hub portion 8010 at least partially supporting the cannula structure 8032, as previously described herein with reference to FIG. 106. Also shown in FIG. 169, engagement surface 9041 of the second locking tab 9034 of the second depending arm 9002 of the safety shield 8064 engages a second ledge 9075 of the front hub portion 8010 at least partially supporting the cannula structure 8032, as also previously described herein with reference to FIG. 106. It is anticipated herein that the engagement surface 9040 of the first locking tab 9032 and the engagement surface 9041 of the second locking tab 9034 may engage the flashback indicator 8060. It is also anticipated herein that the engagement surface 9040 of the first locking tab 9032 and the engagement surface 9041 of the second locking tab 9034 may engage a portion of the housing 8005, such as the hub 8058 at a location that is distal to the flashback indicator 8060. The engagement surfaces 9040, 9041 of the safety shield 8064 are adapted to fixedly engage the housing 8005 to prevent disengagement thereof absent malicious force. Accordingly, the first locking tab 9032 and the second locking tab 9034 releasably engage a portion of the cannula shield 8066 in the restrained position, shown in FIGS. 132-151, and fixedly engage a portion of the housing 8005, such as the front hub portion 8010, in the extended position, shown in FIGS. 160-172.

As shown in FIG. 170, the safety shield 8064 may also include a deformable needle restraint 9077 for deflecting over cannula structure 8032 as the safety shield 8064 is transitioned to the extended position by applying force in the direction of arrow $F_{Extended}$, as shown in FIG. 170. Once the deformable needle restraint 9077 is engaged over the cannula structure 8032, the deformable needle restraint 9077 resists deflection upon application of a reversing force applied to the safety shield 8064 in the direction of arrow $F_{Reverse}$, as also shown in FIG. 170.

As previously described, it is anticipated herein that the housing 8005 of the needle assembly 8000 may or may not include a specimen collection container holder 8011, as shown in FIGS. 132-139. Alternatively, as shown in FIGS. 172A-172B, a needle assembly 9080 may include a non-patient cannula shield 9081 disposed over the proximal needle portion 8004 in place of a specimen collection container holder. This configuration is similarly described herein with reference to FIGS. 107-113, with the exception that, as shown in FIGS. 172A-172B, the needle assembly 9080 includes a cannula shield 8066A having a safety shield engagement 8090A, such as a ridge. As previously described, the safety shield engagement 8090A is releaseably engageable with the safety shield 8064A in the restrained position. The safety shield 8064A is transitionable from the restrained position to the retracted position and is subsequently transitionable from the retracted position to the extended position, as also previously described. The safety shield 8064A is releaseably engaged with the cannula shield 8066A in the restrained position, and is fixedly engaged with a portion of the housing 8005A in the extended position, once the cannula shield 8066A has been removed from engagement with the housing 8005A.

As shown in FIGS. 173-177, assembly of a needle assembly as described herein may be accomplished by assembling a first sub-assembly 9090 and subsequently joining the first sub-assembly 9090 with a second sub-assembly 9091 by press-fit engagement. The first sub-assembly 9090 may include elements previously described herein with reference to FIGS. 132-172 including a hub 8058, a distal hub portion 8010, a flashback indicator 8060, a cannula structure 8032, a cannula shield 8066 removably engaged with the hub 8058, and a pivoting safety shield 8064 fixedly engaged with a portion of the hub 8058. The safety shield 8064 being transitionable from a restricted position to a retracted position, and subsequently transitionable from a retracted position to an extended position. The safety shield 8064 and the cannula shield 8066 being releaseably engaged therewith in the restricted position. The safety shield 8064 fixedly engaged with a portion of the flashback indicator 8060 and/or the distal hub portion 8010 in the extended position. The second sub-assembly 9091 includes a specimen collection container holder 8011 having an interior 8013, as previously described herein with reference to FIGS. 132-139, through which a specimen collection container 8003, shown in FIG. 159, may be engaged with the proximal end of the hub 8058 or proximal rear hub portion 8012.

As shown in FIGS. 176-177, the first sub-assembly 9090 includes a first portion 9092 for press-fit engagement with the second sub-assembly 9091. The second sub-assembly 9091 includes a second portion 9093 for press-fit engagement with the first sub-assembly 9090. The first portion 9092 may include a first abutment surface 9094 for engaging a first restraining surface 9095 of the second portion 9093. The engagement of first abutment surface 9094 and first restraining surface 9095 substantially prevents movement between the first sub-assembly 9090 and the second sub-assembly 9091 in the proximal or rightwardly direction along the longitudinal axis $L_{Sub-Assembly}$ as shown in FIG. 176.

Also shown in FIGS. 176-177, the first sub-assembly 9090 includes a second restraining surface 9096 for restraining a second abutment surface 9097 of the second sub-assembly 9091. The engagement of second abutment surface 9097 and second restraining surface 9096 substantially prevents movement between the first sub-assembly 9090 and the second sub-assembly 9091 in the distal or leftwardly direction along the longitudinal axis $L_{Sub-Assembly}$ as shown in FIG. 176. Additionally, the second sub-assembly 9091 may include a restraining portion 9099 adapted for receipt within a neck portion 9098 of the first sub-assembly 9090 to further secure the first sub-assembly 9090 with the second sub-assembly 9091. The restraining portion 9099 may include an engagement surface 10001 for engaging a restraining tab 10002. In one configuration, engagement of the first sub-assembly 9090 and the second sub-assembly 9091 requires a deflection of at least one of first portion 9092 and the second portion 9093 to provide an interference therebetween. During engagement, an axial force is applied along the longitudinal axis $L_{Sub-Assembly}$ as shown in FIG. 176 to deflect at least one of the first portion 9092 and the second portion 9093 against the other of the first portion 9092 and the second portion 9093. In a further embodiment, the engagement of the first sub-assembly 9090 and the second sub-assembly 9091 includes a two-stage press-fit engagement. In the first stage, during applied axial force a first portion of at least one of the first portion 9092 and the second portion 9093 against the other of the first portion 9092 and the second portion 9093 occurs. In the second stage, still during applied axial force, a second portion of at least one of the first portion 9092 and the second portion 9093 against the other of the first portion 9092 and the second portion 9093 occurs. For example, the restraining portion 9099 may first deflect against the first abutment surface 9094, and subsequently deflect against the second restraining surface 9096.

Alternatively, as shown in FIGS. 178-181, engagement of a first sub-assembly 9090B and a second sub-assembly 9091B may include a portion of the first portion 9092B including locking teeth 10004 for engagement with a corresponding section 10006 of the second portion 9093B. In this configuration, the first sub-assembly 9090B and the second sub-assembly 9091B are engaged in press-fit configuration, and the further engagement of the locking teeth 10004 and the corresponding section 10006 further secure the first sub-assembly 9090B and the second sub-assembly 9091B against proximally or distally applied forces along the longitudinal axis $L_{Sub-Assembly}$ as shown in FIG. 176.

In yet another configuration, as shown in FIGS. 182-185, the first sub-assembly 9090C and the second sub-assembly 9091C may be secured by the above-described press-fit engagement of the first portion 9092C and the second portion 9093C, and by corresponding threaded engagement therebetween. In one configuration, at least a portion of the first portion 9092C and at least a portion of the second portion 9093C include corresponding mating surfaces for threaded engagement therebetween. As shown in FIG. 185, the first portion 9092C includes a plurality of threads 9194 for engagement with a plurality of corresponding recesses 9195 defined within the second portion 9093C. As also shown in FIG. 185, the first sub-assembly 9090C and the second sub-assembly 9091C may be press-fit engaged by interaction between a series of raised annular ridges and corresponding recesses. In one embodiment, the second sub-assembly 9091C may include at least one raised annular ridge 9100 extending outwardly within an interior 9113 of the second sub-assembly 9091C. The first sub-assembly 9090C may include at least one corresponding recess 9115 defined within a portion of the first portion 9092C and adapted to receive the raised annular ridge 9100 therein.

In each of the above-described press-fit engagements between the first sub-assembly 9090 and the second sub-assembly 9091, the press-fit engagement prevents disengagement of the first sub-assembly 9090 from the second sub-assembly 9091 upon engagement of a specimen collection container, such as shown as item 8003 in FIG. 159, with the proximal end of the hub 8058 and/or proximal rear hub portion 8012, each shown for example in FIG. 132. The above-described press-fit engagement mechanisms provide improved stability over sub-assemblies that are affixed together through adhesives, as they are temperature independent and resist additional environmental changes. The above-described press-fit engagement mechanisms also provide improved stability over sub-assemblies that are joined together through threaded engagement alone, as the press-fit mechanisms cannot become engaged through unintentionally applied rotational forces.

While specific embodiments of the invention have been described in detail, it will be appreciated by those skilled in the art that various modifications and alternatives to those details could be developed in light of the overall teachings of the disclosure. The present embodiments described herein are meant to be illustrative only, and not limiting as to the scope of the invention, which is to be given the full breadth of the appended claims and any and all equivalents thereof. Various other embodiments will be apparent to, and readily made by those skilled in the art, without departing from the scope and spirit of the invention.

What is claimed is:

1. A blood collection assembly, comprising:
   a first sub-assembly comprising,
   a hub comprising, a flash indicator, having a distal end and a proximal end engageable with a specimen collection container,
   a cannula extending between a patient end and a non-patient end, defining a cannula interior, the patient end of the cannula projecting at least partially from the distal end of the hub, the cannula interior in fluid communication with the flash indicator,
   a cannula shield removably engaged with the distal end of the hub and shielding at least the patient end of the cannula, the cannula shield comprising a safety shield engagement, and
   a pivoting safety shield engaged with a portion of the hub comprising at least one locking tab, the pivoting safety shield transitionable from a first position in which the locking tab is releasably engaged with the safety shield engagement of the cannula shield wherein at least one of the locking tab and/or the safety shield engagement are configured such that engagement therebetween resists application of axial force to the cannula shield and retains the cannula shield about the cannula, to a second position, in which the locking tab is disengaged from the safety shield engagement and the patient end is exposed, to a third position in which the patient end is shielded by at least a portion of the pivoting safety shield and the locking tab is fixedly locked with a portion of the hub;
wherein the safety shield engagement is a ridge projecting upwardly from an outer surface of the cannula shield and extending along at least a portion of a longitudinal axis of the cannula shield, and at least a portion of the ridge is engageable with at least a portion of the locking tab in a detent arrangement to restrain the pivoting safety shield with the cannula shield,
wherein a second sub-assembly comprising a specimen collection container holder having an interior through which a specimen collection container may be engaged with the proximal end of the hub, and
wherein the first sub-assembly further comprises a first portion for press-fit engagement with the second sub-assembly, and the second sub-assembly comprises a corresponding second portion for press-fit engagement with the first sub-assembly.

2. The blood collection assembly of claim 1, wherein release of the detent arrangement allows the pivoting safety shield to pivot from the first position to the second position.

3. The blood collection assembly of claim 1, wherein removal of the cannula shield from the housing allows for transition of the pivoting safety shield from the second position to the third position.

4. The blood collection assembly of claim 1, wherein the locking tab is releasably engagable with the safety shield engagement in the first position and fixedly engageable with a portion of the housing in the third position.

5. The blood collection assembly of claim 1, wherein engagement of the first portion and the second portion comprises deflection of at least one of the first portion and the second portion to provide an interference therebetween.

6. The blood collection assembly of claim 1, wherein the first portion and the second portion comprise a two-stage press-fit engagement, wherein engagement of the first portion and the second portion comprises a first deflection of at least a portion of at least one of the first portion and the second portion to provide an interference therebetween, and a second deflection of at least a portion of at least one of the first portion and the second portion to provide a second interference therebetween.

7. The blood collection assembly of claim 1, wherein at least a portion of the first portion and at least a portion of the second portion comprise corresponding mating surfaces for threaded engagement therebetween.

8. The blood collection assembly of claim 1, wherein the press-fit engagement of the first portion of the first sub-assembly and the second portion of the second sub-assembly prevents disengagement of the first sub-assembly from the second sub-assembly upon engagement of a specimen collection container with the proximal end of the hub.

9. The blood collection assembly of claim 1 wherein the at least one locking tab is engaged with the safety shield engagement in a detent arrangement that resists unintentional disengagement of the cannula shield from the housing.

10. A needle assembly, comprising:
a housing having a distal end, and a proximal end engageable with a specimen collection container;
a cannula extending distally from the housing, the cannula comprising a patient end;
a cannula shield removably engaged with a portion of the housing and capable of shielding at least the patient end of the cannula, the cannula shield comprising a safety shield engagement, wherein the safety shield engagement is a ridge projecting dorsally from an outer surface of the cannula shield; and
a pivoting safety shield engaged with a portion of the housing and comprising at least one locking tab, the pivoting safety shield transitionable from a first position in which the locking tab is releasably engaged with the safety shield engagement of the cannula shield, to a second position in which the locking tab is disengaged from the safety shield engagement and the patient end of the cannula is exposed, to a third position in which the patient end of the cannula is shielded by at least a portion of the safety shield and the locking tab is fixedly locked with a portion of the housing.

11. The needle assembly of claim 10, wherein removal of the cannula shield from the housing allows for transition of the pivoting safety shield from the second position to the third position.

12. The needle assembly of claim 10, wherein the housing further comprises a flash indicator, and a cannula interior is provided in fluid communication with the flash indicator, the flash indicator visible in the second position and wherein the pivoting safety shield is disposed over the patient end of the cannula and the locking tab engages at least a portion of the flash indicator in the third position.

13. The needle assembly of claim 10, wherein the housing further comprises a flash indicator, and a cannula interior is provided in fluid communication with the flash indicator, the flash indicator visible in the second position and wherein the pivoting safety shield is disposed over the patient end of the cannula and the locking tab engages a portion of the housing distal to the flash indicator in the third position.

14. The needle assembly of claim 10, wherein the housing comprises a forward hub portion and a rear hub portion connectable with the forward hub portion and defining a flash indicator therebetween.

15. The needle assembly of claim 10, wherein the safety shield engagement extends substantially longitudinally along the cannula shield.

16. The needle assembly of claim 10, wherein the ridge comprises a beveled edge and the locking tab comprises an engagement surface corresponding to the beveled edge to provide a resistance interference therebetween.

17. The needle assembly of claim 16, wherein the locking tab comprises a beveled edge and the ridge comprises an engagement surface corresponding to the beveled edge to provide a resistance interference therebetween.

18. The needle assembly of claim 10, wherein at least a portion of the ridge is engageable with at least a portion of the locking tab in a detent arrangement to restrain the pivoting safety shield with the cannula shield.

19. The needle assembly of claim 18, wherein the detent arrangement is adapted to resist disengagement until a force is imparted to the pivoting safety shield in a manner capable of moving the pivtoing safety shield from the first position to the second position.

20. The needle assembly of claim 18, wherein the detent arrangement resists unintentional removal of the cannula shield from the housing.

21. The needle assembly of claim 18, wherein release of the detent arrangement allows the pivoting safety shield to pivot from the first position to the second position.

22. A needle assembly, comprising:
a housing having a distal end and a proximal end;
a cannula extending distally from the housing, the cannula comprising a patient end;
a pivoting safety shield engaged with a portion of the housing and having a locking tab, the safety shield transitionable over the cannula from a retracted position in which the patient end is exposed, to an extended position in which the patient end is shielded by at least a portion of the safety shield and the locking tab fixedly locks with a portion of the housing; and a cannula shield releaseably engaged with a portion of the housing and shielding at least the patient end of the cannula, wherein the cannula shield comprises a safety shield engagement, the safety shield engagement comprising a ridge projecting dorsally from an outer surface of the cannula shield and extending along at least a portion of a longitudinal axis of the cannula shield, the pivoting safety shield releaseably engaged with the safety shield engagement to form a lock, wherein rotation of the pivoting safety shield disengages the lock between the safety shield and the cannula shield.

23. The needle assembly of claim 22, wherein the housing further comprises a flash indicator, and a cannula interior is provided in fluid communication with the flash indicator.

24. A blood collection assembly, comprising:

a first sub-assembly comprising:

a hub, comprising a flash indicator, having a distal end and a proximal end engageable with a specimen collection container;

a cannula extending between a patient end and a non-patient end, defining a cannula interior, the patient end of the cannula projecting at least partially from the distal end of the hub, the cannula interior in fluid communication with the flash indicator;

a cannula shield removably engaged with the distal end of the hub and shielding at least the patient end of the cannula, the cannula shield comprising a safety shield engagement, said safety shield engagement comprising a ridge projecting upwardly from an outer surface of the cannula shield and extending along at least a portion of a longitudinal axis of the cannula shield; and a pivoting safety shield engaged with a portion of the hub comprising at least one locking tab, the pivoting safety shield transitionable from a first position in which the locking tab is releasably engaged with the safety shield engagement of the cannula shield, to a second position, in which the locking tab is disengaged from the safety shield engagement and the patient end is exposed, to a third position in which the patient end is shielded by at least a portion of the pivoting safety shield and the locking tab is fixedly locked with a portion of the hub, wherein at least a portion of the ridge is engageable with at least a portion of the locking tab in a detent arrangement to restrain the pivoting safety shield with the cannula shield; and a second sub-assembly comprising a specimen collection container holder having an interior through which the specimen collection container may be engaged with the proximal end of the hub, wherein the first sub-assembly further comprises a first portion for press-fit engagement with the second sub-assembly, and the second sub-assembly comprises a corresponding second portion for press-fit engagement with the first sub-assembly.

25. The blood collection assembly of claim 24, wherein the locking tab is releasably engagable with the safety shield engagement in the first position and fixedly engageable with a portion of the housing in the third position.

26. The blood collection assembly of claim 24, wherein engagement of the first portion and the second portion comprises deflection of at least one of the first portion and the second portion to provide an interference therebetween.

27. The blood collection assembly of claim 24, wherein the first portion and the second portion comprise a two-stage press-fit engagement, wherein engagement of the first portion and the second portion comprises a first deflection of at least a portion of at least one of the first portion and the second portion to provide an interference therebetween, and a second deflection of at least a portion of at least one of the first portion and the second portion to provide a second interference therebetween.

28. The blood collection assembly of claim 24, wherein at least a portion of the first portion and at least a portion of the second portion comprise corresponding mating surfaces for threaded engagement therebetween.

29. The blood collection assembly of claim 24, wherein the press-fit engagement of the first portion of the first sub-assembly and the second portion of the second sub-assembly prevents disengagement of the first sub-assembly from the second sub-assembly upon engagement of the specimen collection container with the proximal end of the hub.

\* \* \* \* \*